United States Patent
Ebert et al.

(10) Patent No.: US 11,785,925 B2
(45) Date of Patent: Oct. 17, 2023

(54) DISEASE BIOMARKERS AND TREATMENT METHODS RELATED THERETO

(71) Applicants: THE BROAD INSTITUTE, INC., Cambridge, MA (US); THE BRIGHAM AND WOMEN'S HOSPITAL, INC., Boston, MA (US)

(72) Inventors: Benjamin Levine Ebert, Boston, MA (US); Jan Krönke, Boston, MA (US); Steven A. Carr, Cambridge, MA (US); Namrata D. Udeshi, Cambridge, MA (US); Emma Fink, Boston, MA (US)

(73) Assignees: THE BROAD INSTITUTE, INC., Cambridge, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 1086 days.

(21) Appl. No.: 16/408,792

(22) Filed: May 10, 2019

(65) Prior Publication Data

US 2019/0274292 A1    Sep. 12, 2019

Related U.S. Application Data

(63) Continuation of application No. 15/955,073, filed on Apr. 17, 2018, now Pat. No. 10,334,829, which is a continuation of application No. 15/074,920, filed on Mar. 18, 2016, now Pat. No. 9,974,289, which is a continuation-in-part of application No. PCT/US2014/064629, filed on Nov. 7, 2014.

(60) Provisional application No. 61/915,439, filed on Dec. 12, 2013, provisional application No. 61/902,066, filed on Nov. 8, 2013.

(51) Int. Cl.
| | |
|---|---|
| *C12Q 1/6876* | (2018.01) |
| *C12Q 1/6886* | (2018.01) |
| *G01N 33/50* | (2006.01) |
| *G01N 33/574* | (2006.01) |
| *G01N 33/94* | (2006.01) |
| *A01K 67/027* | (2006.01) |

(52) U.S. Cl.
CPC ........ *A01K 67/0278* (2013.01); *C12Q 1/6876* (2013.01); *C12Q 1/6886* (2013.01); *G01N 33/5011* (2013.01); *G01N 33/5088* (2013.01); *G01N 33/57496* (2013.01); *G01N 33/94* (2013.01); *A01K 2217/072* (2013.01); *A01K 2227/105* (2013.01); *A01K 2267/03* (2013.01); *C12Q 2600/106* (2013.01); *C12Q 2600/136* (2013.01); *C12Q 2600/156* (2013.01); *C12Q 2600/158* (2013.01); *G01N 2333/47* (2013.01)

(58) Field of Classification Search
CPC ................ C12Q 1/6876; C12Q 1/6886; C12Q 2600/106; C12Q 2600/136; C12Q 2600/156; G01N 33/5011; G01N 33/5088; G01N 33/57496; G01N 33/94; G01N 2333/47

See application file for complete search history.

(56) References Cited

U.S. PATENT DOCUMENTS

| | | | |
|---|---|---|---|
| 6,358,683 B1 | 3/2002 | Collins | |
| 6,740,495 B1 | 5/2004 | Issakani et al. | |
| 9,611,465 B2 | 4/2017 | Handa et al. | |
| 9,974,289 B2 | 5/2018 | Ebert et al. | |
| 10,334,829 B2 | 7/2019 | Ebert et al. | |
| 11,168,345 B2 | 11/2021 | Mikkelsen et al. | |
| 2010/0240057 A1 | 9/2010 | Downing et al. | |
| 2011/0223157 A1 | 9/2011 | Shafer et al. | |
| 2012/0192297 A1 | 7/2012 | Handa et al. | |
| 2012/0322073 A1 | 12/2012 | Lopez-Girona et al. | |
| 2013/0020590 A1 | 1/2013 | Lin et al. | |
| 2013/0115309 A1 | 5/2013 | Grandori et al. | |
| 2013/0345091 A1 | 12/2013 | Downing et al. | |
| 2014/0127690 A1 | 5/2014 | Bejar et al. | |
| 2014/0162282 A1 | 6/2014 | Schafer et al. | |
| 2015/0126538 A1 | 5/2015 | Muller et al. | |
| 2015/0152511 A1 | 6/2015 | Thakurta et al. | |
| 2016/0282354 A1 | 9/2016 | Ebert et al. | |
| 2016/0338326 A1 | 11/2016 | Ebert et al. | |
| 2018/0343839 A1 | 12/2018 | Ebert et al. | |
| 2019/0071731 A1 | 3/2019 | Mikkelsen et al. | |
| 2022/0017938 A1 | 1/2022 | Mikkelsen et al. | |
| 2022/0251651 A1 | 8/2022 | Ebert et al. | |

FOREIGN PATENT DOCUMENTS

| | | | |
|---|---|---|---|
| CN | 102690877 A | * | 9/2012 |
| WO | 2012125405 | | 9/2012 |
| WO | 2015077058 A2 | | 5/2015 |
| WO | 2015085160 A2 | | 6/2015 |
| WO | 2017044793 A1 | | 3/2017 |

(Continued)

OTHER PUBLICATIONS

Chopra et al., "Cereblon is a direct protein target for immunomoldulatory and antiproliferative activities of lenalidomide and pomalidomide," Leukemia, vol. 26, pp. 2326-2335 (2012).
Egan (British Journal of Haematology, (Jun. 2013), vol. 161, No. 5, pp. 748-751.
Gandhi (British J. Haematology, 2014 (first published Dec. 13, 2013), vol. 164, p. 811-821.
Gouri (J. Hematol Thrombo Dis. 2014, 2:3, p. 1).
He et al., "Ikaros is degraded by proteasome-dependent mechanism in the early phase of apoptosis induction," Biochem and Biophys. Res. Comm., vol. 409, pp. 430-434 (2011).

(Continued)

*Primary Examiner* — Mark Halvorson
*Assistant Examiner* — Dennis J Sullivan
(74) *Attorney, Agent, or Firm* — Melissa Hunter-Ensor; Nathan Hsu; Greenberg Traurig, LLP

(57) ABSTRACT

The present invention features a knock-in mouse comprising a mutation in an endogenous CRBN locus and methods of use thereof.

16 Claims, 79 Drawing Sheets

Specification includes a Sequence Listing.

(56) References Cited

FOREIGN PATENT DOCUMENTS

WO    2017044801 A2    3/2017

OTHER PUBLICATIONS

Holmfelt et al., "The genomic landscape of hypodiploid acute lymphoblastic leukemia," Nature Genetics, vol. 45, No. 3, pp. 242-254 (2013).
Ito (Science, Mar. 12, 2010, vol. 327, No. 5971, p. 1345-1350).
Kim (Biochimica et Biophysica Acta, Sep. 26, 2015, vol. 1852, p. 2662-2670).
Klein et al., "BCR-ABL1 induces aberrant splicing of IKAROS and lineage infidelity in pre-B lymphoblastic leukemia cells," Oncogene, vol. 25, pp. 1118-1124 (2005).
Kronke (Nature, Jul. 9, 2015, vol. 523, No. 7559, p. 183-188).
Kronke (Science, Jan. 17, 2014, vol. 343, p. 301-305).
Kronke, (OncoImmunology, Jul. 1, 2014, vol. 3, No. 7, e941742).
Lee (Biochemical and Biophysical Res. Comm, Jan. 22, 2015, vol. 458, p. 34-39).
Lee (Diabetes, Jun. 2013, vol. 62, p. 1855-1864).
Lopez-Girona (Leukemia, 2012, vol. 26, p. 2326-2335).
Min, Lee et al., Disruption of the Cereblon Gene Enhances Hepatic AMPK Activity and Prevents High-Fat Diet-Induced Obesity and Insulin Resistance in Mice, Diabetes, vol. 62, pp. 1855-1864 (2013).
P. Neri (Dec. 3, 2016, Blood, (Dec. 2, 2016), vol. 128, No. 22, p. 120, Meeting Info.: 58th Annual Meeting and Exposition of the American-Society-of-Hematology, San Diego, CA, USA, Dec. 3-6, 2016. Amer. Soc. Hematol).
R. Maity et al., Blood, Dec. 6, 2014, vol. 124, No. 21, p. 639, Meeting Info: 56th Annual Meeting of the American-Society-of-Hematology, San Francisco, CA, USA, Dec. 6-9, 2014, Amer. Soc. Hematol.).
Rajadhyaksha (Behavioral Brain Res., 2012, available Oct. 4, 2011, vol. 226, p. 428-434).
Sardnal (Leukemia, Apr. 26, 2013, vol. 27, p. 1610-1613).
Sawamura (Biochm. & Biophys. Res. Comm., 2015, vol. 464, p. 1054-1059).
Thakurta (Blood, (Nov. 15, 2013), vol. 122, No. 21, p. 3139, Meeting Info.: 55th Annual Meeting of the American-Society-of-Hematology, New Orleans, LA, USA, Dec. 7-10, 2013, Amer. Soc. Hematol).
Thakurta (Leukemia, 2014, vol. 28, p. 1129-1131, available online Oct. 29, 2013).
Zhu (Blood, Jul. 24, 2014, prepublished online Jun. 9, 2014, vol. 124, No. 4, p. 536-545).
Zhu (Blood, Nov. 16, 2012, vol. 120, No. 21, p. 1807, abstract).
Office Action dated Nov. 7, 2018 in U.S. Appl. No. 15/034,490 (44 pages).
International Search Report and Written Opinion, for corresponding PCT/US2014/064629, dated Mar. 24, 2015 (17 pages).
Ball et al., "Cell type- and estrogen receptor-subtype specific regulation of selective estrogen receptor modulator regulatory elements," Molecular and Cellular Endocrinology, 2009, vol. 299, pp. 204-211.
Baxevanis, Constantin N., "Antibody-based cancer therapy," Expert Opinion on Drug Discovery, 2008, vol. 3, No. 4, pp. 441-452.
Bendall et al., "Prevention of Amino Acid Conversion in SILAC Experiments with Embryonic Stem Cells," Molecular & Cellular Proteomics, 2008, vol. 7, No. 9, pp. 1587-1597.
Chamberlain et al., "Structure of the human Cereblon-DDB1-lenalidomide complex reveals basis for responsiveness to thalidomide analogs," Nature Structural & Molecular Biology, 2014, vol. 21, pp. 803-809.
Dermer, Gerald B., "Another Anniversary for the War on Cancer," Biotechnology, Mar. 12, 1994, vol. 12, p. 320.
Doench et al., "Rational design of highly active sgRNAs for CRISPR-Cas9-mediated gene inactivation," Nature Biotechnology, 2014, vol. 32, No. 12, pp. 1262-1267.
Evans et al., "Pharmacogenomics: Translating Functional Genomics into Rational Therapeutics," Science, Oct. 15, 1999, vol. 286, pp. 487-491.
He et al., "Ikaros is degraded by proteasome-dependent mechanism in the early phase of apoptosis induction," Biochemical and Biophysical Research Communications, 2011, vol. 406, pp. 430-434.
Lee et al., "Depletion of the cereblon gene activates the unfolded protein response and protects cells from ER stress-induced cell death," Biochemical and Biophysical Research Communications, 2015, vol. 458, pp. 34-39.
List et al., "Efficacy of Lenalidomide in Myelodysplastic Syndromes," The New England Journal of Medicine, Feb. 10, 2005, vol. 352, No. 6, pp. 549-557.
Lu et al., "The Myeloma Drug Lenalidomide Promotes the Cereblon-Dependent Destruction of Ikaros Proteins," Science, Jan. 17, 2014, vol. 343, pp. 305-309.
Melnikov et al., "Massively Parallel Reporter Assays in Cultured Mammalian Cells," Journal of Visualized Experiments (joVE), Aug. 2014, vol. 90, e51719, pp. 1-8.
Menard et al., "Cereblon (CRBN) Splicing Could Influence Response To IMiDs: A New PCR Strategy to Easily Detect and Semi-Quantify Loss Of The IMiDs Binding Domain," Blood, 2013, vol. 122, No. 21, p. 3107.
Mertins et al., "Integrated proteomic analysis of post-translational modifications by serial enrichment," Nature Methods, 2013, vol. 10, pp. 634-637.
Mullighan et al., "Genome-wide analysis of genetic alterations in acute lymphoblastic leukaemia," Nature, Apr. 12, 2007, vol. 446, pp. 758-764.
Nash et al., "Multisite phosphorylation of a CDK inhibitor sets a threshold for the onset of DNA replication," Nature, Nov. 29, 2001, vol. 414, pp. 514-521.
Ong et al., "A practical recipe for stable isotope labeling by amino acids in cell culture (SILAC)," Nature Protocols, 2006, vol. 1, No. 6, pp. 2650-2660.
Rajkumar et al., "Combination therapy with lenalidomide plus dexamethasone (Rev/Dex) for newly diagnosed myeloma," Blood, Dec. 15, 2005, vol. 106, No. 13, pp. 4050-4053.
Rappsilber et al., "Protocol for micro-purification, enrichment, pre-fractionation and storage of peptides for proteomics using StageTips," Nature Protocols, 2007, vol. 2, No. 8, pp. 1896-1906.
Rudikoff et al., "Single amino acid substitution altering antigen-binding specificity," Proceedings of the National Academy of Sciences of the United States of America, Mar. 1982, vol. 79, pp. 1979-1983.
Sanjana et al., "Improved vectors and genome-wide libraries for CRISPR screening," Nature Methods, Aug. 2014, vol. 11, No. 8, pp. 783-784.
Schafer et al., "The CUL4 (CRBN) E3 Ubiquitin Ligase Modulator CC-220 Induces Degradation of the Transcription Factors Ikaros and Aiolos: Immunomodulation in Healthy Volunteers and Relevance to Systemic Lupus Erythematosus," Arthritis & Rheumatology, Oct. 2014, vol. 66, Suppl. 10, pp. S1176-S1177.
Shaffer et al., "IRF4 addiction in multiple myeloma," Nature, Jul. 10, 2008, vol. 454, No. 7201, pp. 226-231.
Syvanen, Ann-Christine, "Accessing genetic variation: genotyping single nucleotide polymorphisms," Nature Reviews Genetics, Dec. 2001, vol. 2, pp. 930-942.
Winandy et al., "A Dominant Mutation in the Ikaros Gene Leads to Rapid Development of Leukemia and Lymphoma," Cell, Oct. 20, 1995, vol. 83, pp. 289-299.
Yang et al., "Exploiting Synthetic Lethality for the Therapy of ABC Diffuse Large B Cell Lymphoma," Cancer Cell, Jun. 12, 2012, vol. 21, pp. 723-737.
Zhu et al., "Cereblon expression is required for the antimyeloma activity of lenalidomide and pomalidomide," Blood, Nov. 3, 2011, vol. 118, No. 18, pp. 4771-4779.

\* cited by examiner

FIG. 5B-1

DMSO

| Protein names | M/L DMSO/ Control Rep1 | H/L DMSO/ Control Rep2 |
|---|---|---|
| CUL4B | 3.9 | 3.5 |
| CRBN | 4.0 | 3.3 |
| CUL4A | 3.8 | 3.5 |
| DDB1 | 3.7 | 3.0 |
| SAMD1 | 4.7 | 1.6 |
| COPS4 | 3.2 | 2.8 |
| COPS2 | 2.9 | 2.8 |
| COPS7A | 2.9 | 2.8 |
| GPS1 | 2.8 | 2.8 |
| COPS5 | 2.9 | 2.7 |
| COPS6 | 2.9 | 2.5 |
| COPS7B | 2.8 | 2.5 |
| COPS3 | 2.6 | 2.5 |
| COPS8 | 2.6 | 2.6 |
| LIG4 | 2.4 | 2.9 |
| APTX | 1.8 | 2.9 |
| DDA1 | 2.6 | 2.0 |
| RBX1 | 2.2 | 2.2 |
| IKZF3 | 1.2 | 1.4 |
| IKZF1 | 0.8 | 0.9 |

FIG. 5B-2

Lenalidomide

| Protein names | H/L Len/ Control Rep1 | M/L Len/ Control Rep2 |
|---|---|---|
| DDB1 | 4.0 | 3.6 |
| CUL4B | 4.0 | 3.5 |
| CUL4A | 3.8 | 3.5 |
| CRBN | 3.9 | 3.3 |
| SAMD1 | 4.9 | 2.2 |
| COPS7A | 2.9 | 2.6 |
| COPS4 | 2.9 | 2.6 |
| COPS6 | 2.9 | 2.5 |
| COPS7B | 2.9 | 2.5 |
| COPS5 | 2.9 | 2.4 |
| COPS2 | 2.8 | 2.5 |
| DNAJB12 | 1.1 | 4.2 |
| GPS1 | 2.7 | 2.5 |
| DDA1 | 2.7 | 2.4 |
| COPS3 | 2.6 | 2.3 |
| COPS8 | 2.6 | 2.3 |
| RBX1 | 2.3 | 2.2 |
| IKZF1 | 1.7 | 2.4 |
| IKZF3 | 1.9 | 1.9 |

FIG. 5B-3

Lenalidomide versus DMSO

| Gene names | H/L Len/ DMSO Rep1 | M/H Len/ DMSO Rep2 |
|---|---|---|
| FAM83G | 2.4 | 1.4 |
| IKZF1 | 1.1 | 1.5 |
| SPRYD4 | 0.7 | 1.7 |
| IKZF3 | 0.7 | 0.6 |
| SH3BP1 | 0.5 | 0.6 |
| LIG3 | -0.7 | -2.3 |
| XRCC1 | -0.7 | -2.3 |
| APTX | -0.8 | -2.2 |
| POLB | -1.0 | -2.2 |
| BRCC3 | -1.2 | -3.6 |

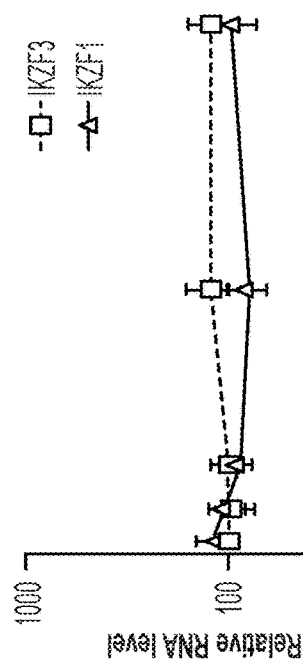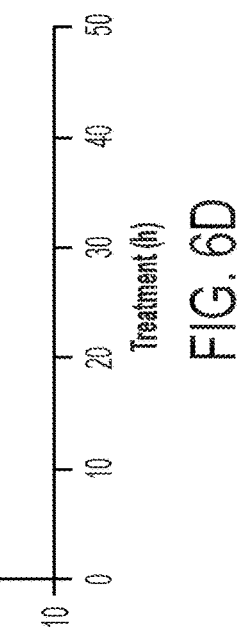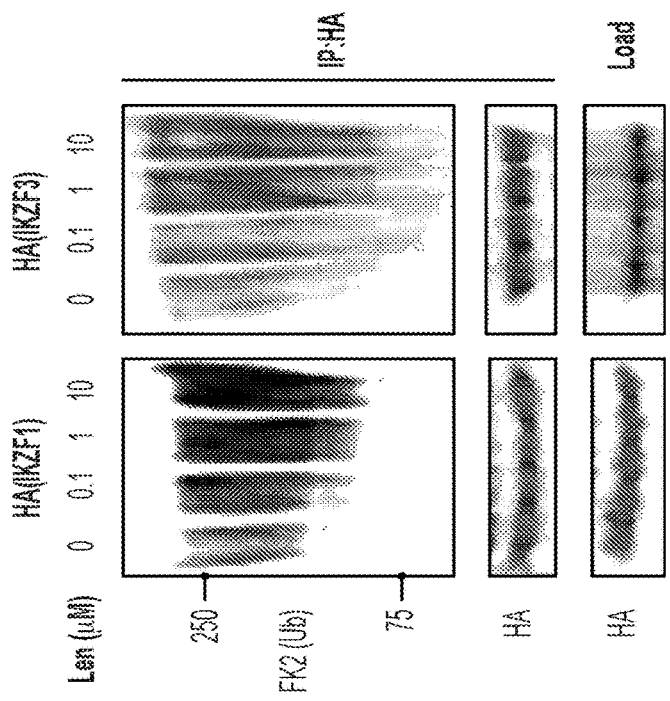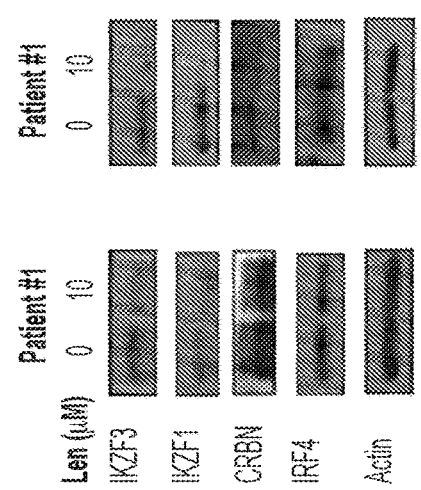
FIG. 6D
FIG. 6E
FIG. 6F

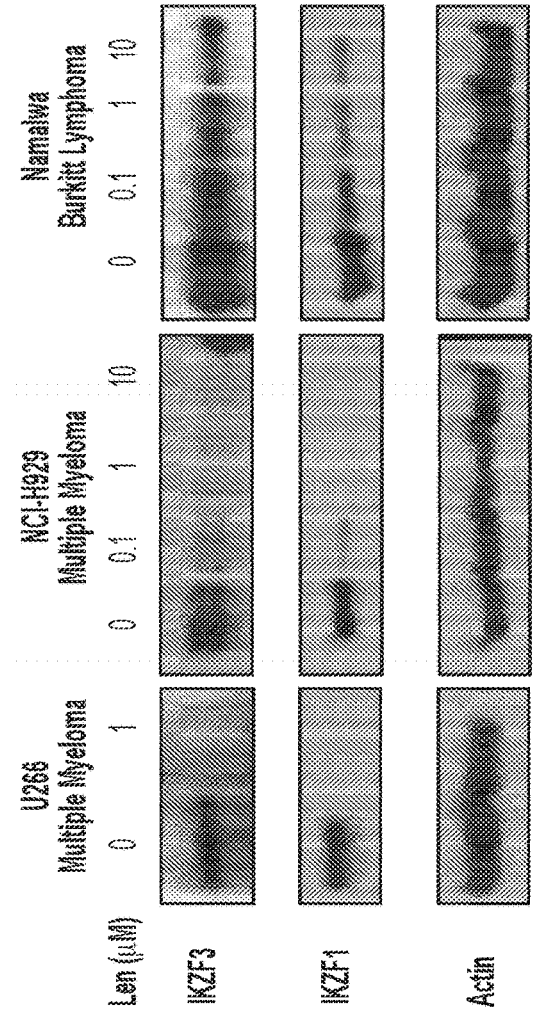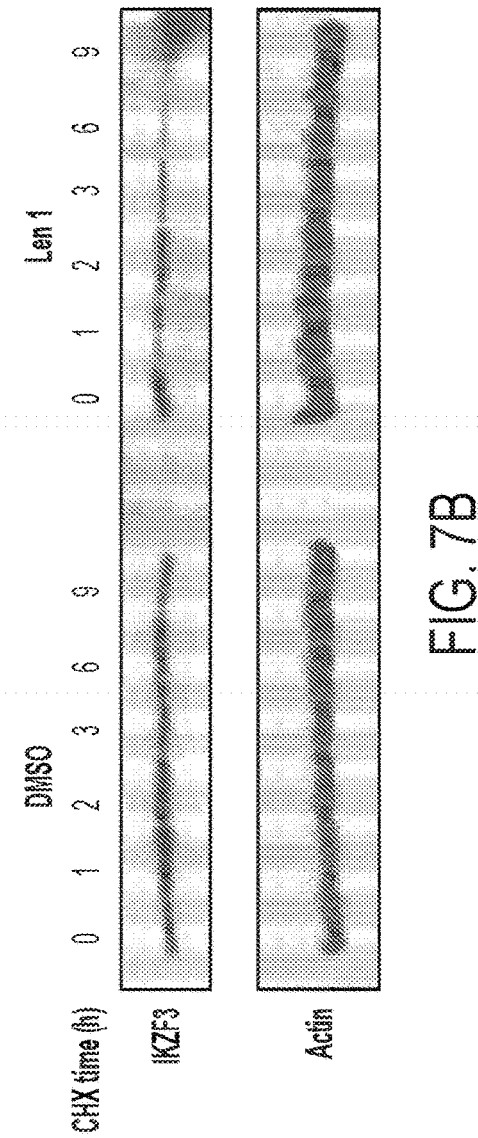
FIG. 7A
FIG. 7B

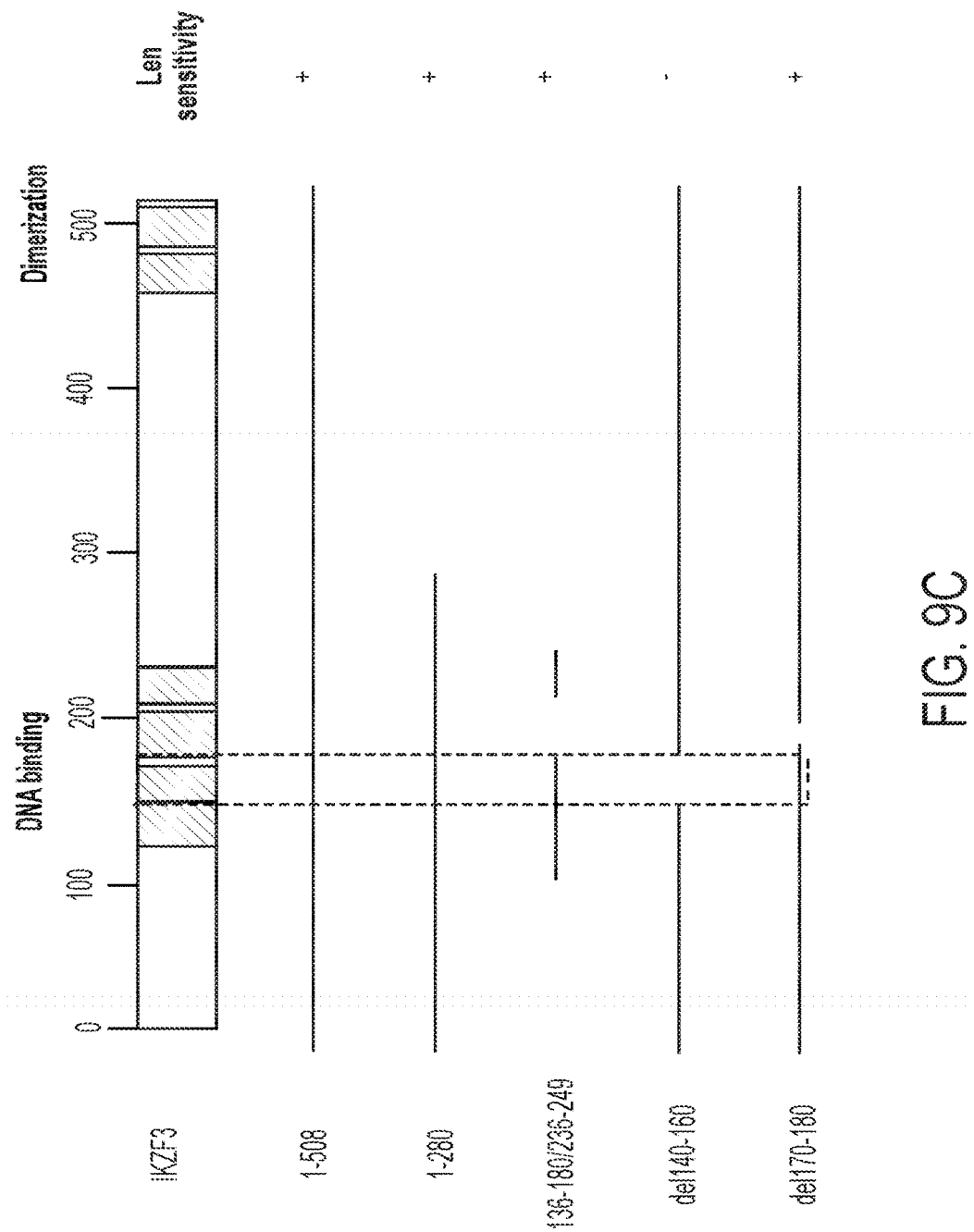

Proteome Analysis
after 12 hrs treatment log$_{2\%}$ FC%
Len/DMSO%

IRF4    70.23
IKZF3   72.09
IKZF1   71.54

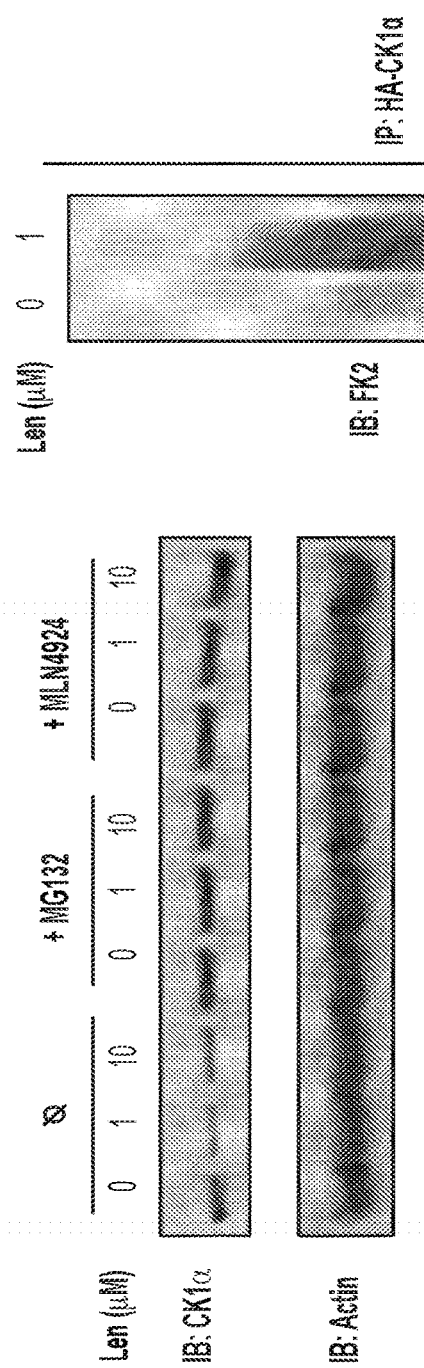
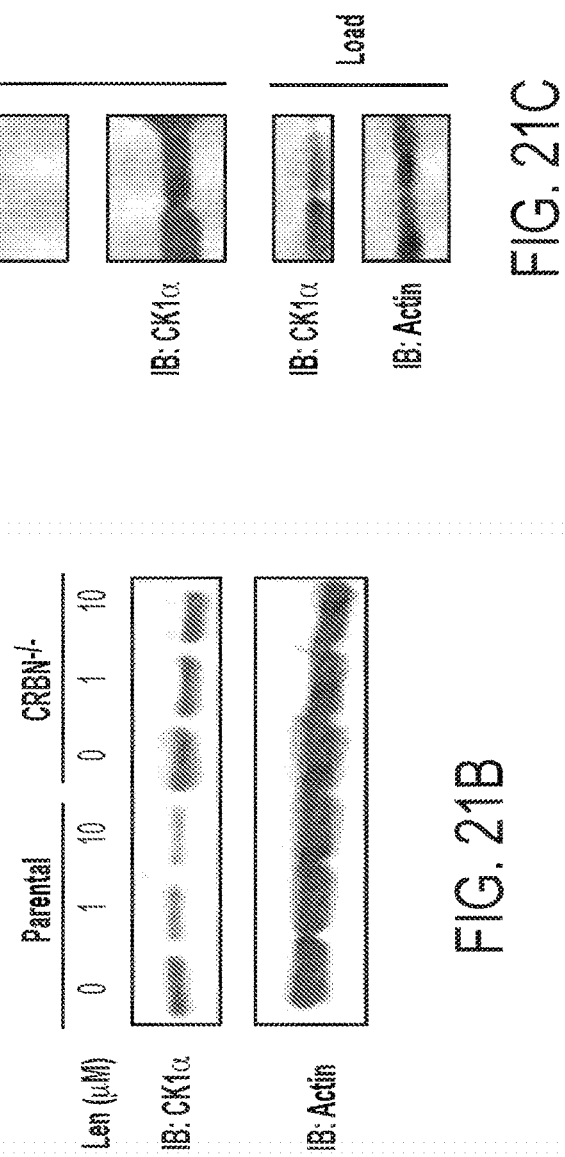
FIG. 21A
FIG. 21B
FIG. 21C

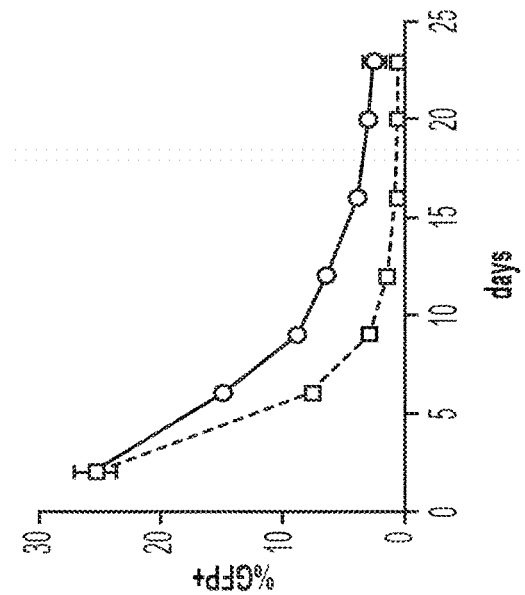
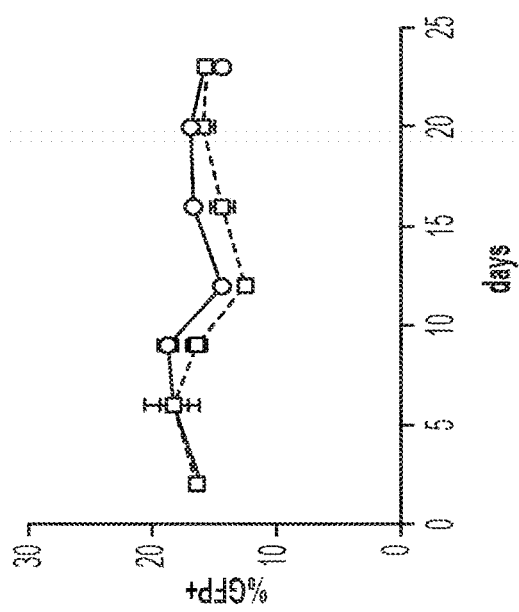
FIG. 21F-1
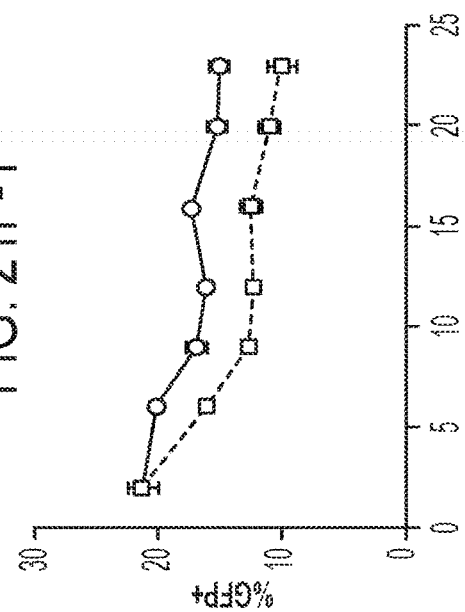
FIG. 21F-2
FIG. 21F-3

| Protein | Chr | 1μM Lenalidomide | | | | | 10μM Lenalidomide | | | | |
|---|---|---|---|---|---|---|---|---|---|---|---|
| | | Top ubiquitinated site | | | Protein | | Top ubiquitinated site | | | Protein | |
| | | Site | Rep#1 | Rep#2 | Rep#1 | Rep#2 | Site | Rep#1 | Rep#2 | Rep#1 | Rep#2 |
| IKZF1 | 7p12.2 | 91 | 2.78 | 2.75 | -1.62 | -1.54 | 91 | 3.18 | 2.62 | -1.73 | -1.67 |
| CK1a | 5q32 | 65 | 1.06 | 0.97 | -1.59 | -1.53 | 65 | 1.08 | 0.95 | -1.54 | -1.96 |
| RNF166 | 16q24.3 | 167 | -1.58 | -1.39 | -1.41 | -1.64 | 167 | -1.79 | -1.60 | -1.38 | -1.56 |
| ZNF692 | 1q44 | NA | NA | NA | -1.89 | -2.20 | NA | NA | NA | -1.91 | -0.60 |
| CRBN | 3q26.2 | 43 | -1.36 | -1.69 | 0.27 | 0.47 | 43 | -0.54 | -1.56 | 0.37 | 0.42 |
| CTNNB1 | 3p22.1 | 133 | -0.13 | -0.14 | 0.67 | 0.60 | 133 | 0.04 | -0.08 | 0.66 | 0.68 |
| C12orf57 | 12p13.31 | NA | NA | NA | 0.66 | 0.70 | NA | NA | NA | 0.82 | 0.64 |
| JUP | 17q21.2 | 149 | -0.67 | NA | 0.46 | 0.59 | 149 | -0.37 | NA | 0.60 | 0.63 |

FIG. 24D

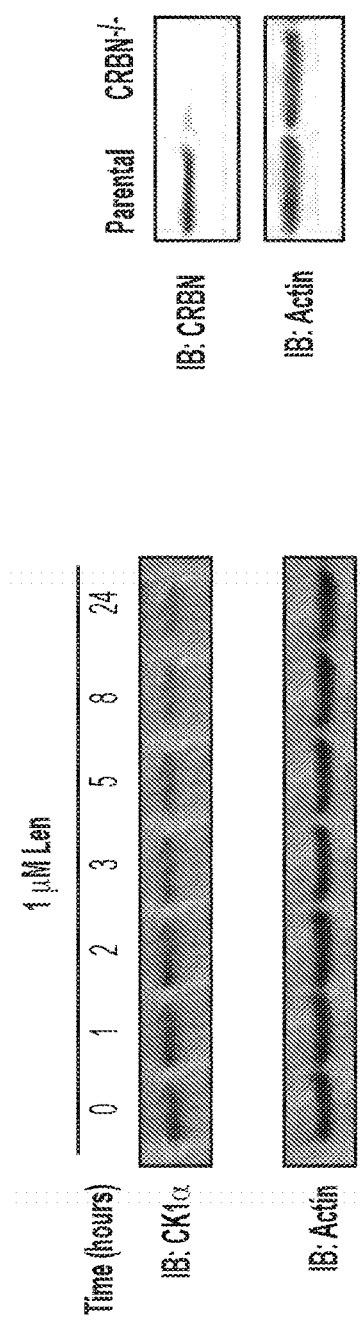
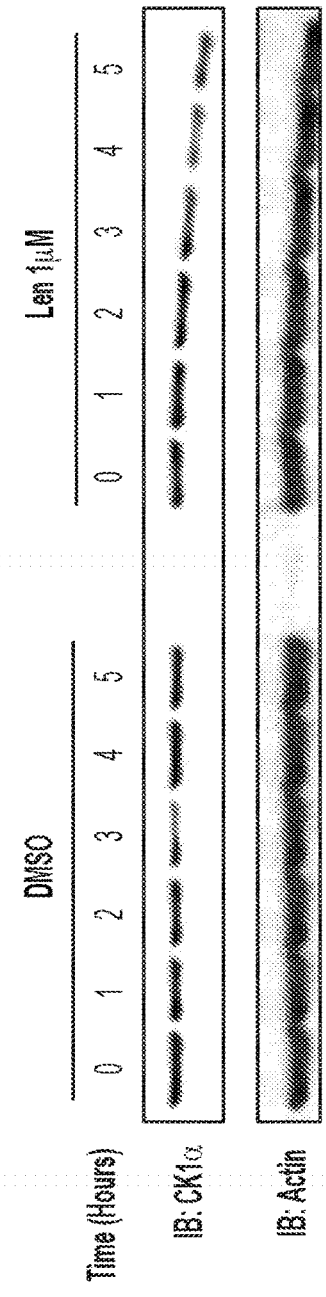
FIG. 25A
FIG. 25B
FIG. 25C

```
  1 MAGEGDQQDAHNWGNHLPLPESFEDEMEVED--QDSKEAKKPNIINEDTSLPTSH  56
  1 ..............ADS.DEDD.I.MEVED...........R............  60

57 TYIGADMEFHGRIHDDSCVIPQVMNLIPSQTIPLQLEHPQVSMVRNLIQKD     116
 61 .....................E..........................S     120

117 RTEAVLAYSNVQEREAQGHAEIVAYREQDFGIETVKVRA-GRQREKVLELRTQSDGI 176
121 ......................V.............E..................  180

177 QQAKVQILPSCVLPSTMSAVQLESLRKCQIPSKPVSREDQCSYKHWQKYQKRKEHCANL 236
181 .........................V..........I..C.................  240

237 FSWPRNLYSLYDAELMDRIKQLRENDENLKDDSLPSN.IDESYRVAACLPIDDVLRIQ  296
241 ...........................E.............................  300

297 LIKIGSAIQRLRCELDIMNKCTSLCKQCQERITKNEIFSLSCGPMAAYVNPHGYVH   356
301 .......................................................  360

357 GTLEVYRACNLMLIGRPSTEHSMRPGYAWTVAQKICASHIGQRETATKKDMSPQKEWGL 416
361 ..........................V.....I..........................  420

417 FRSALLPTIPDEEDEISPDKVLICL*   442
421 ...............E.........   446
```

FIG. 27C

SEQUENCE LISTING

```
<160> NUMBER OF SEQ ID NOS: 69

<210> SEQ ID NO 1
<211> LENGTH: 477
<212> TYPE: PRT
<213> ORGANISM: Homo sapiens

<400> SEQUENCE: 1

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
                20                  25                  30

Ile Pro Glu Asp Leu Ser Thr Thr Ser Gly Gly Gln Gln Ser Ser Lys
            35                  40                  45

Ser Asp Arg Val Val Ala Ser Asn Val Lys Val Glu Thr Gln Ser Asp
        50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95
```

Arg Asp Gln Gly Ser Ser Ala Leu Ser Gly Val Gly Ile Arg Leu
                    100                 105                 110

Pro Asn Gly Lys Leu Lys Cys Asp Ile Cys Gly Ile Ile Cys Ile Gly
                115                 120                 125

Pro Asn Val Leu Met Val His Lys Arg Ser His Thr Gly Glu Arg Pro
130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
                180                 185                 190

Arg Thr His Ser Val Ile Lys Glu Glu Thr Asn His Ser Glu Met Ala
                195                 200                 205

Glu Asp Leu Cys Lys Ile Gly Ser Glu Arg Ser Leu Val Leu Asp Arg
210                 215                 220

Leu Ala Ser Asn Val Ala Lys Arg Lys Ser Ser Met Pro Gln Lys Phe
225                 230                 235                 240

Leu Gly Asp Lys Gly Leu Ser Asp Thr Pro Tyr Asp Ser Ser Ala Ser
                245                 250                 255

Tyr Glu Lys Glu Asn Glu Met Met Lys Ser His Val Met Asp Gln Ala
                260                 265                 270

Ile Asn Asn Ala Ile Asn Tyr Leu Gly Ala Glu Ser Leu Arg Pro Leu
                275                 280                 285

Val Gln Thr Pro Pro Gly Gly Ser Glu Val Val Pro Val Ile Ser Pro
290                 295                 300

Met Tyr Gln Leu His Lys Pro Leu Ala Glu Gly Thr Pro Arg Ser Asn
305                 310                 315                 320

His Ser Ala Gln Asp Ser Ala Val Glu Asn Leu Leu Leu Leu Ser Lys
                325                 330                 335

Ala Lys Leu Val Pro Ser Glu Arg Glu Ala Ser Pro Ser Asn Ser Cys
                340                 345                 350

Gln Asp Ser Thr Asp Thr Glu Ser Asn Asn Glu Glu Gln Arg Ser Gly
                355                 360                 365

Leu Ile Tyr Leu Thr Asn His Ile Ala Pro His Ala Arg Asn Gly Leu
370                 375                 380

Ser Leu Lys Glu Glu His Arg Ala Tyr Asp Leu Leu Arg Ala Ala Ser
385                 390                 395                 400

Glu Asn Ser Gln Asp Ala Leu Arg Val Val Ser Thr Ser Gly Glu Gln
                405                 410                 415

Met Lys Val Tyr Lys Cys Glu His Cys Arg Val Leu Phe Leu Asp His
                420                 425                 430

Val Met Tyr Thr Ile His Met Gly Cys His Gly Phe Arg Asp Pro Phe
                435                 440                 445

Glu Cys Asn Met Cys Gly Tyr His Ser Gln Asp Arg Tyr Glu Phe Ser
                450                 455                 460

Ser His Ile Thr Arg Gly Glu His Arg Phe His Met Ser
465                 470                 475

<210> SEQ ID NO 2
<211> LENGTH: 519
<212> TYPE: PRT
<213> ORGANISM: Homo sapiens

<400> SEQUENCE: 2

-continued

```
Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
                20                  25                  30

Ile Pro Glu Asp Leu Ser Thr Thr Ser Gly Gln Gln Ser Ser Lys
                35                  40                  45

Ser Asp Arg Val Val Ala Ser Asn Val Lys Val Glu Thr Gln Ser Asp
        50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
                100                 105                 110

Pro Asn Gly Lys Leu Lys Cys Asp Ile Cys Gly Ile Ile Cys Ile Gly
                115                 120                 125

Pro Asn Val Leu Met Val His Lys Arg Ser His Thr Gly Glu Arg Pro
                130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
                180                 185                 190

Arg Thr His Ser Val Gly Lys Pro His Lys Cys Gly Tyr Cys Gly Arg
                195                 200                 205

Ser Tyr Lys Gln Arg Ser Ser Leu Glu Glu His Lys Glu Arg Cys His
                210                 215                 220

Asn Tyr Leu Glu Ser Met Gly Leu Pro Gly Thr Leu Tyr Pro Val Ile
225                 230                 235                 240

Lys Glu Glu Thr Asn His Ser Glu Met Ala Glu Asp Leu Cys Lys Ile
                245                 250                 255

Gly Ser Glu Arg Ser Leu Val Leu Asp Arg Leu Ala Ser Asn Val Ala
                260                 265                 270

Lys Arg Lys Ser Ser Met Pro Gln Lys Phe Leu Gly Asp Lys Gly Leu
                275                 280                 285

Ser Asp Thr Pro Tyr Asp Ser Ser Ala Ser Tyr Glu Lys Glu Asn Glu
                290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
                325                 330                 335

Gly Ser Glu Val Val Pro Val Ile Ser Pro Met Tyr Gln Leu His Lys
                340                 345                 350

Pro Leu Ala Glu Gly Thr Pro Arg Ser Asn His Ser Ala Gln Asp Ser
                355                 360                 365

Ala Val Glu Asn Leu Leu Leu Leu Ser Lys Ala Lys Leu Val Pro Ser
                370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
                405                 410                 415
```

```
His Ile Ala Pro His Ala Arg Asn Gly Leu Ser Leu Lys Glu His
                420                 425                 430

Arg Ala Tyr Asp Leu Leu Arg Ala Ala Ser Glu Asn Ser Gln Asp Ala
            435                 440                 445

Leu Arg Val Val Ser Thr Ser Gly Glu Gln Met Lys Val Tyr Lys Cys
450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser His Ile Thr Arg Gly
                500                 505                 510

Glu His Arg Phe His Met Ser
            515

<210> SEQ ID NO 3
<211> LENGTH: 3572
<212> TYPE: DNA
<213> ORGANISM: Homo sapiens

<400> SEQUENCE: 3
```

| | | | | | |
|---|---|---|---|---|---|
| ggcagcagag | gaacctttg | gaggaggaag | aggacacaga | ggccctgtag | ccaggcacca | 60 |
| agatccctcc | caggtggctg | ggtctgaggg | gaactccgag | cagccctagg | tcctcaaagt | 120 |
| ctggatttgt | gtggaaaagg | cagctctcac | ttggccttgg | cgaggcctcg | gttggttgat | 180 |
| aacctgagga | ccatggatgc | tgatgagggt | caagacatgt | cccaagtttc | agggaaggaa | 240 |
| agccccctg  | taagcgatac | tccagatgag | ggcgatgagc | ccatgccgat | ccccgaggac | 300 |
| ctctccacca | cctcgggagg | acagcaaagc | tccaagagtg | acagagtcgt | ggccagtaat | 360 |
| gttaaagtag | agactcagag | tgatgaagag | aatgggcgtg | cctgtgaaat | gaatgggaa  | 420 |
| gaatgtgcgg | aggatttacg | aatgcttgat | gcctcgggag | agaaaatgaa | tggctcccac | 480 |
| agggaccaag | gcagctcggc | tttgtcggga | gttggaggca | ttcgacttcc | taacggaaaa | 540 |
| ctaaagtgtg | atatctgtgg | gatcatttgc | atcgggccca | atgtgctcat | ggttcacaaa | 600 |
| agaagccaca | ctggagaacg | gcccttccag | tgcaatcagt | gcgggcctc  | attcacccag | 660 |
| aagggcaacc | tgctccggca | catcaagctg | cattccgggg | agaagccctt | caaatgccac | 720 |
| ctctgcaact | acgcctgccg | ccggagggac | gccctcactg | gccacctgag | gacgcactcc | 780 |
| gtcattaaag | aagaaactaa | tcacagtgaa | atggcagaag | acctgtgcaa | gataggatca | 840 |
| gagagatctc | tcgtgctgga | cagactagca | agtaacgtcg | ccaaacgtaa | gagctctatg | 900 |
| cctcagaaat | ttcttgggga | caagggcctg | tccgacacgc | cctacgacag | cagcgccagc | 960 |
| tacgagaagg | agaacgaaat | gatgaagtcc | cacgtgatgg | accaagccat | caacaacgcc | 1020 |
| atcaactacc | tgggggccga | gtccctgcgc | ccgctggtgc | agacgccccc | gggcggttcc | 1080 |
| gaggtggtcc | cggtcatcag | cccgatgtac | cagctgcaca | gccgctcgc  | ggagggcacc | 1140 |
| ccgcgctcca | accactcggc | ccaggacagc | gccgtggaga | acctgctgct | gctctccaag | 1200 |
| gccaagttgg | tgccctcgga | gcgcgaggcg | tccccgagca | acagctgcca | agactccacg | 1260 |
| gacaccgaga | gcaacaacga | ggagcagcgc | agcggtctca | tctacctgac | caaccacatc | 1320 |
| gccccgcacg | cgcgcaacgg | gctgtcgctc | aaggaggagc | accgcgccta | cgacctgctg | 1380 |
| cgcgccgcct | ccgagaactc | gcaggacgcg | ctccgcgtgg | tcagcaccag | cggggagcag | 1440 |
| atgaaggtgt | acaagtgcga | acactgccgg | gtgctcttcc | tggatcacgt | catgtacacc | 1500 |

```
atccacatgg gctgccacgg cttccgtgat ccttttgagt gcaacatgtg cggctaccac    1560
agccaggacc ggtacgagtt ctcgtcgcac ataacgcgag gggagcaccg cttccacatg    1620
agctaaagcc ctcccgcgcc cccaccccag accccgagcc accccaggaa aagcacaagg    1680
actgccgcct tctcgctccc gccagcagca tagactggac tggaccagac aatgttgtgt    1740
ttggatttgt aactgttttt tgtttttttgt ttgagttggt tgattggggt ttgatttgct    1800
```

```
tttgaaaaga tttttatttt tagaggcagg gctgcattgg gagcatccag aactgctacc    1860
ttcctagatg tttccccaga ccgctggctg agattccctc acctgtcgct tcctagaatc    1920
cccttctcca aacgattagt ctaaattttc agagagaaat agataaaaca cgccacagcc    1980
tgggaaggag cgtgctctac cctgtgctaa gcacggggtt cgcgcaccag gtgtcttttt    2040
ccagtcccca gaagcagaga gcacagcccc tgctgtgtgg gtctgcaggt gagcagacag    2100
gacaggtgtg ccgccaccca agtgccaaga cacagcaggg ccaacaacct gtgcccaggc    2160
cagcttcgag ctacatgcat ctagggcgga gaggctgcac ttgtgagaga aaatactatt    2220
tcaagtcata ttctgcgtag gaaaatgaat tggttgggga aagtcgtgtc tgtcagactg    2280
ccctgggtgg agggagacgc cgggctagag ccttttgggat cgtcctggat tcactggctt    2340
tgcggaggct gctcagatgg cctgagcctc ccgaggcttg ctgccccgta ggaggagact    2400
gtcttcccgt gggcatatct ggggagccct gttccccgct ttttcactcc cataccttta    2460
atggccccca aaatctgtca ctacaattta acaccagtc ccgaaatttg gatcttcttt    2520 cttttgaat ctctcaaacg gcaacattcc tcagaaacca aagctttatt tcaaatctct    2580
tccttccctg gctggttcca tctagtacca gaggcctctt ttcctgaaga aatccaatcc    2640
tagccctcat tttaattatg tacatctgtt tgtagccaca agcctgaatt tctcagtgtt    2700
ggtaagtttc tttacctacc ctcactatat attattctcg ttttaaaacc cataaaggag    2760
tgatttagaa cagtcattaa ttttcaactc aatgaaatat gtgaagccca gcatctctgt    2820
tgctaacaca cagagctcac ctgtttgaaa ccaagctttc aaacatgttg aagctcttta    2880
ctgtaaaggc aagccagcat gtgtgtccac acatacatag gatggctggc tctgcacctg    2940
taggatattg gaatgcacag ggcaattgag ggactgagcc agaccttcgg agagtaatgc    3000
caccagatcc cctaggaaag aggaggcaaa tggcactgca ggtgagaacc ccgcccatcc    3060
gtgctatgac atggaggcac tgaagcccga ggaaggtgtg tggagattct aatcccaaca    3120
agcaagggtc tccttcaaga ttaatgctat caatcattaa ggtcattact ctcaaccacc    3180
taggcaatga agaatatacc atttcaaata tttacagtac ttgtcttcac caacactgtc    3240
ccaaggtgaa atgaagcaac agagaggaaa ttgtacataa gtacctcagc atttaatcca    3300 aacagggggtt cttagtctca gcactatgac attttgggct gactacttat ttgttaggca    3360
ggagctctcc tgtgcattgt aggataatta gcagtatccc tggtggctac ccaatagacg    3420
ccagtagcac cccgaattga caacccaaac tctccagaca tcaccaactg tcccctgcga    3480
ggagaaatca ctcctggggg agaaccactg acccaaatga attctaaacc aatcaaatgt    3540
ctgggaagcc ctccaagaaa aaaaaaaaa aa                                   3572
```

<210> SEQ ID NO 4
<211> LENGTH: 509
<212> TYPE: PRT
<213> ORGANISM: Homo sapiens

<400> SEQUENCE: 4

Met Glu Asp Ile Gln Thr Asn Ala Glu Leu Lys Ser Thr Gln Glu Gln

```
1               5                   10                  15
Ser Val Pro Ala Glu Ser Ala Val Leu Asn Asp Tyr Ser Leu Thr
            20                  25                  30
Lys Ser His Glu Met Glu Asn Val Asp Ser Gly Glu Gly Pro Ala Asn
            35                  40                  45
Glu Asp Glu Asp Ile Gly Asp Ser Met Lys Val Lys Asp Glu Tyr
50                      55                  60
Ser Glu Arg Asp Glu Asn Val Leu Lys Ser Glu Pro Met Gly Asn Ala
65                  70                  75                  80
Glu Glu Pro Glu Ile Pro Tyr Ser Tyr Ser Arg Glu Tyr Asn Glu Tyr
                85                  90                  95
Glu Asn Ile Lys Leu Glu Arg His Val Val Ser Phe Asp Ser Arg
                100                 105                 110
Pro Thr Ser Gly Lys Met Asn Cys Asp Val Cys Gly Leu Ser Cys Ile
            115                 120                 125
Ser Phe Asn Val Leu Met Val His Lys Arg Ser His Thr Gly Glu Arg
130                 135                 140
Pro Phe Gln Cys Asn Gln Cys Gly Ala Ser Phe Thr Gln Lys Gly Asn
145                 150                 155                 160
Leu Leu Arg His Ile Lys Leu His Thr Gly Glu Lys Pro Phe Lys Cys
                165                 170                 175
His Leu Cys Asn Tyr Ala Cys Gln Arg Arg Asp Ala Leu Thr Gly His
                180                 185                 190
Leu Arg Thr His Ser Val Glu Lys Pro Tyr Lys Cys Glu Phe Cys Gly
            195                 200                 205
Arg Ser Tyr Lys Gln Arg Ser Ser Leu Glu Glu His Lys Glu Arg Cys
210                 215                 220
Arg Thr Phe Leu Gln Ser Thr Asp Pro Gly Asp Thr Ala Ser Ala Glu
225                 230                 235                 240
Ala Arg His Ile Lys Ala Glu Met Gly Ser Glu Arg Ala Leu Val Leu
                245                 250                 255
Asp Arg Leu Ala Ser Asn Val Ala Lys Arg Lys Ser Ser Met Pro Gln
            260                 265                 270
Lys Phe Ile Gly Glu Lys Arg His Cys Phe Asp Val Asn Tyr Asn Ser
            275                 280                 285
Ser Tyr Met Tyr Glu Lys Glu Ser Glu Leu Ile Gln Thr Arg Met Met
            290                 295                 300
Asp Gln Ala Ile Asn Asn Ala Ile Ser Tyr Leu Gly Ala Glu Ala Leu
305                 310                 315                 320
Arg Pro Leu Val Gln Thr Pro Ala Pro Thr Ser Glu Met Val Pro
                325                 330                 335
Val Ile Ser Ser Met Tyr Pro Ile Ala Leu Thr Arg Ala Glu Met Ser
                340                 345                 350
Asn Gly Ala Pro Gln Glu Leu Glu Lys Lys Ser Ile His Leu Pro Glu
            355                 360                 365
Lys Ser Val Pro Ser Glu Arg Gly Leu Ser Pro Asn Asn Ser Gly His
            370                 375                 380
Asp Ser Thr Asp Thr Asp Ser Asn His Glu Arg Gln Asn His Ile
385                 390                 395                 400
Tyr Gln Gln Asn His Met Val Leu Ser Arg Ala Arg Asn Gly Met Pro
                405                 410                 415
Leu Leu Lys Glu Val Pro Arg Ser Tyr Glu Leu Leu Lys Pro Pro
            420                 425                 430
```

```
Ile Cys Pro Arg Asp Ser Val Lys Val Ile Asn Lys Glu Gly Glu Val
            435                 440                 445

Met Asp Val Tyr Arg Cys Asp His Cys Arg Val Leu Phe Leu Asp Tyr
450                 455                 460

Val Met Phe Thr Ile His Met Gly Cys His Gly Phe Arg Asp Pro Phe
465                 470                 475                 480

Glu Cys Asn Met Cys Gly Tyr Arg Ser His Asp Arg Tyr Glu Phe Ser
                485                 490                 495

Ser His Ile Ala Arg Gly Glu His Arg Ala Leu Leu Lys
                500                 505

<210> SEQ ID NO 5
<211> LENGTH: 9686
<212> TYPE: DNA
<213> ORGANISM: Homo sapiens

<400> SEQUENCE: 5
```

| | | | | | |
|---|---|---|---|---|---|
| gcaggagcac | gtggagaggc | cgagtagcca | cagcggcagc | tccagcccgg | cccggcagcg | 60 |
| acatggaaga | tatacaaaca | aatgcggaac | tgaaaagcac | tcaggagcag | tctgtgcccg | 120 |
| cagaaagtgc | agcggttttg | aatgactaca | gtttaaccaa | atctcatgaa | atggaaaatg | 180 |
| tggacagtgg | agaaggccca | gccaatgaag | atgaagacat | aggagatgat | tcaatgaaag | 240 |
| tgaaagatga | atacagtgaa | agagatgaga | atgttttaaa | gtcagaaccc | atgggaaatg | 300 |
| cagaagagcc | tgaaatccct | tacagctatt | caagagaata | taatgaatat | gaaaacatta | 360 |
| agttggagag | acatgttgtc | tcattcgata | gtagcaggcc | aaccagtgga | aagatgaact | 420 |
| gcgatgtgtg | tggattatcc | tgcatcagct | tcaatgtctt | aatggttcat | aagcgaagcc | 480 |
| atactggtga | acgcccattc | cagtgtaatc | agtgtggggc | atcttttact | cagaaaggta | 540 |
| acctcctccg | ccacattaaa | ctgcacacag | gggaaaaacc | ttttaagtgt | cacctctgca | 600 |
| actatgcatg | ccaaagaaga | gatgcgctca | cggggcatct | taggacacat | tctgtggaga | 660 |
| aaccctacaa | atgtgagttt | tgtggaagga | gttacaagca | gagaagttcc | cttgaggagc | 720 |
| acaaggagcg | ctgccgtaca | tttcttcaga | gcactgaccc | aggggacact | gcaagtgcgg | 780 |
| aggcaagaca | catcaaagca | gagatgggaa | gtgaaagagc | tctcgtactg | gacagattag | 840 |
| caagcaatgt | ggcaaaacga | aaaagctcaa | tgcctcagaa | attcattggt | gagaagcgcc | 900 |
| actgctttga | tgtcaactat | aattcaagtt | acatgtatga | gaaagagagt | gagctcatac | 960 |
| agacccgcat | gatggaccaa | gccatcaata | cgccatcag | ctatcttggc | gccgaagccc | 1020 |
| tgcgccccett | ggtccagaca | ccgcctgctc | ccacctcgga | gatggttcca | gttatcagca | 1080 |
| gcatgtatcc | catagccctc | acccgggctg | agatgtcaaa | cggtgcccct | caagagctgg | 1140 |
| aaaagaaaag | catccaccctt | ccagagaaga | gcgtgccttc | tgagagaggc | ctctctccca | 1200 |
| acaatagtgg | ccacgactcc | acggacactg | acagcaacca | tgaagaacgc | agaatcaca | 1260 |
| tctatcagca | aaatcacatg | gtcctgtctc | gggcccgcaa | tgggatgcca | cttctgaagg | 1320 |
| aggttcccccg | ctcttacgaa | ctcctcaagc | cccgcccat | ctgcccaaga | gactccgtca | 1380 |
| aagtgatcaa | caaggaaggg | gaggtgatgg | atgtgtatcg | gtgtgaccac | tgccgcgtcc | 1440 |
| tcttcctgga | ctatgtgatg | ttcacgattc | acatgggctg | ccacggcttc | cgtgacccct | 1500 |
| tcgagtgtaa | catgtgtgga | tatcgaagcc | atgatcggta | tgagttctcg | tctcacatag | 1560 |
| ccagaggaga | acacagagcc | ctgctgaagt | gaatatctgg | tctcagggat | tgctcctatg | 1620 |
| tattcagcat | cgtttctaaa | aaccaatgac | ctcgcctaac | agattgctct | caaaacatac | 1680 |

```
tcagttccaa acttctttc ataccatttt tagctgtgtt cacaggggta gccagggaaa    1740
cactgtcttc cttcagaaat tattcgcagg tctagcatat tattactttt gtgaaacctt    1800
tgttttccca tcagggactt gaattttatg gaatttaaaa gccaaaaagg tatttggtca    1860
ttatcttcta cagcagtgga atgagtggtc ccggagatgt gctatatgaa acattctttc    1920
tgagatatat caaccacacg tggaaaagcc tttcagtcat acatgcaaat ccacaaagag    1980 gaaagagctga ccagctgacc ttgctgggaa gcctcaccct tctgcccttc acaggctgaa    2040
gggttaagat ctaatctccc taatctaaat gacagtctaa gagtaagtaa aagaacagcc    2100
ataaaataag tatctgttac gagtaactga agacccatt ctccaagcat cagatccatt    2160
tcctatcaca acatttttaa aaaatgtcat ctgatggcac ttctgcttct gtcctttacc    2220
ttcccatctc cagtgaaaag ctgagctgct ttgggctaaa ccagttgtct atagaagaaa    2280
atctatgcca gaagaactca tggttttaaa tatagaccat catcgaaact ccagaaattt    2340
atccactgtg gatgatgaca tcgctttcct ttggtcaagg ttggcagagc aagggtataa    2400 aggggggaaat tgtttggcag caccaacaga aaacaaacaa acaaaaaaca gctacctaaa    2460
acttcttgaa agagttcatg gagaattggt gatacagacc caaagcaaat ttgccaatga    2520
tattttccac aaaaaaagtc caaaaagtat ggctcagcct ccccctcccc acaggagagg    2580
aattggagat agatggcatg tgtgtttaga tcggagttga gctccggaat ggggtgagga    2640
gggacacctc tattgagagg ttctccttga tcaggcaggc ttcggccctt ttttttccat    2700
ttaaatggaa ctgctgtatt ccatgaaaat tcctgaaagt ctgatcacgg ttctgcagat    2760
gtataagtca tccttgtcac tcataatatg tacatactat caggaggagt gctgttatca    2820
tggtaaaatt agcactggaa taggaggtca caaaatgctg gctaattagc tatgtgactt    2880
tgagaaatcg tttaactttt ttttttttt ttttttgag acaggatctc actctgttgc    2940
ccaggctgga gtgcagtggt gcaatcatgg ctcagtgcag cctcgacctc ccaggctca    3000 ggtgatcctc ccacctcagc ctcttgagta ctgggacaac aagtgcacac caccatgtct    3060
ggctacattt tgttctttt gtagagatag ggtctcact atgttgccca tgctggtctt    3120
gaactcctgg gctcaagcaa tcagcccgcc tcagcctcct aaagtgctgg gattacaggt    3180
gtgagccacc acaccagcc ttatttaact cttaaaactc agtttccggc caggctcggt    3240
ggctcacacc tgtaatccca cactttggg aagccgaggc aggcgcatca tttgaggtca    3300
ggagttcgag accagcctga cccacatggt gaaaccctgt ctctactaaa aatacaaaaa    3360
ttagctgggg agtagtggca catgcctgta atcccagcta ctccggaggc tgaggcagaa    3420
aaatcgctta agcctgggag gttgaggttg cggtgagtgg agatcacact actgcactcc    3480
agtctgggcg acagagtgag accctgtctc aaacaaaaca aaacaaaaac aaacaaacaa    3540
aaacaaaaaa aactcagttt cctcatccat aaaataggaa ttagatttca atgttctctt    3600
aggtcccttc tagctttaat tcatatgtga ttatgcagta accacaaggt atttttttaaa    3660 cctcctaatg tatggatatt aagcagaaga gtatttatat gaatacatgt ttcacattcc    3720
tttggtatga aaatggtgtg ttaagttttt ccttttaacca ctgagttgtg aatgtgaaga    3780
aggtggtgga gaggaacaaa aaacagaaag gtattttgat cttgccacaa agcatacaca    3840
caaattggca catgcagctg tttgccaaag ccttctttt ttttttactt tttaagaaat    3900
tatgttaggg aaaataaatt ctgcttccag ggacaacttc atggagccta tttacaaatt    3960
aagagtcagc ttaatttgta acatttctac cagagccaag aatcccaaat tcctggtaga    4020
```

```
ttagtgtttt atttctaagg ggcttatgca ttcggctcca actcaactcg tctatgtgct    4080
gccagtaatt aaaatgttcc acctcagact gcacaaatgg cttatccttc tttgtggcat    4140
ggcgtctgtc tcaggaaaaa aggttttatg aaattccatg gcaacagtcc caacatgttt    4200
gagacttcag ctaaaggaat ggatgtattt tggtgtgtag tcttcagtat atcactgtat    4260
ttccgtaata ctagactcca agctatgcca gattgcttat tccctttgtg aaagaggagt    4320
tgctcattac gttcttgaaa tatcgcacat cctgttggtt cttcaaggga caagagaaag    4380
agaatttgga agcagggatt agtagaagag aaaacgaggg aaaggaagcc tttccaccag    4440
attagtgttc aagtctttgc agaggagacc aactttttt gttttctttt gttttgagac    4500
agtctctcgc tctgttgccc aggctggagt gcagtggcgc gatctcggct cacggcaacc    4560
tccgcctccc gggttcaagc aattctcctg cctcagcctc ccaagtagct gggattacag    4620
gtgctcacca ccaagcccgg ctaatttttg tattttagt agagacaagg tttcaccatg    4680
ttggccaggc cagtctcaaa ctcctgacct caggtgatct gcccgccttg cctcccaca    4740 gtgctgggat tacaggcatg agctaccgca cccagcctga ccacctttt tgcatctcaa    4800 gattgtgaaa ccaaggccca ttccaccagc ctggggactc ttttatagaa tatgatcctc    4860 cttttttcctg tgactaatga atttgctgca tgatttctat tcttctgagg ttagttttct    4920
gagtaaggtg accactcaca aaggcacttt cttttgtggca ttctgagcct agattggggc    4980
ccatcaattc cagaaaaaat ttatgtgtgg aaactctgca tccttaagtc ttgaagttga    5040
accagatatg cagtggttac catcacacag ataaacgctg ccttctgtac atacccctta    5100
tgctgtacta attaacaaac cccttgccag ggctggggag gtgagggtga aggagaatct    5160
tagcagaagg gcagagtcag gacttgcatc tgccactgct gggcactgaa gccctggagc    5220
agcttcagat agtacctgta ctttctcatg cagactccct ctgaacaaga gccttgtagg    5280
cccctctcct tcatttccca ccagcctctt atcaggcggg cttttccacca tacacccagg    5340 aggccacggt ctgaggaaca accaaaccca tgcaaaggggc cgggcgcgat agctcacgcc    5400
tgtaatgcca gcactttggg aggctgggc aggcagatca cctgaggttg ggagttcgag    5460
acctgcctga ccaacatgga gaaacccccca tctctactaa aaatacaaaa ttagccgggc    5520
gtgatggcac atgcctgtaa tcccagctac tcaggaggct gaggcaggag aatcgcttga    5580
acccgggagg cggaggttgc ggtgagccga gatggcacca ctgcactcca gcctcggcaa    5640
caagagcgaa actctgtcta aacaaaaac aaacaaacaa acaaaaaaac ccaggcaaag    5700
tttccttgca gccaaggtga cagaactggg ctgagggtgg aaaagaaaca gaaccagtgc    5760
tccaggtgtt ttttaattttt ttaatttatt tttatttttt ttgtatatgt atatatatgt    5820
atgtatattt tagaggacca gggtctcact atgttgccta ggccagactc aaactcctgt    5880
gctcaagcaa tcctgcctca gcctcccaag tagctgggat tacaggcatg cacaaacaat    5940
gcccagctct ccaaatgttt tctgtcacta cctgaagtgt tgcatcggta cttcctacgg    6000
aaagaaaact aaatagaagt gtctctcccg tgagccccca ccactaccac cagaaaaaaa    6060
aaagagagaa aatgaactca tcagtctta gtttcctcaa gttattctcc caaaagaca    6120 ttcgccttgg cacagataag ccagctaatc ttatgcttta tgacccactg tgagctgttc    6180
ctgacacagc ttctgacttt gtcagtgaca aaatttctca ccttttaaat gcagtgctta    6240
acattttgtt aggcccatac tcaaaatcgg ccagatataa aatgacctca gattttgatc    6300
tcctaggctc aaacaatcct cctacctcag cctcccaagt agctgggact ataggcacac    6360
caccatgcac agctaatttt ttttgtattt ttctgcagag atggcgtttc gccatactgc    6420
```

```
ccaggctagt ctcaaaatcc tgggctcaag caatctgccc acctcagcct cccaaagtgc   6480
tggaactaca ggcaagagcc actgcgccca gccacaacct cagatttctt tggcaaacag   6540
aaatgtttaa aaacacaaaa ttttgctcag gtgaaacact gtgttactat caaatctcac   6600
atccacataa agttttctt ttcggctttg tttcgtgagg aacagacaga acaaagtttt    6660
tccaggtagc atctgtatca ctattattct cctatttcct gtaccacccc cacctcccca   6720
agccctactg aatgtgaggt ttagaatgtt ttaaggaggg tcaggtgcgg tggctcacgc   6780
ctgtaatccc agcactttgg gaggccaagg cgggcggatc acctgagttt gggagttcga   6840
gaccagcctg accaacatgg agaaaccctg tctctactaa aaatacaaaa ttagccaggc   6900
gtggtggcac atgcctgtaa tcccagctac ttaggaggct gaggcaggag aatcgcttga   6960
acccaggagg aggaggttgt ggtgagccga gatcgtgcca ttgcactcca gcctgggtga   7020
cagagtgaga ctccatctcg aaaaaaaaaa tacaaaaatt agctgggtgt ggtggtgcac   7080
acctgtaatc ccagctactc gggaggctga cgcaggagaa ttgcttgaac ctgggaggtg   7140
gaggttgcag tgagccgaga tcgcgccatt gcaatccagc ctggacaaca gagtgagact   7200
ccatctcaaa aaaaaaaaa aaagaatgt tttaaggaaa aaaatagtac tgttacatat     7260
aatcccaggt gataagacca caatggaaat gtttaagtcc tcactttaaa gagtaccca    7320 ctgagaagag gtatgttgga ctctagcaga gatttgaaaa ctctgggaca ctcaagatgt   7380
gaaagagcct ggctatctga ggactcaaag agtcagcatc gggacttgtg agctcaagaa   7440
gagaaaaggg agtggtgaaa cttttgtccta aaagttagca ccaggaacag aagaaaaaaa   7500
cccgatatat agtgatacct catctttag agaatgggaa gctattttg tgttcacaca     7560 gaaagtatag ttcaaaaaac ctctatatcc agagttcaga caaggagaat gatttgagat   7620
ataagtgccg atgaaggagg tcaattttga tctgaaacca gcagctggac ctgggccacc   7680
tcaggaaaag gactctgttc tccaaggcag cacgactgaa tggttctgag aataagccag   7740
ggttcaggac tcctgacctt ttaggaccat ggactcagaa gagcctgaag gacaattgtg   7800 ggcttttaaac ttctgagagc ttgtaaagta acacaagact gtgcctctcc cttgccccag   7860
ctgtagatag tctttgcccc accattgtta tgaagataca cagggttttg cagtttgaat   7920
aaattggata caagtttcct cttttttttt ttcttttga gacaaagtct cgctctgttt     7980
ccccaggctg agtgcagtgg cacaatcaag cttacttgc cgcctcaacc tcctgggctc     8040
aagcaacgag ccatcctccc gtcttagcct cccaactagc tgagactaca ggcgtgggtc    8100
accacaccca gctaattttt gtacttttg tagagacagg gtctcaccat gttgcccagg     8160
ctggtcctga actcctgggc tcaagtaatc tgcccacctc agcctcccaa agtgttgggg   8220
ttacaggcgt gaggcaccgc ggctggcctg agtttcttct taatactgta tcacaattgt    8280
gggctgtctt atgtgttgat atcgattgag ctatttgaaa taggaatgtt aatgggtgta   8340 ttaaatttt gtaaggatat aacaatatct accttccaag gatgttgtga ggttttccat     8400
gattttgtat atgagctaat gttaccttg aggggtggtg tgcattatgt tggatgattg    8460
taaattttca gtggaaaatg taccgtgtcc taaatttaaa gacatgaaaa atatcccaag    8520
atcatactag atcataatag caattccttt acaaatgaat tatggaggta actgatctct    8580
aacagtttcc ttcatgttgt tttaatgcac aagggcagag gatctgctga cccttggaac    8640
cagcgtgagc taaccacgtg ctatagacac ttcatggtgt cgcacccagg gaagtcaaag    8700 cgcttttgctc cctcactgtc tgtgagtcct cagccattag taccccaccc ccgctgctc    8760
```

```
                                         -continued
caaaacttga gttatttcaa atgtttctca ctgttcatct ctccactgac cccactccag    8820
aaagcctgga gagagtccca agatgccacc caccttcccc aatccctcgc cacagatctg    8880
tgtctatctc acactctgta agtgccgctt tgcttcttcc tctcttgaaa agactgagaa    8940
cacacatttt aacatgttag gaaaatgggg cagcctaaaa aatgactgat cccaccgcca    9000
gtgactcatg tatactccag gctagcagac aaggcccttt ttggtgggcc tgcttctgtg    9060
ggttcacaga aaccaaatta ctgtgggttg caaagaatta gcaggtcatt tacaaagcag    9120
acatcccttc acccagactg tggttttgca tgctcaggtt ctcagtctat gagctttggt    9180
gcaggatcat tttggctact ggaaaaacca tagcttattt taaatttctg gttgccaaag    9240
ccaccacacg tgtggtctgt ggatgaccat tgtctgcaga atgacgagga aggaacagaa    9300
tgtggtttgg ggctcagggt ggccttccca ctgggaggga aggcgggagg gagcccttgc    9360
cctgggtttt gacacagcct gtgctcacag cctctcctct catctgcatt tctcagaaat    9420
gccctccctg cccagtggtg actttccctc gtcactccta tggagttcta cctggagccc    9480
agccatgtgt ggaactgtga agtttactcc tctgtaaaga tggtttaaag aaagtcagct    9540
tctgaaatgt aacaatgcta acccttgctg gaaccctgta agaaatagcc ctgctgatag    9600
ttttctaggt ttatcatgtt tgattttttac actgaaaaat aaaaaaatcc tggtatgttt    9660
gaaattaaaa aaaaaaaaaa aaaaaa                                         9686

<210> SEQ ID NO 6
<211> LENGTH: 441
<212> TYPE: PRT
<213> ORGANISM: Homo sapiens

<400> SEQUENCE: 6

Met Ala Gly Glu Gly Asp Gln Gln Asp Ala Ala His Asn Met Gly Asn
1               5                   10                  15

His Leu Pro Leu Leu Pro Glu Ser Glu Glu Asp Glu Met Glu Val
                20                  25                  30

Glu Asp Gln Asp Ser Lys Glu Ala Lys Lys Pro Asn Ile Ile Asn Phe
            35                  40                  45

Asp Thr Ser Leu Pro Thr Ser His Thr Tyr Leu Gly Ala Asp Met Glu
        50                  55                  60

Glu Phe His Gly Arg Thr Leu His Asp Asp Ser Cys Gln Val Ile
65                  70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
                100                 105                 110

Ile Gln Lys Asp Arg Thr Phe Ala Val Leu Ala Tyr Ser Asn Val Gln
            115                 120                 125

Glu Arg Glu Ala Gln Phe Gly Thr Thr Ala Glu Ile Tyr Ala Tyr Arg
        130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
            180                 185                 190

Met Ser Ala Val Gln Leu Glu Ser Leu Asn Lys Cys Gln Ile Phe Pro
        195                 200                 205
```

```
Ser Lys Pro Val Ser Arg Glu Asp Gln Cys Ser Tyr Lys Trp Trp Gln
    210                 215                 220

Lys Tyr Gln Arg Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
                245                 250                 255

Lys Lys Gln Leu Arg Glu Trp Asp Glu Asn Leu Lys Asp Asp Ser Leu
                260                 265                 270

Pro Ser Asn Pro Ile Asp Phe Ser Tyr Arg Val Ala Ala Cys Leu Pro
            275                 280                 285

Ile Asp Asp Val Leu Arg Ile Gln Leu Leu Lys Ile Gly Ser Ala Ile
290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
                325                 330                 335

Phe Ser Leu Ser Leu Cys Gly Pro Met Ala Ala Tyr Val Asn Pro His
                340                 345                 350

Gly Tyr Val His Glu Thr Leu Thr Val Tyr Lys Ala Cys Asn Leu Asn
                355                 360                 365

Leu Ile Gly Arg Pro Ser Thr Glu His Ser Trp Phe Pro Gly Tyr Ala
370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
                405                 410                 415

Thr Arg Ser Ala Leu Leu Pro Thr Ile Pro Asp Thr Glu Asp Glu Ile
                420                 425                 430

Ser Pro Asp Lys Val Ile Leu Cys Leu
            435                 440

<210> SEQ ID NO 7
<211> LENGTH: 441
<212> TYPE: PRT
<213> ORGANISM: Homo sapiens

<400> SEQUENCE: 7

Met Ala Gly Glu Gly Asp Gln Gln Asp Ala Ala His Asn Met Gly Asn
1               5                   10                  15

His Leu Pro Leu Leu Pro Glu Ser Glu Glu Asp Glu Met Glu Val
                20                  25                  30

Glu Asp Gln Asp Ser Lys Glu Ala Lys Lys Pro Asn Ile Ile Asn Phe
            35                  40                  45

Asp Thr Ser Leu Pro Thr Ser His Thr Tyr Leu Gly Ala Asp Met Glu
        50                  55                  60

Glu Phe His Gly Arg Thr Leu His Asp Asp Ser Cys Gln Val Ile
65                  70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
            100                 105                 110

Ile Gln Lys Asp Arg Thr Phe Ala Val Leu Ala Tyr Ser Asn Val Gln
        115                 120                 125

Glu Arg Glu Ala Gln Phe Gly Thr Thr Ala Glu Ile Tyr Ala Tyr Arg
130                 135                 140
```

Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
            165                 170                 175

Gln Gln Ala Lys Val Gln Ile Leu Pro Glu Cys Val Leu Pro Ser Thr
            180                 185                 190

Met Ser Ala Val Gln Leu Glu Ser Leu Asn Lys Cys Gln Ile Phe Pro
            195                 200                 205

Ser Lys Pro Val Ser Arg Glu Asp Gln Cys Ser Tyr Lys Trp Trp Gln
210                 215                 220

Lys Tyr Gln Lys Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
            245                 250                 255

Lys Lys Gln Leu Arg Glu Trp Asp Glu Asn Leu Lys Asp Asp Ser Leu
            260                 265                 270

Pro Ser Asn Pro Ile Asp Phe Ser Tyr Arg Val Ala Ala Cys Leu Pro
            275                 280                 285

Ile Asp Asp Val Leu Arg Ile Gln Leu Leu Lys Ile Gly Ser Ala Ile
290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
            325                 330                 335

Phe Ser Leu Ser Leu Cys Gly Pro Met Ala Ala Tyr Val Asn Pro His
            340                 345                 350

Gly Tyr Val His Glu Thr Leu Thr Val Tyr Lys Ala Cys Asn Leu Asn
            355                 360                 365

Leu Ile Gly Arg Pro Ser Thr Glu His Ser Trp Phe Pro Gly Tyr Ala
370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
            405                 410                 415

Thr Arg Ser Ala Leu Leu Pro Thr Ile Pro Asp Thr Glu Asp Glu Ile
            420                 425                 430

Ser Pro Asp Lys Val Ile Leu Cys Leu
            435                 440

<210> SEQ ID NO 8
<211> LENGTH: 2213
<212> TYPE: DNA
<213> ORGANISM: Homo sapiens

<400> SEQUENCE: 8
gcgtgtaaac agacatggcc ggcgaaggag atcagcagga cgctgcgcac aacatgggca    60
accacctgcc gctcctgcct gagagtgagg aagaagatga atggaagtt gaagaccagg   120 atagtaaaga agccaaaaaa ccaaacatca taaattttga caccagtctg ccgacatcac   180
atacatacct aggtgctgat atggaagaat tcatggcag actttgcac gatgacgaca   240 gctgtcaggt gattccagtt cttccacaag tgatgatgat cctgattccc ggacagacat   300
tacctcttca gcttttcac cctcaagaag tcagtatggt gcggaattta attcagaaag   360
atagaacctt tgctgttctt gcatacagca atgtacagga aagggaagca cagtttggaa   420

```
caacagcaga gatatatgcc tatcgagaag aacaggattt tggaattgag atagtgaaag    480
tgaaagcaat tggaagacaa aggttcaaag tccttgagct aagaacacag tcagatggaa    540
tccagcaagc taaagtgcaa attcttcccg aatgtgtgtt gccttcaacc atgtctgcag    600
ttcaattaga atccctcaat aagtgccaga tatttccttc aaaacctgtc tcaagagaag    660
accaatgttc atataaatgg tggcagaaat accagaggag aaagtttcat tgtgcaaatc    720
taacttcatg gcctcgctgg ctgtattcct tatatgatgc tgagacctta atggacagaa    780
tcaagaaaca gctacgtgaa tgggatgaaa atctaaaaga tgattctctt ccttcaaatc    840
caatagattt ttcttacaga gtagctgctt gtcttcctat tgatgatgta ttgagaattc    900
agctccttaa aattggcagt gctatccagc gacttcgctg tgaattagac attatgaata    960
aatgtacttc cctttgctgt aaacaatgtc aagaaacaga ataacaacc aaaaatgaaa     1020 tattcagttt atccttatgt gggccgatgg cagcttatgt gaatcctcat ggatatgtgc    1080
atgagacact tactgtgtat aaggcttgca acttgaatct gataggccgg ccttctacag    1140
aacacagctg gtttcctggg tatgcctgga ctgttgccca gtgtaagatc tgtgcaagcc    1200
atattggatg gaagtttacg gccaccaaaa aagacatgtc acctcaaaaa ttttgggggct   1260 taacgcgatc tgctctgttg cccacgatcc cagacactga agatgaaata agtccagaca    1320
aagtaatact ttgcttgtaa acagatgtga tagagataaa gttagttatc taacaaattg    1380
gttatattct aagatctgct ttggaaatta ttgcctctga tacatacct agtaaacata     1440 acattaatac ctaagtaaac ataacattac ttggagggtt gcagtttcta agtgaaactg    1500
tatttgaaac ttttaagtat actttaggaa acaagcatga acggcagtct agaataccag    1560
aaacatctac ttgggtagct tggtgccatt atcctgtgga atctgatatg tctggtagcg    1620
tgtcattgat gggacatgaa gacatctttg gaaatgatga gattatttcc tgtgttaaaa    1680
aaaaaaaaaa aatcttaaat tcctacaatg tgaaactgaa actaataatt tgatcctgat    1740
gtatgggaca gcgtatctgt accagtgctc taaataacaa aagctagggt gacaagtaca    1800
tgttcctttt ggaaagaagc aaggcaatgt atattaatta ttctaaaagg gctttgttcc    1860 tttccattttt ctttaacttc tctgagatac tgatttgtaa attttgaaaa ttagttaaaa   1920
tatgcagttt tttgagccca cgaatagttg tcatttcctt tatgtgcctg ttagtaaaaa    1980
gtagtattgt gtatttgctc agtatctgaa ctataagccc atttatactg ttccatacaa    2040
aagctatttt tcaaaaatta atttgaacca aaactactac tatagggaaa agatgccaaa    2100
acatgtcccc tcacccaggc taaacttgat actgtattat tttgttcaat gtaaattgaa    2160
gaaaatctgt aagtaagtaa accttaagtg tgaaactaaa aaaaaaaaaa aaa            2213
```

<210> SEQ ID NO 9
<211> LENGTH: 431
<212> TYPE: PRT
<213> ORGANISM: Mus musculus

<400> SEQUENCE: 9

```
Met Gly Asn His Leu Pro Leu Pro Asp Ser Glu Asp Glu Asp
1               5                   10                  15

Glu Ile Glu Met Glu Val Glu Asp Gln Asp Ser Lys Glu Ala Arg Lys
            20                  25                  30

Pro Asn Ile Ile Asn Phe Asp Thr Ser Leu Pro Thr Ser His Thr Tyr
        35                  40                  45

Leu Gly Ala Asp Met Glu Glu Phe His Gly Arg Thr Leu His Asp Asp
```

```
                 50                  55                  60
Asp Ser Cys Gln Val Ile Pro Val Leu Pro Glu Val Leu Met Ile Leu
 65                  70                  75                  80

Ile Pro Gly Gln Thr Leu Pro Leu Gln Leu Ser His Pro Gln Glu Val
                     85                  90                  95

Ser Met Val Arg Asn Leu Ile Gln Lys Asp Arg Thr Phe Ala Val Leu
                100                 105                 110

Ala Tyr Ser Asn Val Gln Glu Arg Glu Ala Gln Phe Gly Thr Thr Ala
            115                 120                 125

Glu Ile Tyr Ala Tyr Arg Glu Gln Glu Phe Gly Ile Glu Val Val
            130                 135                 140

Lys Val Lys Ala Ile Gly Arg Gln Arg Phe Lys Val Leu Glu Leu Arg
145                 150                 155                 160

Thr Gln Ser Asp Gly Ile Gln Gln Ala Lys Val Gln Ile Leu Pro Glu
                165                 170                 175

Cys Val Leu Pro Ser Thr Met Ser Ala Val Gln Val Glu Ser Leu Asn
                180                 185                 190

Lys Cys Gln Val Phe Pro Ser Lys Pro Ile Ser Trp Glu Asp Gln Tyr
            195                 200                 205

Ser Cys Lys Trp Trp Gln Lys Tyr Gln Lys Arg Lys Phe His Cys Ala
            210                 215                 220

Asn Leu Thr Ser Trp Pro Arg Trp Leu Tyr Ser Leu Tyr Asp Ala Glu
225                 230                 235                 240

Thr Leu Met Asp Arg Ile Lys Lys Gln Leu Arg Glu Trp Asp Glu Asn
                245                 250                 255

Leu Lys Asp Asp Ser Leu Pro Glu Asn Pro Ile Asp Phe Ser Tyr Arg
                260                 265                 270

Val Ala Ala Cys Leu Pro Ile Asp Asp Val Leu Arg Ile Gln Leu Leu
            275                 280                 285

Lys Ile Gly Ser Ala Ile Gln Arg Leu Arg Cys Glu Leu Asp Ile Met
290                 295                 300

Asn Lys Cys Thr Ser Leu Cys Cys Lys Gln Cys Gln Glu Thr Glu Ile
305                 310                 315                 320

Thr Thr Lys Asn Glu Ile Phe Ser Leu Ser Leu Cys Gly Pro Met Ala
                325                 330                 335

Ala Tyr Val Asn Pro His Gly Tyr Val His Glu Thr Leu Thr Val Tyr
                340                 345                 350

Lys Ala Ser Asn Leu Asn Leu Ile Gly Arg Pro Ser Thr Val His Ser
            355                 360                 365

Trp Phe Pro Gly Tyr Ala Trp Thr Ile Ala Gln Cys Lys Ile Cys Ala
370                 375                 380

Ser His Ile Gly Trp Lys Phe Thr Ala Thr Lys Lys Asp Met Ser Pro
385                 390                 395                 400

Gln Lys Phe Trp Gly Leu Thr Arg Ser Ala Leu Leu Pro Thr Ile Pro
                405                 410                 415

Glu Thr Glu Asp Glu Ile Ser Pro Asp Lys Val Ile Leu Cys Leu
                420                 425                 430

<210> SEQ ID NO 10
<211> LENGTH: 445
<212> TYPE: PRT
<213> ORGANISM: Mus musculus

<400> SEQUENCE: 10
```

```
Met Ala Gly Glu Gly Asp Gln Gln Asp Ala His Asn Met Gly Asn
1               5                   10                  15

His Leu Pro Leu Pro Ala Asp Ser Glu Asp Glu Asp Asp Glu Ile
            20                  25                  30

Glu Met Glu Val Glu Asp Gln Asp Ser Lys Glu Ala Arg Lys Pro Asn
        35                  40                  45

Ile Ile Asn Phe Asp Thr Ser Leu Pro Thr Ser His Thr Tyr Leu Gly
    50                  55                  60

Ala Asp Met Glu Glu Phe His Gly Arg Thr Leu His Asp Asp Ser
65                  70                  75                  80

Cys Gln Val Ile Pro Val Leu Pro Glu Val Leu Met Ile Leu Ile Pro
                85                  90                  95

Gly Gln Thr Leu Pro Leu Gln Leu Ser His Pro Gln Glu Val Ser Met
            100                 105                 110

Val Arg Asn Leu Ile Gln Lys Asp Arg Thr Phe Ala Val Leu Ala Tyr
            115                 120                 125

Ser Asn Val Gln Glu Arg Glu Ala Gln Phe Gly Thr Thr Ala Glu Ile
    130                 135                 140

Tyr Ala Tyr Arg Glu Glu Gln Glu Phe Gly Ile Glu Val Val Lys Val
145                 150                 155                 160

Lys Ala Ile Gly Arg Gln Arg Phe Lys Val Leu Glu Leu Arg Thr Gln
                165                 170                 175

Ser Asp Gly Ile Gln Gln Ala Lys Val Gln Ile Leu Pro Glu Cys Val
            180                 185                 190

Leu Pro Ser Thr Met Ser Ala Val Gln Leu Glu Ser Leu Asn Lys Cys
            195                 200                 205

Gln Val Phe Pro Ser Lys Pro Ile Ser Trp Glu Asp Gln Tyr Ser Cys
    210                 215                 220

Lys Trp Trp Gln Lys Tyr Gln Lys Arg Lys Phe His Cys Ala Asn Leu
225                 230                 235                 240

Thr Ser Trp Pro Arg Trp Leu Tyr Ser Leu Tyr Asp Ala Glu Thr Leu
                245                 250                 255

Met Asp Arg Ile Lys Lys Gln Leu Arg Glu Trp Asp Glu Asn Leu Lys
            260                 265                 270

Asp Asp Ser Leu Pro Glu Asn Pro Ile Asp Phe Ser Tyr Arg Val Ala
            275                 280                 285

Ala Cys Leu Pro Ile Asp Asp Val Leu Arg Ile Gln Leu Leu Lys Ile
    290                 295                 300

Gly Ser Ala Ile Gln Arg Leu Arg Cys Glu Leu Asp Ile Met Asn Lys
305                 310                 315                 320

Cys Thr Ser Leu Cys Cys Lys Gln Cys Gln Glu Thr Glu Ile Thr Thr
                325                 330                 335

Lys Asn Glu Ile Phe Ser Leu Ser Leu Cys Gly Pro Met Ala Ala Tyr
            340                 345                 350

Val Asn Pro His Gly Tyr Val His Glu Thr Leu Thr Val Tyr Lys Ala
            355                 360                 365

Ser Asn Leu Asn Leu Ile Gly Arg Pro Ser Thr Val His Ser Trp Phe
    370                 375                 380

Pro Gly Tyr Ala Trp Thr Ile Ala Gln Cys Lys Ile Cys Ala Ser His
385                 390                 395                 400

Ile Gly Trp Lys Phe Thr Ala Thr Lys Lys Asp Met Ser Pro Gln Lys
                405                 410                 415

Phe Trp Gly Leu Thr Arg Ser Ala Leu Leu Pro Thr Ile Pro Glu Thr
```

420             425              430
Glu Asp Glu Ile Ser Pro Asp Lys Val Ile Leu Cys Leu
        435                 440                 445

<210> SEQ ID NO 11
<211> LENGTH: 4064
<212> TYPE: DNA
<213> ORGANISM: Mus musculus

<400> SEQUENCE: 11

| | |
|---|---|
| tttcccaggc tcctttgcgg gtaaacagac atggccggcg agggagatca gcaggacgct | 60 |
| gcgcacaaca tgggaaacca cctgccgctt ctgcctgaca gtgaagatga agatgatgaa | 120 |
| attgaaatgg aagttgaaga ccaagatagt aaagaagcca gaaaaccgaa tatcataaac | 180 |
| tttgacacca gtctgccaac ctcacataca tacctgggag ctgatatgga ggagttccac | 240 |
| gggagaactt tgcatgacga cgacagctgc caggtgatcc cagtccttcc tgaggtgctg | 300 |
| atgatcctga ttcctgggca gacactccca ctgcagctct ctcacccaca ggaagtcagc | 360 |
| atggtgcgga acttaatcca gaaagacagg acctttgcag tccttgcata cagtaatgtg | 420 |
| caagaaaggg aagcacagtt tgggacaaca gcagagatcc atgcctatcg agaagagcag | 480 |
| gagtttggaa ttgaagtagt gaaagtgaaa gcaattggaa ggcagcggtt caaggtcctc | 540 |
| gaacttcgaa cacagtcaga tggaatccag caagctaaag tgcagatttt gccagagtgt | 600 |
| gtgttgccgt caaccatgtc tgcagtgcag ttagaatcac tcaataagtg ccaggtattt | 660 |
| ccttcaaaac ccatctcctg gaagaccag tattcatgta atggtggca gaaataccag | 720 |
| aagagaaagt ttcactgtgc aaatctaaca tcatggcctc gctggctgta ttcattatat | 780 |
| gatgctgaaa cattaatgga tagaattaag aaacagctac gtgaatggga tgaaaatctc | 840 |
| aaagatgatt ctcttcctga aaatccaata gacttttctt acagagtagc tgcttgtctt | 900 |
| cctattgatg atgtattgag aattcagctc cttaaaatcg gcagtgctat tcaacggctt | 960 |
| cgctgtgaat tggacatcat gaacaaatgt acttcccttt gctgtaaaca atgtcaagaa | 1020 |
| acagaaataa cgacaaagaa tgaaatattt agtttatcct tatgtggtcc aatggcagca | 1080 |
| tatgtgaatc ctcatggata tgtacatgag acactgactg tgtataaagc gtccaacctg | 1140 |
| aatctgatag gccggccttc tacagtgcac agctggtttc ccgggtatgc atggaccatt | 1200 |
| gcccagtgca agatctgtgc aagccatatt ggatggaaat ttacagccac aaaaaaagac | 1260 |
| atgtcacctc aaaaattttg gggcttaact cgctctgctc tgttaccac aattccagag | 1320 |
| actgaagatg aaataagtcc agacaaagta atactttgtt tataagtgca cctgtaggag | 1380 |
| tgacttcctg acagatattt cctcaagtca gatctgccca gtcatcactg cctctgatat | 1440 |
| atgtgtatag tgggttacag catttgccta ccaagttcaa gagcatattt agggaatgag | 1500 |
| aaagcagtat aaaacataag gctgggttcc aaaatacttg ctttttagta gcttggtgcc | 1560 |
| atggattatc ctgttgagtc tatgtcatga caggatagga aaacacagtt gaataatgg | 1620 |
| gaatggccat ggaacaggat aggggcacca ctgctctaaa tgatgaagct ctaaatgatg | 1680 |
| aatgctccag aaactgggtt ggtaagcaca agatagaggc aaggcagtgt aattttaaaa | 1740 |
| ggactttgct cctttcaatt ttccttagct tgtctgagat actgacctgt acattttgaa | 1800 |
| catattaaag agtaactaag tattctgagc agaaatagca gcatttggtg tagttgcact | 1860 |
| tttgatttga tgagcctgtg atgtgctaga tcccttttaac taatgtatat gtccatttg | 1920 |
| cattttattt gcaaatataa gtgaacagta tatatttcta ggattatacc atttaggaaa | 1980 |

| | |
|---|---|
| caggtttaca taaacataaa tatccaaatc tattctattt ggctgaatta tgtcaaagta | 2040 |
| atcaagtaga atactgaaaa gtgtaagtac gtaataaaat gcaactcaag aataggctgc | 2100 |
| tccttaatgt catttttttca aaagttctac ttgtgtttca ttcaagctgc tgtgatggag | 2160 |
| tggggaatta tgcctttact gctgcagtat aatctgatga tccatggact gtttaccatt | 2220 |
| actttcagat aggactgttt aaaggaatct tacacaatat agcagctttg atgtcactcc | 2280 |
| atctgtgcag atgacaacag cagaaactcc atagtttaaa atccaggtat ttactgacct | 2340 |
| gggtgaagta gattttgaca cgcccttttta tagcacatca ccttatttga cttcaagaaa | 2400 |
| attcaaaatc caaagctgc tgtttacttg tacagtacac agatatctat gagcagctat | 2460 |
| gcagtaagta actatgtaag ctatcagaaa gctaagccat atccatctaa cttgtaaaat | 2520 |
| aaacaatgtg ttcactatct gtggcacctg atataaaggc aagagtctca gcacaagccc | 2580 |
| tcctgttatt cctgcaactt tctgaaatca gaacaatcct gttataaata gatgctacta | 2640 |
| tggactcatt caggaaaacca ctaagaaaac atagtttctc ttcaacagtt actacatttt | 2700 |
| aagatcaaca gcactgctcc acaagcattg ggaaattcag gaggtagact tgagcttagt | 2760 |
| ttttctacct acactcatgc tggttttggg gtctcagtaa cacaggaggg gagaacacca | 2820 |
| gccttaccaa gacttcccct gtttcataca gggctcatct ttaggtcttc tttatgtaac | 2880 |
| ttagtagttc atcttttttcc atccggtaac cactttttctt ccactgttca cgcaactgct | 2940 |
| gtagcagggc cccaatttcc ttccctgaag aaatacccac tttcctgatg tcatgtccac | 3000 |
| tcacagggaa cggcgggaca gaccactgct gcatctcttt gagaagacca tgctctcctt | 3060 |
| ggtacttcag cagctcacaa acacgggcag ttgcatctgg ttccctagac taaatgacac | 3120 |
| agttttatca catactaaac actcacaatt tcattctact atttaaatac ttacatcaaa | 3180 |
| tctacagtgt gaaaaagtta cttttctcta gttagtgaga actatttttct gctcagacct | 3240 |
| aatacatact tacgtctatc acaaagtctt ggtatggttt caatggttct gaactatctg | 3300 |
| ttgctttaat caagtctttc ctgttttttaa ctataaataa acccaggttt ttctcctctt | 3360 |
| ttgaaatttt caatctcaag tccaattttg tgacatcatc ttgtacttttg aataaagaag | 3420 |
| ccaaaagagt cattggttttt ggtgaaaagc cttcaacatt tttactgact ttgttaaatt | 3480 |
| cttctaaatt tgcattagca ggtaaacctg taaacaaaag agaaaagtca ttttttttctt | 3540 |
| aactacaaaa ccctcactca cctcttaaac tatgcagatt tttaagaatg tgtagtgttc | 3600 |
| tttctccact gcttattatc agcccattcg tcactccctt aactcctaga agaaatctat | 3660 |
| catgttcctg tttcctgtag cagcatgtct tgtgaagctc aggagctgtg atcatatcag | 3720 |
| gtaccagcat atgccttctc agtcatgatc ctgtctgcac acattcccta ctcagcaatt | 3780 |
| gtatgttctt gtaaaacagt caaagttact gtctaaaata tactggctat agttattaat | 3840 |
| ttcctttcta tatattaagt gttttgtgaa agagcttatt atacattaac ttattgcttc | 3900 |
| atcctcctct ctatgaagta gcttttattt tgaacccttt gtgattataa accaacccaa | 3960 |
| cctgcaaaac cagtaagctt catcaaattc aggtgttctc tctgaactat tctttaccaa | 4020 |
| taaataaact atttccatct ttaatcccaa aaaaaaaaaa aaaa | 4064 |

<210> SEQ ID NO 12
<211> LENGTH: 4067
<212> TYPE: DNA
<213> ORGANISM: Mus musculus

<400> SEQUENCE: 12

| | |
|---|---|
| tttcccaggc tcctttgcgg gtaaacagac atggccggcg agggagatca gcaggacgct | 60 |

```
gcgcacaaca tgggaaacca cctgccgctt ctgcctgcag acagtgaaga tgaagatgat      120
gaaattgaaa tggaagttga agaccaagat agtaaagaag ccagaaaacc gaatatcata      180
aactttgaca ccagtctgcc aacctcacat acatacctgg gagctgatat ggaggagttc      240
cacgggagaa ctttgcatga cgacgacagc tgccaggtga tcccagtcct tcctgaggtg      300
ctgatgatcc tgattcctgg gcagacactc ccactgcagc tctctcaccc acaggaagtc      360
agcatggtgc ggaacttaat ccagaaagac aggacctttg cagtccttgc atacagtaat      420
gtgcaagaaa gggaagcaca gtttgggaca cagcagaga tctatgccta tcgagaagag      480
caggagtttg aattgaagt agtgaaagtg aaagcaattg gaaggcagcg gttcaaggtc      540
ctcgaacttc gaacacagtc agatggaatc cagcaagcta aagtgcagat tttgccagag      600
tgtgtgttgc cgtcaaccat gtctgcagtg cagttagaat cactcaataa gtgccaggta      660
tttccttcaa aacccatctc ctgggaagac cagtattcat gtaaatggtg cagaaatac      720 cagaagagaa agtttcactg tgcaaatcta acatcatggc ctcgctggct gtattcatta      780
tatgatgctg aaacattaat ggatagaatt aagaaacagc tacgtgaatg ggatgaaaat      840
ctcaaagatg attctcttcc tgaaaatcca atagactttt cttacagagt agctgcttgt      900
cttcctattg atgatgtatt gagaattcag ctccttaaaa tcggcagtgc tattcaacgg      960
cttcgctgtg aattggacat catgaacaaa tgtacttccc tttgctgtaa acaatgtcaa     1020
gaaacagaaa taacgacaaa gaatgaaata tttagtttat ccttatgtgg tccaatggca     1080
gcatatgtga atcctcatgg atatgtacat gagacactga ctgtgtataa agcgtccaac     1140
ctgaatctga taggccggcc ttctacagtg cacagctggt ttcccgggta tgcatggacc     1200
attgcccagt gcaagatctg tgcaagccat attggatgga aatttacagc cacaaaaaaa     1260
gacatgtcac ctcaaaaatt tggggctta actcgctctg ctctgttacc cacaattcca     1320
gagactgaag atgaaataag tccagacaaa gtaatacttt gtttataagt gcacctgtag     1380
gagtgacttc ctgacagata tttcctcaag tcagatctgc ccagtcatca ctgcctctga     1440
tatatgtgta tagtgggtta cagcatttgc ctaccaagtt caagagcata tttagggaat     1500
gagaaagcag tataaaacat aaggctgggt tccaaaatac ttgcttttta gtagcttggt     1560
gccatggatt atcctgttga gtctatgtca tgacaggata ggaaaacaca gttgaaataa     1620
tgggaatggc catggaacag atagggggca ccactgctct aaatgatgaa gctctaaatg     1680
atgaatgctc cagaaactgg gttggtaagc acaagataga ggcaaggcag tgtaatttta     1740
aaaggacttt gctcctttca attttcctta gcttgtctga gatactgacc tgtacatttt     1800
gaacatatta aagagtaact aagtattctg agcagaaata gcagcatttg gtgtagttgc     1860
acttttgatt tgatgagcct gtgatgtgct agatcccttt aactaatgta tatgtccatt     1920 ttgcattta tttgcaaata taagtgaaca gtatatattt ctaggattat accatttagg     1980
aaacaggttt acataaacat aaatatccaa atctattcta tttggctgaa ttatgtcaaa     2040
gtaatcaagt agaatactga aaagtgtaag tacgtaataa aatgcaactc aagaataggc     2100
tgctccttaa tgtcattttt tcaaaagttc tacttgtgtt tcattcaagc tgctgtgatg     2160
gagtggggaa ttatgccttt actgctgcag tataatctga tgatccatgg actgtttacc     2220
attactttca gataggactg tttaaaggaa tcttacacaa tatagcagct ttgatgtcac     2280
tccatctgtg cagatgacaa cagcagaaac tccatagttt aaaatccagg tatttactga     2340
cctgggtgaa gtagattttg acacgcccctt ttatagcaca tcaccttatt tgacttcaag     2400
```

-continued

```
aaaattcaaa atccaaaagc tgctgtttac ttgtacagta cacagatatc tatgagcagc    2460
tatgcagtaa gtaactatgt aagctatcag aaagctaagc catatccatc taacttgtaa    2520
aataaacaat gtgttcacta tctgtggcac ctgatataaa ggcaagagtc tcagcacaag    2580
ccctcctgtt attcctgcaa ctttctgaaa tcagaacaat cctgttataa atagatgcta    2640
ctatggactc attcaggaaa ccactaagaa aacatagttt ctcttcaaca gttactacat    2700
tttaagatca acagcactgc tccacaagca ttgggaaatt caggaggtag acttgagctt    2760 agttttcta cctacactca tgctggtttt ggggtctcag taacacagga ggggagaaca    2820
ccagccttac caagacttcc cctgtttcat acagggctca tctttaggtc ttctttatgt    2880
aacttagtag ttcatctttt tccatccggt aaccacttt cttccactgt tcacgcaact    2940
gctgtagcag ggccccaatt tccttccctg aagaaatacc cactttcctg atgtcatgtc    3000
cactcacagg gaacggcggg acagaccact gctgcatctc tttgagaaga ccatgctctc    3060
cttggtactt cagcagctca caaacacggg cagttgcatc tggttcccta gactaaatga    3120
cacagtttta tcacatacta aacactcaca atttcattct actatttaaa tacttacatc    3180
aaatctacag tgtgaaaaag ttacttttct ctagttagtg agaactattt tctgctcaga    3240
cctaatacat acttacgtct atcacaaagt cttggtatgg tttcaatggt tctgaactat    3300
ctgttgcttt aatcaagtct ttcctgtttt taactataaa taaacccagg ttttttctcct    3360 cttttgaaat tttcaatctc aagtccaatt ttgtgacatc atcttgtact ttgaataaag    3420
aagccaaaag agtcattggt tttggtgaaa agccttcaac attttttactg actttgttaa    3480 attcttctaa atttgcatta gcaggtaaac ctgtaaacaa aagagaaaag tcatttttt    3540 cttaactaca aaaccctcac tcacctctta aactatgcag attttttaaga atgtgtagtg    3600 ttctttctcc actgcttatt atcagcccat tcgtcactcc cttaactcct agaagaaatc    3660
tatcatgttc ctgtttcctg tagcagcatg tcttgtgaag ctcaggagct gtgatcatat    3720
caggtaccag catatgcctt ctcagtcatg atcctgtctg cacacattcc ctactcagca    3780
attgtatgtt cttgtaaaac agtcaaagtt actgtctaaa atatactggc tatagttatt    3840
aatttccttt ctatatatta agtgttttgt gaaagagctt attatacatt aacttattgc    3900
ttcatcctcc tctctatgaa gtagctttta ttttgaaccc tttgtgatta taaaccaacc    3960
caacctgcaa aaccagtaag cttcatcaaa ttcaggtgtt ctctctgaac tattctttac    4020
caataaataa actatttcca tctttaatcc caaaaaaaaa aaaaaaa                  4067
```

<210> SEQ ID NO 13
<211> LENGTH: 337
<212> TYPE: PRT
<213> ORGANISM: Homo sapiens

<400> SEQUENCE: 13

```
Met Ala Ser Ser Gly Ser Lys Ala Glu Phe Ile Val Gly Gly Lys
1               5                   10                  15

Tyr Lys Leu Val Arg Lys Ile Gly Ser Gly Ser Phe Gly Asp Ile Tyr
                20                  25                  30

Leu Ala Ile Asn Ile Thr Asn Gly Glu Glu Val Ala Val Lys Leu Glu
            35                  40                  45

Ser Gln Lys Ala Arg His Pro Gln Leu Leu Tyr Glu Ser Lys Leu Tyr
        50                  55                  60

Lys Ile Leu Gln Gly Gly Val Gly Ile Pro His Ile Arg Trp Tyr Gly
65                  70                  75                  80
```

Gln Glu Lys Asp Tyr Asn Val Leu Val Met Asp Leu Leu Gly Pro Ser
            85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
            115                 120                 125

Thr Lys Asn Phe Ile His Arg Asp Ile Lys Pro Asp Asn Phe Leu Met
130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
            165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
            195                 200                 205

Tyr Val Leu Met Tyr Phe Asn Arg Thr Ser Leu Pro Trp Gln Gly Leu
            210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
            245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
            275                 280                 285

Asn His Gln Tyr Asp Tyr Thr Phe Asp Trp Thr Met Leu Lys Gln Lys
            290                 295                 300

Ala Ala Gln Gln Ala Ala Ser Ser Ser Gly Gln Gly Gln Gln Ala Gln
305                 310                 315                 320

Thr Pro Thr Gly Lys Gln Thr Asp Lys Thr Leu Ser Asn Met Lys Gly
            325                 330                 335

Phe

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atgtttacta cactcggata t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cttcgaaatg tccgttcggt t                                              21

<210> SEQ ID NO 16
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cgctggctgt attccttata t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caggatagta agaagccaa a                                               21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cttaacgcga tctgctctgt t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccgcttccac atgagctaaa g                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcatttggaa acgggaataa a                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgatatctg tgggatcatt t                                              21

<210> SEQ ID NO 22
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 22
ccgcttccac atgagctaaa g                                                21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcatttggaa acgggaataa a                                                21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gtgatatctg tgggatcatt t                                                21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
catctatttg gcgatcaaca t                                                21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcagaatttg cgatgtactt a                                                21

<210> SEQ ID NO 27
<211> LENGTH: 30
<212> TYPE: PRT
<213> ORGANISM: Homo sapiens

<400> SEQUENCE: 27

His Thr Gly Glu Arg Pro Phe Gln Cys Asn Gln Cys Gly Ala Ser Phe
1               5                   10                  15

Thr Gln Lys Gly Asn Leu Leu Arg His Ile Lys Leu His Thr
            20                  25                  30

<210> SEQ ID NO 28
<211> LENGTH: 30
<212> TYPE: PRT

<213> ORGANISM: Homo sapiens

<400> SEQUENCE: 28

His Thr Gly Glu Arg Pro Phe Gln Cys Asn Gln Cys Gly Ala Ser Phe
1               5                   10                  15

Thr Gln Lys Gly Asn Leu Leu Arg His Ile Lys Leu His Ser
            20                  25                  30

<210> SEQ ID NO 29
<211> LENGTH: 30
<212> TYPE: PRT
<213> ORGANISM: Homo sapiens

<400> SEQUENCE: 29

His Thr Gly Glu Arg Pro Phe His Cys Asn Gln Cys Gly Ala Ser Phe
1               5                   10                  15

Thr Gln Lys Gly Asn Leu Leu Arg His Ile Lys Leu His Ser
            20                  25                  30

<210> SEQ ID NO 30
<211> LENGTH: 30
<212> TYPE: PRT
<213> ORGANISM: Homo sapiens

<400> SEQUENCE: 30

His Thr Gly Glu Arg Pro Phe His Cys Asn Gln Cys Gly Ala Ser Phe
1               5                   10                  15

Thr Gln Lys Gly Asn Leu Leu Arg His Ile Lys Leu His Ser
            20                  25                  30

<210> SEQ ID NO 31
<211> LENGTH: 30
<212> TYPE: PRT
<213> ORGANISM: Homo sapiens

<400> SEQUENCE: 31

His Thr Gly Glu Lys Pro His Arg Cys His Leu Cys Pro Phe Ala Ser
1               5                   10                  15

Ala Tyr Glu Arg His Leu Glu Ala Ile Met Ala Ser His Thr
            20                  25                  30

<210> SEQ ID NO 32
<211> LENGTH: 60
<212> TYPE: PRT
<213> ORGANISM: Homo sapiens

<400> SEQUENCE: 32

Glu Thr Leu Thr Val Tyr Lys Ala Cys Asn Leu Asn Leu Ile Gly Arg
1               5                   10                  15

Pro Ser Thr Glu His Ser Trp Phe Pro Gly Tyr Ala Trp Thr Val Ala
            20                  25                  30

Gln Cys Lys Ile Cys Ala Ser His Ile Gly Trp Lys Phe Thr Ala Thr
        35                  40                  45

Lys Lys Asp Met Ser Pro Gln Lys Phe Trp Gly Leu
    50                  55                  60

<210> SEQ ID NO 33
<211> LENGTH: 60
<212> TYPE: PRT
<213> ORGANISM: Mus musculus

<400> SEQUENCE: 33

```
Glu Thr Leu Thr Val Tyr Lys Ala Ser Asn Leu Asn Leu Ile Gly Arg
1               5                   10                  15

Pro Ser Thr Val His Ser Trp Phe Pro Gly Tyr Ala Trp Thr Ile Ala
            20                  25                  30

Gln Cys Lys Ile Cys Ala Ser His Ile Gly Trp Lys Phe Thr Ala Thr
        35                  40                  45

Lys Lys Asp Met Ser Pro Gln Lys Phe Trp Gly Leu
    50                  55                  60

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucloetide

<400> SEQUENCE: 34
agctggagcc aacagcaaca tatag                                    25

<210> SEQ ID NO 35
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 35
ggtccatgca tacctataaa atgaagg                                  27

<210> SEQ ID NO 36
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 36
taggtatgca tggaccgtgg cccagtgcaa gatctg                        36

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37
gctcttgaac ttggtaggca aatgc                                    25

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
gagtgcacca tatggacata ttgt                                     24

<210> SEQ ID NO 39
<211> LENGTH: 25
<212> TYPE: DNA
<213> ORGANISM: Artificial Sequence
<220> FEATURE:
```

<223> OTHER INFORMATION: Synthetic oligonucleotide

<400> SEQUENCE: 39
taatgcaggt taacctggct tatcg                                          25

<210> SEQ ID NO 40
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 40
tgcgaggcca gaggccactt gtgtagc                                        27

<210> SEQ ID NO 41
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 41
agtatggctt tccttcccga tgg                                            23

<210> SEQ ID NO 42
<211> LENGTH: 838
<212> TYPE: DNA
<213> ORGANISM: Mus musculus

<400> SEQUENCE: 42
gctacaatgg aatccttact gttaattttc taacttaagt tgaattgcag acgtgcctct     60
catgtagata cttcctgttc tctacagagc ctttacaagt gaagctggct ccatgactta    120
ctttgatatg tcatctctat ttgtttataa gtcacttcaa gtatatgttt gacttaaagg    180
aaagtgactg aagtgtatat taatgactcc taagtttaaa gcctgcaaac ctctctgtct    240
tttaagactt ttcttacaga gtagctgctt gtcttcctat tgatgatgta ttgagaattc    300
agctccttaa aatcggcagt gctattcaac ggcttcgctg tgaattggac atcatgaaca    360
aagtgagtaa agcctccacg tcatcattta gtcagtcagg ctacatagac acataagaga    420
gtcgagatca caagctacct cgactgtgta gtaatacaag cagatgctac aagtacttgt    480
ttacctgcca cagtttgcag taatctgaca tgctttataa cttagaccat tcaaatttg     540 gaggattagg aatgtatcaa caataaagtc ttgtccaact ttgaataagg tatattcagt    600
gtgaaaattt gagccattta ttttgcagt caatataaat ttgcctgctt aggtatgatc     660
tacagcccaa gacattagtg ccatagaaag gtttgtttat tcatcatctg ggtaacatgc    720
ctatttctcc atttaacctt tgtagtgtac ttcccttgc tgtaaacaat gtcaagaaac     780
agaaataacg acaaagaatg aaatatttag gtaagatctt tattacattt ttaatata     838

<210> SEQ ID NO 43
<211> LENGTH: 835
<212> TYPE: DNA
<213> ORGANISM: Mus musculus

<400> SEQUENCE: 43
gctacaatgg aatccttact gttaattttc taacttaagt tgaattgcag acgtgcctct     60
catgtagata cttcctgttc tctacagagc ctttacaagt gaagctggct ccatgactta    120
ctttgatatg tcatctctat ttgtttataa gtcacttcaa gtatatgttt gacttaaagg    180

```
aaagtgactg aagtgtatat taatgactcc taagttaaa gcctgcaaac ctctctgtct    240
tttaagactt ttcttacaga gtagctgctt gtcttcctat tgatgatgta ttgagaattc    300
agctccttaa aatcggcagt gctattcaac ggcttcgctg tgaattggac atcatgaaca    360
aagtgagtaa agcctccacg tcatcattta gtcagtcagg ctacatagac acataagaga    420
gtcgagatca caagctacct cgactgtgta gtaatacaag cagatgctac aagtacttgt    480
ttacctgcca cagtttgcag taatctgaca tgctttataa cttagaccat ttcaaatttg    540
gaggattagg aatgtatcaa caataaagtc ttgtccaact ttgaataaag gtatattcag    600
tgtgaaaatt tgagccattt atttttgcag tcaatataaa tttgcctgct taggtatgat    660
ctacagccca agacattagt gccatagaaa ggtttgttta ttcatcatct gggtaacatg    720
cctatttctc catttaaccc tttgtagtgt acttcccttt gctgtaacaa tgtcagaaac    780
agaaataacg acaagaatga aatatttagg tagatcttta ttacatttta atata          835
```

<210> SEQ ID NO 44
<211> LENGTH: 903
<212> TYPE: DNA
<213> ORGANISM: Mus musculus

<400> SEQUENCE: 44

```
ggatccctca gtgttaggat tataggcata tccaccacca tatcttgtca tttataataa     60
taaagttaga gataagagtt aaataatctg gacacaaaaa gccaagtaat gcataataca    120
catgtaacca aactagggta agctgaggac taggatatgt tagttgactt atccatgagg    180
actaaggtac aaggacacag atgacattct catcactgct gcaaagtaga gggactacag    240
ataaccaaaa agttcacaag gggattgaat gcttttagcc taaacatgat agctttgagg    300
gaagagatgt gtttaccttc aataccaatg tatcaagaca ttatatatac atgtataact    360
agtgtttatg catcagttaa aaatctacaa aaattaaaac cactaatacc cacacaacta    420
tcactgcatt tcacacttag ccagtttctc aacttttaa gtatcggaat actctgattt    480
gttgtaccac ttgctagcac tctctttctg tgtcattttt tggtgaggca ccgaatatgt    540
tccagaacat cgactctagg tccttgaggt agagcacagc ttaagtcatt tctctgtagt    600
aagatcaccg agcacaatac ctggcctgtg gcaagaattt aaactacaca atcaatgaag    660 gaaaagaca ttaatgatgt aaagctttta tataaaacat actacaaaga acggtttgat    720
tatgtatact tctgaataaa agccacagaa tgctactcaa cagctacttg ggtgtctcaa    780
agggtgacac gcaaaactaa aattttctag tgttgaaatt tataagttct tacctgaaat    840
accttaaaat tcgaagataa tcttcctgaa ttctctgttt tgcatgtcca acaaatcgaa    900
cct                                                                  903
```

<210> SEQ ID NO 45
<211> LENGTH: 903
<212> TYPE: DNA
<213> ORGANISM: Mus musculus

<400> SEQUENCE: 45

```
ggatccctca gtgttaggat tataggcata tccaccacca tatcttgtca tttataataa     60
taaagttaga gataagagtt aaataatctg gacacaaaaa gccaagtaat gcataataca    120
catgtaacca aactagggta agctgaggac taggatatgt tagttgactt atccatgagg    180
actaaggtac aaggacacag atgacattct catcactgct gcaaagtaga gggactacag    240
```

| ataaccaaaa agttcacaag gggattgaat gcttttagcc taaacatgat agctttgagg | 300 |
| gaagagatgt gtttaccttc aataccaatg tatcaagaca ttatatatac atgtataact | 360 |
| agtgtttatg catcagttaa aaatctacaa aaattaaaac cactaatacc cacacaacta | 420 |
| tcactgcatt tcacacttag ccagtttctc caacttttaa gtatcggaat actctgattt | 480 |
| gttgtaccac ttgctagcac tctctttctg tgtcattttt tggtgaggca ccgaatatgt | 540 |
| tccagaacat cgactctagg tccttgaggt agagcacagc ttaagtcatt tctctgtagt | 600 |
| aagatcaccg agcacaatac ctggcctgtg gcaagaattt aaactacaca atcaatgaag | 660 |
| gaaaaagaca ttaatgatgt aaagctttta tataaaacat actacaaaga acggtttgat | 720 |
| tatgtatact tctgaataaa agccacagaa tgctactcaa cagctacttg ggtgtctcaa | 780 |
| agggtgacac gcaaaactaa aattttctag tgttgaaatt tataagttct tacctgaaat | 840 |
| accttaaaat tcgaagataa tcttcctgaa ttctctgttt tgcatgtcca acaaatcgaa | 900 |
| cct | 903 |

<210> SEQ ID NO 46
<211> LENGTH: 897
<212> TYPE: DNA
<213> ORGANISM: Mus musculus

<400> SEQUENCE: 46

| agctggagcc aacagcaaca tatagacacg tgcagtaata aattatccag ttataacagg | 60 |
| gtggctttgt aaatttgagg tgtcagagaa atctcacgag aagcctagta caaaggctaa | 120 |
| aaataggttt taacttatat ctttccttca ttttataggt atgcatggac cattgcccag | 180 |
| tgcaagatct gtgcaagcca tattggatgg aaatttacag ccacaaaaaa agacatgtca | 240 |
| cctcaaaaat tttggggctt aactcgctct gctctgttac ccacaattcc agagactgaa | 300 |
| gatgaaataa gtccagacaa agtaatactt tgtttataag tgcacctgta ggagtgactt | 360 |
| cctgacagat atttcctcaa gtcagatctg cccagtcatc actgcctctg atatatgtgt | 420 |
| atagtgggtt acagcatttg cctaccaagt tcaagagcat atttagggaa tgagaaagca | 480 |
| gtataaaaca taaggctggg ttccaaaata cttgcttttt agtagcttgg tgccatggat | 540 |
| tatcctgttg agtctatgtc atgacaggat aggaaaacac agttgaaata tgggaatgg | 600 |
| ccatggaaca ggataggggc accactgctc taaatgatga agctctaaat gatgaatgct | 660 |
| ccagaaactg ggttggtaag cacaagatag aggcaaggca gtgtaatttt aaaaggactt | 720 |
| tgctcctttc aatttttcctt agcttgtctg agatactgac ctgtacattt tgaacatatt | 780 |
| aaagagtaac taagtattct gagcagaaat agcagcattt ggtgtagttg cacttttgat | 840 |
| ttgatgagcc tgtgatgtgc tagatcccett taactaatgt atatgtccat tttgcat | 897 |

<210> SEQ ID NO 47
<211> LENGTH: 899
<212> TYPE: DNA
<213> ORGANISM: Mus musculus

<400> SEQUENCE: 47

| agctggagcc aacagcaaca tatagacacg tgcagtaata aattatccag ttataacagg | 60 |
| gtggctttgt aaatttgagg tgtcagagaa atctcacgag aagcctagta caaaggctaa | 120 |
| aaataggttt taacttatat ctttccttca ttttataggt atgcatggac cgtggcccag | 180 |
| tgcaagatct gtgcaagcca tattggatgg aaatttacag ccacaaaaaa agacatgtca | 240 |
| cctcaaaaat tttggggctt aactcgctct gctctgttac ccacaattcc agagactgaa | 300 |

```
gatgaaataa gtccagacaa agtaatactt tgtttataag tgcacctgta ggagtgactt        360
cctgacagat atttcctcaa gtcagatctg cccagtcatc actgcctctg atatatgtgt        420
atagtgggtt acagcatttg cctaccaagt tcaagagcat atttagggaa tgagaaagca        480
gtataaaaca taaggctggg ttccaaaata cttgcttttt agtagcttgg tgccatggat        540
tatcctgttg agtctatgtc atgacaggat aggaaaacac agttgaaata atgggaatgg        600
ccatggaaca ggataggggc accactgctc taaatgatga agctctaaat gatgaatgct        660
ccagaaactg ggttggtaag cacaagatag aggcaaggca gtgtaatttt aaaaggactt        720
tgctcctttc aatttteett agcttgtctg agatactgac ctgtacattt ttgacatatt        780
aagagtaact aagtattctg agcagaaata gcagcatttg gtgtagttgc acttttgatt        840
tgatgagcct gtgatgtgct agatcccttt aactaatgta ttatgtccaa ttttggcat         899

<210> SEQ ID NO 48
<211> LENGTH: 1050
<212> TYPE: DNA
<213> ORGANISM: Artificial Sequence
<220> FEATURE:
<223> OTHER INFORMATION: Recombinant polynucleotide

<400> SEQUENCE: 48
agcgaacctg ccggggcctg cttaaggcgc atgcttccag actgccttgg gaaaagcgcc         60
tcccctaccc ggtagaatga agttcctata ctttctagag aataggaact tcgttggtac        120
cgtacgcgga cgaccaacgg gcccaattgc tagctggagc caacagcaac atatagacac        180
gtgcagtaat aaattatcca gttataacag ggtggctttg taaatttgag gtgtcagaga        240
aatctcacga gaagcctagt acaaaggcta aaaataggtt ttaacttata tctttccttc        300
attttatagg tatgcatgga ccgtggccca gtgcaagatc tgtgcaagcc atattggatg        360
gaaatttaca gccacaaaaa aagacatgtc acctcaaaaa ttttggggct taactcgctc        420
tgctctgtta cccacaattc cagagactga agatgaaata agtccagaca agtaatact         480 ttgtttataa gtgcacctgt aggagtgact tcctgacaga tatttcctca gtcagatct         540 gcccagtcat cactgcctct gatatatgtg tatagtgggt tacagcattt gcctaccaag        600
ttcaagagca tatttaggga tgagaaagc agtataaaac ataaggctgg gttccaaaat         660
acttgctttt tagtagcttg tgccatgga ttatcctgtt gagtctatgt catgacagga         720
taggaaaaca cagttgaaat aatgggaatg ccatggaac aggataggg caccactgct         780 ctaaatgatg aagctctaaa tgatgaatgc tccagaaact gggttggtaa gcacaagata        840
gaggcaaggc agtgtaattt taaaaggact tgctcctttt caattttcct tagcttgtct        900
gagatactga cctgtacatt tttgacatat taagagtaac taagtattct gagcagaaat        960
agcagcattt ggtgtagttg cacttttgat ttgatgagcc tgtgatgtgc tagatccctt       1020
taactaatgt attatgtcca attttggcat                                       1050

<210> SEQ ID NO 49
<211> LENGTH: 858
<212> TYPE: DNA
<213> ORGANISM: Mus musculus

<400> SEQUENCE: 49
aggtcaggaa actgatatgt aggtaaagta actaaatgtc caaagatgaa acatgacct          60 cactaggctt tgtaaacaca tatatttacc tttgaatcat caaagaacat ttttaagcaa        120
```

| | |
|---|---:|
| cagaatatct gccaacctcc tgtatacttg tcttacattt tacacaaagt actatataat | 180 |
| atctaaaatt caaaggttaa aaagcataac ttatgtccca ataagtaaa aaactgggat | 240 |
| tactattttt cttttcattg tcttattctc cacattattt ctttgtctgt agtttatcct | 300 |
| tatgtggtcc aatggcagca tatgtgaatc ctcatggata tgtacatgag acactgactg | 360 |
| tgtataaagc gtccaacctg aatctgatag gccggccttc tacagtgcac agctggtttc | 420 |
| ccgggtaata cagctgttta cttttcttgt tgactcttca tttagttta gatgaacttt | 480 |
| ctaggaagat acaaaacaaa caggacagga atagtttgat cacttcatga atgggttaaa | 540 |
| agcagggaca tgagatgtag aaaccagtaa atcctgcttt ctctagcttg ctttaacctt | 600 |
| gctctcccct ttactttgga agtggcagaa gaattaggga ttagtgactt attatcttat | 660 |
| tatccttgaa caaaatcctc ttatttggca tcattcttga ggactgtaaa gctaacatta | 720 |
| atatgcagaa tcctctacct gagaaaaatg gtaccctgag agcagaagtg ccttgcctgt | 780 |
| cttccagggg ttcatgctct cctgcatcac cttcacgtgc atctccaaca gaaatggaga | 840 |
| agaaagctgt gaggttaa | 858 |

<210> SEQ ID NO 50
<211> LENGTH: 859
<212> TYPE: DNA
<213> ORGANISM: Mus musculus

<400> SEQUENCE: 50

| | |
|---|---:|
| aggtcaggaa actgatatgt taggtaaagt aactaaatgt ccaaagatga aaacatgact | 60 |
| cactaggctt tgtaaacaca taatatttac ctttgaatca tcaagaaca tttttaagca | 120 |
| acagaatatc tgccaactcc ttgtatactt gtcttacatt ttacacaaag tactatataa | 180 |
| tatctaaaat tcaaaggtta aaaagcataa cttatgtccc aaataagtaa aaaactggga | 240 |
| ttactatttt tcttttcatt gtcttattct ccacattatt tctttgtctg tagtttatcc | 300 |
| ttatgtggtc caatggcagc atatgtgaat cctcatggat atgtacatga gacactgact | 360 |
| gtgtataaag cgtccaacct gaatctgata ggccggcctt ctacagtgca cagctggttt | 420 |
| cccgggtaat acagctgttt acttttcttg ttgactcttc atttagtttt agatgaactt | 480 |
| tctaggaaga tacaaaacaa acaggacagg aatagtttga tcacttcatg aatgggttaa | 540 |
| aagcagggac atgagatgta gaaaccagta atcctgcttt ctctagcttg ctttaacct | 600 |
| tgctctccct tttactttgg aagtggcaga agaattaggg attagtgact tattatctta | 660 |
| ttatccttga acaaaatcct cttatttggc atcattcttg aggactgtaa agctaacatt | 720 |
| aatatgcaga atcctctacc tgagaaaaat ggtaccctga gagcagaagt gccttgcctg | 780 |
| tcttccaggg gttcatgctc tcctgcatca ccttcacgtg catctccaac agaaatggag | 840 |
| aagaaagctg tgaggttaa | 859 |

<210> SEQ ID NO 51
<211> LENGTH: 1040
<212> TYPE: DNA
<213> ORGANISM: Artificial Sequence
<220> FEATURE:
<223> OTHER INFORMATION: Recombinant polynucleotide

<400> SEQUENCE: 51

| | |
|---|---:|
| cctcacccgg cccgataaaa attggccact ggattgcaga aggtctcttc ctggatcacc | 60 |
| tgacaactca ctcccatgtc ttccagactt ctgtcttact ctagatcggg aagttcctat | 120 |
| tctctagaaa gtataggaac ttcgcgacac ggacacaatc ccacgaacgt acgcctaggt | 180 |

```
taacctcaca gctttcttct ccatttctgt tggagatgca cgtgaaggtg atgcaggaga    240
gcatgaaccc ctggaagaca ggcaaggcac ttctgctctc agggtaccat ttttctcagg    300
tagaggattc tgcatattaa tgttagcttt acagtcctca agaatgatgc caaataagag    360
gattttgttc aaggataata agataataag tcactaatcc ctaattcttc tgccacttcc    420
aaagtaaaag ggagagcaag gttaaagcaa gctagagaaa gcaggattta ctggtttcta    480
catctcatgt ccctgctttt aacccattca tgaagtgatc aaactattcc tgtcctgttt    540
gttttgtatc ttcctagaaa gttcatctaa aactaaatga agagtcaaca agaaaagtaa    600
acagctgtat tacccgggaa accagctgtg cactgtagaa ggccggccta tcagattcag    660
gttggacgct ttatacacag tcagtgtctc atgtacatat ccatgaggat tcacatatgc    720
tgccattgga ccacataagg ataaactaca gacaaagaaa taatgtggag aataagacaa    780
tgaaaagaaa aatagtaatc ccagttttt acttatttgg gacataagtt atgctttta     840 acctttgaat tttagatatt atatagtact ttgtgtaaaa tgtaagacaa gtatacaagg    900
agttggcaga tattctgttg cttaaaaatg ttctttgatg attcaaaggt aaatattatg    960
tgtttacaaa gcctagtgag tcatgttttt c atctttggac atttagttac tttacctaac  1020
atatcagttt cctgacctct                                                1040
```

```
<210> SEQ ID NO 52
<211> LENGTH: 2441
<212> TYPE: DNA
<213> ORGANISM: Artificial Sequence
<220> FEATURE:
<223> OTHER INFORMATION: Recombinant polynucleotide

<400> SEQUENCE: 52
catcgatgat gggccacatt ggcctcgacg atatcgcgat cgccgataag ccaggttaac     60
ctgcattaac gcgccgtcga cgcggcgcgt ttgcgtattg ggcgctcttc cgcttcctcg    120
ctcactgact cgctgcgctc ggtcgttcgg ctgcggcgag cggtatcagc tcactcaaag    180
gcggtaatac ggttatccac agaatcaggg gataacgcag gaaagaacat gtgagcaaaa    240
ggccagcaaa aggccaggaa ccgtaaaaag gccgcgttgc tggcgttttt ccataggctc    300
cgcccccctg acgagcatca caaaaatcga cgctcaagtc agaggtggcg aaacccgaca    360
ggactataaa gataccaggc gtttccccct ggaagctccc tcgtgcgctc tcctgttccg    420
accctgccgc ttaccggata cctgtccgcc tttctccctt cgggaagcgt ggcgctttct    480
catagctcac gctgtaggta tctcagttcg gtgtaggtcg ttcgctccaa gctgggctgt    540
gtgcacgaac cccccgttca gcccgaccgc tgcgccttat ccggtaacta tcgtcttgag    600
tccaacccgg taagacacga cttatcgcca ctggcagcag ccactggtaa caggattagc    660
agagcgaggt atgtaggcgg tgctacagag ttcttgaagt ggtggcctaa ctacggctac    720
actagaagaa cagtatttgg tatctgcgct ctgctgaagc cagttacctt cggaaaaaga    780
gttggtagct cttgatccgg caaacaaacc accgctggta gcggtggttt ttttgtttgc    840
aagcagcaga ttacgcgcag aaaaaaagga tctcaagaag atcctttgat cttttctacg    900
gggtctgacg ctcagtggaa cgaaaactca cgttaaggga ttttggtcat gagattatca    960
aaaaggatct tcacctagat ccttttaaat taaaaatgaa gttttaaatc aatctaaagt   1020
atatatgagt aaacttggtc tgacagttac caatgcttaa tcagtgaggc acctatctca   1080
gcgatctgtc tatttcgttc atccatagtt gcctgactcc ccgtcgtgta gataactacg   1140
```

| | |
|---|---|
| atacgggagg gcttaccatc tggccccagt gctgcaatga taccgcgaga cccacgctca | 1200 |
| ccggctccag atttatcagc aataaaccag ccagccggaa gggccgagcg cagaagtggt | 1260 |
| ctgcaacttt atccgcctcc atccagtcta ttaattgttg ccgggaagct agagtaagta | 1320 |
| gttcgccagt taatagtttg cgcaacgttg ttgccattgc tacaggcatc gtggtgtcac | 1380 |
| gctcgtcgtt tggtatggct tcattcagct ccggttccca acgatcaagg cgagttacat | 1440 |
| gatcccccat gttgtgcaaa aaagcggtta gctccttcgg tcctccgatc gttgtcagaa | 1500 |
| gtaagttggc cgcagtgtta tcactcatgg ttatggcagc actgcataat tctcttactg | 1560 |
| tcatgccatc cgtaagatgc ttttctgtga ctggtgagta ctcaaccaag tcattctgag | 1620 |
| aatagtgtat gcggcgaccg agttgctctt gcccggcgtc aatacgggat aataccgcgc | 1680 |
| cacatagcag aactttaaaa gtgctcatca ttggaaaacg ttcttcgggg cgaaaactct | 1740 |
| caaggatctt accgctgttg agatccagtt cgatgtaacc cactcgtgca cccaactgat | 1800 |
| cttcagcatc ttttactttc accagcgttt ctgggtgagc aaaaacagga aggcaaaatg | 1860 |
| ccgcaaaaaa gggaataagg gcgacacgga aatgttgaat actcatactc ttccttttc | 1920 |
| aatattattg aagcatttat cagggttatt gtctcatgag cggatacata tttgaatgta | 1980 |
| tttagaaaaa taaacaaata gggttccgc gcacatttcc ccgaaaagtg ccacctgacg | 2040 |
| tctaagaaac cattattatc atgacattaa cctataaaaa taggcgtatc acgaggccct | 2100 |
| ttcgtctcgc gcgtttcggt gatgacggtg aaaacctctg acacatgcag ctcccggaga | 2160 |
| cggtcacagc ttgtctgtaa gcggatgccg ggagcagaca agcccgtcag ggcgcgtcag | 2220 |
| cgggtgttgg cgggtgtcgg ggctggctta actatgcggc atcagagcag attgtactga | 2280 |
| gagtgcacca tatggacata ttgtcgttag aacgcggcta caattaatac ataaccttat | 2340 |
| gtatcataca catacgattt aggtgacact atagaactcg atgcggcccc tgcaggcgcg | 2400 |
| ccatttaaat gcggccgcac ctcaggatgt cccctgaagc t | 2441 |

<210> SEQ ID NO 53
<211> LENGTH: 2019
<212> TYPE: DNA
<213> ORGANISM: Artificial Sequence
<220> FEATURE:
<223> OTHER INFORMATION: Recombinant polynucleotide

<400> SEQUENCE: 53

| | |
|---|---|
| cctaggcgta cgttcgtggg attgtgtccg tgtcgcgaag ttcctatact ttctagagaa | 60 |
| taggaacttc ccgcggttgt aagttctcca gatctagagt aagacagaag tctggaagac | 120 |
| atgggagtga gttgtcaggt gatccaggaa gagaccttct gcaatccagt gaccaattaa | 180 |
| ttacagcaga aaggaccatc gggaaggaaa gccatactct ccaggaacgt cattagtcgg | 240 |
| gatcttcagt tgctacaaga agcagatgtc aaacggcctt cccctaacca tgtgagaagt | 300 |
| gagctttcac tggcccgggt gtgaagtgat tctaatggaa taaatggatt tgctaaggaa | 360 |
| tagtttcctc agaagaaatc ctgggagcaa gtggggaaag ctgactcagc aaaacagagc | 420 |
| tgtttcttga ggacgatgcc aatagcaatc atttgaccaa actgaagtgg ccgtcaggag | 480 |
| gcatgaggat ctgatatcag ggagctctca gacgtcgctt ggtcggtctt tattcgaacc | 540 |
| ccagagtccc gctcagaaga actcgtcaag aaggcgatag aaggcgatgc gctgcgaatc | 600 |
| gggagcggcg ataccgtaaa gcacgaggaa gcggtcagcc cattcgccgc caagctcttc | 660 |
| agcaatatca cgggtagcca acgctatgtc ctgatagcgg tccgccacac ccagccggcc | 720 |
| acagtcgatg aatccagaaa agcggccatt ttccaccatg atattcggca agcaggcatc | 780 |

```
gccatgggtc acgacgagat cctcgccgtc gggcatgcgc gccttgagcc tggcgaacag    840
ttcggctggc gcgagcccct gatgctcttc gtccagatca tcctgatcga caagaccggc    900
ttccatccga gtacgtgctc gctcgatgcg atgtttcgct tggtggtcga atgggcaggt    960
agccggatca agcgtatgca gccgccgcat tgcatcagcc atgatggata ctttctcggc   1020
aggagcaagg tgagatgaca ggagatcctg ccccggcact tcgcccaata gcagccagtc   1080
ccttcccgct tcagtgacaa cgtcgagcac agctgcgcaa ggaacgcccg tcgtggccag   1140
ccacgatagc cgcgctgcct cgtcctgcag ttcattcagg gcaccggaca ggtcggtctt   1200
gacaaaaaga accgggcgcc cctgcgctga cagccggaac acggcggcat cagagcagcc   1260
gatcgtctgt tgtgcccagt catagccgaa tagcctctcc acccaagcgg ccggagaacc   1320
tgcgtgcaat ccatcttgtt caatggccga tcccatggtt tagttcctca ccttgtcgta   1380
ttatactatg ccgatatact atgccgatga ttaattgtca acacgtgctg ctgcaggtcg   1440
aaaggctcgg agatgaggaa gaggagaaca gcgcggcaga cgtgcgcttt tgaagcgtgc   1500
agaatgccgg gcctccggag gaccttcggg cgcccgcccc gccctgagc ccgcccctga   1560 gcccgcccc ggacccaccc cttcccagcc tctgagccca gaaagcgaag gagcaaagct   1620
gctattggcc gctgccccaa aggcctaccc gcttccattg ctcagcggtg ctgtccatct   1680
gcacgagact agtgagacgt gctacttcca tttgtcacgt cctgcacgac gcgagctgcg   1740 gggcggggg gaacttcctg actaggggag gagtggaagg tggcgcgaag gggccaccaa   1800
agaacggagc cggttggcgc ctaccggtgg atgtggaatg tgtgcgaggc cagaggccac   1860
ttgtgtagcg ccaagtgccc agcggggctg ctaaagcgca tgctccagac tgccttggga   1920
aaagcgcctc ccctacccgg tagaatgaag ttcctatact ttctagagaa taggaacttc   1980
gttggtaccg tacgcggacg accaacgggc ccaattgct                          2019

<210> SEQ ID NO 54
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 54
acagacatcg tacgtggtct cag                                             23

<210> SEQ ID NO 55
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 55
gctccagact gccttgggaa aagc                                            24

<210> SEQ ID NO 56
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 56
gctcttgaac ttggtaggca aatgc                                           25
```

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 57
tcccatgtct tccagacttc tgtc                                        24

<210> SEQ ID NO 58
<211> LENGTH: 217
<212> TYPE: DNA
<213> ORGANISM: Artificial Sequence
<220> FEATURE:
<223> OTHER INFORMATION: Recombinant polynucleotide

<400> SEQUENCE: 58
agctggagcc aacagcaaca tatagacacg tgcagtaata aattatccag ttataacagg   60
gtggctttgt aaatttgagg tgtcagagaa atctcacgag aagcctagta caaaggctaa  120
aaataggttt taacttatat ctttccttca ttttataggt atgcatggac cgtggcccag  180
tgcaagatct gtgcaagcca tattggatgt aaattta                          217

<210> SEQ ID NO 59
<211> LENGTH: 217
<212> TYPE: DNA
<213> ORGANISM: Mus musculus

<400> SEQUENCE: 59
agctggagcc aacagcaaca tatagacacg tgcagtaata aattatccag ttataacagg   60
gtggctttgt aaatttgagg tgtcagagaa atctcacgag aagcctagta caaaggctaa  120
aaataggttt taacttatat ctttccttca ttttataggt atgcatggac cattgcccag  180
tgcaagatct gtgcaagcca tattggatgg aaattta                          217

<210> SEQ ID NO 60
<211> LENGTH: 359
<212> TYPE: DNA
<213> ORGANISM: Artificial Sequence
<220> FEATURE:
<223> OTHER INFORMATION: Recombinant polynucleotide

<400> SEQUENCE: 60
gtgagttgtc aggtgatcca ggaagagacc ttctgcaatc cagtgaccaa ttaattacag   60
cagaaaggac catcgggaag gaaagccata ctctccagga acgtcattag tcgggatctt  120
cagttgctac aagaagcaga tgtcaaacgg ccttccccta accatgtgag aagtgagctt  180
tcactggccc gggtgtgaag tgattctaat ggaataaatg gatttgctaa ggaatagttt  240
cctcagaaga atcctggga gcaagtgggg aaagctgact cagcaaaaca gagctgtttc  300
ttgaggacga tgccaatagc aatcatttga ccaaactgaa gtggccgtca ggaggcatg   359

<210> SEQ ID NO 61
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 61
actttggaag tggcagaaga attaggg                                      27

<210> SEQ ID NO 62
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 62
gaaagtatag gaacttcgcg acacggac                                      28

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
gctcttgaac ttggtaggca aatgc                                         25

<210> SEQ ID NO 64
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 64
cactgatatt gtaagtagtt tgc                                           23

<210> SEQ ID NO 65
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 65
ctagtgcgaa gtagtgatca gg                                            22

<210> SEQ ID NO 66
<211> LENGTH: 540
<212> TYPE: DNA
<213> ORGANISM: Artificial Sequence
<220> FEATURE:
<223> OTHER INFORMATION: Recombinant polynucleotide

<400> SEQUENCE: 66
ggactgtaaa gctaacatta atatgcagaa tcctctacct gagaaaaatg gtaccctgag    60
agcagaagtg ccttgcctgt cttccagggg ttcatgctct cctgcatcac cttcacgtgc   120
atctccaaca gaaatggaga agaaagctgt gaggttaacc taggcgtacg ttcgtgggat   180
tgtgtccgtg tcgcgaagtt cctatacttt ctagagaata ggaacttcgt tcgaacataa   240
cttcgtatag catacattat acgaagttat ggtacgcgga cgaccaacgg gcccaattgc   300
tagctggagc caacagcaac atatagacac gtgcagtaat aaattatcca gttataacag   360
ggtggctttg taaatttgag gtgtcagaga atctcacga gaagcctagt acaaaggcta   420
aaaataggtt ttaacttata tctttccttc attttatagg tatgcatgga ccgtggccca   480
gtgcaagatc tgtgcaagcc atattggatg gaaatttaca gccacaaaaa aagacatgtc   540

<210> SEQ ID NO 67

```
<211> LENGTH: 540
<212> TYPE: DNA
<213> ORGANISM: Artificial Sequence
<220> FEATURE:
<223> OTHER INFORMATION: Recombinant polynucleotide

<400> SEQUENCE: 67
ggactgtaaa gctaacatta atatgcagaa tcctctacct gagaaaaatg gtaccctgag      60
agcagaagtg ccttgcctgt cttccagggg ttcatgctct cctgcatcac cttcacgtgc     120
atctccaaca gaaatggaga agaaagctgt gaggttaacc taggcgtacg ttcgtgggat     180
tgtgtccgtg tcgcgaagtt cctatacttt ctagagaata ggaacttcgt tcgaacataa     240
cttcgtatag catacattat acgaagttat ggtacgcgga cgaccaacgg gcccaattgc     300
tagctggagc caacagcaac atatagacac gtgcagtaat aaattatcca gttataacag     360
ggtggctttg taaatttgag gtgtcagaga atctcacga gaagcctagt acaaaggcta      420
aaaataggtt ttaacttata tctttccttc attttatagg tatgcatgga ccgtggccca     480
gtgcaagatc tgtgcaagcc atattggatg gaaatttaca gccacaaaaa aagacatgtc     540

<210> SEQ ID NO 68
<211> LENGTH: 424
<212> TYPE: DNA
<213> ORGANISM: Artificial Sequence
<220> FEATURE:
<223> OTHER INFORMATION: Recombinant polynucleotide

<400> SEQUENCE: 68
actatccata atatctatgc agtgatgact gggcagatct gactttgagg aaatatctgt      60
caggaagtca ctcctactgg tgcacttata aacaaagtat tactttgtct ggacttattt     120
catcttcagt ctctggaatt gtgggtaaca gagcagagcg agttaagccc caaaattttt     180
gaggtgacat gtctttttt gtggctgtaa atttccatcc aatatggctt gcacagatct      240
tgcactgggc cacggtccat gcataccttat aaaatgaagg aaagatataa gttaaaacct    300
attttagcc tttgtactag gcttctcgtg agatttctct gacacctcaa atttacaaag      360
ccaccctgtt ataactggat aatttattac tgcacgtgtc tatatgttgc tgttggctcc     420
agct                                                                 424

<210> SEQ ID NO 69
<211> LENGTH: 425
<212> TYPE: DNA
<213> ORGANISM: Artificial Sequence
<220> FEATURE:
<223> OTHER INFORMATION: Recombinant polynucleotide

<400> SEQUENCE: 69
actatacaca tatatcagag gcagtgatga ctgggcagat ctgacttgag gaaatatctg      60
tcaggaagtc actcctacag gtgcacttat aaacaaagta ttactttgtc tggacttatt    120
tcatcttcag tctctggaat tgtgggtaac agagcagagc gagttaagcc ccaaaatttt     180
tgaggtgaca tgtctttttt gtggctgtaa atttccatc caatatggct tgcacagatc      240
ttgcactggg caatggtcca tgcatacctta taaatgaag gaaagatata agttaaaacc    300
tatttttagc ctttgtacta ggcttctcgt gagatttctc tgcacctca aatttacaaa     360
gccaccctgt tataactgga taatttatta ctgcacgtgt ctatatgttg ctgttggctc     420
cagct                                                                425
```

DISEASE BIOMARKERS AND TREATMENT METHODS RELATED THERETO

CROSS REFERENCE TO RELATED APPLICATIONS

This application is a continuation of U.S. patent Ser. No. 15/955,073, filed Apr. 17, 2018, which is a continuation of application U.S. Ser. No. 15/074,920, issued as U.S. Pat. No. 9,974,289 on May 22, 2018, which is a continuation-in-part of and claims priority to International PCT Application No. PCT/US2014/064629, filed Nov. 7, 2014, which claims the benefit of and priority to U.S. Provisional Application No. 61/915,439, filed Dec. 12, 2013, and U.S. Provisional Application No. 61/902,066, filed Nov. 8, 2013, the contents of all of which are incorporated by reference herein in their entireties.

STATEMENT OF RIGHTS TO INVENTIONS MADE UNDER FEDERALLY SPONSORED RESEARCH

This invention was made with government support under Grant Nos: HL082945, P01 CA108631, and F30CA199988-01 awarded by the National Institutes of Health. The government has certain rights in the invention

SEQUENCE LISTING

This application contains a Sequence Listing which has been submitted electronically in ASCII format and is hereby incorporated by reference in its entirety. The ASCII copy, created on Jun. 6, 2016, is named 364950_00097SL.txt and is 95504 bytes in size.

BACKGROUND OF THE INVENTION

B lymphocytes are an important cellular component of the adaptive immune system. When normal B-cell development goes awry, B-cell neoplasia can result. B cell neoplasms include multiple myeloma, mantle cell lymphoma and chronic lymphocytic leukemia. Multiple myeloma is a malignant plasma cell disorder and is the second most common hematologic malignancy in the United States, with about 20 000 patients diagnosed annually. Most patients diagnosed with multiple myeloma survive for only 2-3 years. In contrast, patients with mantle cell lymphoma may survive between 5 and 7 years. However, for most multiple myeloma patients, the disease eventually progresses or returns, and over time treatment resistance often develops. Chronic lymphocytic leukemia (CLL) is the most common form of adult leukemia. In the U.S. alone, about 15,000 patients will be diagnosed with CLL in 2013, and almost 5,000 deaths from CLL will occur. MDS is diagnosed in more than 15,000 new patients per year, and deletions of chromosome 5q are the most common cytogenetic abnormality. As with virtually all cancers, prognosis is improved by the early identification of disease and initiation of an appropriate therapeutic regimen. Similarly, it is important to detect treatment resistance to a particular agent early, so that alternate forms of therapy can be provided. IMiDs, such as lenalidomide, pomalidomide and thalidomide may be useful for the treatment of CLL and related disorders. The therapeutic development of such agents would be advanced by the availability of a rodent model capable of responding to these agents, as human cells do. To date, such models have been lacking.

SUMMARY OF THE INVENTION

As described below, the present invention features a knock-in mouse responsive to treatment with lenalidomide and lenalidomide related compounds and methods of using the knock-in mouse.

In one aspect, the invention provides a knock-in mouse containing a polynucleotide encoding a mutant murine CRBN polypeptide or a human CRBN polypeptide. In one embodiment, the mutant CRBN polypeptide comprises one or more of the following substitutions: S369C, V380E, and I391V.

In another aspect, the invention provides a knock-in mouse containing a single point mutation (I391V) in the mouse endogenous CRBN locus. In one embodiment, the mouse is a wild type mouse.

In another aspect, the invention provides a pregnant knock-in mouse containing a single point mutation (I391V) in the mouse endogenous CRBN locus.

In another aspect, the invention provides a method for assessing teratogenicity of lenalidomide or an analog thereof, the method involving contacting the pregnant mouse of a previous aspect with lenalidomide or an analog thereof, and assessing teratogenicity in the murine pups produced by the pregnant mouse. In other embodiments of the above aspects, teratogenicity is assessed prenatally or postnatally.

In another aspect, the invention provides a method of assessing lenalidomide sensitivity in the knock-in mouse of a previous aspect, the method involving contacting the mouse with lenalidomide or an analog thereof, and assessing lenalidomide sensitivity.

In another aspect, the invention provides a murine cell containing a single point mutation (I391V) in the mouse endogenous CRBN locus.

In another aspect, the invention provides a method of assessing lenalidomide sensitivity in the murine cell of a previous aspect, the method involving contacting the murine cell of the previous aspect with lenalidomide or an analog thereof, and assessing lenalidomide sensitivity.

In another aspect, the invention provides a method of screening for agents that activate ubiquitin ligase using the murine cell of a previous aspect, the method involving contacting the cells with lenalidomide or an analog thereof and detecting ubiquitin ligase activation.

In various embodiments of the above aspects or any other aspect of the invention delineated herein, global protein ubiquitination and alterations in global protein levels are assayed. In other embodiments of the above aspects, the method involves detecting increased IKZF1 or IKZF3 ubiquitination, increased IKZF1 or IKZF3 degradation, or increased IKZF1 or IKZF3 binding to CRBN. In other embodiments of the above aspects, the mutation confers sensitivity to ImiDs. In still other embodiments of the above aspects, the mutation confers sensitivity to an agent that is thalidomide, lenalidomide, pomalidomide. In other embodiments of the above aspects, lenalidomide sensitivity is assessed by assaying IKZF1 or IKZF3 levels or ubiquitination, by assessing CRBN binding, by assaying for an alteration in the immune system, or by assaying neoplastic cell proliferation. In still other embodiments of the above aspects, the immune system is assayed by analyzing B cell or T cell function. In other embodiments of the above aspects, lenalidomide sensitivity is assessed by assaying IKZF1 or IKZF3 levels or ubiquitination, or by assessing CRBN binding. In other embodiments of the above aspects, binding to CRBN is assayed by detecting the affinity of binding, by detecting ubiquination of IKZF1 or IKZF3, by detecting degradation of IKZF1 or IKZF3.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "IKZF1 polypeptide" is meant a polypeptide having at least about 85% amino acid sequence identity to a sequence provided at NCBI Accession No. AAH18349, NP_006051, NP_001207694, or a fragment thereof and having DNA binding or transcriptional regulatory activity.

For IKZF1 Isoform 1, the degron is from 130-270. For IKZF1 Isoform 2, the degron is from amino acid 136-180/ 236-249. Both isoforms are responsive to lenalidomide. Exemplary amino acid sequences for the two isoforms are provided below:

```
IKZF1 isoform 2 NCBI Reference No. NP_001207694
                                                       (SEQ ID NO: 1)
    1   mdadegqdms qvsgkesppv sdtpdegdep mpipedlstt sggqqssksd rvvasnvkve 61   tqsdeengra cemngeecae dlrmldasge kmngshrdqg ssalsgvggi rlpngklkcd 121   icgiicigpn vlmvhkrsht gerpfqcnqc gasftqkgnl lrhiklhsge kpfkchlcny 181   acrrrdaltg hlrthsvike etnhsemaed lckigsersl vldrlasnva krkssmpqkf 241   lgdkglsdtp ydssasyeke nemmkshvmd qainnainyl gaeslrplvq tppggsevvp 301   vispmyqlhk plaegtprsn hsaqdsaven llllskaklv psereaspsn scqdstdtes 361   nneeqrsgli yltnhiapha rnglslkeeh raydllraas ensqdalrvv stsgeqmkvy 421   kcehcrvlfl dhvmytihmg chgfrdpfec nmcgyhsqdr yefsshitrg ehrfhms IKZF1 isoform 1 NCBI Reference No. NP_006051
                                                       (SEQ ID NO: 2)
    1   mdadegqdms qvsgkesppv sdtpdegdep mpipedlstt sggqqssksd rvvasnvke 61   tqsdeengra cemngeecae dlrmldasge kmngshrdqg ssalsgvggi rlpngklkcd 121   icgiicigpn vlmvhkrsht gerpfqcnqc gasftqkgnl lrhiklhsge kpfkchlcny 181   acrrrdaltg hlrthsvgkp hkcgycgrsy kqrssleehk erchnylesm glpgtlypvi 241   keetnhsema edlckigser slvldrlasn vakrkssmpq kflgdkglsd tpydssasye 301   kenemmkshv mdqainnain ylgaeslrpl vqtppggsev vpvispmyql hkplaegtpr 361   snhsaqdsav enllllskak lvpsereasp snscqdstdt esnneeqrsg liyltnhiap 421   harnglslke ehraydllra asensqdalr vvstsgeqmk vykcehcrvl fldhvmytih 481   mgchgfrdpf ecnmcgyhsq dryefsshit rgehrfhms
```

By "IKZF1 polynucleotide" is meant a polynucleotide encoding an IKZF1 polypeptide. An exemplary IKZF1 polynucleotide is provided at NM_006060.4 and reproduced below:

```
                                                       (SEQ ID NO: 3)
    1   ggcagcagag gaaccttttg gaggaggaag aggacacaga ggccctgtag ccaggcacca 61   agatccctcc caggtggctg ggtctgaggg gaactccgag cagccctagg tcctcaaagt 121   ctggatttgt gtggaaaagg cagctctcac ttggccttgg cgaggcctcg gttggttgat 181   aacctgagga ccatggatgc tgatgagggt caagacatgt cccaagtttc agggaaggaa 241   agcccccctg taagcgatac tccagatgag ggcgatgagc ccatgccgat ccccgaggac 301   ctctccacca cctcgggagg acagcaaagc tccaagagtg acagagtcgt ggccagtaat 361   gttaaagtag agactcagag tgatgaagag aatgggcgtg cctgtgaaat gaatggggaa 421   gaatgtgcgg aggatttacg aatgcttgat gcctcgggag agaaaatgaa tggctcccac
```

-continued

```
 481   agggaccaag gcagctcggc tttgtcggga gttggaggca ttcgacttcc taacggaaaa
 541   ctaaagtgtg atatctgtgg gatcatttgc atcgggccca atgtgctcat ggttcacaaa
 601   agaagccaca ctggagaacg gcccttccag tgcaatcagt gcggggcctc attcacccag
 661   aagggcaacc tgctccggca catcaagctg cattccgggg agaagccctt caaatgccac
 721   ctctgcaact acgcctgccg ccggagggac gccctcactg gccacctgag gacgcactcc
 781   gtcattaaag aagaaactaa tcacagtgaa atggcagaag acctgtgcaa gataggatca
 841   gagagatctc tcgtgctgga cagactagca agtaacgtcg ccaaacgtaa gagctctatg
 901   cctcagaaat ttcttgggga caagggcctg tccgacacgc cctacgacag cagcgccagc
 961   tacgagaagg agaacgaaat gatgaagtcc cacgtgatgg accaagccat caacaacgcc
1021   atcaactacc tggggccga gtccctgcgc cgctggtgc agacgccccc gggcggttcc
1081   gaggtggtcc cggtcatcag cccgatgtac cagctgcaca agccgctcgc ggagggcacc
1141   ccgcgctcca accactcggc ccaggacagc gccgtggaga acctgctgct gctctccaag
1201   gccaagttgg tgccctcgga gcgcgaggcg tccccgagca acagctgcca agactccacg
1261   gacaccgaga gcaacaacga ggagcagcgc agcggtctca tctacctgac caaccacatc
1321   gccccgcacg cgcgcaacgg gctgtcgctc aaggaggagc accgcgccta cgacctgctg
1381   cgcgccgcct ccgagaactc gcaggacgcg ctccgcgtgg tcagcaccag cggggagcag
1441   atgaaggtgt acaagtgcga acactgccgg gtgctcttcc tggatcacgt catgtacacc
1501   atccacatgg gctgccacgg cttccgtgat ccttttgagt gcaacatgtg cggctaccac
1561   agccaggacc ggtacgagtt ctcgtcgcac ataacgcgag gggagcaccg cttccacatg
1621   agctaaagcc ctcccgcgcc cccaccccag accccgagcc acccaggaa aagcacaagg
1681   actgccgcct ctcgctcccc gccagcagca tagactggac tggaccagac aatgttgtgt
1741   ttggatttgt aactgttttt tgttttttgt ttgagttggt tgattgggggt ttgatttgct
1801   tttgaaaaga ttttattttt tagaggcagg gctgcattgg gagcatccag aactgctacc
1861   ttcctagatg tttccccaga ccgctggctg agattccctc acctgtcgct tcctagaatc
1921   cccttctcca aacgattagt ctaaattttc agagagaaat agataaaaca cgccacagcc
1981   tgggaaggag cgtgctctac cctgtgctaa gcacggggtt cgcgcaccag gtgtcttttt
2041   ccagtcccca gaagcagaga gcacagcccc tgctgtgtgg gtctgcaggt gagcagacag
2101   gacaggtgtg ccgccaccca agtgccaaga cacagcaggg ccaacaacct gtgcccaggc
2161   cagcttcgag ctacatgcat ctagggcgga gaggctgcac ttgtgagaga aaatactatt
2221   tcaagtcata ttctgcgtag gaaaatgaat tggttgggga aagtcgtgtc tgtcagactg
2281   ccctggggtgg agggagacgc cgggctagag cctttgggat cgtcctggat tcactggctt
2341   tgcggaggct gctcagatgg cctgagcctc ccgaggcttg ctgccccgta ggaggagact
2401   gtcttcccgt gggcatatct ggggagccct gttccccgct ttttcactcc catacccttta
2461   atggccccca aaatctgtca ctacaattta aacaccagtc ccgaaatttg gatcttcttt
2521   cttttgaat ctctcaaacg gcaacattcc tcagaaacca aagctttatt tcaaatctct
2581   tccttccctg gctggttcca tctagtacca gaggcctctt ttcctgaaga aatccaatcc
2641   tagccctcat tttaattatg tacatctgtt tgtagccaca agcctgaatt tctcagtgtt
2701   ggtaagtttc tttacctacc ctcactatat attattctcg ttttaaaacc cataaaggag
2761   tgatttagaa cagtcattaa ttttcaactc aatgaaatat gtgaagccca gcatctctgt
2821   tgctaacaca cagagctcac ctgtttgaaa ccaagctttc aaacatgttg aagctcttta
```

-continued

```
2881    ctgtaaaggc aagccagcat gtgtgtccac acatacatag gatggctggc tctgcacctg 2941    taggatattg gaatgcacag ggcaattgag ggactgagcc agaccttcgg agagtaatgc 3001    caccagatcc cctaggaaag aggaggcaaa tggcactgca ggtgagaacc ccgcccatcc 3061    gtgctatgac atggaggcac tgaagcccga ggaaggtgtg tggagattct aatcccaaca 3121    agcaagggtc tccttcaaga ttaatgctat caatcattaa ggtcattact ctcaaccacc 3181    taggcaatga agaatatacc atttcaaata tttacagtac ttgtcttcac caacactgtc 3241    ccaaggtgaa atgaagcaac agagaggaaa ttgtacataa gtacctcagc atttaatcca 3301    aacaggggtt cttagtctca gcactatgac attttgggct gactacttat ttgttaggca 3361    ggagctctcc tgtgcattgt aggataatta gcagtatccc tggtggctac ccaatagacg 3421    ccagtagcac cccgaattga caacccaaac tctccagaca tcaccaactg tccctgcga 3481    ggagaaatca ctcctggggg agaaccactg acccaaatga attctaaacc aatcaaatgt 3541    ctgggaagcc ctccaagaaa aaaaaaaaa aa
```

By "IKZF3 polypeptide" is meant a protein having at least about 85% amino acid sequence identity to NCBI Accession No. NP_036613.2 (UnitPro Identifier No. Q9UKT9-1) or a fragment thereof and having DNA binding or transcriptional regulatory activity. An exemplary amino acid sequence of IKZF3 is provided below.

```
                                                        (SEQ ID NO: 4)
         10         20         30         40         50         60
MEDIQTNAEL KSTQEQSVPA ESAAVLNDYS LTKSHEMENV DSGEGPANED EDIGDDSMKV 70         80         90        100        110        120
KDEYSERDEN VLKSEPMGNA EEPEIPYSYS REYNEYENIK LERHVVSFDS SRPTSGKMNC 130        140        150        160        170        180
DVCGLSCISF NVLMVHKRSH TGERPFQCNQ CGASFTQKGN LLRHIKLHTG EKPFKCHLCN 190        200        210        220        230        240
YACQRRDALT GHLRTHSVEK PYKCEFCGRS YKQRSSLEEH KERCRTFLQS TDPGDTASAE 250        260        270        280        290        300
ARHIKAEMGS ERALVLDRLA SNVAKRKSSM PQKFIGEKRH CFDVNYNSSY MYEKESELIQ 310        320        330        340        350        360
TRMMDQAINN AISYLGAEAL RPLVQTPPAP TSEMVPVISS MYPIALTRAE MSNGAPQELE 370        380        390        400        410        420
KKSIHLPEKS VPSERGLSPN NSGHDSTDTD SNHEERQNHI YQQNHMVLSR ARNGMPLLKE 430        440        450        460        470        480
VPRSYELLKP PPICPRDSVK VINKEGEVMD VYRCDHCRVL FLDYVMFTIH MGCHGFRDPF 490        500
ECNMCGYRSH DRYEFSSHIA RGEHRALLK
```

By "IKZF3 polynucleotide is meant a nucleic acid sequence encoding an IKZF3 polypeptide. An exemplary polynucleotide sequence is provided at NCBI Accession No. NM_012481, which is reproduced below:

```
                                                        (SEQ ID NO: 5)
  1    gcaggagcac gtggagaggc cgagtagcca cagcggcagc tccagcccgg cccggcagcg 61    acatggaaga tatacaaaca aatgcggaac tgaaaagcac tcaggagcag tctgtgcccg 121    cagaaagtgc agcggttttg aatgactaca gtttaaccaa atctcatgaa atggaaaatg 181    tggacagtgg agaaggccca gccaatgaag atgaagacat aggagatgat tcaatgaaag 241    tgaaagatga atacagtgaa agagatgaga atgttttaaa gtcagaaccc atgggaaatg
```

-continued

```
 301   cagaagagcc tgaaatccct tacagctatt caagagaata taatgaatat gaaaacatta
 361   agttggagag acatgttgtc tcattcgata gtagcaggcc aaccagtgga agatgaact
 421   gcgatgtgtg tggattatcc tgcatcagct tcaatgtctt aatggttcat aagcgaagcc
 481   atactggtga acgcccattc cagtgtaatc agtgtggggc atcttttact cagaaaggta
 541   acctcctccg ccacattaaa ctgcacacag gggaaaaacc ttttaagtgt cacctctgca
 601   actatgcatg ccaaagaaga gatgcgctca cggggcatct taggacacat tctgtggaga
 661   aaccctacaa atgtgagttt tgtggaagga gttacaagca gagaagttcc cttgaggagc
 721   acaaggacg ctgccgtaca tttcttcaga gcactgaccc aggggacact gcaagtgcgg
 781   aggcaagaca catcaaagca gagatgggaa gtgaaagagc tctcgtactg gacagattag
 841   caagcaatgt ggcaaaacga aaaagctcaa tgcctcagaa attcattggt gagaagcgcc
 901   actgctttga tgtcaactat aattcaagtt acatgtatga gaaagagagt gagctcatac
 961   agacccgcat gatggaccaa gccatcaata acgccatcag ctatcttggc gccgaagccc
1021   tgcgccctt ggtccagaca ccgcctgctc ccactcgga gatggttcca gttatcagca
1081   gcatgtatcc catagccctc acccgggctg agatgtcaaa cggtgcccct caagagctgg
1141   aaaagaaaag catccacctt ccagaagaga gcgtgccttc tgagagagc ctctctccca
1201   acaatagtgg ccacgactcc acggacactg acagcaacca tgaagaacgc cagaatcaca
1261   tctatcagca aaatcacatg gtcctgtctc gggcccgcaa tgggatgcca cttctgaagg
1321   aggttccccg ctcttacgaa ctcctcaagc ccccgcccat ctgcccaaga gactccgtca
1381   aagtgatcaa caaggaaggg gaggtgatgg atgtgtatcg gtgtgaccac tgccgcgtcc
1441   tcttcctgga ctatgtgatg ttcacgattc acatgggctg ccacggcttc cgtgacccttt
1501   tcgagtgtaa catgtgtgga tatcgaagcc atgatcggta tgagttctcg tctcacatag
1561   ccagaggaga acacagagcc ctgctgaagt gaatatctgg tctcagggat gctcctatg
1621   tattcagcat cgtttctaaa aaccaatgac ctcgcctaac agattgctct caaaacatac
1681   tcagttccaa acttctttttc ataccatttt tagctgtgtt cacagggta gccagggaaa
1741   cactgtcttc cttcagaaat tattcgcagg tctagcatat tattacttttt gtgaaacctt
1801   tgtttttccca tcagggactt gaatttatg gaatttaaaa gccaaaaagg tatttggtca
1861   ttatcttcta cagcagtgga atgagtggtc ccggagatgt gctatatgaa acattctttc
1921   tgagatatat caaccacacg tggaaaagcc tttcagtcat acatgcaaat ccacaaagag
1981   gaaagctga ccagctgacc ttgctgggaa gcctcaccct tctgccctttc acaggctgaa
2041   gggttaagat ctaatctccc taatctaaat gacagtctaa gagtaagtaa aagaacagcc
2101   ataaaataag tatctgttac gagtaactga agaccccatt ctccaagcat cagatccatt
2161   tcctatcaca acattttttaa aaaatgtcat ctgatggcac ttctgcttct gtcctttacc
2221   ttcccatctc cagtgaaaag ctgagctgct ttgggctaaa ccagttgtct atagaagaaa
2281   atctatgcca gaagaactca tggttttaaa tatagaccat catcgaaact ccagaaattt
2341   atccactgtg gatgatgaca tcgctttcct ttggtcaagg ttgcagagc aagggtataa
2401   agggggaaat tgtttggcag caccaacaga aaacaaacaa acaaaaaaca gctacctaaa
2461   acttcttgaa agagttcatg gagaattggt gatacagacc caaagcaaat ttgccaatga
2521   tattttccac aaaaaaagtc caaaaagtat ggctcagcct ccccctcccc acaggagagg
2581   aattggagat agatggcatg tgtgtttaga tcggagttga gctccggaat ggggtgagga
2641   gggacacctc tattgagagg ttctccttga tcaggcaggc ttcggccctt ttttttccat
2701   ttaaatggaa ctgctgtatt ccatgaaaat tcctgaaagt ctgatcacgg ttctgcagat
```

-continued

```
2761  gtataagtca tccttgtcac tcataatatg tacatactat caggaggagt gctgttatca
2821  tggtaaaatt agcactggaa taggaggtca caaaatgctg gctaattagc tatgtgactt
2881  tgagaaatcg tttaactttt tttttttttt tttttttgag acaggatctc actctgttgc
2941  ccaggctgga gtgcagtggt gcaatcatgg ctcagtgcag cctcgacctc cccaggctca
3001  ggtgatcctc ccacctcagc ctcttgagta ctgggacaac aagtgcacac caccatgtct
3061  ggctacattt tgttcttttt gtagagatag gggtctcact atgttgccca tgctggtctt
3121  gaactcctgg gctcaagcaa tcagcccgcc tcagcctcct aaagtgctgg gattacaggt
3181  gtgagccacc acacccagcc ttatttaact cttaaaactc agtttccggc caggctcggt
3241  ggctcacacc tgtaatccca cactttggg aagccgaggc aggcgcatca tttgaggtca
3301  ggagttcgag accagcctga cccacatggt gaaaccctgt ctctactaaa aatacaaaaa
3361  ttagctgggc gtagtggca catgcctgta atcccagcta ctccggaggc tgaggcagaa
3421  aaatcgctta agcctgggag gttgaggttg cggtgagtgg agatcacact actgcactcc
3481  agtctgggcg acagagtgag accctgtctc aaacaaaaca aacaaaaac aaacaaacaa
3541  aaacaaaaaa aactcagttt cctcatccat aaaataggaa ttagatttca atgttctctt
3601  aggtcccttc tagctttaat tcatatgtga ttatgcagta accacaaggt atttttttaaa
3661  cctcctaatg tatggatatt aagcagaaga gtatttatat gaatacatgt ttcacattcc
3721  tttggtatga aaatggtgtg ttaagttttt cctttaacca ctgagttgtg aatgtgaaga
3781  aggtggtgga gaggaacaaa aaacagaaag gtattttgat cttgccacaa agcatacaca
3841  caaattggca catgcagctg tttgccaaag ccttcttttt ttttttactt tttaagaaat
3901  tatgttaggg aaaataaatt ctgcttccag ggacaacttc atggagccta tttacaaatt
3961  aagagtcagc ttaatttgta acatttctac cagagccaag aatcccaaat tcctggtaga
4021  ttagtgtttt atttctaagg ggcttatgca ttcggctcca actcaactcg tctatgtgct
4081  gccagtaatt aaaatgttcc acctcagact gcacaaatgg cttatccttc tttgtggcat
4141  ggcgtctgtc tcaggaaaaa aggtttttatg aaattccatg gcaacagtcc caacatgttt
4201  gagacttcag ctaaaggaat ggatgtattt tggtgtgtag tcttcagtat atcactgtat
4261  ttccgtaata ctagactcca agctatgcca gattgcttat tcccttttgtg aaagaggagt
4321  tgctcattac gttcttgaaa tatcgcacat cctgttggtt cttcaaggga caagagaaag
4381  agaatttgga agcagggatt agtagaagag aaaacgaggg aaaggaagcc tttccaccag
4441  attagtgttc aagtcttttgc agaggagacc aactttttt gttttcttt gttttgagac
4501  agtctctcgc tctgttgccc aggctggagt gcagtggcgc gatctcggct cacggcaacc
4561  tccgcctccc gggttcaagc aattctcctg cctcagcctc ccaagtagct gggattacag
4621  gtgctcacca ccaagcccgg ctaattttg tattttagt agagacaagg tttcaccatg
4681  ttggccaggc cagtctcaaa ctcctgacct caggtgatct gcccgccttg gcctcccaca
4741  gtgctgggat tacaggcatg agctaccgca cccagcctga daccaccttt tgcatctcaa
4801  gattgtgaaa ccaaggccca ttccaccagc ctggggactc tttttataga tatgatcctc
4861  cttttcctg tgactaatga atttgctgca tgatttctat tcttctgagg ttagttttct
4921  gagtaaggtg accactcaca aaggcacttt cttttgtggca ttctgagcct agattggggc
4981  ccatcaattc cagaaaaat ttatgtgtgg aaactctgca tccttaagtc ttgaagttga
5041  accagatatg cagtggttac catcacacag ataaacgctg ccttctgtac ataccccta
5101  tgctgtacta attaacaaac cccttgccag ggctggggag gtgagggtga aggagaatct
```

-continued

```
5161  tagcagaagg gcagagtcag gacttgcatc tgccactgct gggcactgaa gccctggagc
5221  agcttcagat agtacctgta ctttctcatg cagactccct ctgaacaaga gccttgtagg
5281  cccctctcct tcatttccca ccagcctctt atcaggcggg ctttccacca tacacccagg
5341  aggccacggt ctgaggaaca accaaaccca tgcaaagggc cgggcgcgat agctcacgcc
5401  tgtaatgcca gcactttggg aggctggggc aggcagatca cctgaggttg ggagttcgag
5461  acctgcctga ccaacatgga gaaccccca tctctactaa aaatacaaaa ttagccgggc
5521  gtgatggcac atgcctgtaa tcccagctac tcaggaggct gaggcaggag aatcgcttga
5581  acccgggagg cggaggttgc ggtgagccga gatggcacca ctgcactcca gcctcggcaa
5641  caagagcgaa actctgtcta aaacaaaaac aaacaaacaa acaaaaaaac ccaggcaaag
5701  tttccttgca gccaaggtga cagaactggg ctgagggtgg aaaagaaaca gaaccagtgc
5761  tccaggtgtt ttttaatttt ttaatttatt tttattttt ttgtatatgt atatatatgt
5821  atgtatattt tagaggacca gggtctcact atgttgccta ggccagactc aaactcctgt
5881  gctcaagcaa tcctgcctca gcctcccaag tagctgggat tacaggcatg cacaaacaat
5941  gcccagctct ccaaatgttt tctgtcacta cctgaagtgt tgcatcggta cttcctacgg
6001  aaagaaaact aaatagaagt gtctctcccg tgagccccca ccactaccac cagaaaaaaa
6061  aaagagagaa aatgaactca tcagtctttta gtttcctcaa gttattctcc caaaaagaca
6121  ttcgccttgg cacagataag ccagctaatc ttatgcttta tgacccactg tgagctgttc
6181  ctgacacagc ttctgacttt gtcagtgaca aaatttctca ccttttaaat gcagtgctta
6241  acattttgtt aggcccatac tcaaaatcgg ccagatataa aatgacctca gattttgatc
6301  tcctaggctc aaacaatcct cctacctcag cctcccaagt agctgggact ataggcacac
6361  caccatgcac agctaatttt ttttgtattt ttctgcagag atggcgtttc gccatactgc
6421  ccaggctagt ctcaaaatcc tgggctcaag caatctgccc acctcagcct cccaaagtgc
6481  tggaactaca ggcaagagcc actgcgccca gccacaacct cagatttctt tggcaaacag
6541  aaatgtttaa aaacacaaaa ttttgctcag gtgaaacact gtgttactat caaatctcac
6601  atccacataa agttttttctt ttcggctttg tttcgtgagg aacagacaga acaaagtttt
6661  tccaggtagc atctgtatca ctattattct cctatttcct gtaccacccc cacctcccca
6721  agccctactg aatgtgaggt ttagaatgtt ttaaggaggg tcaggtgcgg tggctcacgc
6781  ctgtaatccc agcactttgg gaggccaagg cgggcggatc acctgagttt gggagttcga
6841  gaccagcctg accaacatgg agaaccctg tctctactaa aaatacaaaa ttagccaggc
6901  gtggtggcac atgcctgtaa tcccagctac ttaggaggct gaggcaggag aatcgcttga
6961  acccaggagg aggaggttgt ggtgagccga gatcgtgcca ttgcactcca gcctgggtga
7021  cagagtgaga ctccatctcg aaaaaaaaaa tacaaaaatt agctgggtgt ggtggtgcac
7081  acctgtaatc ccagctactc gggaggctga cgcaggagaa ttgcttgaac ctgggaggtg
7141  gaggttgcag tgagccgaga tcgcgccatt gcaatccagc ctggacaaca gagtgagact
7201  ccatctcaaa aaaaaaaaa aaagaatgt ttaaggaaa aaaatagtac tgttacatat
7261  aatcccaggt gataagacca caatggaaat gtttaagtcc tcactttaaa gagtaccca
7321  ctgagaagag gtatgttgga ctctagcaga gatttggaaa ctctgggaca ctcaagatgt
7381  gaaagagcct ggctatctga ggactcaaag agtcagcatc gggacttgtg agctcaagaa
7441  gagaaagggg agtggtgaaa ctttgtccta aaagttagca ccaggaacag aagaaaaaaa
7501  cccgatatat agtgatacct catcttttag agaatgggaa gctattttttg tgttcacaca
7561  gaaagtatag ttcaaaaaac ctctatatcc agagttcaga caaggagaat gatttgagat
```

```
-continued 7621  ataagtgccg atgaaggagg tcaattttga tctgaaacca gcagctggac ctgggccacc
7681  tcaggaaaag gactctgttc tccaaggcag cacgactgaa tggttctgag aataagccag
7741  ggttcaggac tcctgaccct ttaggaccat ggactcagaa gagcctgaag acaattgtg
7801  ggctttaaac ttctgagagc ttgtaaagta acacaagact gtgcctctcc cttgcccag
7861  ctgtagatag tctttgcccc accattgtta tgaagataca cagggttttg cagtttgaat
7921  aaattggata caagtttcct cttttttttt ttcttttga dacaaagtct cgctctgttt
7981  ccccaggctg agtgcagtgg cacaatcaag gcttacttgc cgcctcaacc tcctgggctc
8041  aagcaacgag ccatcctccc gtcttagcct cccaactagc tgagactaca ggcgtgggtc
8101  accacaccca gctaattttt gtactttttg tagagacagg gtctcaccat gttgcccagg
8161  ctggtcctga actcctgggc tcaagtaatc tgcccacctc agcctcccaa agtgttggg
8221  ttacaggcgt gaggcaccgc ggctggcctg agtttcttct taatactgta tcacaattgt
8281  gggctgtctt atgtgttgat atcgattgag ctatttgaaa taggaatgtt aatgggtgta
8341  ttaaatttt gtaaggatat aacaatatct accttccaag gatgttgtga ggttttccat
8401  gattttgtat atgagctaat gttacctttg aggggtggtg tgcattatgt tggatgattg
8461  taaattttca gtggaaaatg taccgtgtcc taaatttaaa gacatgaaaa atatcccaag
8521  atcatactag atcataatag caattccttt acaaatgaat tatggaggta actgatctct
8581  aacagtttcc ttcatgttgt tttaatgcac aagggcagag gatctgctga cccttggaac
8641  cagcgtgagc taaccacgtg ctatagacac ttcatggtgt cgcacccagg gaagtcaaag
8701  cgctttgctc cctcactgtc tgtgagtcct cagccattag taccccaccc ccgctgctc
8761  caaaactga gttatttcaa atgtttctca ctgttcatct ctccactgac cccactccag
8821  aaagcctgga gagtccca agatgccacc caccttcccc aatccctcgc cacagatctg
8881  tgtctatctc acactctgta agtgccgctt tgcttcttcc tctcttgaaa agactgagaa
8941  cacacatttt aacatgttag gaaaatgggg cagcctaaaa aatgactgat cccaccgcca
9001  gtgactcatg tatactccag gctagcagac aaggcccttt ttggtgggcc tgcttctgtg
9061  ggttcacaga accaaatta ctgtgggttg caaagaatta gcaggtcatt tacaaagcag
9121  acatccctc acccagactg tggttttgca tgctcaggtt ctcagtctat gagctttggt
9181  gcaggatcat tttggctact ggaaaaacca tagcttattt taaatttctg gttgccaaag
9241  ccaccacacg tgtggtctgt ggatgaccat tgtctgcaga atgacgagga aggaacagaa
9301  tgtggtttgg ggctcagggt ggccttccca ctgggaggga aggcgggagg gagcccttgc
9361  cctgggtttt gacacagcct gtgctcacag cctctcctct catctgcatt tctcagaaat
9421  gccctccctg cccagtggta actttccctc gtcactccta tggagttcta cctggagccc
9481  agccatgtgt ggaactgtga agtttactcc tctgtaaaga tggtttaaag aaagtcagct
9541  tctgaaatgt aacaatgcta acccttgctg gaaccctgta agaaatagcc ctgctgatag
9601  ttttctaggt ttatcatgtt tgattttac actgaaaaat aaaaaaatcc tggtatgttt
9661  gaaattaaaa aaaaaaaaaa aaaaaa
```

By "human CRBN polypeptide" is meant an amino acid sequence or fragment thereof having at least 85% amino acid sequence identity to NCBI Accession No. AAH67811.1 or NP_001166953.1 and having IKZF3 binding activity. Exemplary CRBN polypeptide sequences are provided below:

```
AAH67811.1
                                                           (SEQ ID NO: 6)
  1    magegdqqda ahnmgnhlpl lpeseeedem evedqdskea kkpniinfdt slptshtylg
 61    admeefhgrt lhdddscqvi pvlpqvmmil ipgqtlplql fhpqevsmvr nliqkdrtfa
121    vlaysnvqer eaqfgttaei yayreeqdfg ieivkvkaig rqrfkvlelr tqsdgiqqak
181    vqilpecvlp stmsavqles lnkcqifpsk pvsredqcsy kwwqkyqrrk fhcanltswp
241    rwlyslydae tlmdrikkql rewdenlkdd slpsnpidfs yrvaaclpid dvlriqllki
301    gsaiqrlrce ldimnkctsl cckqcqetei ttkneifsls lcgpmaayvn phgyvhetlt
361    vykacnlnli grpstehswf pgyawtvaqc kicashigwk ftatkkdmsp qkfwgltrsa
421    llptipdted eispdkvilc l NP_001166953.1
                                                           (SEQ ID NO: 7)
  1    magegdqqda ahnmgnhlpl lpeseeedem evedqdskea kkpniinfdt slptshtylg
 61    admeefhgrt lhdddscqvi pvlpqvmmil ipgqtlplql fhpqevsmvr nliqkdrtfa
121    vlaysnvqer eaqfgttaei yayreeqdfg ieivkvkaig rqrfkvlelr tqsdgiqqak
181    vqilpecvlp stmsavqles lnkcqifpsk pvsredqcsy kwwqkyqkrk fhcanltswp
241    rwlyslydae tlmdrikkql rewdenlkdd slpsnpidfs yrvaaclpid dvlriqllki
301    gsaiqrlrce ldimnkctsl cckqcqetei ttkneifsls lcgpmaayvn phgyvhetlt
361    vykacnlnli grpstehswf pgyawtvaqc kicashigwk ftatkkdmsp qkfwgltrsa
421    llptipdted eispdkvilc l
```

By "human CRBN polynucleotide" is meant a nucleic acid molecule encoding a CRBN polypeptide. An exemplary CRBN polynucleotide sequence is provided at NCBI Accession No. BC067811, which is reproduced below:

```
                                                           (SEQ ID NO: 8)
  1   gcgtgtaaac agacatggcc ggcgaaggag atcagcagga cgctgcgcac aacatgggca
 61   accacctgcc gctcctgcct gagagtgagg aagaagatga aatggaagtt gaagaccagg
121   atagtaaaga agccaaaaaa ccaaacatca taaattttga caccagtctg ccgacatcac
181   atacatacct aggtgctgat atggaagaat tcatggcag actttgcac gatgacgaca
241   gctgtcaggt gattccagtt cttccacaag tgatgatgat cctgattccc ggacagacat
301   tacctcttca gcttttcac cctcaagaag tcagtatggt gcggaattta attcagaaag
361   atagaacctt tgctgttctt gcatacagca atgtacagga aagggaagca cagtttggaa
421   caacagcaga gatatatgcc tatcgagaag aacaggattt tggaattgag atagtgaaag
481   tgaaagcaat tggaagacaa aggttcaaag tccttgagct aagaacacag tcagatggaa
541   tccagcaagc taaagtgcaa attcttcccg aatgtgtgtt gccttcaacc atgtctgcag
601   ttcaattaga atccctcaat aagtgccaga tatttccttc aaaacctgtc tcaagagaag
661   accaatgttc atataaatgg tggcagaaat accagaggag aaagtttcat tgtgcaaatc
721   taacttcatg gcctcgctgg ctgtattcct tatatgatgc tgagacctta atggacagaa
781   tcaagaaaca gctacgtgaa tgggatgaaa atctaaaaga tgattctctt ccttcaaatc
```

```
-continued
 841 caatagattt tcttacaga gtagctgctt gtcttcctat tgatgatgta ttgagaattc 901 agctccttaa aattggcagt gctatccagc gacttcgctg tgaattagac attatgaata 961 aatgtacttc cctttgctgt aaacaatgtc aagaaacaga ataacaacc aaaaatgaaa 1021 tattcagttt atccttatgt gggccgatgg cagcttatgt gaatcctcat ggatatgtgc 1081 atgagacact tactgtgtat aaggcttgca acttgaatct gataggccgg ccttctacag 1141 aacacagctg gtttcctggg tatgcctgga ctgttgccca gtgtaagatc tgtgcaagcc 1201 atattggatg gaagtttacg gccaccaaaa aagacatgtc acctcaaaaa ttttggggct 1261 taacgcgatc tgctctgttg cccacgatcc cagacactga agatgaaata agtccagaca 1321 aagtaatact ttgcttgtaa acagatgtga tagagataaa gttagttatc taacaaattg 1381 gttatattct aagatctgct ttggaaatta ttgcctctga tacataccta agtaaacata 1441 acattaatac ctaagtaaac ataacattac ttggagggtt gcagtttcta agtgaaactg 1501 tatttgaaac ttttaagtat actttaggaa acaagcatga acggcagtct agaataccag 1561 aaacatctac ttgggtagct tggtgccatt atcctgtgga atctgatatg tctggtagcg 1621 tgtcattgat gggacatgaa gacatctttg gaaatgatga gattatttcc tgtgttaaaa 1681 aaaaaaaaaa aatcttaaat tcctacaatg tgaaactgaa actaataatt tgatcctgat 1741 gtatgggaca gcgtatctgt accagtgctc taaataacaa aagctagggt gacaagtaca 1801 tgttcctttt ggaagaagc aaggcaatgt atattaatta ttctaaaagg gctttgttcc 1861 tttccatttt ctttaacttc tctgagatac tgatttgtaa attttgaaaa ttagttaaaa 1921 tatgcagttt tttgagccca cgaatagttg tcatttcctt tatgtgcctg ttagtaaaaa 1981 gtagtattgt gtatttgctc agtatctgaa ctataagccc atttatactg ttccatacaa 2041 aagctatttt tcaaaaatta atttgaacca aaactactac tatagggaaa agatgccaaa 2101 acatgtcccc tcacccaggc taaacttgat actgtattat tttgttcaat gtaaattgaa 2161 gaaaatctgt aagtaagtaa accttaagtg tgaaactaaa aaaaaaaaaa aaa
```

By "murine CRBN polypeptide" is meant an amino acid sequence or fragment thereof having at least 85% amino acid sequence identity to NCBI Accession No. BC086488.1 or NP_067424 and having IKZF3 binding activity. Exemplary CRBN polypeptide sequence is provided below:

```
BC086488.1
                                                    (SEQ ID NO: 9)
  1mgnhlpllpd sededdeiem evedqdskea rkpniinfdt slptshtylg admeefhgrt 61lhdddscqvi pvlpevlmil ipgqtlplql shpqevsmvr nliqkdrtfa vlaysnvqer 121eaqfgttaei yayreeqefg ievvkvkaig rqrfkvlelr tqsdgiqqak vqilpecvlp 181stmsavqves lnkcqvfpsk piswedqysc kwwqkyqkrk fhcanltswp rwlyslydae 241tlmdrikkql rewdenlkdd slpenpidfs yrvaaclpid dvlriqllki gsaiqrlrce 301ldimnkctsl cckqcqetei ttkneifsls lcgpmaayvn phgyvhetlt vykasnlnli 361grpstvhswf pgyawtiaqc kicashigwk ftatkkdmsp qkfwgltrsa llptipeted 421eispdkvilc l NP_067424
                                                    (SEQ ID NO: 10)
  1magegdqqda ahnmgnhlpl lpadsededd eiemevedqd skearkpnii nfdtslptsh 61tylgadmeef hgrtlhddds cqvipvlpev lmilipgqtl plqlshpqev smvrnliqkd 121rtfavlaysn vgereaqfgt taeiyayree qefgievvkv kaigrqrfkv lelrtqsdgi
```

-continued

```
181 qqakvqilpe cvlpstmsav qleslnkcqv fpskpiswed qysckwwqky qkrkfhcanl 241 tswprwlysl ydaetlmdri kkqlrewden lkddslpenp idfsyrvaac lpiddvlriq 301 llkigsaiqr lrceldimnk ctslcckqcq eteittknei fslslcgpma ayvnphgyvh 361 etltvykasn lnligrpstv hswfpgyawt iaqckicash igwkftatkk dmspqkfwgl 421 trsallptip etedeispdk vilcl
```

By "murine CRBN polynucleotide" is meant a nucleic acid molecule encoding a murine CRBN polypeptide. An exemplary murine CRBN polynucleotide sequence is provided at NCBI Accession No. NM_021449 or NM_175357, which are reproduced below:

NM_021449

(SEQ ID NO: 11)

```
   1 tttcccaggc tcctttgcgg gtaaacagac atggccggcg agggagatca gcaggacgct 61 gcgcacaaca tgggaaacca cctgccgctt ctgcctgaca gtgaagatga agatgatgaa 121 attgaaatgg aagttgaaga ccaagatagt aaagaagcca gaaaaccgaa tatcataaac 181 tttgacacca gtctgccaac ctcacataca tacctgggag ctgatatgga ggagttccac 241 gggagaactt tgcatgacga cgacagctgc aggtgatcc cagtccttcc tgaggtgctg 301 atgatcctga ttcctgggca gacactccca ctgcagctct ctcacccaca ggaagtcagc 361 atggtgcgga acttaatcca gaaagacagg acctttgcag tccttgcata cagtaatgtg 421 caagaaaggg aagcacagtt tgggacaaca gcagagatct atgcctatcg agaagagcag 481 gagtttggaa ttgaagtagt gaaagtgaaa gcaattggaa ggcagcggtt caaggtcctc 541 gaacttcgaa cacagtcaga tggaatccag caagctaaag tgcagatttt gccagagtgt 601 gtgttgccgt caaccatgtc tgcagtgcag ttagaatcac tcaataagtg ccaggtattt 661 ccttcaaaac ccatctcctg ggaagaccag tattcatgta atggtggca gaaataccag 721 aagagaaagt tcactgtgc aaatctaaca tcatggcctc gctggctgta ttcattatat 781 gatgctgaaa cattaatgga tagaattaag aaacagctac gtgaatggga tgaaaatctc 841 aaagatgatt ctcttcctga aaatccaata gactttctt acagagtagc tgcttgtctt 901 cctattgatg atgtattgag aattcagctc cttaaaatcg gcagtgctat tcaacggctt 961 cgctgtgaat tggacatcat gaacaaatgt acttcccttt gctgtaaaca atgtcaagaa 1021 acagaaataa cgacaaagaa tgaaatattt agtttatcct tatgtggtcc aatggcagca 1081 tatgtgaatc ctcatggata tgtacatgag acactgactg tgtataaagc gtccaacctg 1141 aatctgatag gccggccttc tacagtgcac agctggtttc ccgggtatgc atggaccatt 1201 gcccagtgca gatctgtgc aagccatatt ggatggaaat ttacagccac aaaaaaagac 1261 atgtcacctc aaaaattttg gggcttaact cgctctgctc tgttacccac aattccagag 1321 actgaagatg aaataagtcc agacaaagta atactttgtt tataagtgca cctgtaggag 1381 tgacttcctg acagatattt cctcaagtca gatctgccca gtcatcactg cctctgatat 1441 atgtgtatag tgggttacag catttgccta ccaagttcaa gagcatattt agggaatgag 1501 aaagcagtat aaaacataag gctgggttcc aaaatacttg cttttagta gcttggtgcc 1561 atggattatc ctgttgagtc tatgtcatga caggatagga aaacagtt gaaataatgg 1621 gaatggccat ggaacaggat aggggcacca ctgctctaaa tgatgaagct ctaaatgatg 1681 aatgctccag aaactgggtt ggtaagcaca agatagaggc aaggcagtgt aattttaaaa 1741 ggactttgct cctttcaatt ttccttagct tgtctgagat actgacctgt acattttgaa
```

-continued

```
1801 catattaaag agtaactaag tattctgagc agaaatagca gcatttggtg tagttgcact
1861 tttgatttga tgagcctgtg atgtgctaga tccctttaac taatgtatat gtccattttg
1921 cattttattt gcaaatataa gtgaacagta tatatttcta ggattatacc atttaggaaa
1981 caggtttaca taaacataaa tatccaaatc tattctattt ggctgaatta tgtcaaagta
2041 atcaagtaga atactgaaaa gtgtaagtac gtaataaaat gcaactcaag aataggctgc
2101 tccttaatgt catttttca aaagttctac ttgtgtttca ttcaagctgc tgtgatggag
2161 tggggaatta tgcctttact gctgcagtat aatctgatga tccatggact gtttaccatt
2221 actttcagat aggactgttt aaaggaatct tacacaatat agcagctttg atgtcactcc
2281 atctgtgcag atgacaacag cagaaactcc atagtttaaa atccaggtat ttactgacct
2341 gggtgaagta gattttgaca cgcccttta tagcacatca ccttatttga cttcaagaaa
2401 attcaaaatc caaaagctgc tgtttacttg tacagtacac agatatctat gagcagctat
2461 gcagtaagta actatgtaag ctatcagaaa gctaagccat atccatctaa cttgtaaaat
2521 aaacaatgtg ttcactatct gtggcacctg atataaaggc aagagtctca gcacaagccc
2581 tcctgttatt cctgcaactt tctgaaatca gaacaatcct gttataaata gatgctacta
2641 tggactcatt caggaaaacca ctaagaaaac atagtttctc ttcaacagtt actacatttt
2701 aagatcaaca gcactgctcc acaagcattg ggaaattcag gaggtagact tgagcttagt
2761 ttttctacct acactcatgc tggttttggg gtctcagtaa cacaggaggg gagaacacca
2821 gccttaccaa gacttcccct gtttcataca gggctcatct ttaggtcttc tttatgtaac
2881 ttagtagttc atcttttcc atccggtaac cacttttctt ccactgttca cgcaactgct
2941 gtagcagggc cccaatttcc ttccctgaag aaatacccac tttcctgatg tcatgtccac
3001 tcacagggaa cggcgggaca gaccactgct gcatctcttt gagaagacca tgctctcctt
3061 ggtacttcag cagctcacaa acacgggcag ttgcatctgg ttccctagac taaatgacac
3121 agttttatca catactaaac actcacaatt tcattctact atttaaatac ttacatcaaa
3181 tctacagtgt gaaaaagtta cttttctcta gttagtgaga actattttct gctcagacct
3241 aatacatact tacgtctatc acaaagtctt ggtatggttt caatggttct gaactatctg
3301 ttgctttaat caagtctttc ctgttttaa ctataaataa acccaggttt ttctcctctt
3361 ttgaaatttt caatctcaag tccaattttg tgacatcatc ttgtactttg aataaagaag
3421 ccaaaagagt cattggtttt ggtgaaaagc cttcaacatt tttactgact tgttaaatt
3481 cttctaaatt tgcattagca ggtaaacctg taaacaaaag agaaaagtca ttttttctt
3541 aactacaaaa ccctcactca cctcttaaac tatgcagatt tttaagaatg tgtagtgttc
3601 tttctccact gcttattatc agcccattcg tcactccctt aactcctaga agaaatctat
3661 catgttcctg tttcctgtag cagcatgtct tgtgaagctc aggagctgtg atcatatcag
3721 gtaccagcat atgccttctc agtcatgatc ctgtctgcac acattcccta ctcagcaatt
3781 gtatgttctt gtaaaacagt caaagttact gtctaaaata tactggctat agttattaat
3841 ttcctttcta tatattaagt gttttgtgaa agagcttatt atacattaac ttattgcttc
3901 atcctcctct ctatgaagta gctttatttt tgaaccctt tgtgattataa accaacccaa
3961 cctgcaaaac cagtaagctt catcaaattc aggtgttctc tctgaactat tctttaccaa
4021 taaataaact atttccatct ttaatcccaa aaaaaaaaa aaaa
```

NM_175357

(SEQ ID NO: 12)

```
  1 tttcccaggc tcctttgcgg gtaaacagac atggccggcg agggagatca gcaggacgct
 61 gcgcacaaca tgggaaacca cctgccgctt ctgcctgcag acagtgaaga tgaagatgat
```

-continued

```
 121 gaaattgaaa tggaagttga agaccaagat agtaaagaag ccagaaaacc gaatatcata
 181 aactttgaca ccagtctgcc aacctcacat acatacctgg gagctgatat ggaggagttc
 241 cacgggagaa ctttgcatga cgacgacagc tgccaggtga tcccagtcct tcctgaggtg
 301 ctgatgatcc tgattcctgg gcagacactc ccactgcagc tctctcaccc acaggaagtc
 361 agcatggtgc ggaacttaat ccagaaagac aggacctttg cagtccttgc atacagtaat
 421 gtgcaagaaa gggaagcaca gtttgggaca acagcagaga tctatgccta tcgagaagag
 481 caggagtttg gaattgaagt agtgaaagtg aaagcaattg aaggcagcg gttcaaggtc
 541 ctcgaacttc gaacacagtc agatggaatc cagcaagcta aagtgcagat tttgccagag
 601 tgtgtgttgc cgtcaaccat gtctgcagtg cagttagaat cactcaataa gtgccaggta
 661 tttccttcaa aacccatctc ctgggaagac cagtattcat gtaaatggtg gcagaaatac
 721 cagaagagaa agtttcactg tgcaaatcta acatcatggc ctcgctggct gtattcatta
 781 tatgatgctc aaacattaat ggatagaatt aagaaacagc tacgtgaatg ggatgaaaat
 841 ctcaaagatg attctcttcc tgaaaatcca atagacttttt cttacagagt agctgcttgt
 901 cttcctattg atgatgtatt gagaattcag ctccttaaaa tcggcagtgc tattcaacgg
 961 cttcgctgtg aattggacat catgaacaaa tgtacttccc tttgctgtaa acaatgtcaa
1021 gaaacagaaa taacgacaaa gaatgaaata tttagtttat ccttatgtgg tccaatggca
1081 gcatatgtga atcctcatgg atatgtacat gagacactga ctgtgtataa agcgtccaac
1141 ctgaatctga taggccggcc ttctacagtg cacagctggt ttcccgggta tgcatggacc
1201 attgcccagt gcaagatctg tgcaagccat attggatgga aatttacagc cacaaaaaaa
1261 gacatgtcac ctcaaaaatt tggggctta actcgctctg ctctgttacc cacaattcca
1321 gagactgaag atgaaataag tccagacaaa gtaatacttt gtttataagt gcacctgtag
1381 gagtgacttc ctgacagata tttcctcaag tcagatctgc ccagtcatca ctgcctctga
1441 tatatgtgta tagtgggtta cagcatttgc ctaccaagtt caagagcata tttagggaat
1501 gagaaagcag tataaaacat aaggctgggt tccaaaatac ttgcttttta gtagcttggt
1561 gccatggatt atcctgttga gtctatgtca tgacaggata ggaaaacaca gttgaaataa
1621 tgggaatggc catggaacag gatagggca ccactgctct aaatgatgaa gctctaaatg
1681 atgaatgctc cagaaactgg gttggtaagc acaagataga ggcaaggcag tgtaatttta
1741 aaaggacttt gctcctttca atttccttta gcttgtctga gatactgacc tgtacatttt
1801 gaacatatta aagagtaact aagtattctg agcagaaata gcagcatttg gtgtagttgc
1861 acttttgatt tgatgagcct gtgatgtgct agatcccttt aactaatgta tatgtccatt
1921 ttgcatttta tttgcaaata taagtgaaca gtatatattt ctaggattat accatttagg
1981 aaacaggttt acataaacat aaatatccaa atctattcta tttggctgaa ttatgtcaaa
2041 gtaatcaagt agaatactga aaagtgtaag tacgtaataa aatgcaactc aagaataggc
2101 tgctccttaa tgtcattttt tcaaaagttc tacttgtgtt tcattcaagc tgctgtgatg
2161 gagtggggaa ttatgccttt actgctgcag tataatctga tgatccatgg actgtttacc
2221 attactttca gataggactg tttaaaggaa tcttacacaa tatagcagct ttgatgtcac
2281 tccatctgtg cagatgacaa cagcagaaac tccatagttt aaaatccagg tatttactga
2341 cctgggtgaa gtagattttg acacgccctt ttatagcaca tcaccttatt tgacttcaag
2401 aaaattcaaa atccaaaagc tgctgtttac ttgtacagta cacagatatc tatgagcagc
2461 tatgcagtaa gtaactatgt aagctatcag aaagctaagc catatccatc taacttgtaa
```

```
-continued
2521 aataaacaat gtgttcacta tctgtggcac ctgatataaa ggcaagagtc tcagcacaag 2581 ccctcctgtt attcctgcaa ctttctgaaa tcagaacaat cctgttataa atagatgcta 2641 ctatggactc attcaggaaa ccactaagaa aacatagttt ctcttcaaca gttactacat 2701 tttaagatca acagcactgc tccacaagca ttgggaaatt caggaggtag acttgagctt 2761 agtttttcta cctacactca tgctggtttt ggggtctcag taacacagga ggggagaaca 2821 ccagccttac caagacttcc cctgtttcat acagggctca tctttaggtc ttctttatgt 2881 aacttagtag ttcatctttt tccatccggt aaccactttt cttccactgt tcacgcaact 2941 gctgtagcag ggccccaatt tccttccctg aagaaatacc cactttcctg atgtcatgtc 3001 cactcacagg gaacggcggg acagaccact gctgcatctc tttgagaaga ccatgctctc 3061 cttggtactt cagcagctca caaacacggg cagttgcatc tggttcccta gactaaatga 3121 cacagtttta tcacatacta aacactcaca atttcattct actatttaaa tacttacatc 3181 aaatctacag tgtgaaaaag ttacttttct ctagttagtg agaactattt tctgctcaga 3241 cctaatacat acttacgtct atcacaaagt cttggtatgg tttcaatggt tctgaactat 3301 ctgttgcttt aatcaagtct ttcctgtttt taactataaa taaacccagg ttttttctcct 3361 cttttgaaat tttcaatctc aagtccaatt ttgtgacatc atcttgtact ttgaataaag 3421 aagccaaaag agtcattggt tttggtgaaa agccttcaac attttttactg actttgttaa 3481 attcttctaa atttgcatta gcaggtaaac ctgtaaacaa aagagaaaag tcattttttt 3541 cttaactaca aaaccctcac tcacctctta aactatgcag attttttaaga atgtgtagtg 3601 ttctttctcc actgcttatt atcagcccat tcgtcactcc cttaactcct agaagaaatc 3661 tatcatgttc ctgtttcctg tagcagcatg tcttgtgaag ctcaggagct gtgatcatat 3721 caggtaccag catatgcctt ctcagtcatg atcctgtctg cacacattcc ctactcagca 3781 attgtatgtt cttgtaaaac agtcaaagtt actgtctaaa atatactggc tatagttatt 3841 aatttccttt ctatatatta agtgttttgt gaaagagctt attatacatt aacttattgc 3901 ttcatcctcc tctctatgaa gtagctttta ttttgaaccc tttgtgatta taaaccaacc 3961 caacctgcaa aaccagtaag cttcatcaaa ttcaggtgtt ctctctgaac tattctttac 4021 caataaataa actatttcca tctttaatcc caaaaaaaaa aaaaaaa
```

By "casein kinase 1A1 polypeptide" is meant a protein having at least about 85% or greater identity to Unit Pro Accession No. P48729-1 or P48729-2 (having a phosphor serine at position 156) and having kinase activity.

```
                                              (SEQ ID NO: 13)
         10         20         30         40
MASSSGSKAE FIVGGKYKLV RKIGSGSFGD IYLAINITNG 50         60         70         80
EEVAVKLESQ KARHPQLLYE SKLYKILQGG VGIPHIRWYG 90        100        110        120
QEKDYNVLVM DLLGPSLEDL FNFCSRRFTM KTVLMLADQM 130        140        150        160
ISRIEYVHTK NFIHRDIKPD NFLMGIGRHC NKLFLIDFGL 170        180        190        200
AKKYRDNRTR QHIPYREDKN LTGTARYASI NAHLGIEQSR 210        220        230        240
RDDMESLGYV LMYFNRTSLP WQGLKAATKK QKYEKISEKK 250        260        270        280
MSTPVEVLCK GFPAEFAMYL NYCRGLRFEE APDYMYLRQL 290        300        310        320
FRILFRTLNH QYDYTFDWTM LKQKAAQQAA SSSGQGQQAQ

330
TPTGKQTDKT KSNMKGF
```

By "casein kinase 1A1 polynucleotide" is meant a polynucleotide encoding a casein kinase 1A1 polypeptide.

By "B cell neoplasia" is meant any neoplasia arising from a B-cell progenitor or other cell of B cell lineage. In particular embodiments, a B cell neoplasia arises from a cell type undergoing B cell differentiation. In other embodiments, a B cell neoplasia includes plasma cells.

By "knock-in rodent" is meant any rodent which expresses an exogenous polynucleotide in an endogenous locus. In one embodiment, a knock-in mouse comprises a targeted insertion of a DNA construct containing the engineered gene of interest (e.g., a mutated CRBN). The engineered gene (or portion thereof) is flanked by sequences identical to those in the target locus and introduced into ES cells, where homologous sequences align and recombine, thereby introducing the altered gene into an endogenous locus. In one embodiment, the rodent is a knock-in mouse or rat comprising a mutation in CRBN.

By "mutant CRBN" is meant any mutation of murine CRBN to include at least one of S369C, V380E, I391V, or any other substitution, deletion or addition of the murine CRBN that confers lenalidomide sensitivity to CSNK1A1.

By "myeloid malignancy" is meant a condition associated with a defect in the proliferation of a hematopoietic cell. Myelodysplastic syndrome with deletion of 5q.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change. In one embodiment, an alteration characterized in accordance with the methods of the invention is a change in the sequence of a polypeptide or polynucleotide. In another embodiment, an alteration characterized in accordance with the methods of the invention is an increase or decrease in the level, biological activity, or post-transcriptional modification of a polypeptide (e.g., IKZF1, IKZF3) as detected by standard art known methods such as those described herein. As used herein, an alteration includes 10%, 25%, 50%, 75%, 85%, 95% or greater increase or decrease in level or biological activity.

By "lenalidomide sensitivity" is meant that at least one symptom of a pathological condition is ameliorated by treatment with lenalidomide or a lenalidomide analog.

By "lenalidomide resistant" is meant that a neoplastic cell has acquired an alteration that allows it to escape an anti-neoplastic effect of lenalidomide. Exemplary anti-neoplastic effects include, but are not limited to, any effect that reduces proliferation, reduces survival, and/or increases cell death (e.g., increases apoptosis).

By "analog" is meant a molecule that is not identical, but has analogous functional or structural features. Lenalidomide analogs include, but are not limited to, thalidomide or pomalidomide. By "biological sample" is meant any liquid, cell, or tissue obtained from a subject.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "effective amount" is meant the amount of an agent required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention which has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" or "biomarker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, or feline.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammalian (e.g., rodents such as rats or mice) and the DNA (transgene) is inserted by artifice into the nuclear genome. In one embodiment, the transgenic mouse is a knock-in mouse comprising an exogenous CRBN sequence.

By "transformation" is meant any method for introducing foreign molecules into a cell. Lipofection, calcium phosphate precipitation, retroviral deliver, electroporation and biolistic transformation are just a few of the teachings which may be used. For example, Biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "positioned for expression" is meant that the DNA molecule is positioned adjacent to a DNA sequence which directs transcription and translation of the sequence (i.e., facilitates the production of, e.g., an IAP polypeptide, a recombinant protein or a RNA molecule).

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a schematic diagram showing the experimental design for SILAC-based assessment of global changes in ubiquitination and protein levels. Cells were treated for 12 hours with DMSO, lenalidomide, or thalidomide. For ubiquitination analysis 5 µM MG132 were added for the last 3 hours. FIG. 1B is a ubiquitin analysis. $Log_2$ ratios for individual K-ε-GG sites of lenalidomide versus DMSO treated cells for replicate 1 and 2. Each dot represents a unique K-ε-GG site. FIG. 1C shows a proteome analysis. $Log_2$ ratios of changes of protein abundance of lenalidomide versus DMSO treated cells. Each dot represents a distinct protein group. FIG. 1D shows a CRBN interaction analysis in cells treated for 6 hours with 1 µM lenalidomide. Scatter plot shows $log_2$ changes of proteins pulled down by HA-CBRN in lenalidomide versus DMSO treated control cells.

FIG. 2A shows the synthesis of a lenalidomide derivative immobilized to a bead that was used to pull down proteins binding lenalidomide. FIG. 2B-1 is a graph showing the viability (CellTiter-Glo® Luminescent Cell Viability Assay, Promega) of lenalidomide sensitive MM1S cells. FIG. 2B-2 is a graph showing lenalidomide insensitive K562 cells treated with lenalidomide or lenalidomide derivative for 6 days. FIG. 2C shows a schematic overview of pull down of candidate protein binders to lenalidomide beads. K562 cells were cultured in light (R0K0) or heavy (R10K6) SILAC media for 14 days to allow for quantitative assessment of proteins binding the lenalidomide derivative bead by LC-MS/MS. In the second condition cell lysates were additionally incubated with soluble lenalidomide to compete off binding proteins. The ratio of proteins pulled down in the lenalidomide beads only versus lenalidomide beads with soluble lenalidomide represent proteins that specifically bind lenalidomide. For a biological replicate SILAC labeling for the two conditions was switched.

FIGS. 3A-1, 3A-2 and 3B-1, 3B-2 show the results of a proteomic assessment of thalidomide induced in vivo changes of global ubiquitination and proteome. FIG. 3A-1 is a scatter plot for $\log_2$ ratios for individual K-ε-GG sites of lenalidomide versus DMSO treated cells for replicate 1 and 2. Each dot represents an individual K-ε-GG site. FIG. 3A-2 is a table showing median $\log_2$ ratios from all 3 replicates. FIG. 3B-1 is a scatter plot for $\log_2$ ratios of changes of protein abundance in lenalidomide versus DMSO treated cells. Each dot represents an individual protein. FIG. 3B-2 is a table showing median $\log_2$ ratios from 2 replicates.

FIGS. 5A-1. 5A-2 and 5B-1-5B-3 show results of CRBN co-immunoprecipitation, continued from FIG. 1G. FIG. 5A-1 is a scatter plot with $\log_2$ ratios for (HA-CRBN expressing) DMSO treated versus (FLAG-CRBN expressing) control cells. FIG. 5A-2 is a scatter plot with $\log_2$ ratios for lenalidomide versus DMSO treated cells (both expressing HA-CRBN. FIG. 5B-1 is a list of top (co-)immunoprecipitated proteins from DMSO treated versus control. FIG. 5B-2 is a list of top (co-)immunoprecipitated proteins from lenalidomide treated versus control. FIG. 5B-3 is a list of top (co-)immunoprecipitated proteins from lenalidomide versus DMSO treated cells. For $\log_2$ ratios of lenalidomide versus DMSO treated cells only proteins that bound to CRBN in presence of lenalidomide and/or DMSO with a $\log_2$ ratio>0.5 in both replicates were considered.

FIGS. 6A-6F show the effect of lenalidomide on IKZF1 and IKZF3 protein levels. FIG. 6A is a graph. 293T cells transfected with vectors expressing the indicated cDNA fused to firefly luciferase and control renilla luciferase were treated with DMSO or 1 µM lenalidomide for 24 hours. Bars represent the firefly to renilla luciferase ratio, normalized to DMSO-treated cells. FIG. 6B is a Western blot showing the effects of lenalidomide on endogenous IKZF1 and IKZF3 in MM cells treated for 24 hours. FIG. 6C is a Western blot showing a time course of lenalidomide treatment in MM1S cells for IKZF1 and IKZF3 protein levels and FIG. 6D mRNA levels. FIG. 6E provides immunoblots. Primary multiple myeloma samples were treated for 6 hours and analyzed by immunoblot. FIG. 6F shows an in vivo ubiquitination analysis of HA-tagged IKZF1 and IKZF3 expressed in MM1S cells treated for 1.5 hours with 100 nM Epoxomicin and the indicated concentrations of lenalidomide. The FK2 antibody detects covalently linked ubiquitin.

FIGS. 7A and 7B show that Lenalidomide induced decrease of IKZF1 and IKZF3 in different cell lines. Cells were treated in the presence of the respective lenalidomide concentrations for 24 hours. MM cells were treated with DMSO or 1 µM lenalidomide in the presence of 100 µg/ml Cycloheximide.

FIG. 8A shows results in 293T cells expressing stably transduced with a retrovirus expressing FLAG-IKZF3. FIG. 8B shows results in MM1S cells stably expressing HA-IKZF1. FIG. 8C shows endogenous IKZF3 of MM1S cells was immunoprecipitated by a polyclonal IKZF3 antibody.

FIGS. 9A-9D-1, 9D-2 show that CRBN is a substrate receptor for IKZF1 and IKZF3. FIG. 9A is a Western blot showing the immunoprecipitiation of endogenous CRBN in MM1S cells treated for 1 hour with the indicated drugs. FIG. 9B is shows the results of an in vitro ubiquitination reaction of HA-IKZF3 co-immunoprecipitated by FLAG-CRBN from 293T cells and incubated in the presence or absence of E1 and E2 ubiquitin conjugating enzymes. FIG. 9C is a schematic diagram showing the mapping of the degron that confers lenalidomide sensitivity. Blue boxes in the IKZF3 protein represent zinc finger domains. FIG. 9D-1 shows a sequence alignment of the core lenalidomide degron between the 5 Ikaros proteins (SEQ ID NOs: 27-31, respectively, in order of appearance). FIG. 9D-2 shows Western blots of 293T cells lysates 48 hours after co-transfection of FLAG-tagged IKZF3 or IKZF4 with HA-tagged CRBN and 24 hours drug treatment.

FIG. 11A provides a representation of all IKZF3 mutants tested. Response to lenalidomide was assessed with an ORF-luciferase reporter. The red box indicates the critical peptide sequence (amino acids 140 to 180 of IKZF3) necessary for lenalidomide sensitivity. Substitution in the H177P/L178F mutant is based on the sequence alignment of IKZF1 and IKZF3 versus IKZF2 and IKZF4 and does not affect lenalidomide sensitivity in contrast to the Q147H substitution in IKZF3. FIG. 11B shows validation of lenalidomide response by western blot for several IKZF3 mutants. FLAG-tagged versions were cloned into the RSF91 vector, transfected into 293T cells together with a plasmid expressing HA-CRBN. After 24 hours media was replaced with media containing lenalidomide in the indicated concentrations and incubated another 24 hours before lysis. FIG. 11C shows the co-immunoprecipitation of FLAG-IKZF3 and its mutants by HA-CRBN. 293T cells were transfected with the indicated plasmids. After 48 hours 1 µM lenalidomide was added for 1 hour before lysis and HA-immunoprecipitation.

FIGS. 12A-1, 12A-2. 12A-3-12F shows the biological role of IKZF1 and IKZF3 in multiple myeloma cell lines and T cells. FIG. 12A-1 shows Lenalidomide insensitive and Lenalidomide sensitive cell lines. FIG. 12A-2 is a graph showing the results of Lenalidomide-sensitive and insensitive cell lines infected with lentivirus expressing IKZF1 specific shRNAs and GFP. FIG. 12A-3 is a graph showing the results of Lenalidomide-sensitive and insensitive cell lines infected with lentivirus expressing IKZF3 specific shRNAs and GFP. Relative depletion was assessed by flow cytometry and normalized to day 2 post infection.

In FIG. 14A MM1S cells were treated for up to 48 hours with lenalidomide and IRF4 protein levels determined by immunoblot. FIG. 14B shows IRF4, IZKF1 and IKZF3 protein changes after 12 hours of lenalidomide treatment assessed by quantitative MS. FIG. 14C is a graph showing results of an RQ-PCR analysis of IRF4 RNA levels after 24 and 48 hour treatment with 1 µM lenalidomide. FIG. 14D shows an IRF4 Immunoblot of MM cells that were transduced with lentivirus expressing luciferase or IKZF3-specific shRNAs. FIG. 14E is a graph showing IRF4 RNA expression levels after IKZF3 knockdown.

FIGS. 15A-1, 15A-2, 15B-1, 15B-2, 15C-1 and 15C-2 include graphs and immunoblots. FIG. 15A-1 is a graph showing knockdown of shRNAs assessed by RQ-PCR in MM1S cells for IKZF1. FIG. 15A-2 shows knockdown of expression in MM1S cells assessed by immunoblot for IKZF1. FIG. 15B-1 is a graph showing knockdown of shRNAs assessed by RQ-PCR in MM1S cells for IKZF3. FIG. 15B-2 shows knockdown of expression in MM1S cells assessed by immunoblot for IKZF3. FIG. 15C-1 is a graph showing knockdown of shRNAs assessed by RQ-PCR in MM1S cells for CRBN. FIG. 15C-2 shows knockdown of expression in MM1S cells assessed by immunoblot for CRBN.

FIG. 16A shows results of SILAC-based quantitative MS studies used to characterize changes in the ubiquitinome in the MM1S multiple myeloma cell line cultured in the presence of lenalidomide. FIG. 16B show results of SILAC-based quantitative MS studies used to characterize changes in the proteome in the MM1S multiple myeloma cell line cultured in the presence of lenalidomide.

FIG. 20A shows the log$_2$ ratios for individual K-ε-GG sites of lenalidomide- (1 µM) versus DMSO-treated cells for replicates 1 and 2. Each dot represents a unique K-ε-GG site. FIG. 20B shows the log$_2$ ratios of changes of protein abundance of lenalidomide- (1 µM) versus DMSO-treated cells for replicates 1 and 2. Each dot represents a unique protein group. FIG. 20C shows the effects of lenalidomide on endogenous CSNK1A1 levels in KG-1 cells after 24-hour treatment. FIG. 20D shows a time course of lenalidomide treatment in KG-1 cells for CSNK1A1 mRNA levels.

FIGS. 21A-21F-1, 21F-2, 21F-3 show lenalidomide induces degradation of CSNK1A1 by CRBN-CRL4. FIG. 21A shows CSNK1A1 protein levels in KG-1 cells treated with DMSO or 1 µM or 10 µM lenalidomide alone or with MG-132 or MLN4924 for 6 hours. FIG. 21B shows CRBN knockout 293T cells were generated using CRISPR/Cas9-mediated deletion. The effect of lenalidomide on CSNK1A1 protein was assessed in normal and CRBN knockout 293T cells. FIG. 21C shows immunoprecipitation of HA-CRBN in 293T cells treated for 4 hours with MG132 and DMSO or lenalidomide. FIG. 21D shows in vivo ubiquitination analysis of tagged CSNK1A1 transiently expressed in 293T cells with or without CRBN. Cells were treated for 4 hours with the indicated concentrations of lenalidomide. The FK2 antibody was used to detect ubiquitination of immunoprecipitated HA-CSNK1A1. FIG. 21E shows CD34$^+$ cells isolated from cord blood were transduced with either luciferase control specific shRNA or CSNK1A1-specific shRNA expressing GFP labeled lentivirus. After 48 hours cells were either treated with DMSO or 1 µM lenalidomide. FIG. 21F-1 shows numbers of GFP positive cells as assessed by flow cytometry. 21F-2 shows numbers of GFP positive cells as assessed by flow cytometry. 21F-3 shows numbers of GFP positive cells as assessed by flow cytometry.

FIG. 22A shows murine Baf3 cells or primary murine AML cells transformed with an MLL-AF9 expressing retrovirus were treated with lenalidomide for 24 hours in vitro. CSNK1A1 protein levels were assessed by immunoblot. FIG. 22B shows murine Baf3 cells were transduced with a retrovirus expressing murine CRBN (m), human CRBN (h), human CRBN with single amino acid substitutions based on corresponding residues in murine CRBN, or empty vector. After selection with puromycin cells were treated for 24 hours with DMSO (−) or 1 µM lenalidomide (+) and CSNK1A1 protein levels were assessed by immunoblot. FIG. 22C shows alignment of human and murine CRBN_ (SEQ ID NOs: 32 and 33, respectively, in order of appearance). Non-conserved amino acids are indicated by red bars. In the enlarged segment of the lenalidomide binding region the critical non-conserved amino acid determining response to IMiDs (human V387, murine I391) is indicated in red, the previously described human CBRN mutant that does not bind IMiDs (Y383A/W385A) is indicated in green. FIG. 22D shows murine Baf3 cells were transduced with retrovirus expressing murine CRBN, human CRBN, murine CRBN$^{I391I}$, or empty vector. After selection with puromycin cells were treated for 24 hours with DMSO or lenalidomide and CSNK1A1 protein levels were assessed by immunoblot. FIG. 22E shows human 293T cells were transfected with a IKZF3-luciferase fusion protein together with a human or murine CRBN. Cells were treated with DMSO or 1 µM lenalidomide for 4 hours.

FIG. 23A is an illustration showing the experimental setup for in vitro competition experiments. Primary hematopoietic progenitors (cKIT+) were isolated from the bone marrow of CSNK1A1$^{+/-}$ MxCre$^+$ or MxCre$^+$ mice treated with poly I:C 4 weeks before. When applicable, excision of exon 3 of CSNK1A1 on one allele was confirmed by excision PCR. One day after harvest cells were transduced with a retrovirus expressing murine CRBN$^{I391I}$ and GFP. 72 hours after infection cells were sorted, mixed with SJL cells and treated with DMSO or lenalidomide. FIG. 23B is a graph showing the effects of 1 µM and 10 µM lenalidomide on CSNK1A1$^{+/-}$MxCre$^+$ or MxCre$^+$ cells as analyzed by flow cytometry. FIG. 23C shows the quantitative RT-PCR analysis of p21 expression in CSNK1A1$^{+/-}$MxCre$^+$ or MxCre$^+$ cells treated with DMSO or lenalidomide. FIG. 23D is a graph showing the effects of lenalidomide in p53$^{+/-}$ and p53$^{+/+}$ cells.

FIGS. 24A, 24B, 24C-1, 24C-2, 24C-3 and 24D show lenalidomide-induced changes in ubiquitination and protein levels. FIG. 24A shows the log$_2$ ratios for individual K-ε-GG sites of lenalidomide- (10 µM) versus DMSO treated cells for replicates 1 and 2. Each dot represents a unique K-ε-GG site. FIG. 24B shows the log$_2$ ratios of changes of protein abundance of lenalidomide- (10 µM) versus DMSO treated cells for replicates 1 and 2. Each dot represents a unique protein group. FIG. 24C-1 is a graph showing log$_2$ ratios for different lysine residues in CK1α. FIG. 24C-2 is a graph showing log$_2$ ratios for different lysine residues in IKZF1. FIG. 24C-3 is a graph showing log$_2$ ratios for different lysine residues in CRBN for 1 or 10 µM lenalidomide treated cells versus DMSO treated cells. FIG. 24D shows a list of significantly regulated K-ε-GG sites with 1 µM or 10 µM lenalidomide vs. DMSO. P-value is adjusted as described in the methods section.

FIGS. 25A-25C show the effect of lenalidomide in human cells. FIG. 25A shows a time course of effect of lenalidomide treatment on CK1α protein levels in KG-1 cells. FIG. 25B shows the half-life of CK1α was assessed in 293T cells treated with 100 µg/ml cycloheximide in the absence or presence of 1 µM lenalidomide. FIG. 25C shows an immunoblot confirming the loss of CRBN expression in 293T cells with the CRBN gene disrupted by CRISPR/Cas genome editing.

FIGS. 26A, 26B, 26C and 26D-1, 26D-2 show sensitivity of human cells to growth inhibition by lenalidomide. FIG. 26A shows 293T cells treated with different concentrations of lenalidomide for 24 hours. CK1α protein levels were detected by western blot. FIG. 26B shows CSNK1A1 mRNA expression levels as measured by RQ-PCR. FIG. 26C shows CK1α protein levels as detected hourly by western blot in cells treated with 1 µM lenalidomide. FIG. 26D-1 is a graph showing CSNK1A1 mRNA expression levels measured by RQ-PCR from MM1S cells treated with different concentrations of lenalidomide for 24 hours. FIG. 26D-2 shows a western blot to detect CK1α protein levels in MOLM13 cells treated with different concentrations of lenalidomide for 24 hours.

FIGS. 27A-27C show the effects of lenalidomide on mouse cells. FIG. 27A shows CK1α protein levels in Ba/F3 cells transduced with empty vector, mouse CRBN or human CRBN and treated with lenalidomide. FIG. 27B shows dual luciferase IKZF3 degradation assay in 293T cells expressing different CRBN chimeras and mutants. FIG. 27C shows the amino acid sequence alignment of mouse and human CRBN_(SEQ ID NOs: 7 and 10, respectively, in order of appearance).

FIG. 31A is an immunoblot showing lenalidomide-induced casein kinase 1α (CK1α) degradation in cKit$^+$ cells derived from wild type (WT), CRBN$^{I391V/+}$, CRBN$^{I391V/I391V}$ mice. Cells were treated with lenalidomide at 0, 1, and 10 µM. The protein level of the casein kinase 1α and actin was detected by immunoblot (IB). FIG. 31B is an immunoblot showing lenalidomide-induced IKZF1 protein and casein kinase 1 1α (CK1α) degradation in CRBN$^{I391V/I391V}$ mice. CRBN$^{I391V/I391V}$ mice were treated with lenalidomide (Len) (10 or 100 mg/kg) or thalidomide (Thal) (250 mg/kg) by oral gavage or intraperitoneal injection. T cells were isolated from these mice 14 hours after treatment and subjected to Western Blotting for IKZF1 and Ck1α.

Each expanded clone was denoted by the clone number (e.g. 144) followed by a "x". "100 bp" refers to the reference 100 bp DNA ladder. No DNA (--) and DNA from wild-type (wt) cells were used as controls. DNA from an individual clone (before reconfirmation) was used as a positive control (+).

Figure 38:
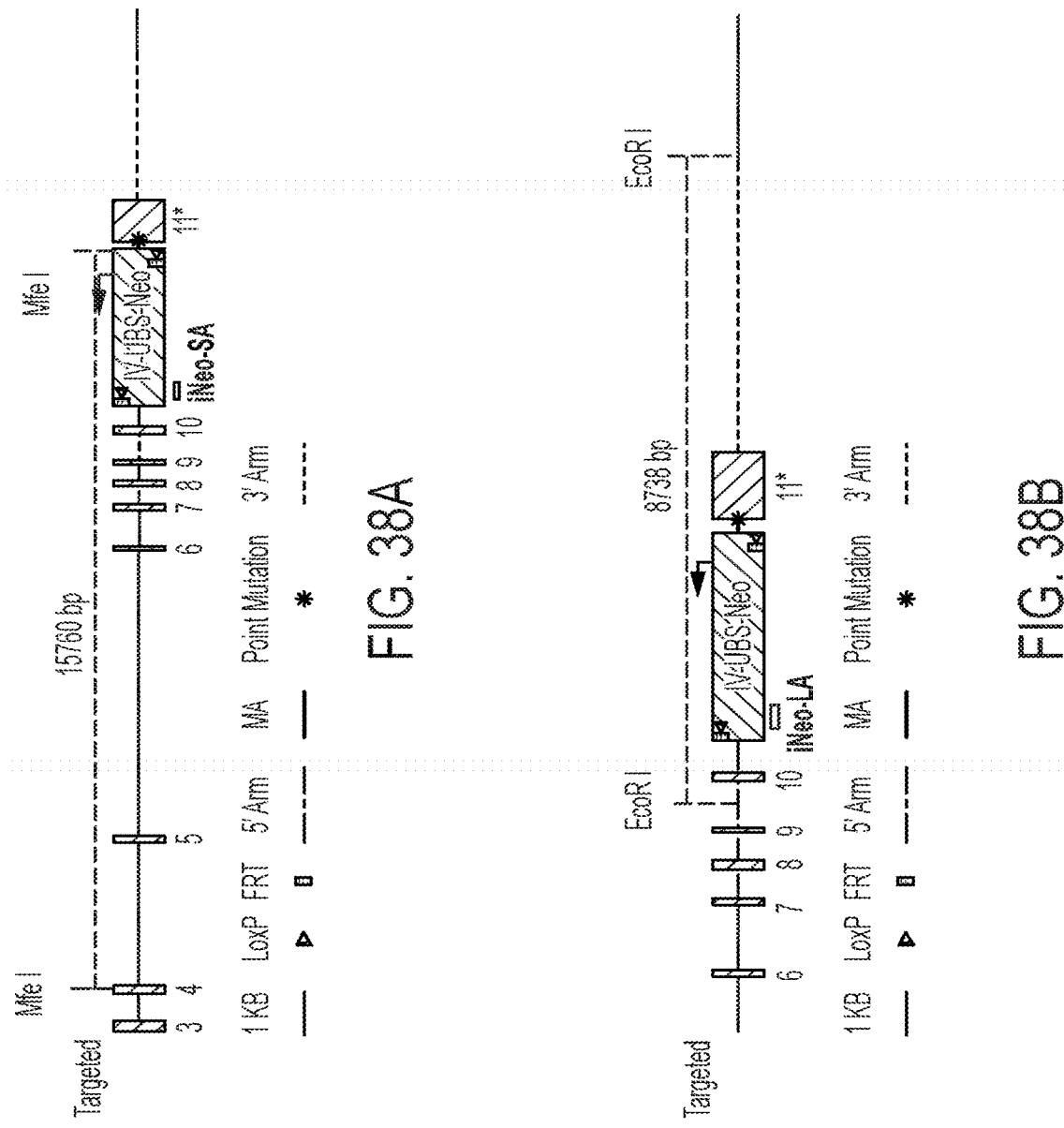

FIGS. 38A-38B are schematic diagram for Southern Blot strategy to confirmation the integration of the targeting vector. FIG. 38A shows the expected DNA fragment size from cells carrying the I391V mutation and the Neo cassette after MfeI restriction digestion. FIG. 38B shows the expected DNA fragment size from cells carrying the I391V mutation and the Neo cassette after EcoRI restriction digestion.

Figure 39:
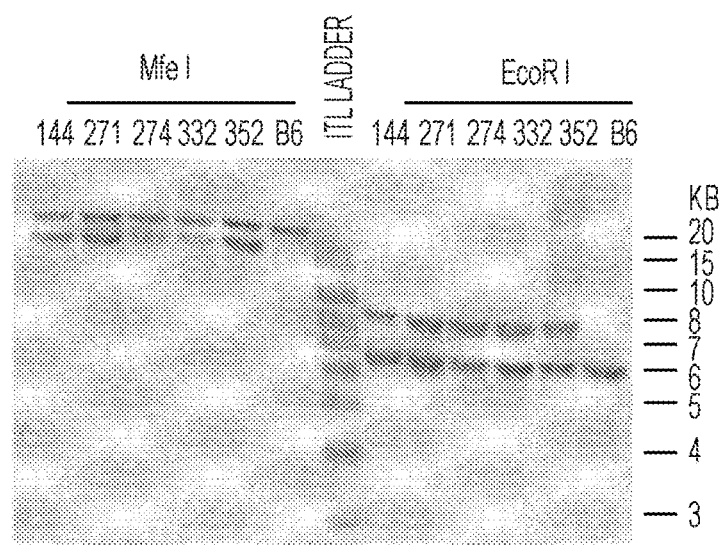

FIG. 39 shows the result of a Southern Blot on DNA from cells of an expanded clone. Each expanded clone was denoted by the clone number (e.g. 144). DNA from the expanded clones and wild type C57BL/6(B6) were digested with MfeI and EcoRI and separated on a 0.8% agarose gel. An ITL ladder is a reference DNA ladder used to show the size of DNA band on the agarose gel.

Figure 40A:
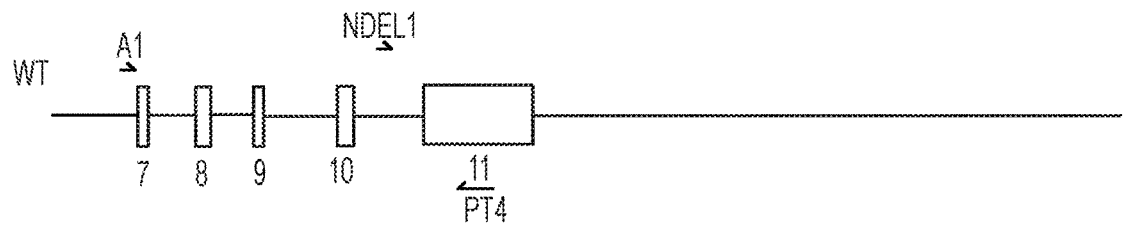
Figure 40B:
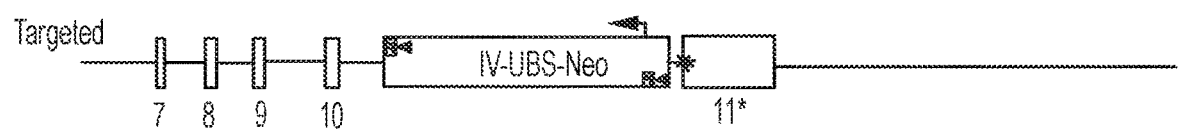
Figure 40C:
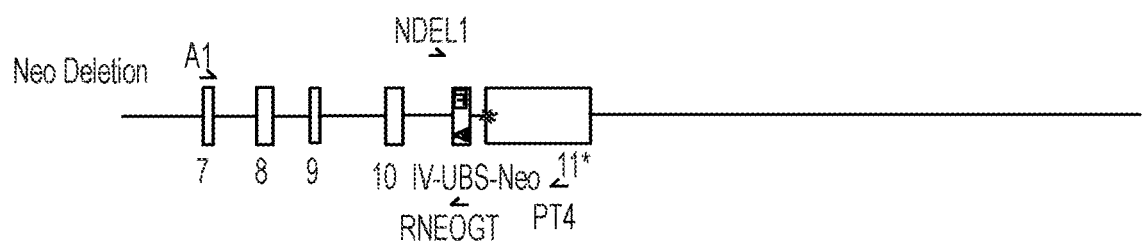

FIGS. 40A-40C are schematic diagrams showing the primers (A1, NDEL1, PT4, and RNEOGT) used to identify a knock-in mouse with the Neo cassette removed.

Figure 41:
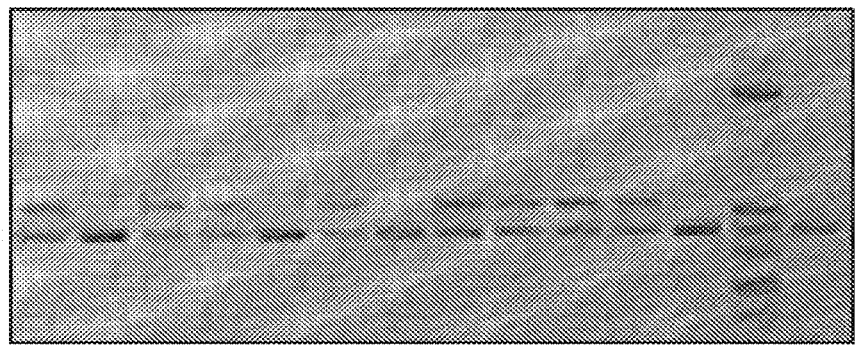

FIG. 41 shows the result of PCR screening of knock-in mice. Each mouse was denoted by a number (e.g. 582). Wild type mouse (WT) DNA was used as negative control (−). "100 BP" refers to the reference 100 bp DNA ladder.

Figure 42:
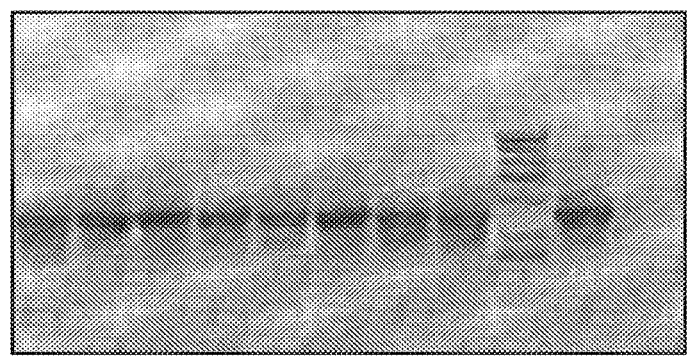

FIG. 42 shows the results of PCR used to confirm the integration of the short homology arm. Each mouse was denoted by a number (e.g. 582). Wild type mouse (WT) DNA was used as negative control (−). "1 KB" refers to the reference 1 kb DNA ladder.

Figure 43:
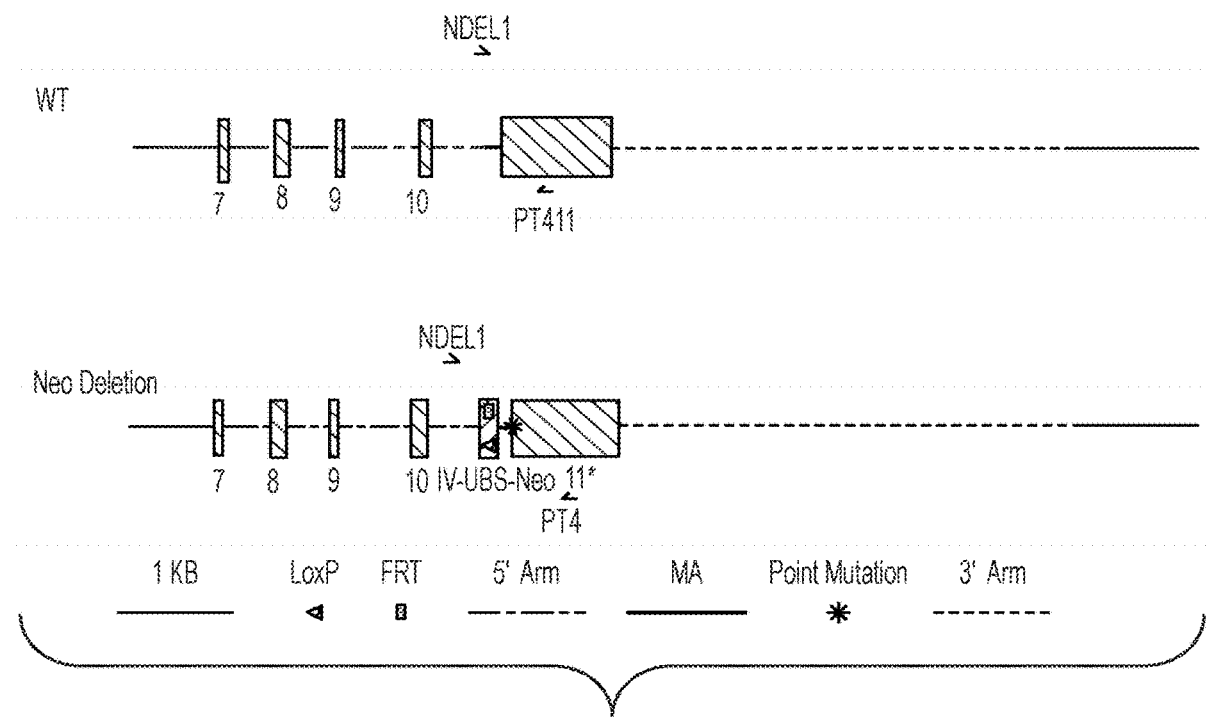

FIG. 43 is a schematic diagram showing the position of primers (NDEL1 and PT4) used for PCR screening of germline Neo deleted mice.

Figure 44:
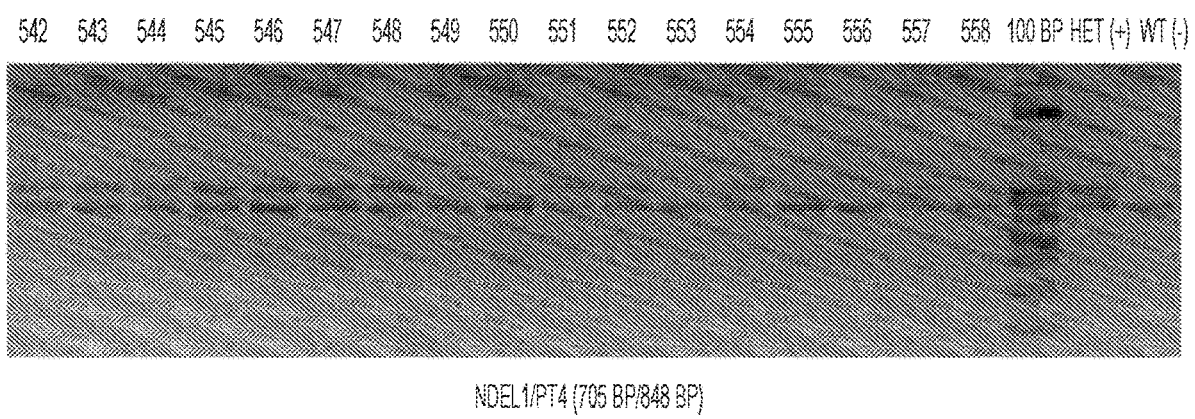

FIG. 44 shows the results of PCR screening for Neo Deletion. Each mouse was denoted by a number (e.g. 542). Wild type mouse (WT) DNA was used as negative control (−). DNA from a mouse that is heterozygous for Neo deletion (HET) was used a positive control (+).

Figure 45:
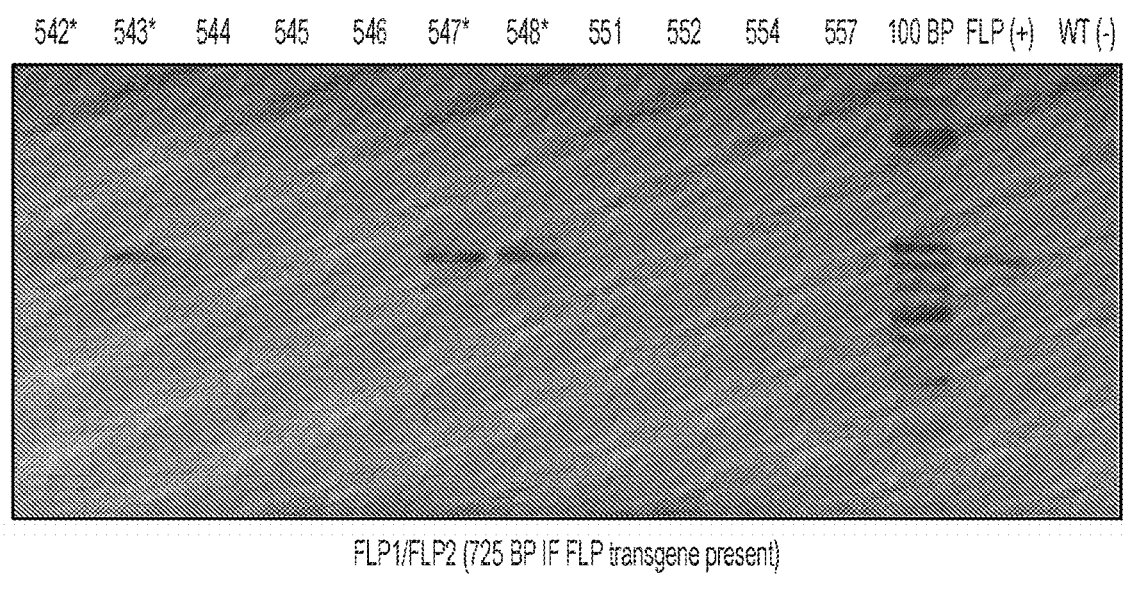

FIG. 45 shows the results of PCR screening for the absence of the FLP gene (encoding flippase enzyme). Each mouse was denoted by a number (e.g. 542). Asterisk (*) symbol indicates the presence of FLP gene. DNA from wild type (WT) mouse was used as negative control (−). FLP was used as positive control (+).

Figure 46A:
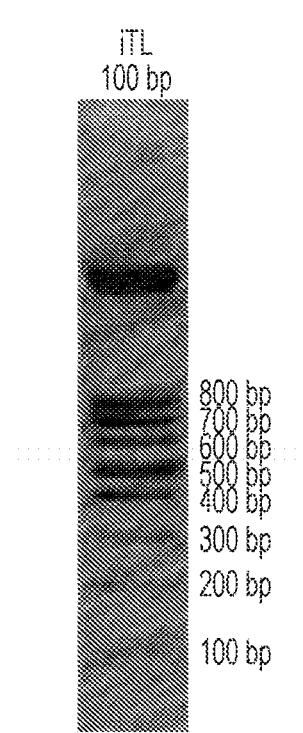
Figure 46B:
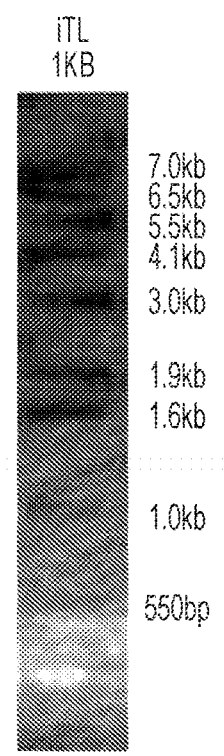

FIGS. 46A and 46B show the reference DNA ladders used to estimate the size of DNA fragment. FIG. 46A shows a 100 bp reference DNA ladder. FIG. 46B shows a 1kb reference DNA ladder.

DETAILED DESCRIPTION OF THE INVENTION

As described below, the present invention features a knock-in mouse responsive to treatment with lenalidomide and lenalidomide related compounds and methods of using the knock-in mouse.

The invention is based, at least in part, on the discovery that lenalidomide causes selective ubiquitination and degradation of two lymphoid transcription factors, IKZF1 and IKZF3, by the CRBN-CRL4 ubiquitin ligase. IKZF1 and IKZF3 are essential transcription factors for terminal B cell differentiation. A single amino acid substitution of IKZF3 conferred resistance to lenalidomide-induced degradation and rescued lenalidomide-induced inhibition of cell growth. Similarly, it was found that lenalidomide-induced IL2 production in T cells is due to depletion of IKZF3. These findings reveal a novel mechanism of action for a therapeutic agent, alteration of the activity of an E3 ubiquitin ligase leading to selective degradation of specific targets.

In other aspects, the invention features the discovery that casein kinase 1A1 (CSNK1A1) is a target of lenalidomide in del(5q) myelodysplastic syndrome (MDS). Myelodysplastic syndrome (MDS) is a heterogeneous clonal haematopoietic stem cell disorder characterised by ineffective haematopoiesis and a high risk of progression to acute myeloid leukemia (AML). Lenalidomide is often used for the treatment of patients with MDS with 5q deletion cytogenetic abnormalities. However, analysis of lenalidomide activity has been hampered by the relative insensitivity of murine cells to lenalidomide and related compounds. Expression of human CRBN in murine cells was sufficient to confer lenalidomide sensitivity to CSNK1A1. Accordingly, the present invention provides murine cells and transgenic animals expressing human CRBN or mutant CRBN.

Selection of Therapies for the Treatment of B Cell Neoplasia

As reported in detail below, lenalidomide causes the selective ubiquitination and degradation of lymphoid transcription factors, IKZF1 and IKZF3. IKZF1 and IKZF3 are expressed by B cell neoplasias that are sensitive to treatment with lenalidomide or a related compound, such as thalidomide or palidomide.

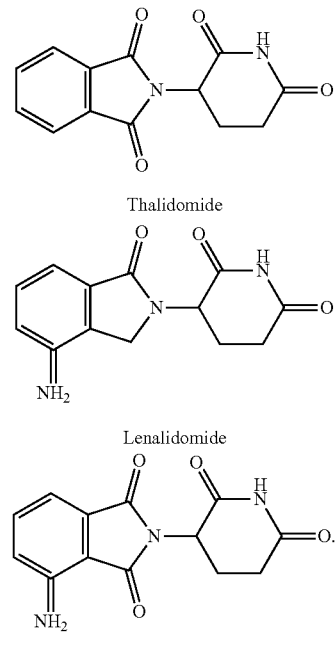

Thalidomide

Lenalidomide

Pomalidomide

Lenalidomide, pomalidomide, and thalidomide have been shown to have immunomodulatory activity in multiple myeloma. Thus, these compounds are termed IMiDs.

The invention provides methods for selecting IMiD therapy for a subject having a B cell neoplasia by detecting an increased level of biomarkers IKZF1 and/or IKZF3 in a biological sample of the subject relative to the level present in a reference. Methods for detecting IKZF1 and IKZF3 are known in the art and described herein at Example 2.

The CRBN-CRL4 ubiquitin ligase selectively ubiquinates IKZF1 and IKZF3, thereby targeting IKZF1 and IKZF3 for lenalidomide-induced degradation. In one embodiment, the invention provides methods for selecting a therapy for a subject having a B cell neoplasia by detecting the lenalidomide-induced ubiquitination of IKZF1 and/or IKZF3 polypeptides in a biological sample from the subject. In other embodiments, the method involves detecting a decrease in ubiquitination of lysine residues of IKZF1 and IKZF3 prior to addition of a proteasome inhibitor (e.g., MG132). Methods for detecting ubiquination are known in the art and described, for example, herein at Example 1.

In other embodiments, the invention provides methods for selecting lenalidomide as a therapy for a subject having a B cell neoplasia. The method involves detecting a reduction in the level of IKZF1 and/or IKZF3 polypeptides in response to lenalidomide in a biological sample obtained from a subject.

Over time, many patients treated with lenalidomide acquire resistance to the therapeutic effects of lenalidomide. The early identification of lenalidomide resistance is important to patient survival because it allows for the selection of alternate therapies. As reported herein below, the anti-proliferative effect of lenalidomide in B cell neoplasias is mediated by depletion of IKZF1 and IKZF3. Accordingly, the invention provides methods for identifying the presence of lenalidomide resistant B cells by detecting IKZF1 and/or IKZF3 polypeptides that are resistant to lenalidomide-induced degradation. In one embodiment, a lenalidomide resistant B cell neoplasia is identified by detection of mutant IKZF1 or IKZF3 proteins that are not degraded in response to lenalidomide treatment or that are not ubiquitinated in response to lenalidomide treatment.

Subjects identified as having a lenalidomide resistant B cell neoplasia are identified as in need of alternative treatment. Subjects identified as having a lenalidomide resistant myeloma, for example, are treated with [(1R)-3-methyl-1-[[(2S)-3-phenyl-2-(pyrazine-2-carbonylamino)propanoyl]amino]butyl]boronic acid (VELCADE® or bortezomib), corticosteroids, or other anti-neoplastic therapy. For subjects identified as having lenalidomide resistant myelodysplastic syndrome are treated, for example, with azacitidine or decitabine.

Ubiquitination of IKZF1 and IKZF3 in response to lenalidomide requires binding to CRBN. Mutations that reduce or inhibit IKZF1 and IKZF3 binding to CRBN also render the B cell neoplasia resistant to lenalidomide. Accordingly, the invention provides methods for detecting a reduction in IKZF1 and/or IKZF3 binding to CRBN. Methods for detecting CRBN binding to IKZF1 and/or IKZF3 are known in the art and described, for example, at Examples 2 and 3. B cell neoplasias having a reduction in IKZF1 and/or IKZF3 binding to CRBN are identified as resistant to lenalidomide.

In still other embodiments, a lenalidomide resistant B cell neoplasia is identified by detecting a mutation in an IKZF3 degron sequence, such as a mutation in any one or more of amino acids 141-180 or 160-180. In particular embodiments, the invention provides for the detection of a mutation at amino acid 147, 150, 161, or 162. In still other embodiments, the invention provides for the detection of is Q147H, Q150H, L161R, or L162R. Methods for detecting a mutation of the invention include immunoassay, direct sequencing, and probe hybridization to a polynucleotide encoding the mutant polypeptide.

Monitoring

Methods of monitoring the sensitivity of a B cell neoplasia to lenalidomide in a subject are useful in managing subject treatment. Provided are methods where alterations in a IKZF1 and/or IKZF3 polypeptide (e.g., sequence, level, post-transcriptional modification, biological activity) are analyzed, such as before and again after subject management or treatment. In these cases, the methods are used to monitor the status of lenalidomide sensitivity (e.g., response to lenalidomide treatment, resistance to lenalidomide, amelioration of the disease or progression of the disease).

For example, IKZF1 and/or IKZF3 polypeptide biomarkers can be used to monitor a subject's response to certain treatments of B cell neoplasia. The level, biological activity, sequence, post-transcriptional modification, or sensitivity to lenalidomide induced degradation of a IKZF1 and/or IKZF3 polypeptide may be assayed before treatment, during treatment, or following the conclusion of a treatment regimen. In some embodiments, multiple assays (e.g., 2, 3, 4, 5) are made at one or more of those times to assay resistance to lenalidomide.

Diagnostic Methods

Alterations in IKZF1 and/or IKZF3 polypeptides (e.g., sequence, level, post-transcriptional modification, biological activity) are detected in a biological sample obtained from a patient that has or has a propensity to develop a B cell neoplasia. Such biological samples include, but are not limited to, peripheral blood, bone marrow, or lymphoid tissue obtained from the subject relative to the level of such biomarkers in a reference.

Alterations in the levels of IKZF1 and/or IKZF3 polypeptide biomarkers (or any other marker delineated herein) are detected using standard methods. In one embodiment, the level of IKZF1 or IKZF3 is detected using an antibody that specifically binds the polypeptide. Exemplary antibodies that specifically bind such polypeptides are known in the art and described herein. Such antibodies are useful for the diagnosis of a B cell neoplasia that is sensitive to treatment with lenalidomide. Methods for measuring an antibody-biomarker complex include, for example, detection of fluorescence, luminescence, chemiluminescence, absorbance, reflectance, transmittance, birefringence or refractive index. Optical methods include microscopy (both confocal and non-confocal), imaging methods and non-imaging methods. Methods for performing these assays are readily known in the art. Useful assays include, for example, an enzyme immune assay (EIA), such as enzyme-linked immunosorbent assay (ELISA), a radioimmune assay (RIA), a Western blot assay, or a slot blot assay. Other assays useful for detecting changes in IKZF1 or IKZF3 are immunohistochemistry and quantitative fluorescent microscopy. These methods are also described in, e.g., Methods in Cell Biology: Antibodies in Cell Biology, volume 37 (Asai, ed. 1993); Basic and Clinical Immunology (Stites & Ten, eds., 7th ed. 1991); and Harlow & Lane, supra. Immunoassays can be used to determine the quantity of marker in a sample, where an increase or decrease in the level of the biomarker polypeptide is diagnostic of a patient having a B cell neoplasia that is sensitive or resistant to treatment with lenalidomide.

In general, the measurement of a IKZF1 and/or IKZF3 polypeptide in a subject sample is compared with an amount present in a reference. A diagnostic amount distinguishes between a B cell neoplasia that is sensitive to treatment with lenalidomide and a B cell neoplasia that is resistant to treatment with lenalidomide. The skilled artisan appreciates that the particular diagnostic amount used can be adjusted to increase sensitivity or specificity of the diagnostic assay depending on the preference of the diagnostician. In general, any significant alteration (e.g., at least about 10%, 15%, 30%, 50%, 60%, 75%, 80%, or 90%) in the level of a biomarker polypeptide in the subject sample relative to a reference may be used to diagnose a B cell neoplasia that is sensitive or resistant to treatment with lenalidomide. In one embodiment, the reference is the level of biomarker polypeptide present in a corresponding control sample obtained from a patient that does not have a B cell neoplasia. In another embodiment, the reference is a baseline level of IKZF1 and/or IKZF3 markers present in a biologic sample derived from a patient prior to, during, or after treatment with lenalidomide. In yet another embodiment, the reference is a standardized curve. In another example, levels of IKZF1 or IKZF3 are measured relative to the level of other B cell markers or actin.

Clinical Indicators

The present invention provides methods for detecting alterations in an IKZF1 and/or IKZF3 polypeptide biomarker in a biological sample (e.g., peripheral blood, bone marrow) derived from a subject having a B cell neoplasia to determine whether the B cell neoplasia is sensitive to treatment with lenalidomide or whether it has acquired lenalidomide resistance. Alterations in IKZF1 and/or IKZF3 are useful individually, or in combination with other markers typically used in characterizing a B cell neoplasia.

B-cell neoplasms typically recapitulate the normal stages of B-cell differentiation, and can be classified according to their putative cell of origin. Accordingly, alterations in IKZF1 and IKZF3 may be assayed alone or in combination with the neoplasm's cytogenetic profile, genotype, and immunophenotype. B cell markers useful in the methods of the invention include, but are not limited to, characterization of CD5, CD10, CD19, CD20, CD22, CD23, FMC7, CD79a, CD40, CD38, and CD138.

Microarrays

The methods of the invention may also be used for microarray-based assays that provide for the high-throughput analysis of an IKZF1 and/or IKZF3 polypeptide or polynucleotide. The IKZF1 and/or IKZF3 polypeptides, polynucleotides, or capture molecules that specifically bind to IKZF1 and/or IKZF3 polypeptides of the invention are useful as hybridizable array elements. If desired, arrays of the invention include, for example, other markers useful in the differential diagnosis of a B cell neoplasia (e.g., CD5, CD10, CD19, CD20, CD22, CD23, FMC7, CD79a, CD40, and CD38). The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28:e3.i-e3.vii, 2000), MacBeath et al., (Science 289:1760-1763, 2000), Zhu et al. (Nature Genet. 26:283-289), and in U.S. Pat. No. 6,436,665, hereby incorporated by reference.

IKZF1 and/or IKZF3 polypeptide may also be analyzed using protein microarrays. Typically, protein microarrays feature a protein, or fragment thereof, bound to a solid support. In particular embodiments, the proteins are antibodies that specifically bind a biomarker of the invention (e.g., IKZF1 and/or IKZF3 polypeptide). Suitable solid supports include membranes (e.g., membranes composed of nitrocellulose, paper, or other material), polymer-based films (e.g., polystyrene), beads, or glass slides. For some applications, biomarker polypeptides or antibodies recognizing such biomarkers are spotted on a substrate using any convenient method known to the skilled artisan (e.g., by hand or by inkjet printer).

Biomarker levels present in a biological sample taken from a patient, such as a bodily fluid (e.g. Peripheral blood) may be measured using an antibody or other molecule derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Kits

In one aspect, the invention provides kits for monitoring lenalidomide sensitivity, including the development of lenalidomide resistance. For example, the kits can be used to detect an alteration in an IKZF1 and/or IKZF3 polypeptide (e.g., sequence, level, post-transcriptional modification, biological activity). If desired a kit includes any one or more of the following: capture molecules that bind IKZF1 and/or IKZF3. The kits have many applications. For example, the kits can be used to determine if a subject has a lenalidomide sensitive B cell neoplasia or if the subject has developed resistance to lenalidomide.

The kits may include instructions for the assay, reagents, testing equipment (test tubes, reaction vessels, needles, syringes, etc.), standards for calibrating the assay, and/or equipment provided or used to conduct the assay. The instructions provided in a kit according to the invention may be directed to suitable operational parameters in the form of a label or a separate insert.

Inhibitory Nucleic Acids

As reported herein below, the anti-proliferative effect of lenalidomide in B cell neoplasias is mediated by depletion of IKZF1 and/or IKZF3. Accordingly, the invention provides oligonucleotides that inhibit the expression of IKZF1 and/or IKZF3. Such inhibitory nucleic acid molecules include single and double stranded nucleic acid molecules (e.g., DNA, RNA, and analogs thereof) that bind a nucleic acid molecule that encodes an IKZF1 and/or IKZF3 polypeptide (e.g., antisense molecules, siRNA, shRNA).

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an siRNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of a gene can be used to design small interfering RNAs (siRNAs). The 21 to 25 nucleotide siRNAs may be used, for example, as therapeutics to treat a B cell neoplasia.

The inhibitory nucleic acid molecules of the present invention may be employed as double-stranded RNAs for RNA interference (RNAi)-mediated knock-down of IKZF1 and/or IKZF3 expression. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418:244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the invention, a double-stranded RNA (dsRNA) molecule is made that includes between eight and nineteen consecutive nucleobases of a nucleobase oligomer of the invention. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Genes & Devel. 16:948-958, 2002. Paul et al. Nature Biotechnol. 20:505-508, 2002; Sui et al. Proc. Natl. Acad. Sci. USA 99:5515-5520, 2002; Yu et al. Proc. Natl. Acad. Sci. USA 99:6047-6052, 2002; Miyagishi et al. Nature Biotechnol. 20:497-500, 2002; and Lee et al. Nature Biotechnol. 20:500-505 2002, each of which is hereby incorporated by reference.

Small hairpin RNAs (shRNAs) comprise an RNA sequence having a stem-loop structure. A "stem-loop structure" refers to a nucleic acid having a secondary structure that includes a region of nucleotides which are known or predicted to form a double strand or duplex (stem portion) that is linked on one side by a region of predominantly single-stranded nucleotides (loop portion). The term "hairpin" is also used herein to refer to stem-loop structures. Such structures are well known in the art and the term is used consistently with its known meaning in the art. As is known in the art, the secondary structure does not require exact base-pairing. Thus, the stem can include one or more base mismatches or bulges. Alternatively, the base-pairing can be exact, i.e. not include any mismatches. The multiple stem-loop structures can be linked to one another through a linker, such as, for example, a nucleic acid linker, a miRNA flanking sequence, other molecule, or some combination thereof.

As used herein, the term "small hairpin RNA" includes a conventional stem-loop shRNA, which forms a precursor miRNA (pre-miRNA). While there may be some variation in range, a conventional stem-loop shRNA can comprise a stem ranging from 19 to 29 bp, and a loop ranging from 4 to 30 bp. "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. In some instances, the precursor miRNA molecule can include more than one stem-loop structure. MicroRNAs are endogenously encoded RNA molecules that are about 22-nucleotides long and generally expressed in a highly tissue- or developmental-stage-specific fashion and that post-transcriptionally regulate target genes. More than 200 distinct miRNAs have been identified in plants and animals. These small regulatory RNAs are believed to serve important biological functions by two prevailing modes of action: (1) by repressing the translation of target mRNAs, and (2) through RNA interference (RNAi), that is, cleavage and degradation of mRNAs. In the latter case, miRNAs function analogously to small interfering RNAs (siRNAs). Thus, one can design and express artificial miRNAs based on the features of existing miRNA genes.

shRNAs can be expressed from DNA vectors to provide sustained silencing and high yield delivery into almost any cell type. In some embodiments, the vector is a viral vector. Exemplary viral vectors include retroviral, including lentiviral, adenoviral, baculoviral and avian viral vectors, and including such vectors allowing for stable, single-copy genomic integrations. Retroviruses from which the retroviral plasmid vectors can be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus. A retroviral plasmid vector can be employed to transduce packaging cell lines to form producer cell lines. Examples of packaging cells which can be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, Human Gene Therapy 1:5-14 (1990), which is incorporated herein by reference in its entirety. The vector can transduce the packaging cells through any means known in the art. A producer cell line generates infectious retroviral vector particles which include polynucleotide encoding a DNA replication protein. Such retroviral vector particles then can be employed, to transduce eukaryotic cells, either in vitro or in vivo. The transduced eukaryotic cells will express a DNA replication protein.

Catalytic RNA molecules or ribozymes that include an antisense sequence of the present invention can be used to inhibit expression of a IKZF1 and/or IKZF3 nucleic acid molecule in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Essentially any method for introducing a nucleic acid construct into cells can be employed. Physical methods of introducing nucleic acids include injection of a solution containing the construct, bombardment by particles covered by the construct, soaking a cell, tissue sample or organism in a solution of the nucleic acid, or electroporation of cell membranes in the presence of the construct. A viral construct packaged into a viral particle can be used to accomplish both efficient introduction of an expression construct into the cell and transcription of the encoded shRNA. Other methods known in the art for introducing nucleic acids to cells can be used, such as lipid-mediated carrier transport, chemical mediated transport, such as calcium phosphate, and the like. Thus, the shRNA-encoding nucleic acid construct can be introduced along with components that perform one or more of the following activities: enhance RNA uptake by the cell, promote annealing of the duplex strands, stabilize the annealed strands, or otherwise increase inhibition of the target gene.

For expression within cells, DNA vectors, for example plasmid vectors comprising either an RNA polymerase II or RNA polymerase III promoter can be employed. Expression of endogenous miRNAs is controlled by RNA polymerase II (Pol II) promoters and in some cases, shRNAs are most efficiently driven by Pol II promoters, as compared to RNA polymerase III promoters (Dickins et al., 2005, Nat. Genet. 39: 914-921). In some embodiments, expression of the shRNA can be controlled by an inducible promoter or a conditional expression system, including, without limitation, RNA polymerase type II promoters. Examples of useful promoters in the context of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types. A certain embodiment uses tetracycline-responsive promoters, one of the most effective conditional gene expression systems in in vitro and in vivo studies. See International Patent Application PCT/US2003/030901 (Publication No. WO 2004-029219 A2) and Fewell et al., 2006, Drug Discovery Today 11: 975-982, for a description of inducible shRNA.

Delivery of Polynucleotides

Naked polynucleotides, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120,798, 6,221,959, 6,346,613, and 6,353,055, each of which is hereby incorporated by reference).

Therapy

Therapy may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the kind of cancer being treated, the age and condition of the patient, the stage and type of the patient's disease, and how the patient's body responds to the treatment. Drug administration may be performed at different intervals (e.g., daily, weekly, or monthly).

Oligonucleotides and Other Nucleobase Oligomers

At least two types of oligonucleotides induce the cleavage of RNA by RNase H: polydeoxynucleotides with phosphodiester (PO) or phosphorothioate (PS) linkages. Although 2′-OMe-RNA sequences exhibit a high affinity for RNA targets, these sequences are not substrates for RNase H. A desirable oligonucleotide is one based on 2′-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed, including covalently-closed multiple antisense (CMAS) oligonucleotides (Moon et al., Biochem J. 346:295-303, 2000; PCT Publication No. WO 00/61595), ribbon-type antisense (RiAS) oligonucleotides (Moon et al., J. Biol. Chem. 275: 4647-4653, 2000; PCT Publication No. WO 00/61595), and large circular antisense oligonucleotides (U.S. Patent Application Publication No. US 2002/0168631 A1).

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2′, 3′ or 5′ hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3′ to 5′ phosphodiester linkage.

Specific examples of preferred nucleobase oligomers useful in this invention include oligonucleotides containing modified backbones or non-natural internucleoside linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3′-alkylene phosphonates and chiral phosphonates, phosphinates, phosphoramidates including 3′-amino phosphoramidate and aminoalkylphosphoramidates, thionophosphoramidates, thionoalkylphosphonates, thionoalkylphosphotriest-ers, and boranophosphates having normal 3′-5′ linkages, 2′-5′ linked analogs of these, and those having inverted polarity, wherein the adjacent pairs of nucleoside units are linked 3′-5′ to 5′-3′ or 2′-5′ to 5′-2′. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. The nucleobase units are maintained for hybridization with a gene listed in Table 2 or 3. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$NH$_2$, O($CH_2$)$_n$$CH_3$, O($CH_2$)$_n$ONH$_2$, and O($CH_2$)$_n$ON[($CH_2$)$_n$$CH_3$)]$_2$, where n and m are from 1 to about 10. Other preferred nucleobase oligomers include one of the following at the 2' position: C1 to C10 lower alkyl, substituted lower alkyl, alkaryl, aralkyl, O-alkaryl, or O-aralkyl, SH, SCH$_3$, OCN, Cl, Br, CN, CF$_3$, OCF$_3$, SOCH$_3$, SO$_2$CH$_3$, ONO$_2$, NO$_2$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O-methyl and 2'-methoxyethoxy (2'-O—$CH_2$$CH_2$O$CH_3$, also known as 2'-O-(2-methoxyethyl) or 2'-MOE). Another desirable modification is 2'-dimethylaminooxyethoxy (i.e., O($CH_2$)$_2$ON($CH_3$)$_2$), also known as 2'-DMAOE. Other modifications include, 2'-aminopropoxy (2'-O$CH_2$$CH_2$$CH_2$NH$_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-S-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241; 5,391,723; 5,414,077; 5,416,203; 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The nucleobase oligomers used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Casein Kinase 1A1

As reported in detail herein below, casein kinase 1A1 (CSNK1A1) was identified as a target of lenalidomide in del(5q) myelodysplastic syndrome (MDS). Methods for characterizing the biological activity of lenalidomide, thalidomide, and pomalidomide have been hampered because mice have been largely unresponsive to the activity of these compounds. Significantly, as reported herein below, expression of human CRBN in murine cells was sufficient to confer lenalidomide sensitivity to CSNK1A1. Moreover, mutation of murine CRBN to include at least one of I391V, or any other substitution, deletion or addition of the murine CRBN that confers lenalidomide sensitivity to CSNK1A1, IKZF1 and IKZF3 is also included. Accordingly, the present invention provides murine cells and transgenic animals expressing human CRBN or mutant CRBN.

In other embodiments, the invention provides for the use of casein kinase 1A1 inhibitors for the treatment of a B cell neoplasia or related condition. Casein kinase 1A1 and casein kinase 1 inhibitors are useful in the methods of the invention. In particular embodiments, casein kinase 1 inhibitors include, but are not limited to, Casein Kinase I Inhibitor, D4476 (CAS 301836-43-1), (Santa Cruz Biotechnology).

In yet other embodiments, the invention includes knockdown or inhibition of casein kinase 1A1 expression for the treatment of a B cell neoplasia or related condition. Knockdown or inhibition of expression of casein kinase 1A1 is useful in the methods of the invention to confer sensitivity to lenalidomide or a lenalidomide analog. In particular embodiments, casein kinase 1 expression is decreased by a method including, but are not limited to, antisense nucleic acid molecule, siRNA molecule, shRNA, CRISPR, CRISPRi (Cell 152 (5): 1173-83, 2013) and other known method for decreasing gene expression.

Generation of a Transgenic Mouse that is Responsive to Lenalidomide and Other IMiDs Generating transgenic mice involves five basic steps: purification of a transgenic construct, harvesting donor zygotes, microinjection of transgenic construct, implantation of microinjected zygotes into the pseudo-pregnant recipient mice, and genotyping and analysis of transgene expression in founder mice. Methods for the generation of transgenic mice are known in the art and described, for example, by Cho et al., Curr Protoc Cell Biol. 2009 March; CHAPTER: Unit-19.11, which is incorporated herein in its entirety.

An expression vector, such as an expression vector encoding human CRBN or an expression vector encoding a mutant CRBN (e.g., S369C, V380E, or I391V), is generated using standard methods known in the art. Construction of transgenes can be accomplished using any suitable genetic engineering technique, such as those described in Ausubel et al. (Current Protocols in Molecular Biology, John Wiley & Sons, New York, 2000). Many techniques of transgene construction and of expression constructs for transfection or transformation in general are known and may be used to generate the desired human CRBN-expressing construct.

One skilled in the art will appreciate that a promoter is chosen that directs expression of the CRBN gene in all tissues or in a preferred tissue. In particular embodiments, CRBN expression is driven by a phosphoglycerate kinase 1 promoter (PGK1), (Qin et al. (2010) PLoS ONE 5(5): e10611. doi:10.1371/journal.pone.0010611), the spleen focus-forming virus (SFFV) (Gonzalez-Murillo et al., Hum Gene Ther. 2010 May; 21(5):623-30, using knockin technology (Cohen-Tannoudji et al., Mol Hum Reprod 4:929-938, 1998; Rossant et al., Nat Med 1:592-594, 1995; tet-off promoter (Clontech), human EF1s, CMV or endogenous CRBN promoter. The modular nature of transcriptional regulatory elements and the absence of position-dependence of the function of some regulatory elements, such as enhancers, make modifications such as, for example, rearrangements, deletions of some elements or extraneous sequences, and insertion of heterologous elements possible. Numerous techniques are available for dissecting the regulatory elements of genes to determine their location and function. Such information can be used to direct modification of the elements, if desired. Preferably, an intact region that includes all of the transcriptional regulatory elements of a gene is used.

Following its construction, the transgene construct is amplified by transforming bacterial cells using standard techniques. Plasmid DNA is then purified and treated to remove endogenous bacterial sequences. A fragment suitable for expression of a transgenic CRBN under the control of a suitable promoter, such as an endogenous murine CRBN promoter, and optionally additional regulatory elements is purified (e.g., by a sucrose gradient or a gel-purification method) in preparation for microinjection.

Foreign DNA is transferred into a mouse zygote by microinjection into the pronucleus. A fragment of the transgene DNA isolated above is microinjected into the male pronuclei of fertilized mouse eggs derived from, for example, a C57BL/6 or C3B6 F1 strain, using the techniques described in Gordon et al. (Proc. Natl. Acad. Sci. USA 77:7380, 1980). The eggs are transplanted into pseudopregnant female mice for full-term gestation, and resultant litters are analysed to identify transgenic mice.

In other embodiments, the knock-in of a mutant allele in the mouse genome can be achieved using homologous recombination (HR) in embryonic stem (ES) cells (Thomas and Capecchi 1987), similar to the methods used to generate conditional knockout mice. Specific mutations can be introduced into endogenous genes and transmitted throughout the mouse germline. A DNA construct containing the engineered gene of interest (e.g., a mutated oncogene) is flanked by sequences identical to those in the target locus and introduced into ES cells, where homologous sequences align and recombine, thereby introducing the altered gene into an endogenous locus. This technology allows for the expression of mutant genes from their endogenous promoter, or another promoter of interest, and avoids issues of variability and founder effects that are frequently observed with randomly integrated transgenes.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: DNA Damage Binding Protein 1 (DDB1) and Carbonyl Reductase 1 (CBR1) Bind to Lenolidomide Lenalidomide is a highly effective drug for the treatment of multiple myeloma (Rajkumar et al., *Blood* 106, 4050 (Dec. 15, 2005).) and del(5q) MDS (List et al., *N Engl J Med* 352, 549 (Feb. 10, 2005)), and its use in a range of other conditions is being actively explored, but the precise mechanism of action of lenalidomide has not been established. In addition, lenalidomide and its analogues thalidomide and pomalidomide have multiple additional biological effects, including stimulation of IL-2 production by T cells, and inhibition of TNF production by monocytes, but the molecular basis of these pleiotropic activities is unknown.

Figure 2A:
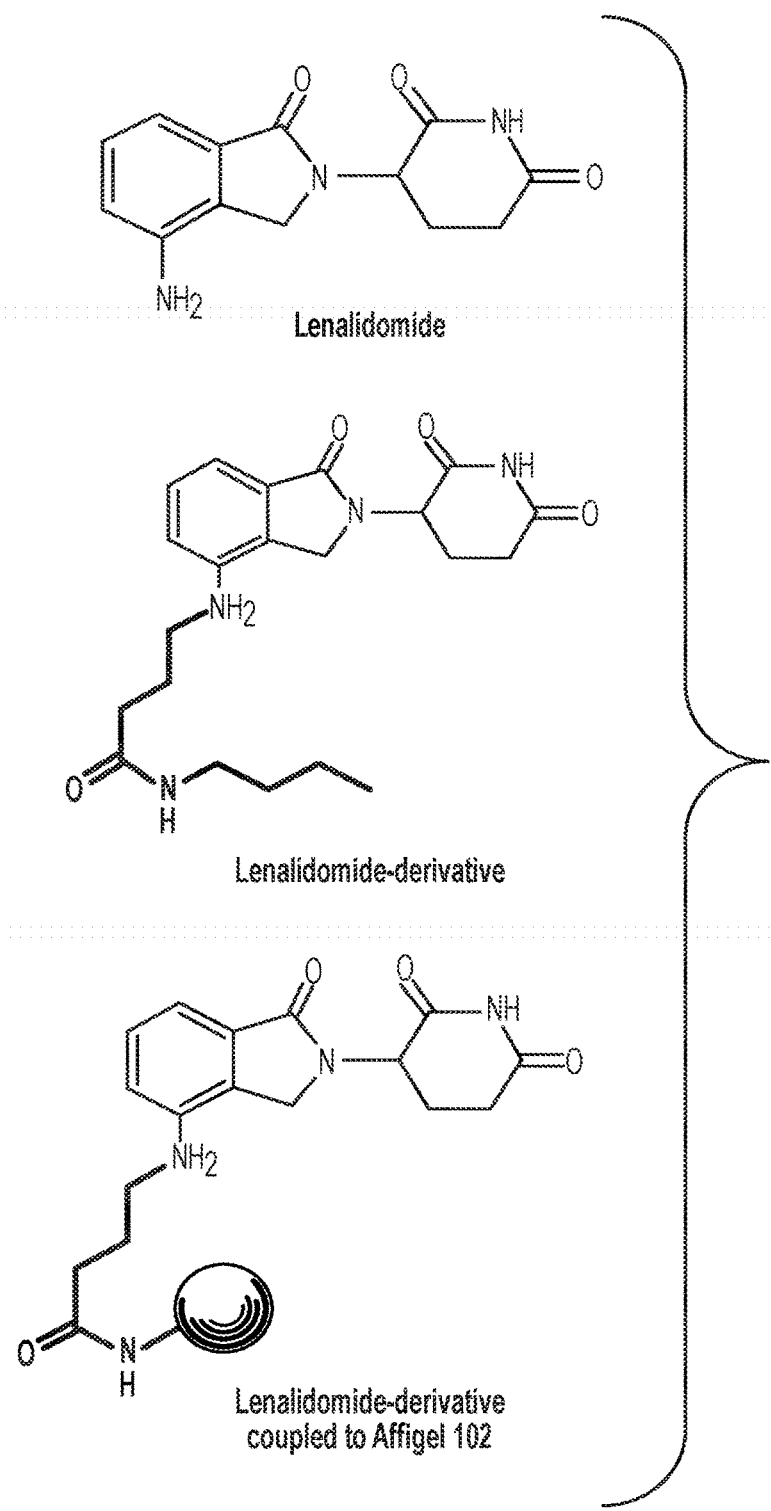
FIGS. 2A, 2B-1, 2B-2 and 2C are provided.
Figures 1, 2B:
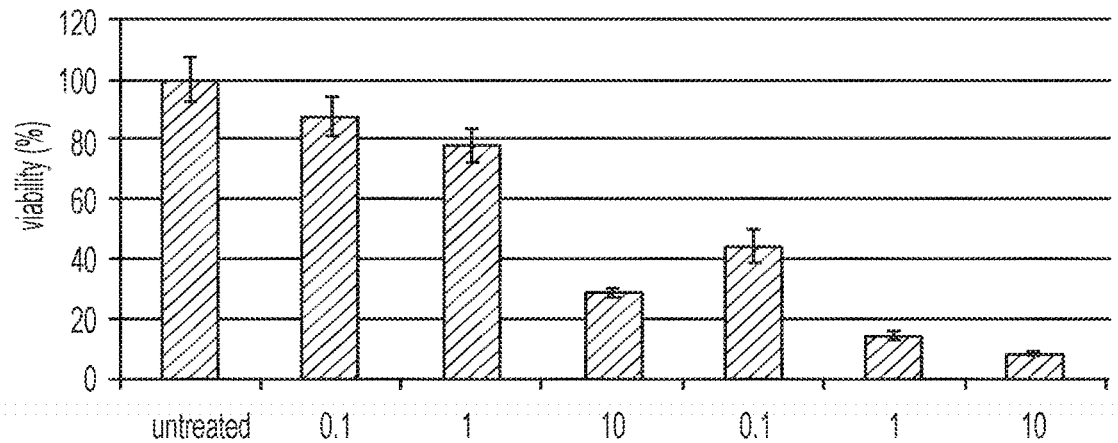
Figures 2, 2B:
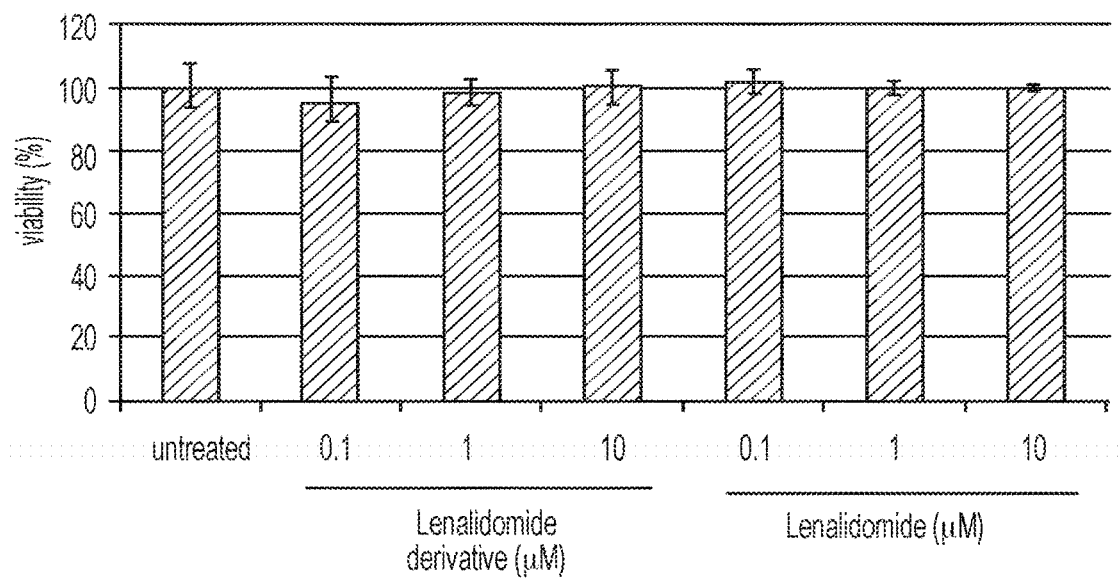
Figure 2C:
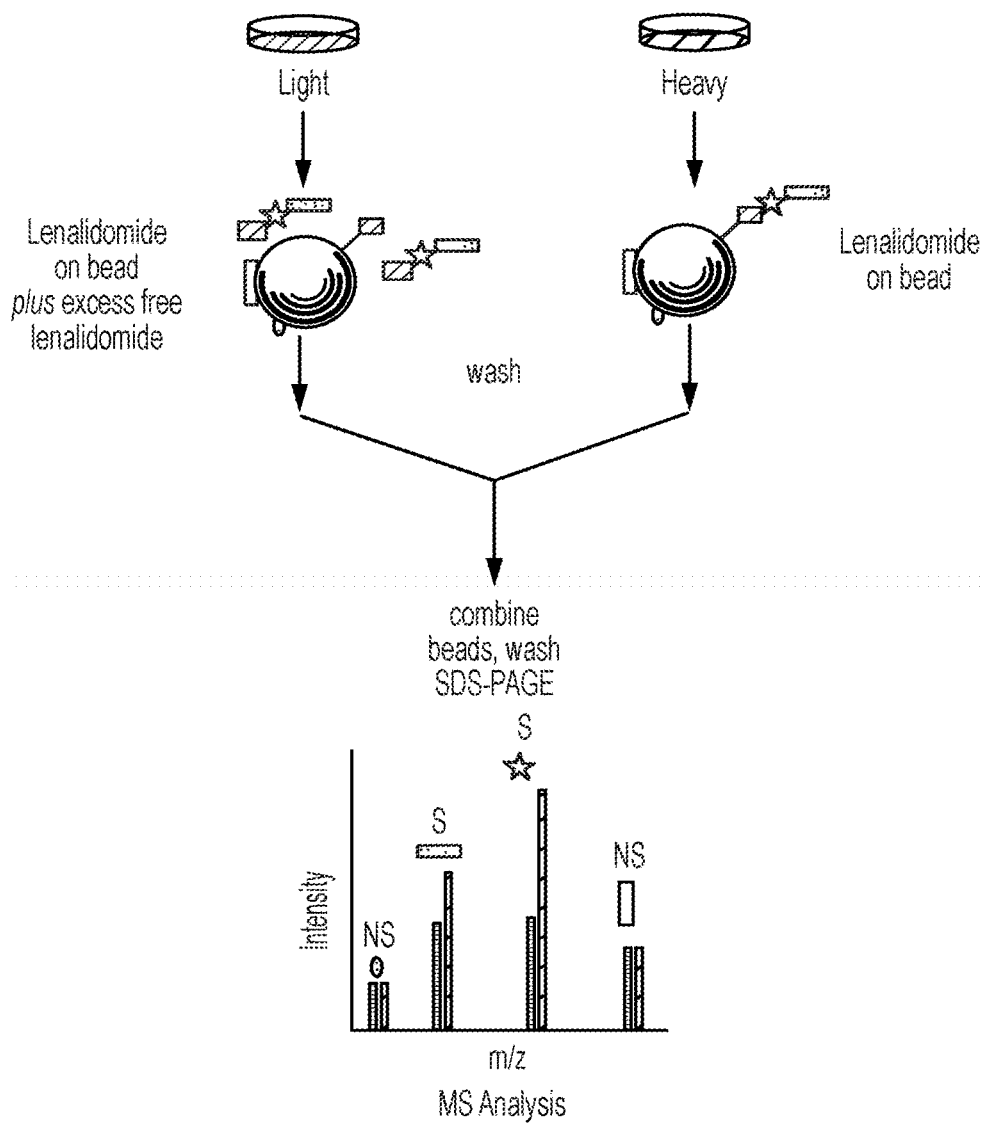
Figures 1, 2, 3A:
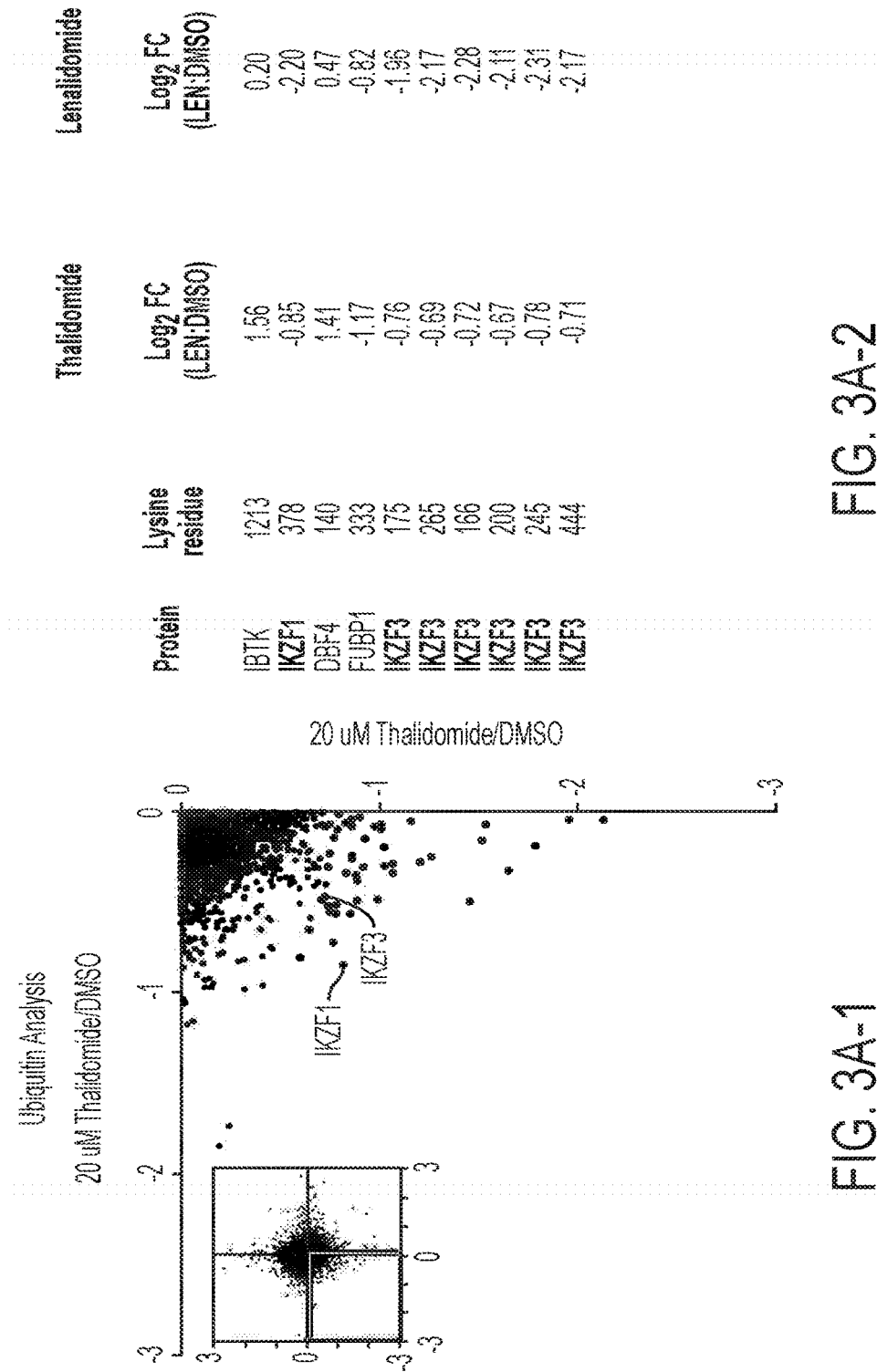
Figures 1, 2, 3B:
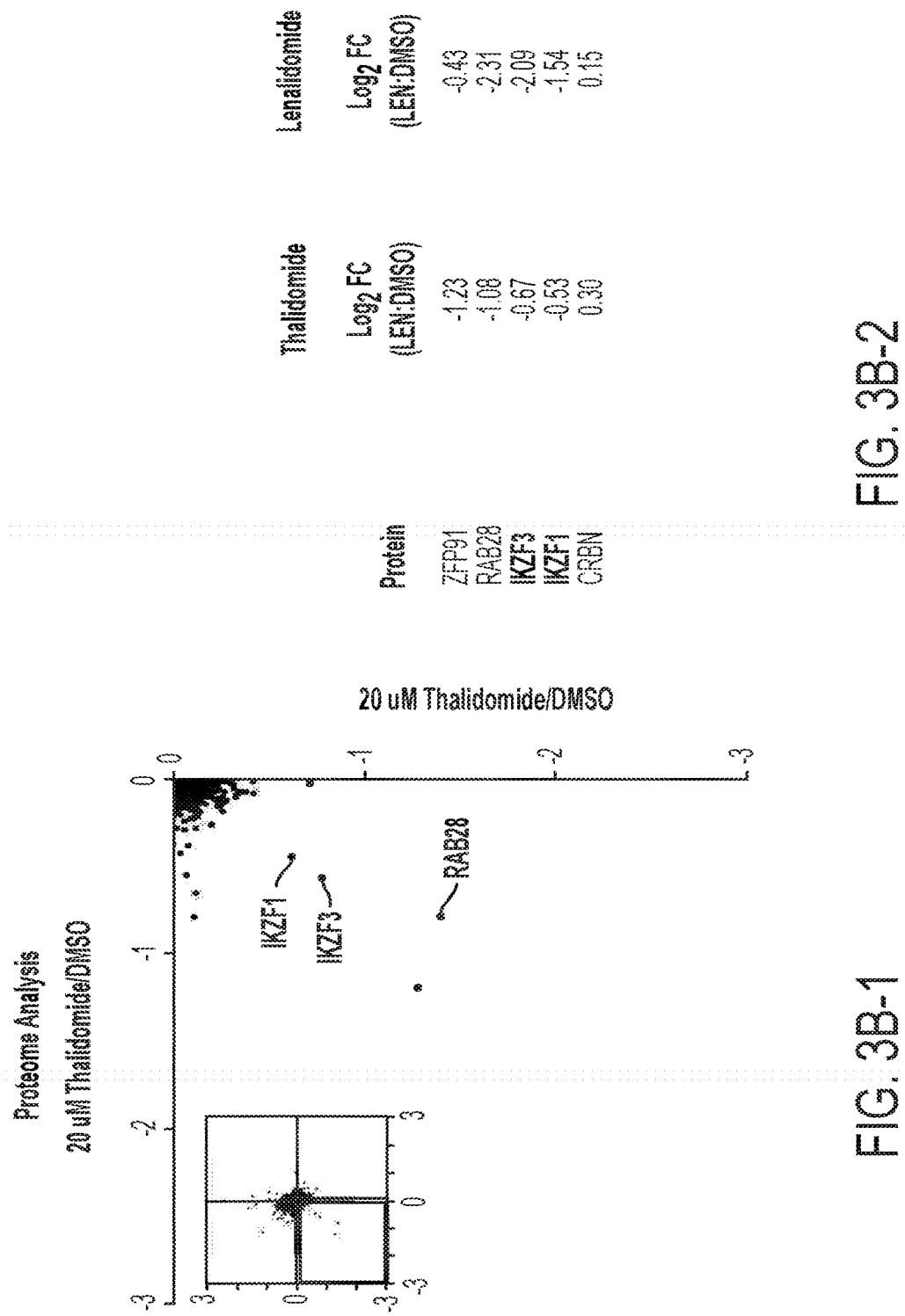

In order to identify direct protein targets of lenalidomide, a derivative of lenalidomide was synthesized that allowed immobilization of the molecule to a bead (FIG. 2A). This derivative retained the biological activity of lenalidomide, including selective growth inhibition of multiple myeloma cells (FIGS. 2B-1, 2B-2). To identify proteins that bind to the lenalidomide derivative immobilized on a solid support, SILAC (Stable Isotope Labeling of Amino Acids in Cell Culture)-based quantitative mass spectrometry (MS) was used to compare proteins pulled down by beads in the presence or absence of 100-fold excess soluble lenalidomide, enabling discrimination between proteins that bind lenalidomide from those binding the bead or linker (FIG. 2C).

This approach identified two candidate proteins binding specifically to lenalidomide, DNA damage binding protein 1 (DDB1) and carbonyl reductase 1 (CBR1). DDB1 binds the lenalidomide derivative-immobilized beads, and was competed off by lenalidomide, thalidomide, and pomalidomide. Lenalidomide did not interact with CBR1 in direct binding assays or inhibit CBR1 in biochemical assays so it was not pursued further. Recently, Ito et al. reported a similar proteomic strategy leading to the finding that thalidomide binds to DDB1 via CRBN, and that this interaction is necessary for thalidomide's teratogenic effects. DDB1 forms an E3 ubiquitin ligase (CRL4) with Cullin 4A and 4B (Cul4A/4B) and regulator of cullins 1(RBX1). Consistent with these findings, it was found that DDB1 and CRBN each bound the lenalidomide derivative beads and were competed off by soluble lenalidomide. The finding that CRBN-DDB1 binds both lenalidomide and thalidomide in independent proteomic studies provided powerful evidence that this ubiquitin ligase complex is a major direct protein binding partner for this class of molecules.

Figure 1A:
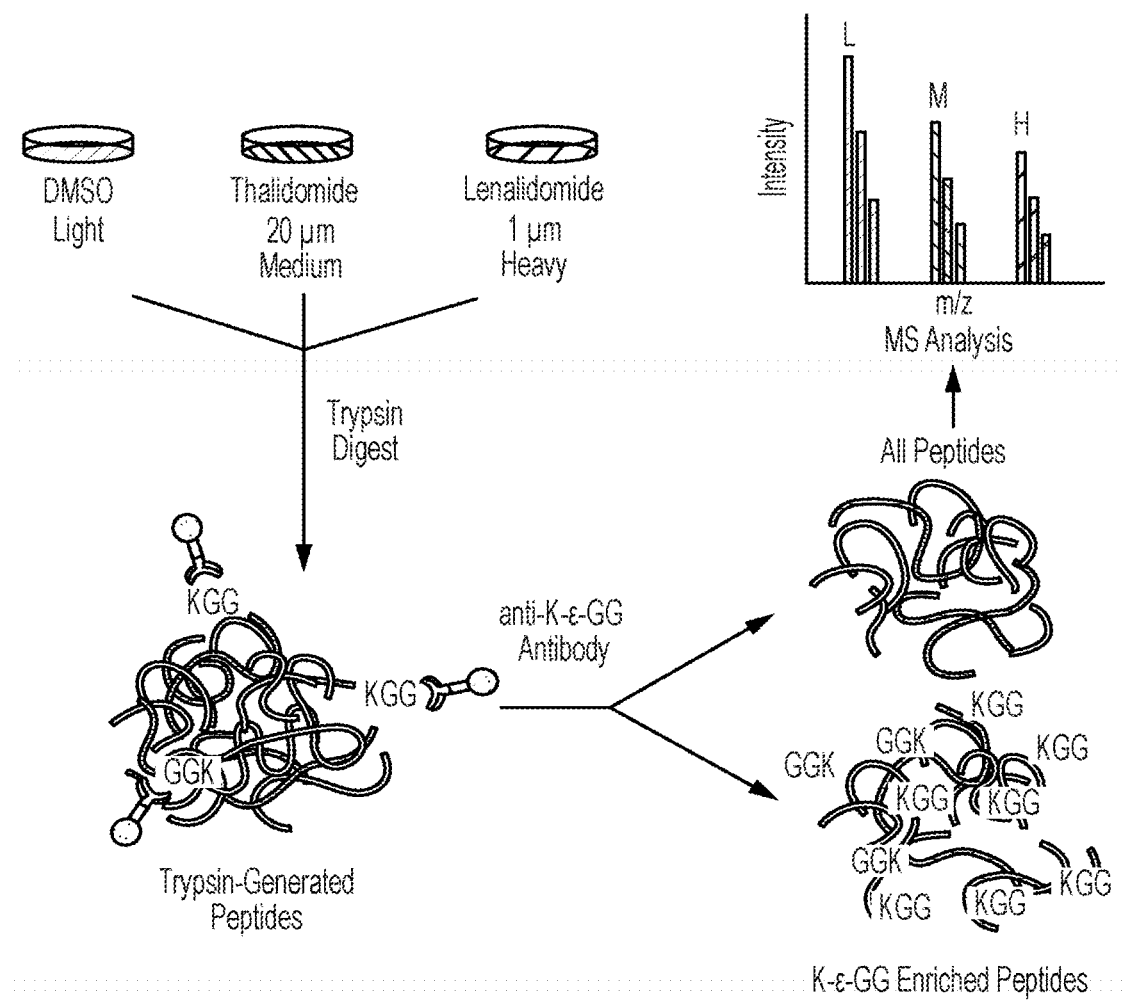
FIGS. 1A-1D provide a proteomic analysis of lenalidomide-induced changes in ubiquitination, protein abundance and CRBN interaction in MM1S cells.
Figure 1B:
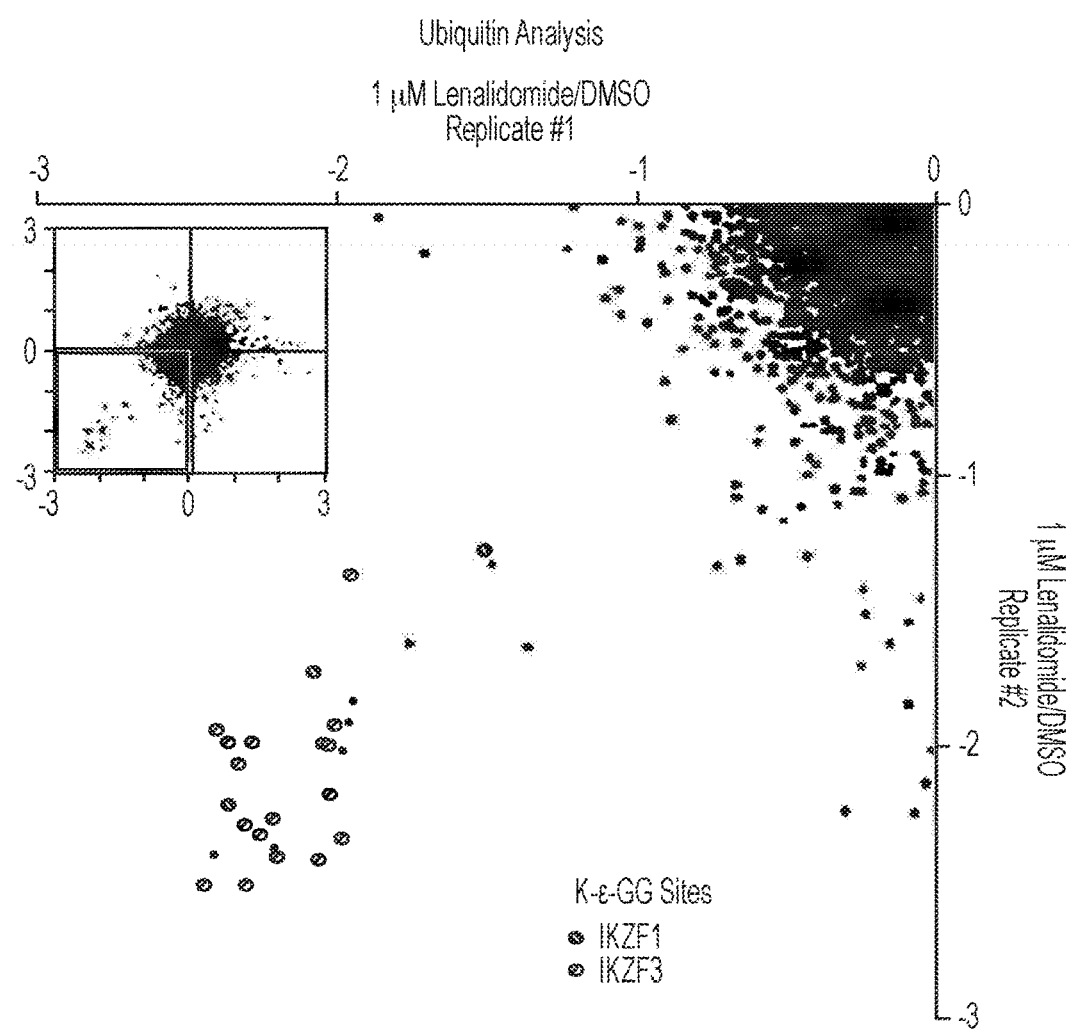
Figure 1C:
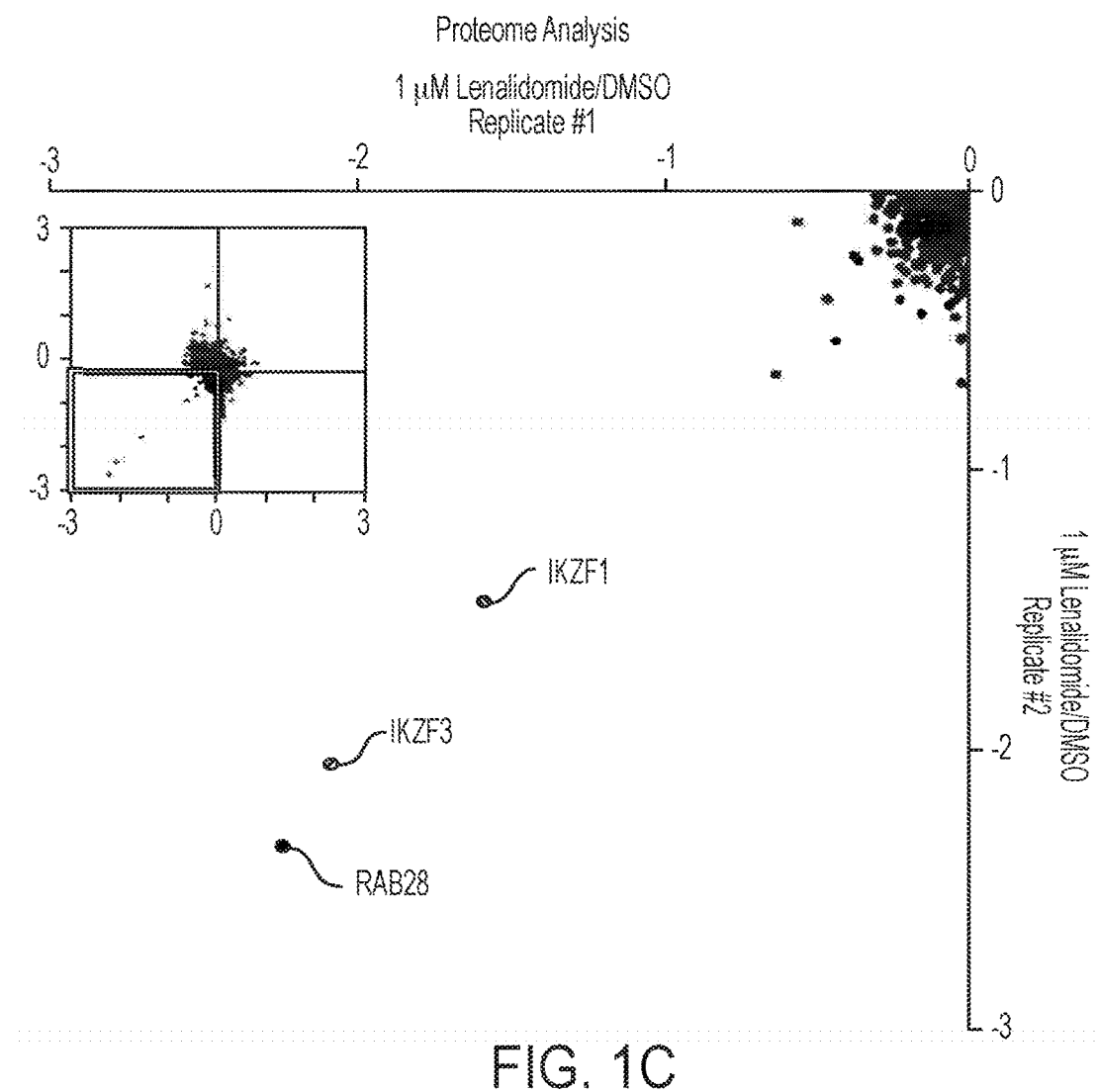
Figure 4A:
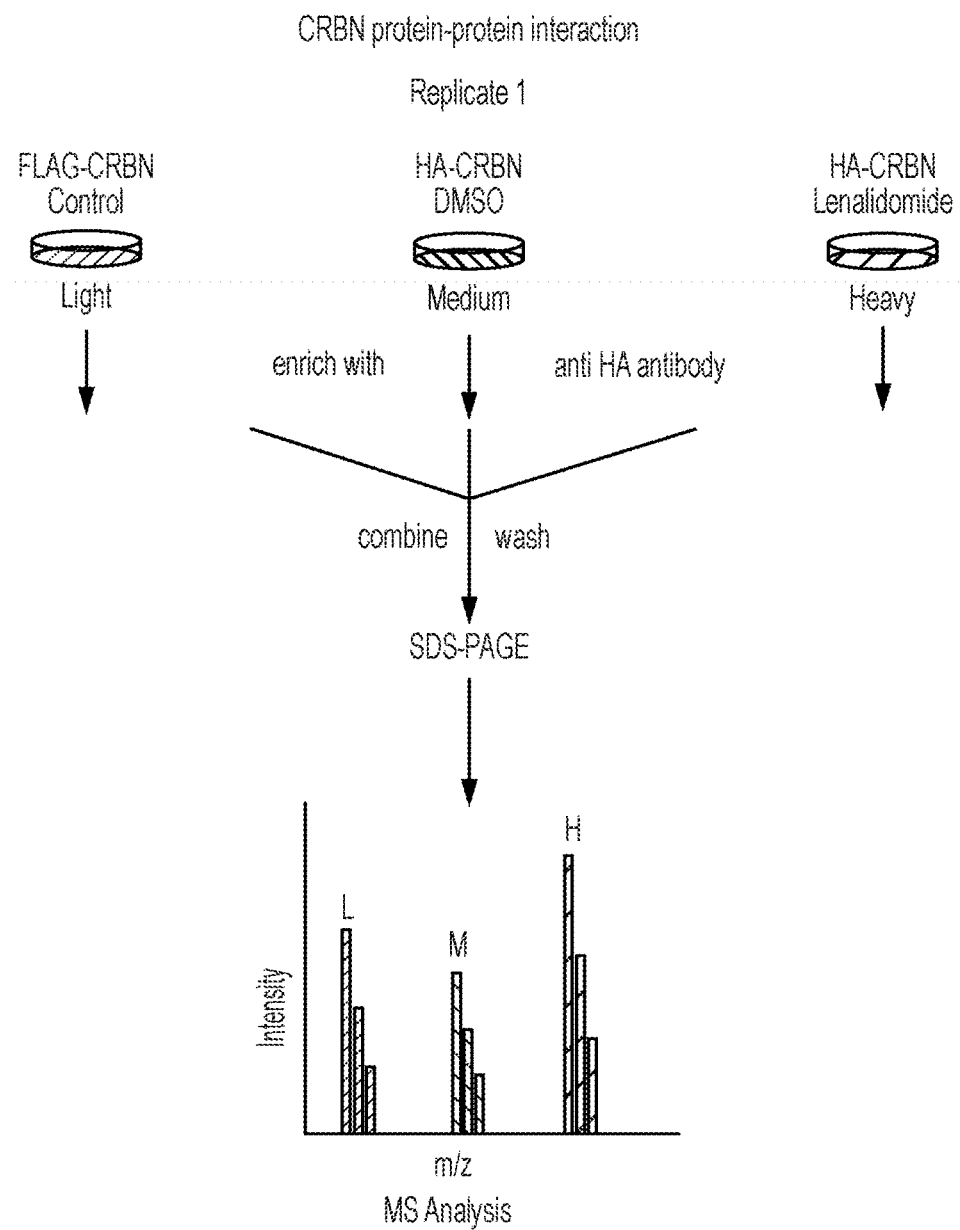
FIGS. 4A and 4B provides schematic diagrams illustrating the experimental design for SILAC-based assessment of CRBN interaction analysis in MM1S cells. HA-CRBN of DMSO and lenalidomide treated cells was immunoprecipitated with anti-HA Sepharose conjugate beads. Lysates of FLAG-CRBN expressing cells served as a negative control to exclude non-specific binding to the antibody-sepharose conjugate.
Figure 4B:
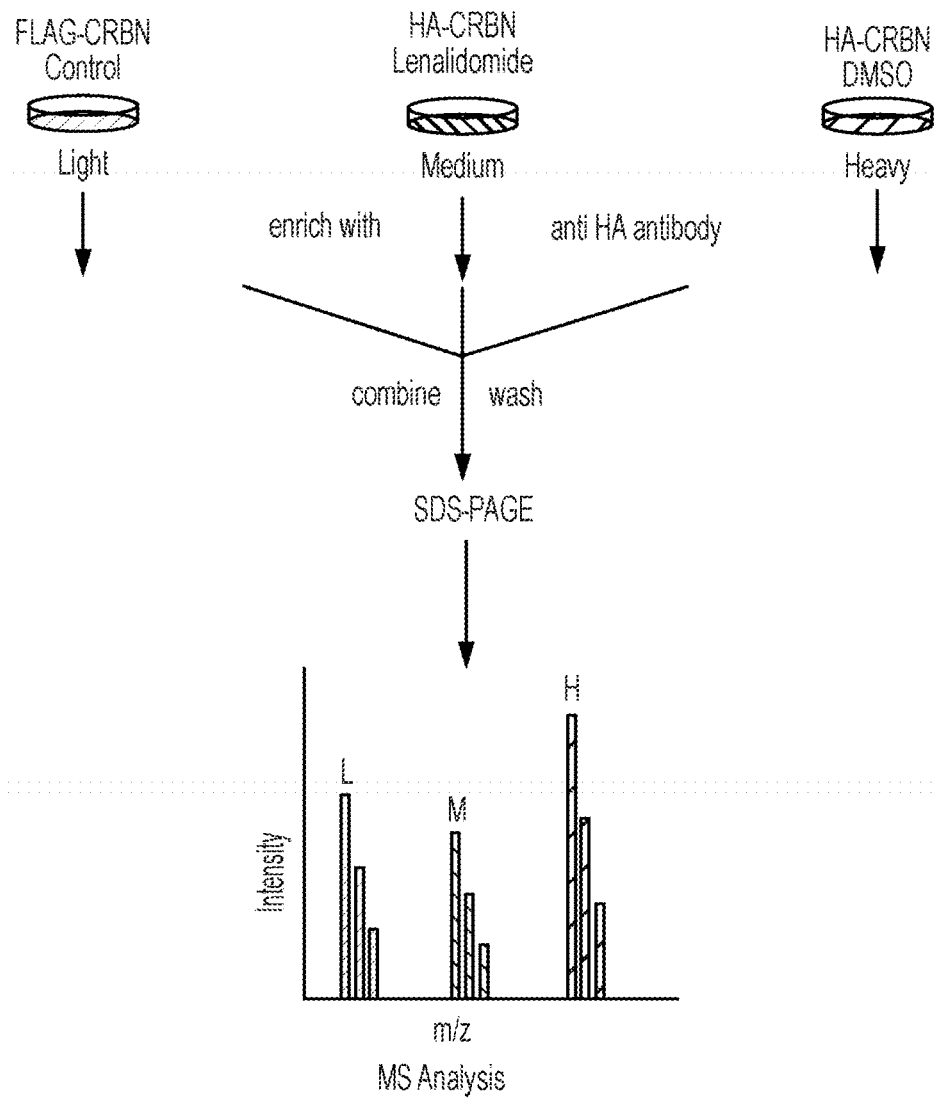

It was hypothesized that the pleiotropic effects of lenalidomide might be caused by altered ubiquitination of target proteins. Specificity of the CRL4 ubiquitin ligase is mediated by an interchangeable substrate receptor, but no targets have been identified for CRBN, a putative substrate receptor. To characterize drug-induced modulation of CRL4-CRBN ubiquitin ligase activity, SILAC-based quantitative MS studies were used to characterize changes in the ubiquitinome and proteome in the MM1S multiple myeloma cell line cultured in the presence of lenalidomide or thalidomide for 12 hours (FIGS. 1A, 1C). Ubiquitination profiling was completed by enrichment of formerly ubiquitinated peptides with an anti-K-ε-GG antibody (FIG. 1B). In parallel, the landscape of lenalidomide-dependent CRBN protein interactions was examined (FIGS. 1D, 4).

Example 2: Lenalidomide Regulates Ikaros (IKZF1) and Aiolos (IKZF3)

Figure 1D:
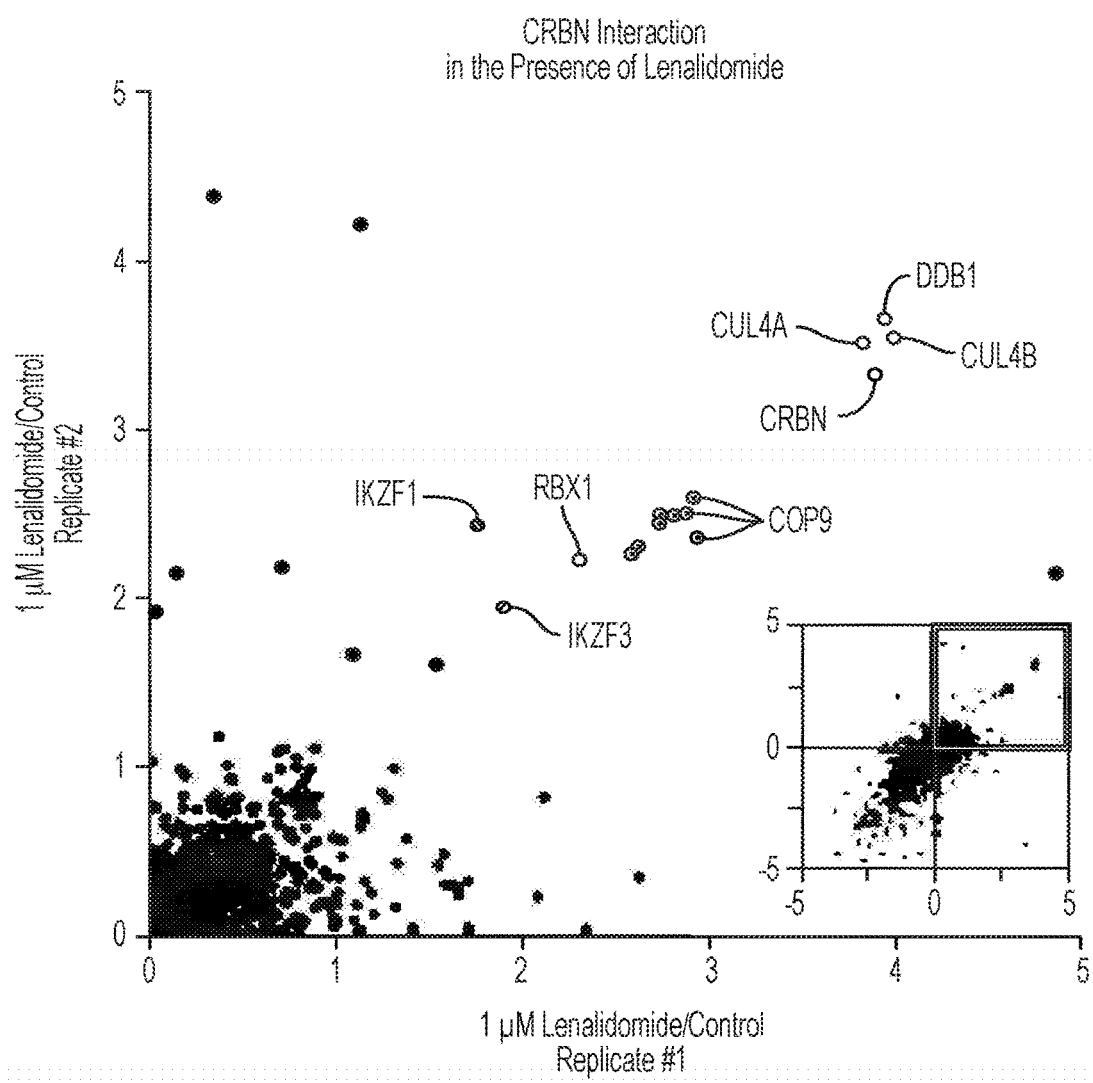

Two proteins, Ikaros (IKZF1) and Aiolos (IKZF3), scored at the top of the lists of proteins regulated by lenalidomide at both the protein and ubiquitin-site level (FIG. 1C, 1D). Lenalidomide decreased the abundance of IKZF3 ($log_2$ ratio–2.09) and IKZF1 ($log_2$ ratio –1.54). While increased ubiquitination would be expected to be associated with decreased protein abundance, a decrease in ubiquitination of multiple lysine residues of IKZF1 and IKZF3 was observed after treating cells with lenalidomide for 12 hours prior to addition of the proteasome inhibitor MG132. A likely interpretation of these results is that IKZF1 and IKZF3 are rapidly ubiquitinated, targeting them for degradation and thereby resulting in a decrease in abundance of both ubiquitinated and absolute levels of these proteins. IKZF1 and IKZF3 also scored at the top of the list of thalidomide-regulated proteins, consistent with the similar biological activity of the molecules (FIGS. 3A-1, 3A-2, 3B-1, and 3B-2).

Figures 1, 5A:
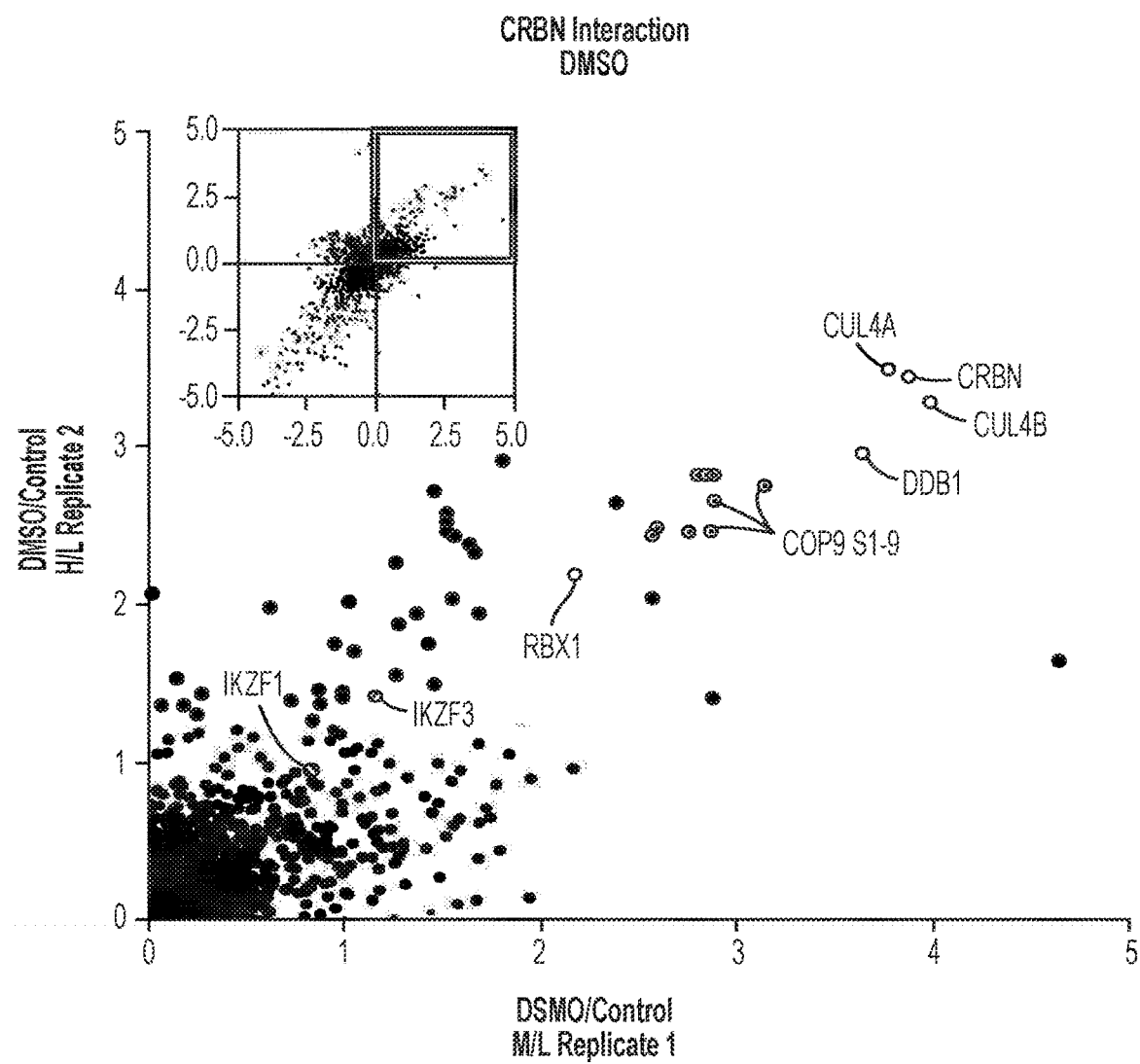
Figures 2, 5A:
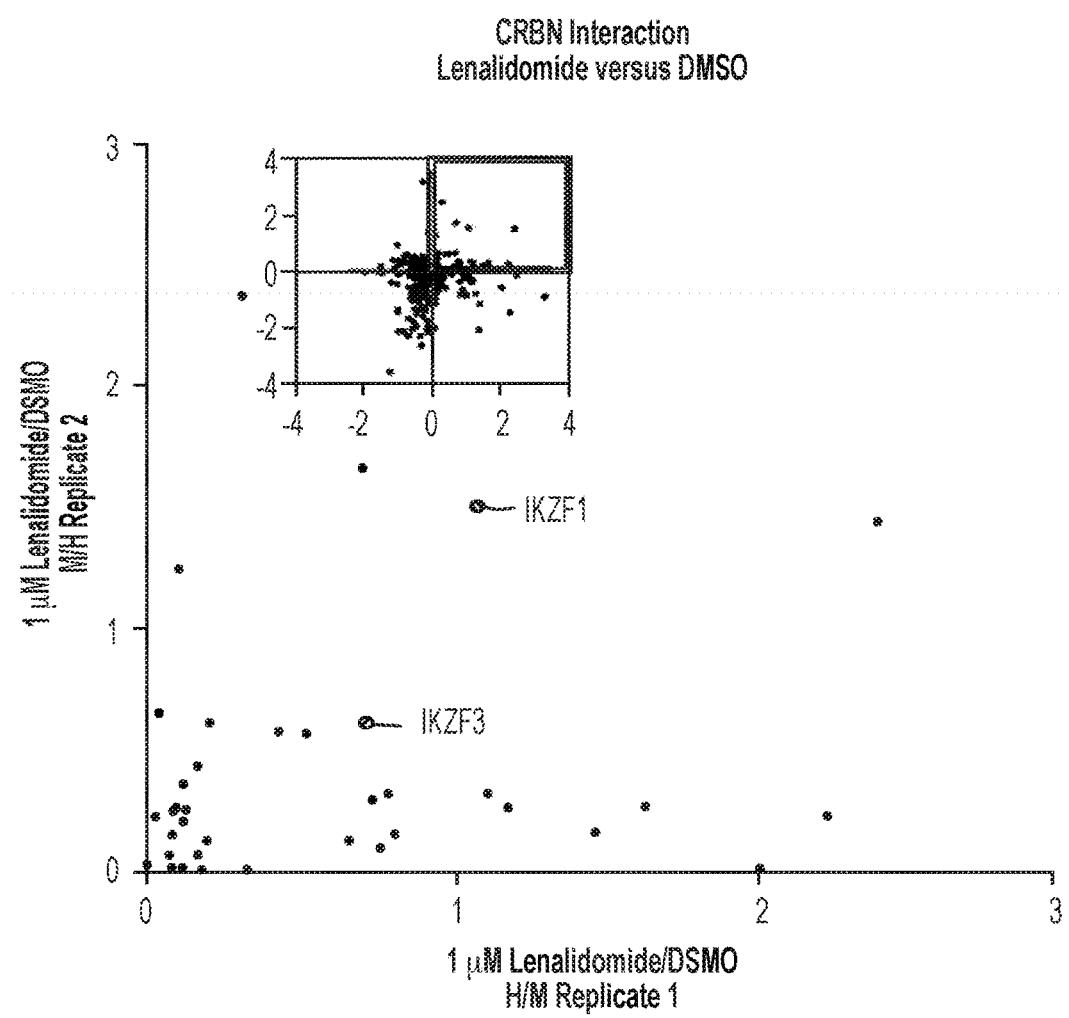

Strikingly, the protein interaction study using HA-CRBN revealed binding of IKZF1 and IKZF3 to the putative CRBN substrate receptor in the presence of lenalidomide (FIGS. 5A and 5B). As expected, all of the members of the CRBN-CRL4 ubiquitin ligase and proteins known to interact with DDB1 including subunits 1 to 8 of the COPS signalosome complex CSN, DDA1, and DNA ligase 4 were pulled down in both untreated or lenalidomide treated cells. No other substrate receptors for DDB1 were co-immunoprecipitated. Based on these results it is likely that CRBN is a substrate receptor and precludes binding of alternative receptors to DDB1. In aggregate, the proteomic data indicate that lenalidomide increases the binding of IKZF1 and IKZF3 to the CRBN-DDB1 ubiquitin ligase complex, leading to increased ubiquitination and consequent degradation.

Figure 6A:
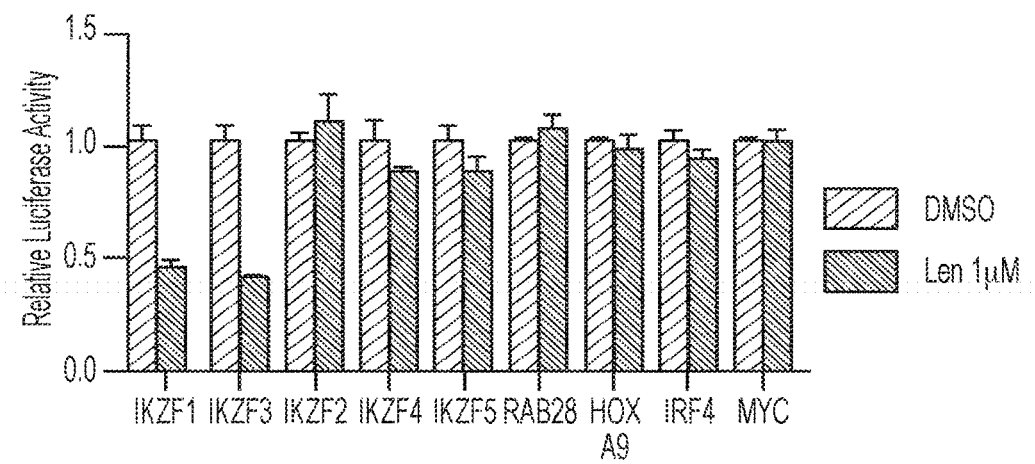
Figure 6B:
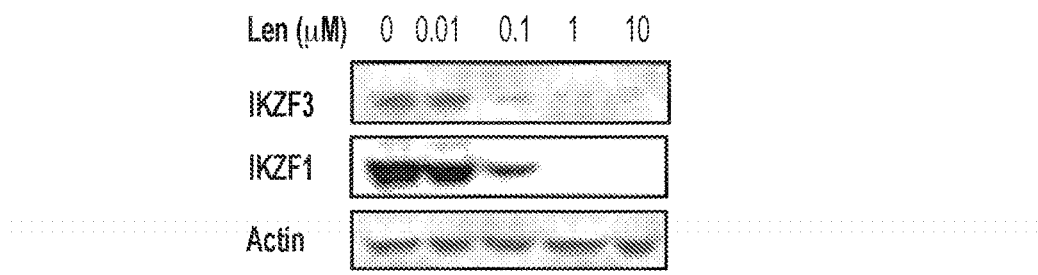

To validate this putative mechanism, the question of whether lenalidomide causes post-transcriptional regulation of IKZF1 and IKZF3 protein abundance was analyzed. The cDNAs of candidate genes, fused to firefly luciferase (FFluc), were expressed in 293T cells. IKZF1 and IKZF3 conferred a lenalidomide-regulated decrease in protein abundance onto the fused FFLuc. In contrast, luciferase levels were not altered after lenalidomide treatment when FFluc was fused to RAB28, a protein that decreased in abundance after lenalidomide treatment but did not bind to CRBN. Similarly, lenalidomide did not alter the abundance of FFluc fused to three other transcription factors of the Ikaros family, Helios (IKZF2), Eos (IKZF4) and Pegasus (IKZF5); IRF4, a protein implicated in lenalidomide activity; or the transcription factors HOXA9 and Myc (FIG. 6A). It was confirmed that, in MM1S multiple myeloma cells stably expressing HA-IKZF1 or HA-IKZF3, lenalidomide caused a dose-dependent reduction of both proteins (FIG. 6B). Taken together, these results demonstrate the selective regulation of IKZF1 and IKZF3 levels in response to lenalidomide.

Figure 6C:
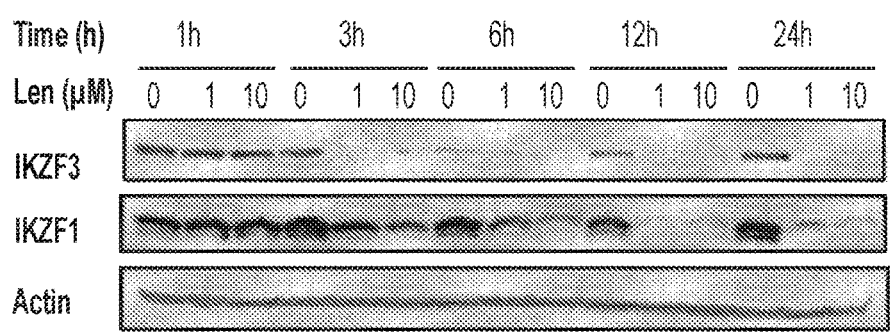

Endogenous protein expression was examined in response to lenalidomide. Lenalidomide strongly decreased the abundance of IKZF1 and IKZF3 in a dose-dependent manner in MM1S cells (FIG. 6C), in primary cells (FIG. 6E) and other cell lines (FIGS. 7A and 7B). Depletion of these proteins was evident in as little as 3 hours after treatment. In contrast, IKZF1 and IZKF3 mRNA levels were not altered by lenalidomide treatment (FIG. 6D). FIG. 6F shows an in vivo ubiquitination analysis of HA-tagged IKZF1 and IKZF3 expressed in MM1S cells treated for 1.5 hours with 100 nM Epoxomicin and the indicated concentrations of lenalidomide. The FK2 antibody detects covalently linked ubiquitin.

Example 3: Lenalidomide Induced Ubiquitination of IKZF1 and IKZF3

Figure 8A:
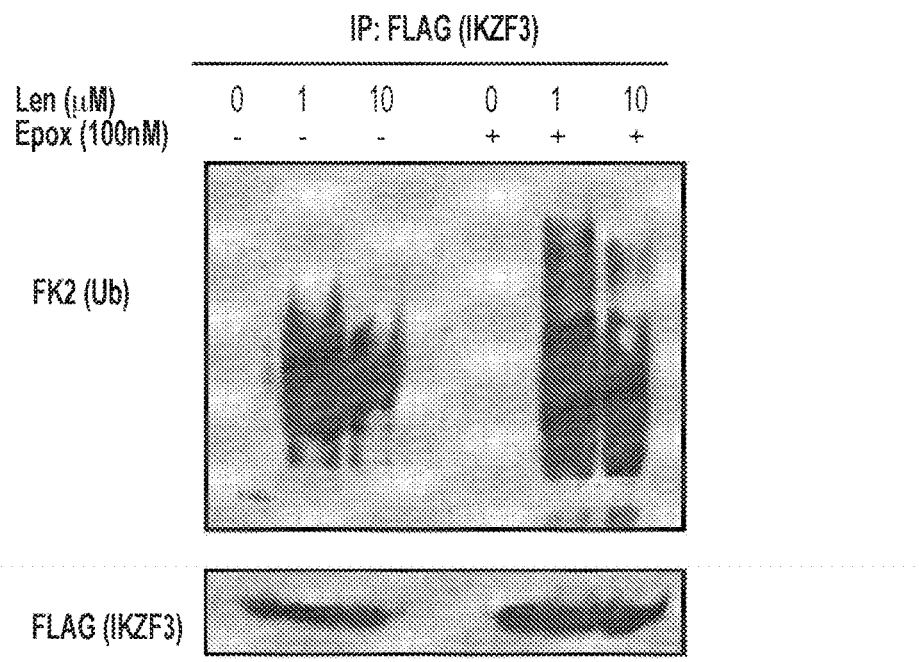
FIGS. 8A-8C show the in vivo ubiquitination of IKZF1 and IKZF3. Cells were treated with the indicated concentrations of lenalidomide and/or 100 nM epoxomicin for 1.5 hours.
Figures 8B, 8C:
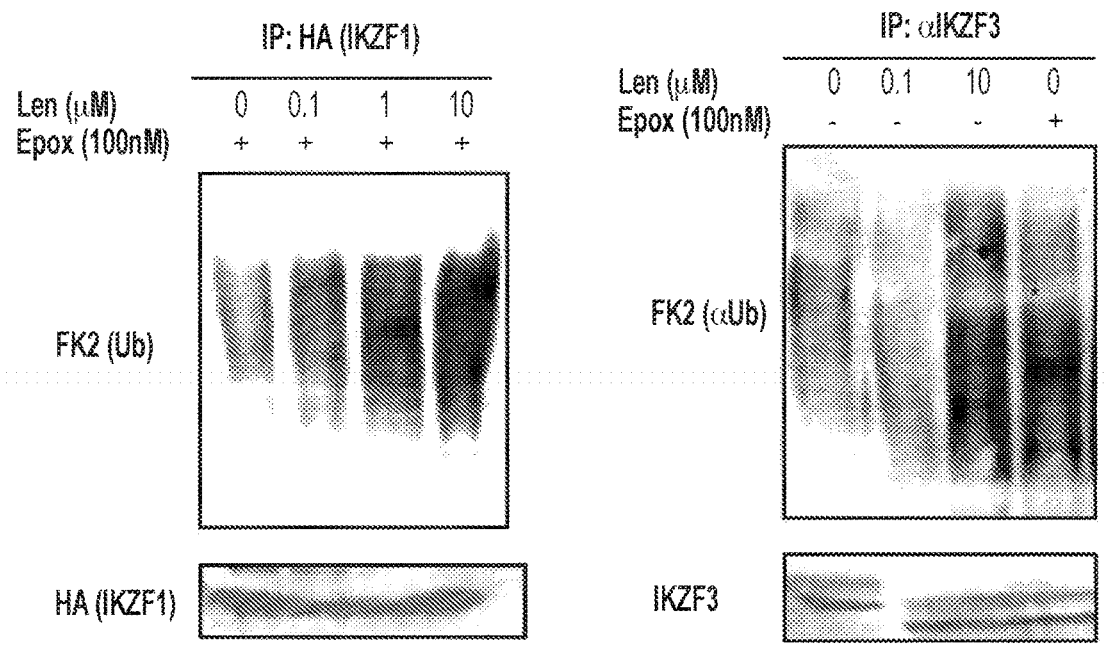

The direct effect of lenalidomide on ubiquitination of IKZF1 and IKZF3 was assessed. Lenalidomide induced dose-dependent ubiquitination of tagged IKZF1 and IKZF3 in MM and 293T cells (FIGS. 8A-8C). Cullin-RING ubiquitin ligase (CRL) activity depends on NEDDylation and can be inhibited by the Nedd8 enzyme inhibitor MLN4924. Treatment with 1 µM MLN-4924 prevented the lenalidomide-induced decrease of endogenous IKZF1 and IKZF3 in MM1S cells and of FFluc-fused IKZF3 in 293T cells. These experiments demonstrate that lenalidomide-induced degradation of IKZF1 and IKZF3 involves ubiquitination by a cullin-based E3 ubiquitin ligase.

Figures 9A, 9B:
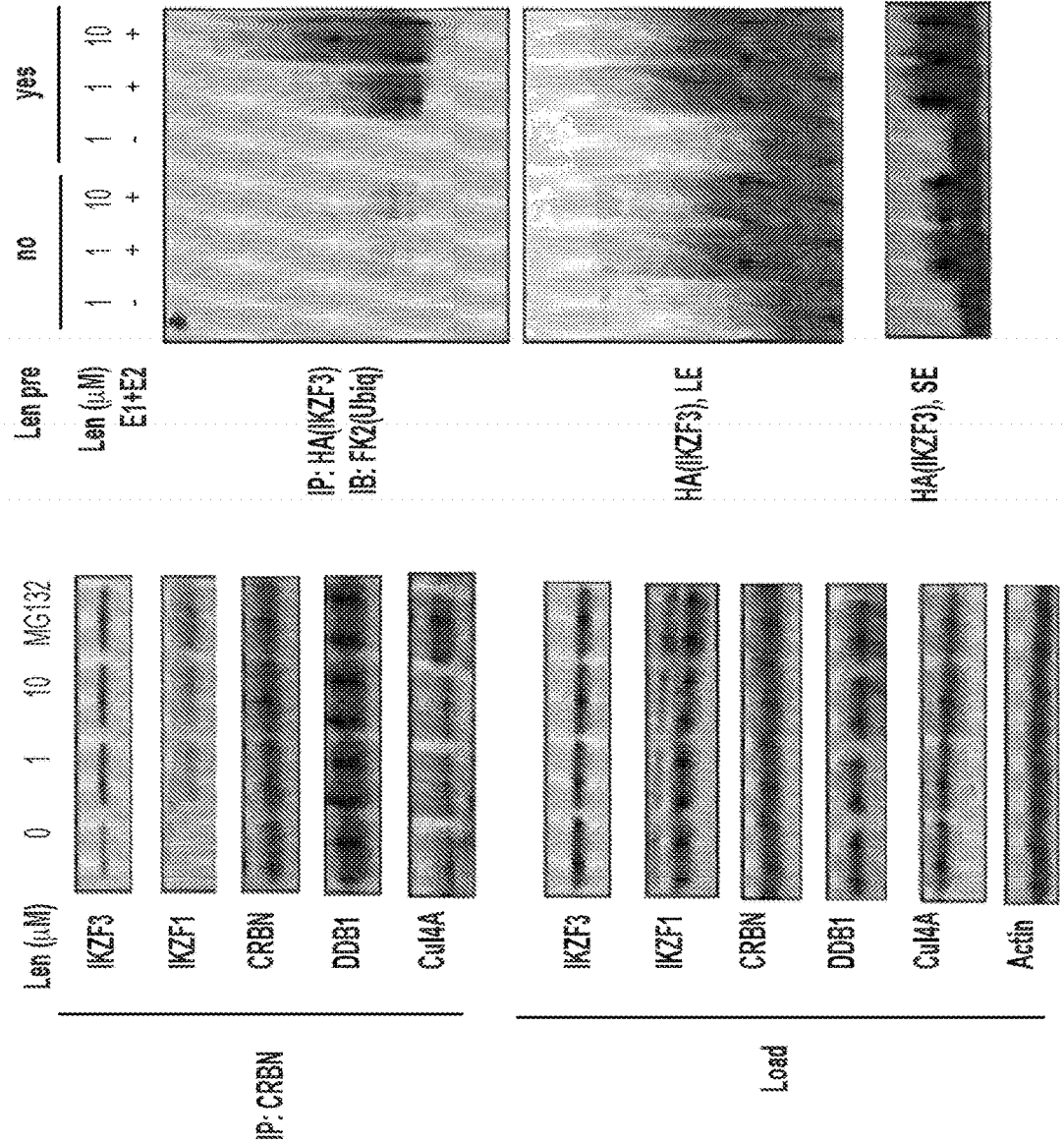
Figures 1, 9D:
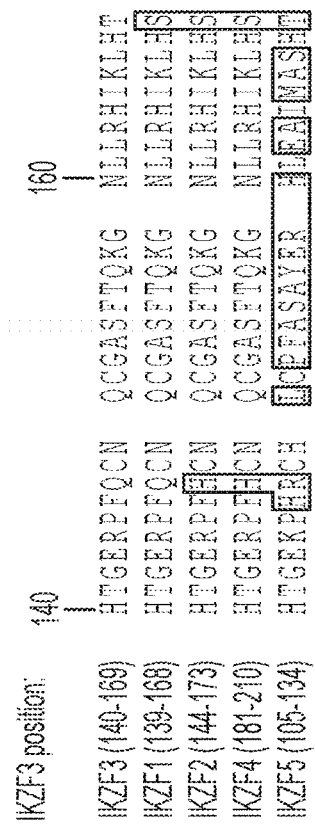
Figures 2, 9D:
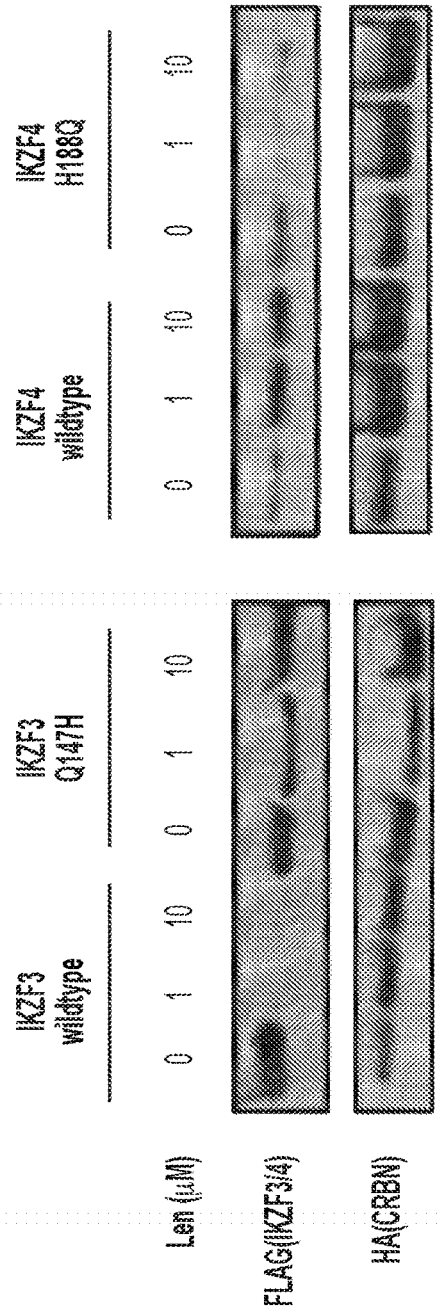

Experiments were carried out to determine whether lenalidomide-induced ubiquitination of IKZF1 and IKZF3 is caused by altered binding of these proteins to CRBN, as observed in our proteomic studies. These experiments confirmed that more IKZF1 and IKZF3 co-immunoprecipitate with HA-CRBN after 3 hours of lenalidomide treatment, despite a dramatic decrease of protein levels in the whole cell lysate at the same time (FIG. 9A). If CRBN is essential for lenalidomide-induced degradation of IKZF1 and IKZF3, then loss or mutation of CRBN would inhibit the effect of the drug. Consistent with this, it was found that shRNA knockdown of CRBN prevented lenalidomide-induced degradation of luciferase fusions of IKZF1 and IKZF3, and prevented degradation of HA tagged IKZF3 in 293T cells (FIGS. 9B, 9C). Similarly, the CRBN$^{YW44}$ mutant that does not bind lenalidomide abrogated degradation of IKZF1 and IKZF3 (FIGS. 9D-1, 9D-2) and conferred lenalidomide resistance to MM1S cells (FIG. 10), consistent with previous studies that have shown CRBN to be essential for lenalidomide activity in multiple myeloma. These studies demonstrate that lenalidomide causes increased binding of IKZF1 and IKZF3 to CRBN, and that CRBN is critical for the effects of lenalidomide on these proteins.

To assess whether IKZF3 is an enzymatic substrate of the CRBN-DDB1 E3 ubiquitin ligase, an in vitro ubiquitination assay was performed. HA-IKZF3 was co-immunoprecipitated by FLAG-CRBN from 293T cells treated with DMSO or lenalidomide. Lenalidomide was added to the protein lysate in order to achieve efficient co-immunoprecipitation of IKZF3. The eluted complex was then incubated in the ubiquitin reaction mixture. Ubiquitinated IKZF3 could only be detected in reactions containing E1 and E2 ubiquitin ligase enzymes and was increased in cells pre-treated with lenalidomide, demonstrating that IZKF3 gets ubiquitinated when bound to CRBN.

Example 4: Amino Acids 131 to 270 of IKZF3 Mediate Lenalidomide Sensitivity

Figure 10:
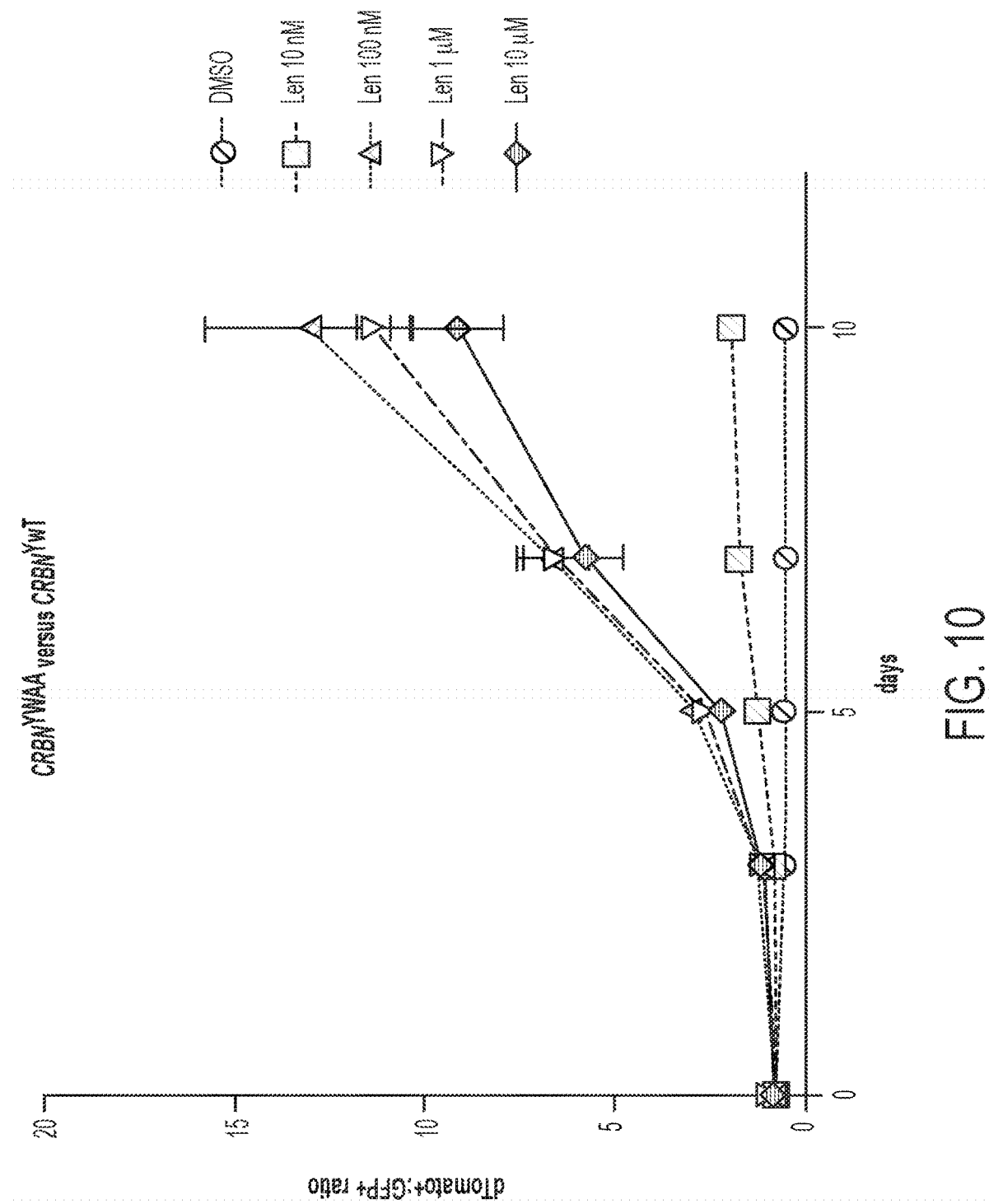
FIG. 10 is a graph showing rescue of lenalidomide induced growth inhibition by expression of $CRBN^{YWAA}$ that does not bind lenalidomide. NCI-H929 cells were transduced with a retroviral vector expressing CRBN wildtype and GFP or $CRBN^{YWAA}$ and dTomato. Two days after transduction cells were mixed and treated with the indicated concentrations of lenalidomide. The ratio of dTomato versus GFP expressing cells was assessed by flow cytometry.
Figure 11A:
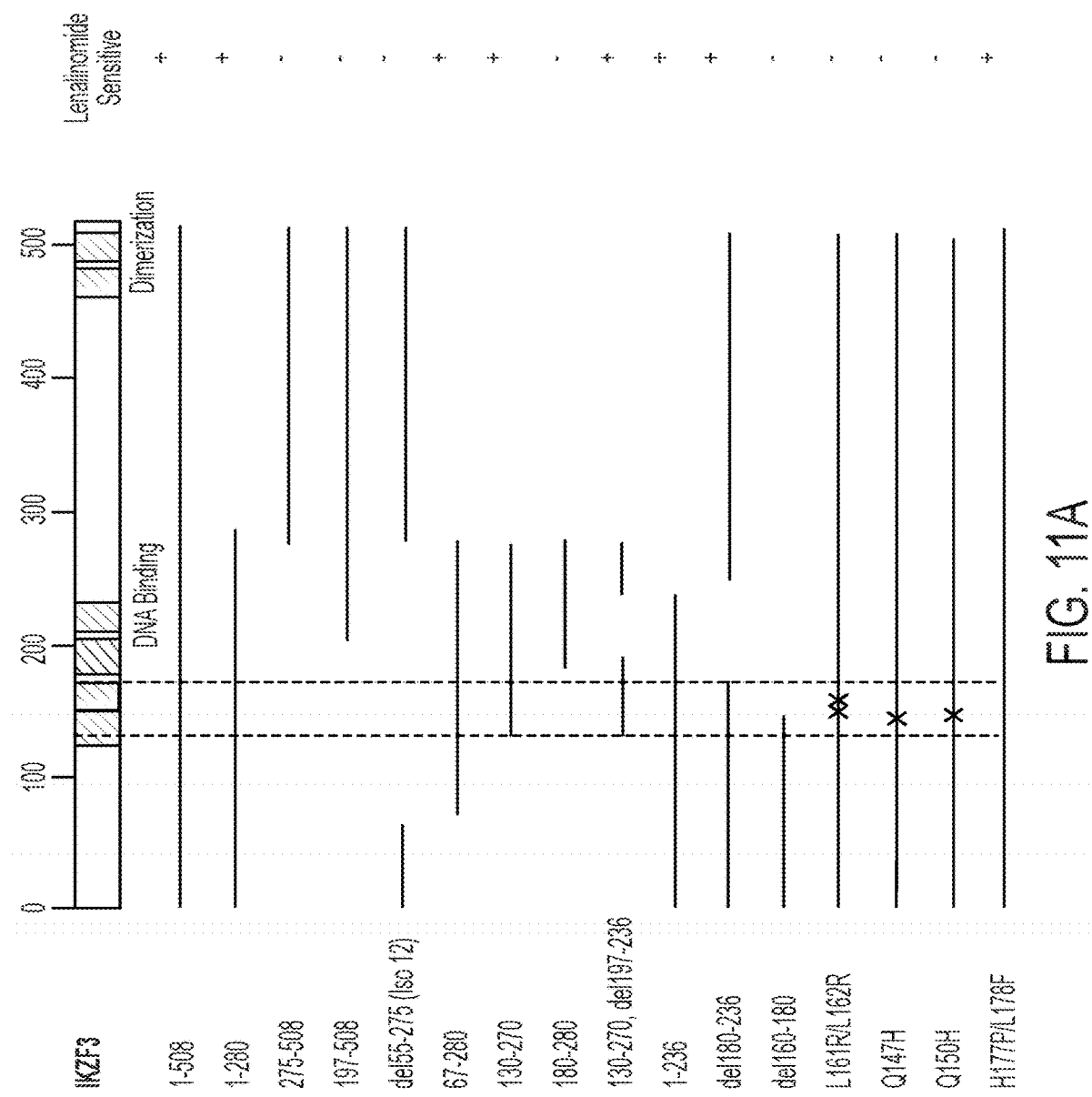
FIG. 11A-11C shows deletion mapping of IZKF3.
Figure 11B:
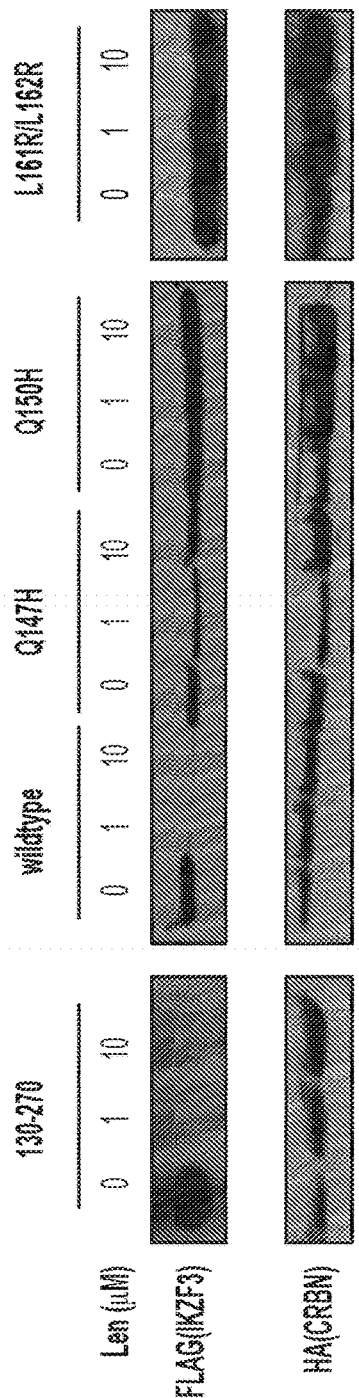
Figure 11C:
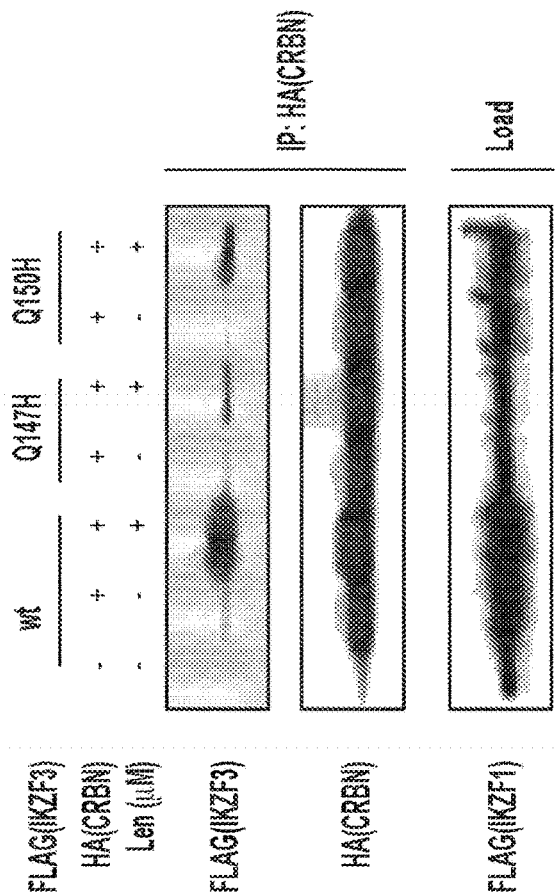

In order to identify a degron sequence in IKZF3 responsible for lenalidomide sensitivity, a series of IKZF3 cDNA deletion mutants was generated. Amino acids 131 to 270 of IKZF3 were identified as necessary and sufficient for lenalidomide sensitivity. Amino acids 141 to 180 were necessary for the lenalidomide response. The critical amino acid sequence lies within zinc finger domain 2, which is highly homologous between IKZF1 and IKZF3. IKZF2, IKZF4, and IKZF5, proteins that are not sensitive to lenalidomide-induced degradation, differ from IKZF1 and IKZF3 at three amino acids within this region. Substitution of Q147 in IKZF3 with a histidine residue (IKZF3 Q147H), which is present at this corresponding site in IKZF2 and IKZF4 resulted in resistance to lenalidomide-induced degradation (FIG. 10). Conversely, when the corresponding histidine (H188) in IKZF4 is changed to glutamine (IKZF4 H188Q), IKZF4 was degraded after lenalidomide treatment (FIG. 9G). In addition, Q150H and further point mutations in the essential region of IKZF3 were identified that rendered IKZF3 resistant towards lenalidomide (FIGS. 11A-11C). Binding to CRBN in the presence of lenalidomide is decreased for Q147H and Q150H mutants compared to wildtype IKZF3 (FIG. 11C). This domain is therefore necessary and sufficient for lenalidomide-induced binding to CRBN and subsequent protein degradation, and amino acid changes in this region provide the basis for differential sensitivity to lenalidomide between Ikaros family members.

Figures 1, 12A:
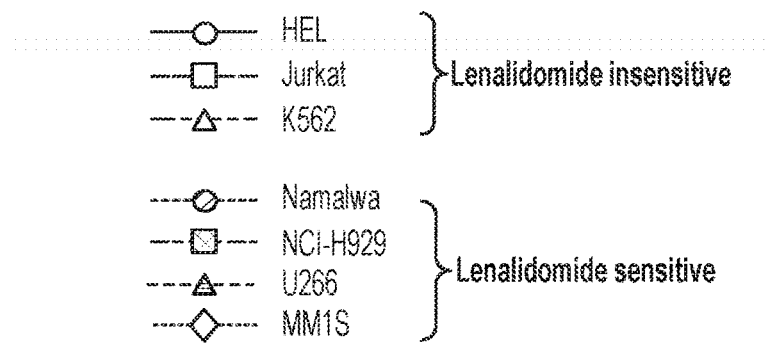
Figures 2, 12A:
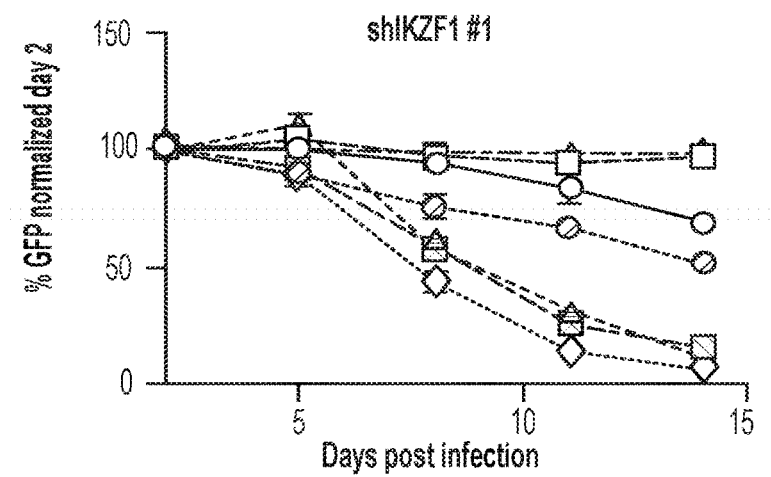
Figures 3, 12A:
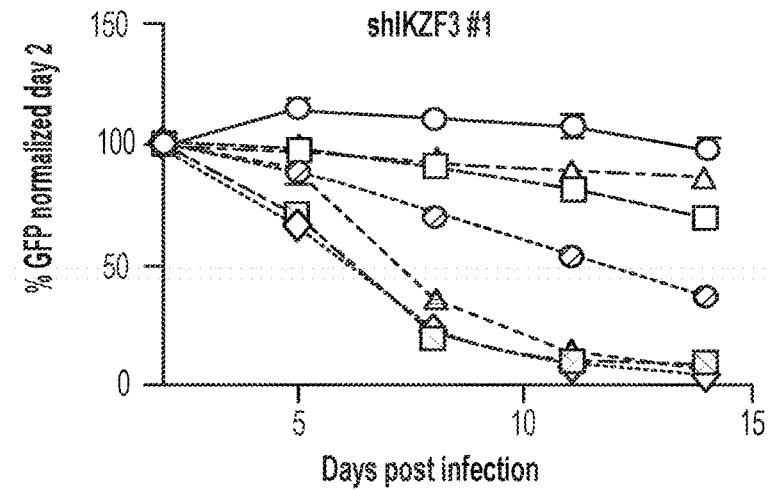
Figure 12B:
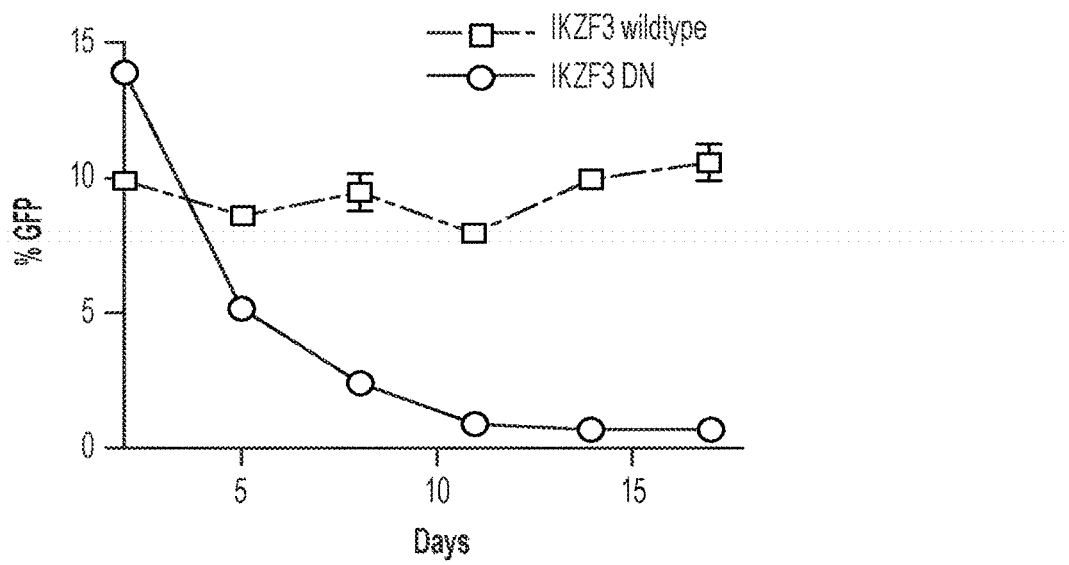
FIG. 12B is a graph showing that MM1S cells were transduced with retrovirus expressing GFP and wild-type IKZF3 or a dominant negative IKZF3 Isoform with deletion of the complete DNA binding region.
Figure 12C:
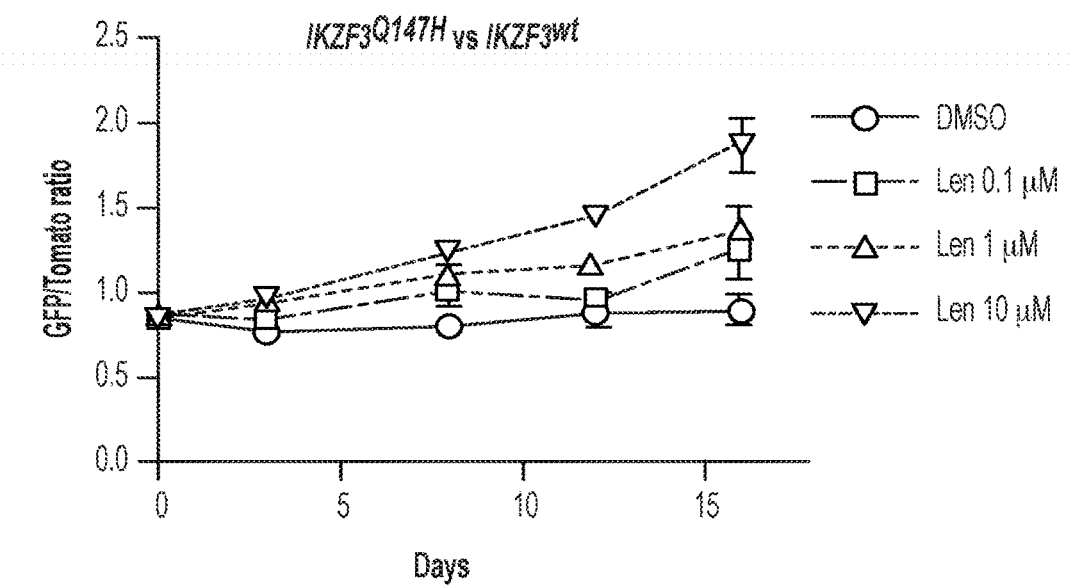
FIG. 12C includes two graphs showing that MM1S cells were infected with different retrovirus and competed against each other in media containing DMSO or lenalidomide. Left panel: IKZF3$^{wt}$/GFP versus empty vector/dTomato. Right panel: IKZF3$^{Q150H}$/GFP versus IKZF3$^{wt}$/dTomato.
Figures 1, 15A:
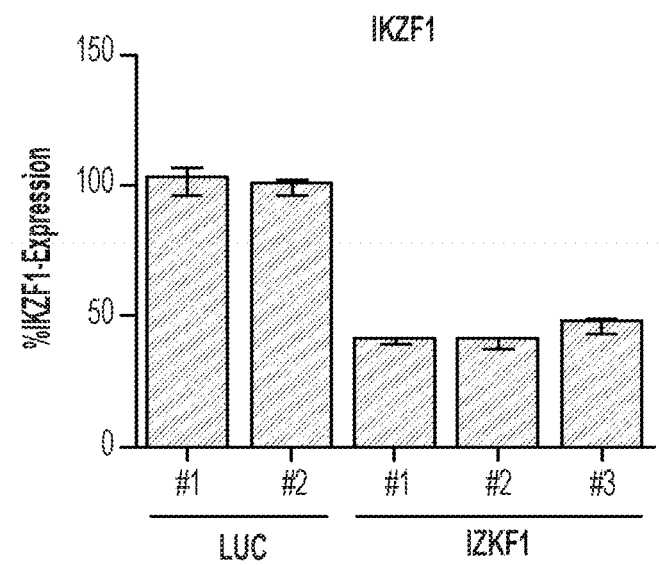
Figures 2, 15A:
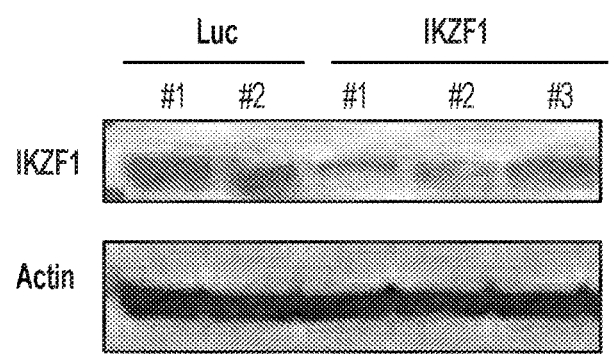
Figures 1, 15B:
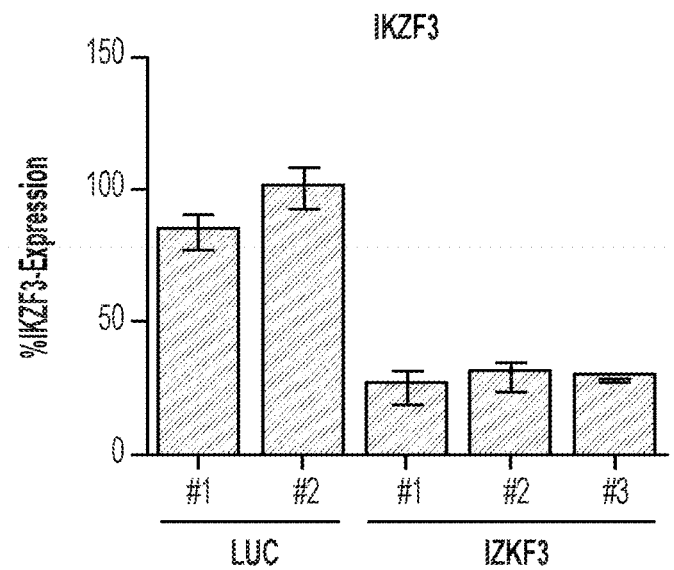
Figures 2, 15B:
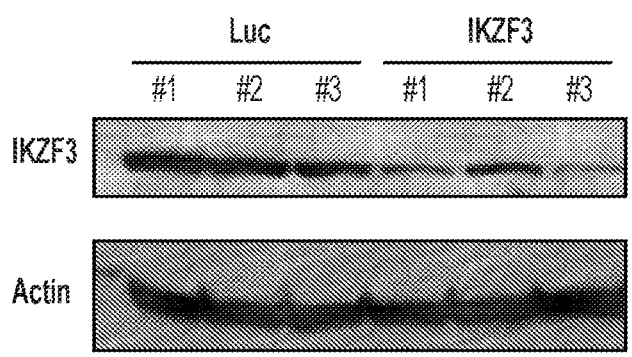
Figures 1, 15C:
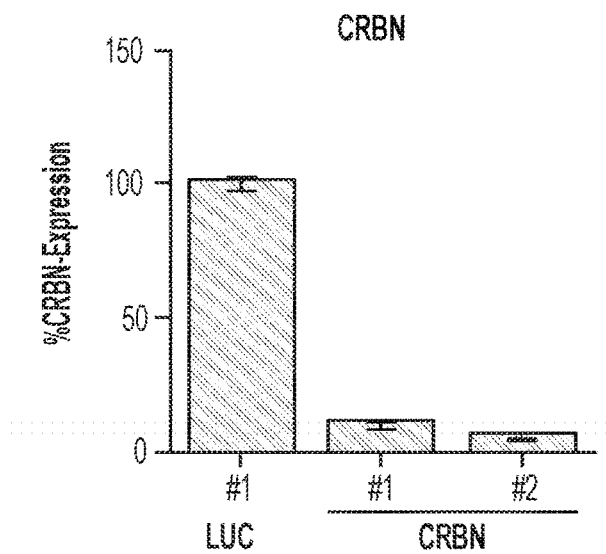
Figures 2, 15C:
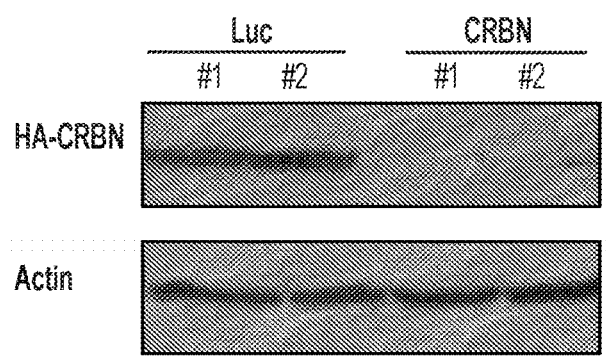

Example 5: IKZF1 and IKZF3 Depletion Mediates Lenalidomide's Anti-Proliferative Effect in Multiple Myeloma Cells Having demonstrated that lenalidomide regulates IKZF1 and IKZF3 ubiquitination and abundance, experiments were carried out to determine whether these proteins mediate specific biological and therapeutic effects of lenalidomide. IKZF1 and IKZF3 are essential transcription factors for terminal differentiation of B and T cell lineages. While IKZF1 is highly expressed in early lymphoid progenitors, IKZF3 is expressed at high levels in more mature B cell neoplasms, and murine studies have demonstrated that IKZF3 is required for the generation of plasma cells, the physiologic counterparts of multiple myeloma cells. Therefore, the dependence of multiple myeloma cells on IKZF1 and IKZF3 expression by genetic silencing of these proteins was assessed using RNA interference. IKZF1 and IKZF3 shRNAs that effectively decreased expression of the target proteins (FIGS. 15A-15C) inhibited growth of lenalidomide-sensitive multiple myeloma cell lines, while lenalidomide insensitive cell lines were unaffected (FIGS. 12A-1, 12A-2, 12A-3 and FIG. 13). Similarly, expression of a dominant negative IKZF3 isoform that lacks the complete DNA binding region resulted in depletion of MM1S cells (FIG. 12B). Over-expression of IKZF3 conferred relative lenalidomide-resistance to MM1S cells when competed with MM1S cells infected with a control retrovirus (FIG. 12C). Moreover, MM1S cells expressing the lenalidomide-resistant IKZF3 Q150H mutation were relatively resistant towards lenalidomide when competed to MM1S cells expressing wild-type IKZF3. These studies indicate that the anti-proliferative effect of lenalidomide in multiple myeloma cells is mediated by depletion of IKZF1 and IKZF3.

The transcription factor IRF4 was previously reported to be an important gene in multiple myeloma, and was implicated in the activity of lenalidomide in this disease (Y. Yang et al., *Cancer Cell* 21, 723 (Jun. 12, 2012)., A. L. Shaffer et al., *Nature* 454, 226 (Jul. 10, 2008).). While IRF4 levels were only slightly decreased in a proteomic analysis, performed on cells treated with lenalidomide for 12 hours, a significant decrease of IRF4 mRNA and protein was observed when cells were treated for 24 hours and longer. Knockdown of IKZF3 also suppressed IRF4 mRNA levels, suggesting that lenalidomide regulates IRF4 through Ikaros-mediated transcriptional repression (FIG. 14A-14E).

Example 6: Knockdown of IKZF3 Induced IL2 Expression

Figure 12D:
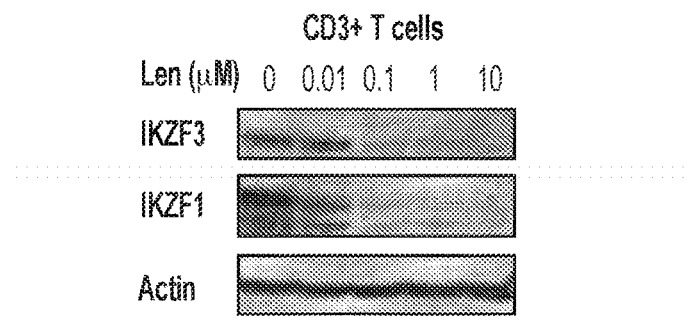
FIG. 12D shows results from human CD3+ T cells isolated from buffy coats of healthy blood donors were stimulated with plate-bound anti-CD3 and anti-CD28 and treated with different concentrations of lenalidomide for 24 hours.
Figure 12E:
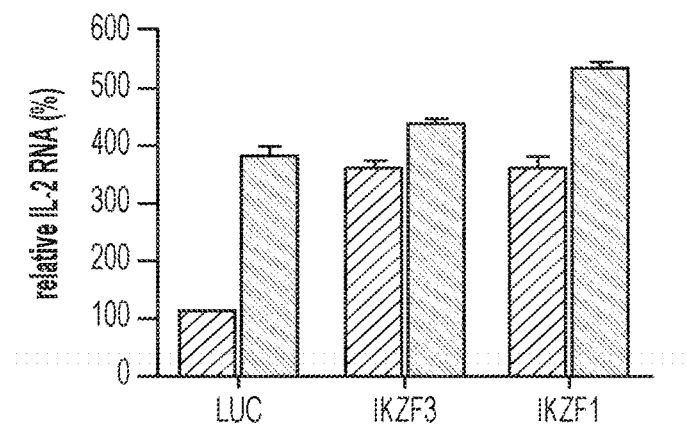
FIG. 12E is a graph. T cells were infected with lentiviral vectors expressing shRNAs targeting the indicated genes. After selection with puromycin, T cells were stimulated with anti-CD3/CD28 Dynabeads and treated with DMSO or 1 µM lenalidomide for 12 hours before lysis. IL-2 RNA expression levels were analyzed by quantitative RT-PCR using GAPDH expression as an internal control.
Figure 12F:
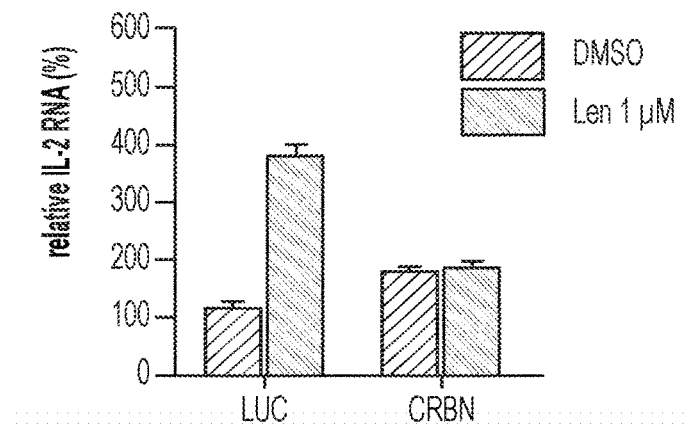
FIG. 12F is a graph. IL2 expression was measured in lenalidomide treated T cells expressing CRBN or control shRNAs.
Figure 13A:
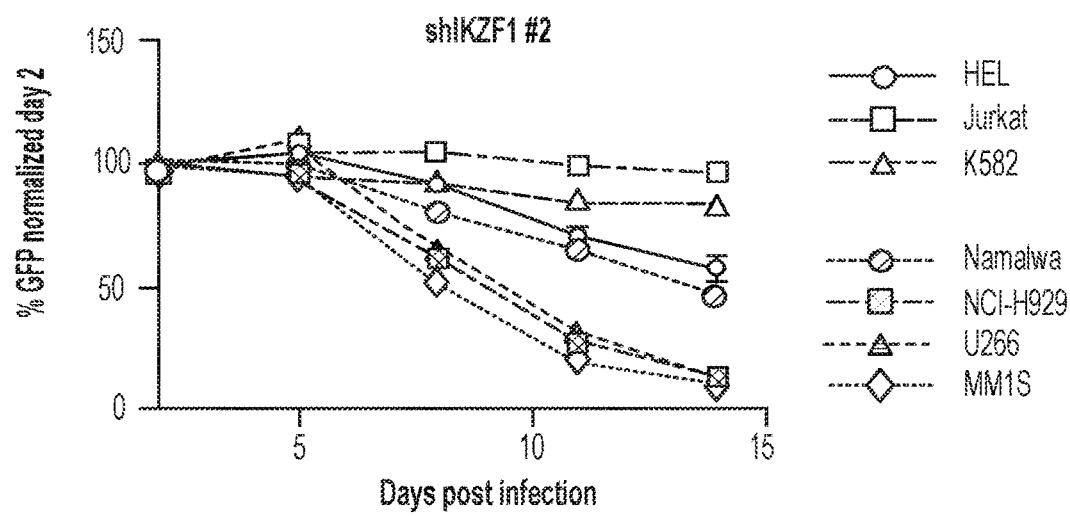
FIGS. 13A and 13B show the effect of a 2$^{nd}$ shRNA for IKZF1 (FIG. 13A) and IKZF3 (FIG. 13B), respectively on cell growth of multiple myeloma and lenalidomide-insensitive cell lines. Same experimental setup as in FIG. 4A.
Figure 13B:
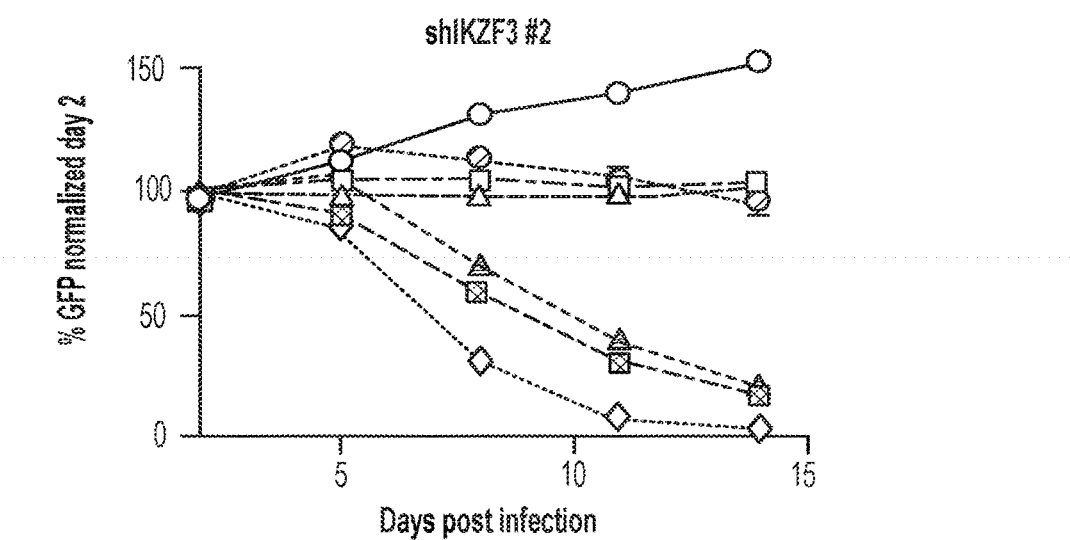
Figure 14A:
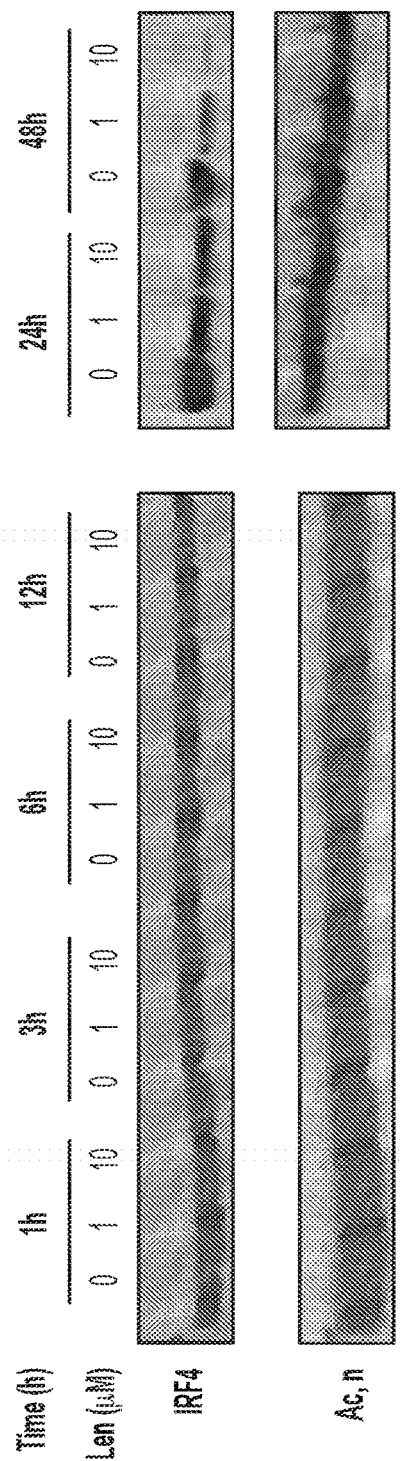
FIGS. 14A-14E show that lenalidomide and IKZF3 depletion result in decreased expression of IRF4 in MM1S cells.
Figures 14B, 14C:
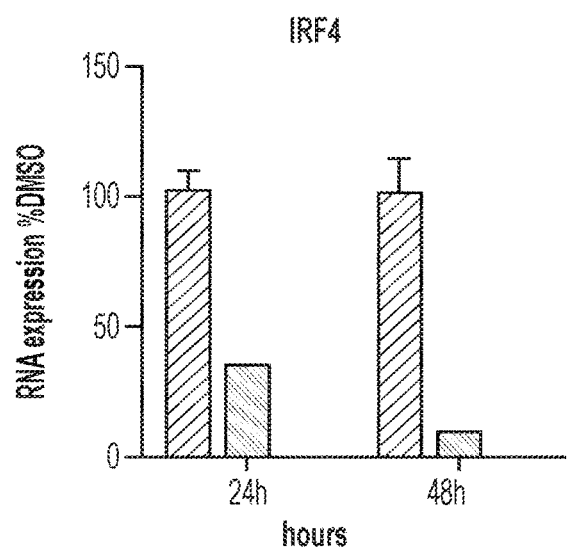
Figure 14D:
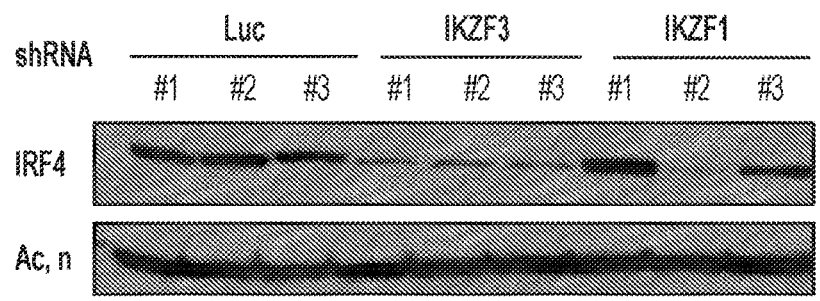
Figure 14E:
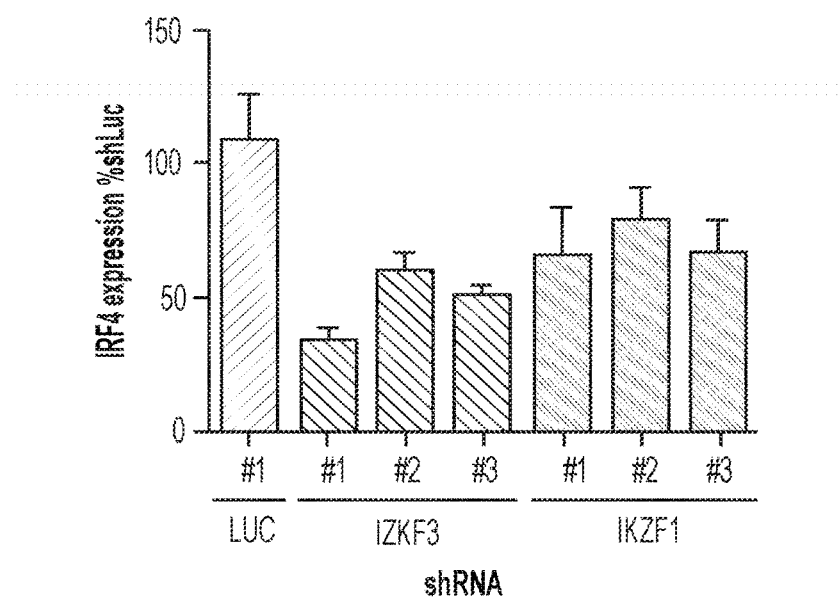

IKZF3 binds the IL2 gene promoter and repressed IL2 transcription in T cells. Experiments were carried out to determine whether lenalidomide regulates IL2 levels by modulating IKZF3 expression. Both IKZF1 and IKZF3 protein levels decreased markedly in primary human T cells treated with lenalidomide (FIG. 12D). Lentiviral shRNA-mediated knockdown of IKZF3 induced IL2 expression. Lenalidomide induced IL2 mRNA expression by 3.3-fold in T cells expressing a control shRNA, and this induction was blocked by IKZF3 knockdown (FIG. 12E). Similarly, the effect of lenalidomide on IL2 expression was abrogated by shRNA knockdown of CRBN (FIG. 12F). These studies demonstrated that one of the primary immunomodulatory activities of lenalidomide, induction of IL2, is mediated by de-repression of the IL2 promoter by depletion of IKZF3.

In aggregate, the studies reported herein above demonstrate that lenalidomide acts via a novel mechanism of drug activity, enforced binding of the substrate receptor CRBN to IKZF1 and IKZF3, resulting in selective ubiquitination and degradation of the target proteins. IKZF1 and IKZF3 play central roles in the biology of B and T cells, and ablation of protein expression for these transcription factors explains the activity of lenalidomide in lymphoid cells. In particular, IKZF3 is critical for plasma cell development, and these data indicate that IKZF3 is important in multiple myeloma, a plasma cell malignancy, providing a mechanistic basis for therapeutic efficacy in this disorder. Moreover, the activity of lenalidomide in other B cell neoplasms, including mantle cell lymphoma and chronic lymphocytic leukemia, may be explained by high IKZF3 expression in these disorders. In contrast to the high expression and essentiality of IKZF1 and IKZF3 in mature B cells, somatic genetic inactivation of the IKZF1 and IKZF3 occurs in acute lymphoblastic leukemia, resulting in an accumulation of immature lymphoid progenitor cells (C. G. Mullighan et al., Nature 446, 758 (Apr. 12, 2007); S. Winandy et al., Cell 83, 289 (Oct. 20, 1995)). In T cells, ablation of IKZF3-mediated repression of IL2 gene expression provides a mechanism for increased IL2 production in response to lenalidomide. The teratogenicity of thalidomide and the efficacy of lenalidomide in MDS may be mediated by alternative substrates in different cellular lineages.

RING-based E3 ubiquitin ligases are characterized by a high specificity for their substrates and therefore represent promising drug targets in cancer and other diseases. Following the identification of an E3 ubiquitin ligase as a target of thalidomide and lenalidomide, inhibition of enzymatic activity would have seemed a more likely mechanism of action. The results reported herein reveal that lenalidomide modulates the activity of the CRL4-CRBN complex to increase ubiquitination of two transcription factors, IKZF1 and IKZF3 that would otherwise be considered "undruggable." A plant hormone, auxin, appears to act similarly, increasing the interaction between a ubiquitin ligase and a specific substrate, suggesting that this mechanism might be operative in additional biological contexts. Selective ubiquitination and degradation of specific targets provides a novel mechanism of therapeutic activity for proteins that are not otherwise amenable to small-molecule inhibition.

Figures 16A, 16B:
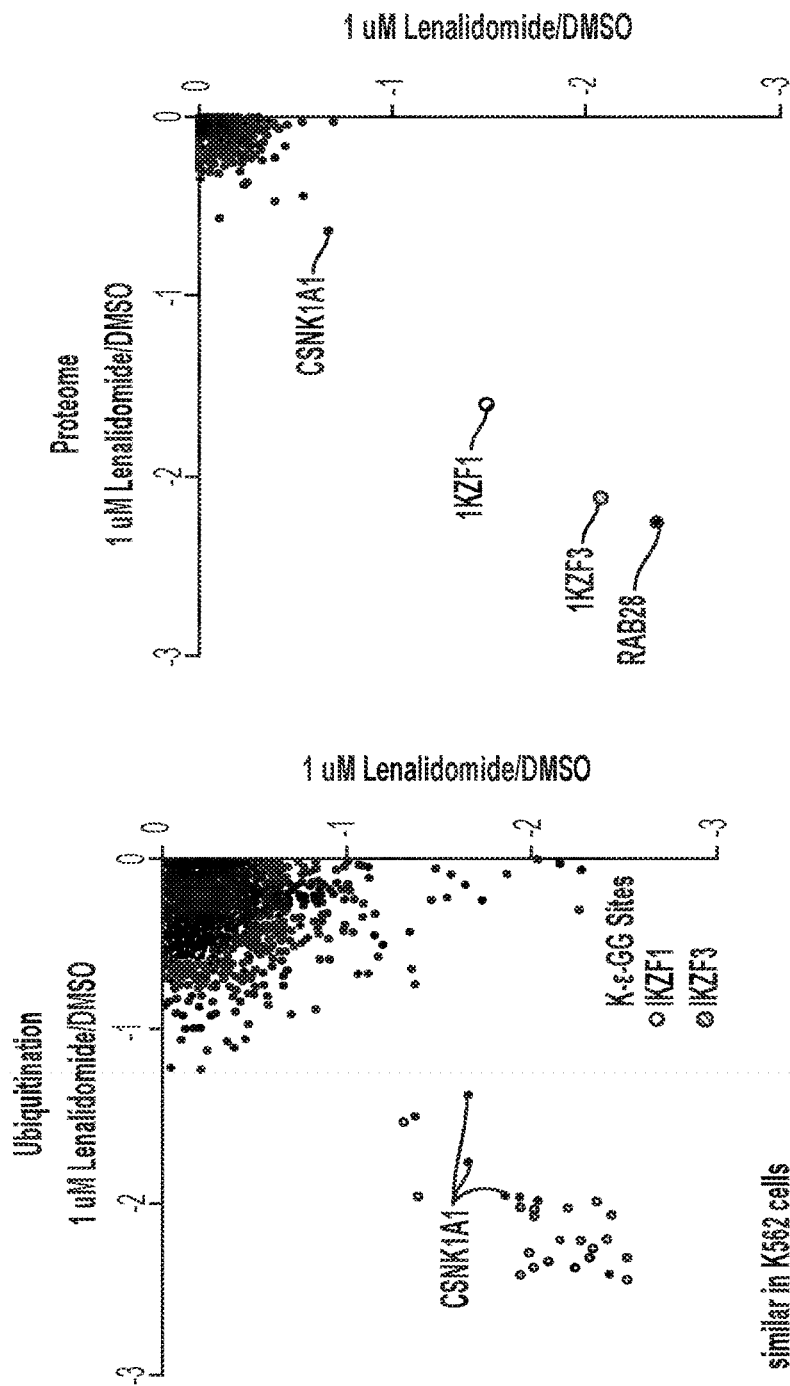
FIGS. 16A and 16B show results of SILAC-based quantitative MS studies.
Figure 17:
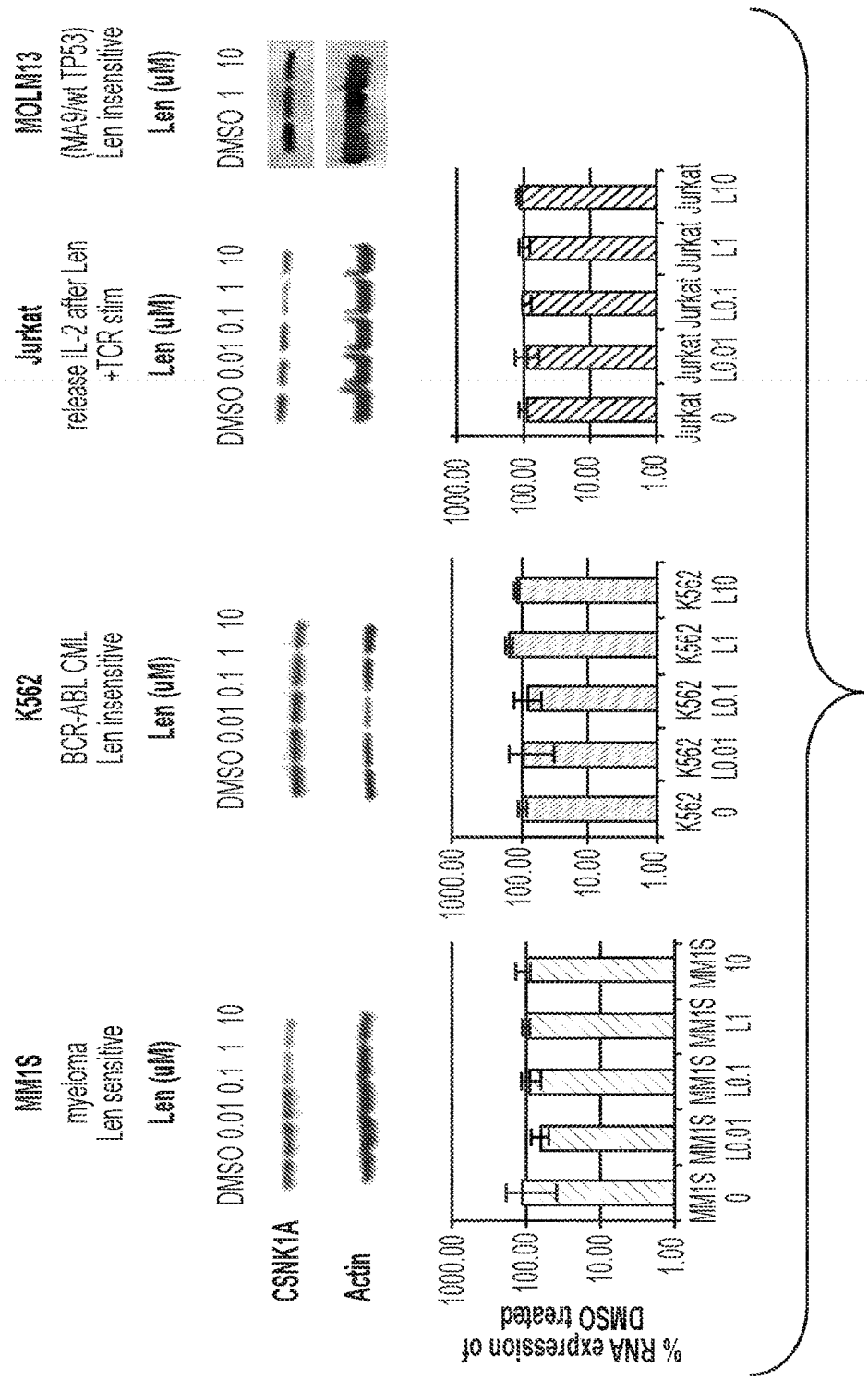
FIG. 17 shows that lenalidomide treatment results in a dose-dependent decrease in casein kinase 1A1 (CSNK1A) protein levels in lenalidomide sensitive multiple myeloma cells. No significant change is observed in RNA expression.
Figure 18:
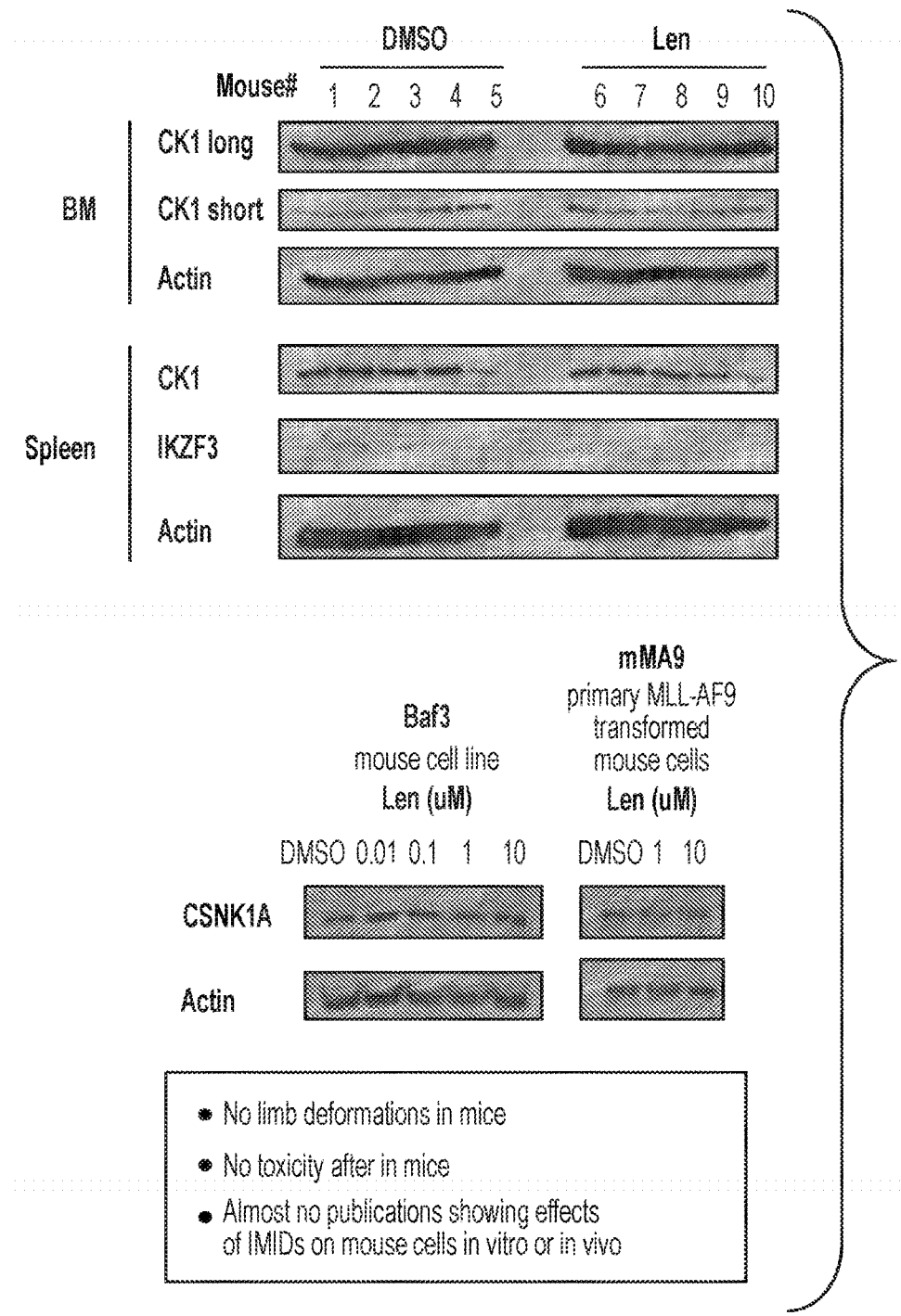
FIG. 18 shows that lenalidomide treatment did not alter casein kinase 1A1 (CSNK1A) protein levels in mice.
Figure 19:
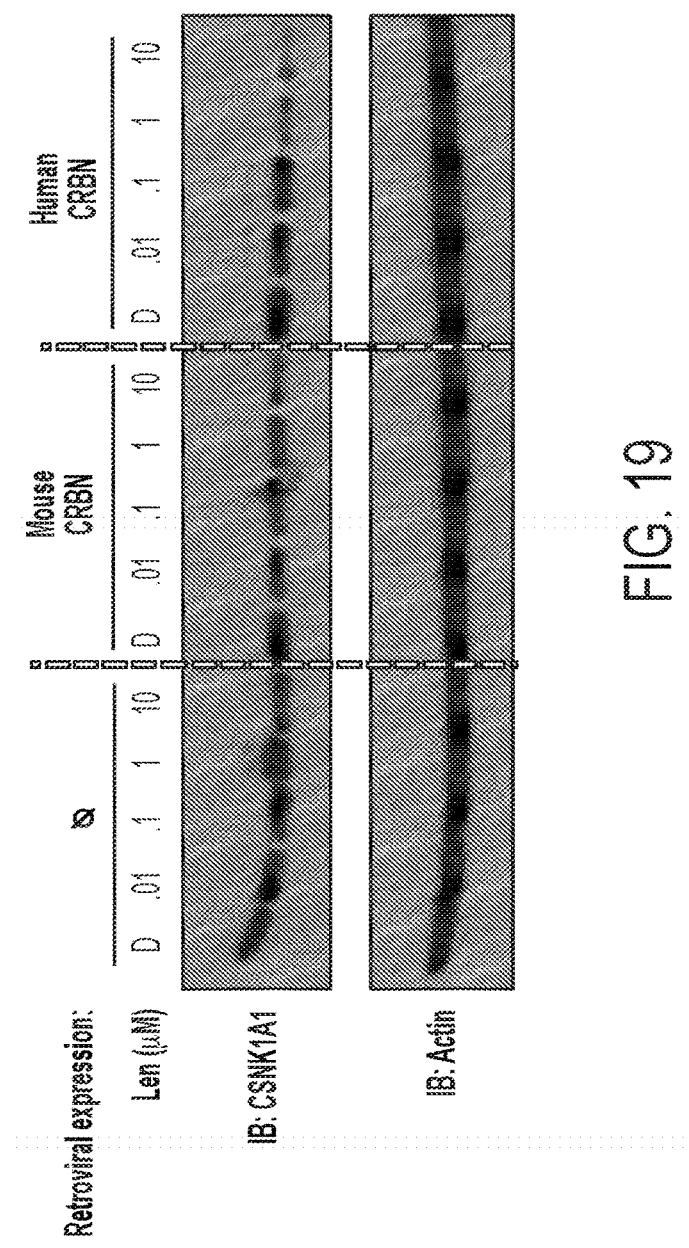
FIG. 19 shows that expression of human CRBN in murine cells was sufficient to confer lenalidomide sensitivity to CSNK1A1.

Example 7: Lenalidomide Treatment Reduced CSNK1A1 Levels in Murine Cells Over-Expressing Human CRBN To determine whether mouse and human cells responded similarly, cell lines were treated with lenolidomide (FIG. 16). Lenalidomide decreased CSNK1A levels in all human cell lines expressing CRBN (see FIG. 17). FIG. 18 shows that levels of the short and long forms of casein kinase were not reduced in bone marrow from mice treated with lenalidomide. Similarly, murine casein kinase 1 levels were not reduced in spleen in response to lenalidomide (FIG. 18). No change in CSKN1A levels was seen in Murine baf-3 cells or in primary MLL-AF9 transformed mouse cells. In contrast, lenalidomide treatment reduced CSNK1A1 levels in murine cells over-expressing human CRBN (FIG. 19). CSNK1A1 was used as a readout because CSNK1A1 decreased after being treated with Lenolidomide. hCRBN was clearly more sensitive to Lenalidomide than mCRBN (FIG. 19).

Example 8: Lenalidomide Induces Ubiquitination and Degradation of Casein Kinase 1A1 Via CRL4$^{CRBN}$ Lenalidomide is a highly effective treatment for myelodysplastic syndrome (MDS) with deletion of chromosome 5q (del(5q)), inducing cytogenetic remission in more than 50% of patients. No biallelic deletions or loss of function mutations on the remaining allele have been detected in any of the genes located in the commonly deleted regions of in del(5q) MDS, implying that del(5q) MDS is a haploinsufficiency disease. MDS patients without del(5q) are much less sensitive to lenalidomide, suggesting that haploinsufficiency for a gene on chromosome 5q causes selective sensitivity of the MDS cells to the drug. Recently, it has been demonstrated that lenalidomide acts to modulate CRBN-CRL4 E3 ubiquitin ligase. Ubiquitination and degradation of the transcription factors, IKZF1 and IKZF3, by lenalidomide is responsible for two major properties of IMiDs: growth inhibition of multiple myeloma cells and interleukin-2 release from T-cells. However, it is unlikely that degradation of these lymphoid transcription factors also accounts for therapeutic activity in del (5q) MDS. Instead, it is possible that ubiquitination of a different CRBN substrate in myeloid cells accounts for the efficacy of lenalidomide in del(5q) MDS.

In order to identify such substrates, SILAC (stable isotope labeling of amino acids in cell culture)-based quantitative mass spectrometry was applied to assess global changes in ubiquitination and protein levels in the myeloid cell line KG-1. Similar to the analysis in multiple myeloma, lenalidomide altered the ubiquitination and protein levels of a strikingly low number of proteins, demonstrating the highly specific effects of the drug on ubiquitin ligase function. Consistent with previous studies, lenalidomide treatment decreased ubiquitination of CRBN and increased ubiquitination of IKZF1, followed by the corresponding changes in protein levels. Aside from IKZF1, casein kinase 1A1 (CSNK1A1, also known as CK1α) had the greatest increase in ubiquitination and decrease in protein abundance following lenalidomide treatment. CSNK1A1 is encoded by a gene in the del(5q) commonly deleted region and has been shown to be a therapeutic target in AML, and is thus an attractive candidate for mediating the effects of lenalidomide in del (5q) MDS (FIGS. 20A, 20B and FIGS. 24A, 24B, 24C-1, 24C-2, and 24C-3).

Figure 20A:
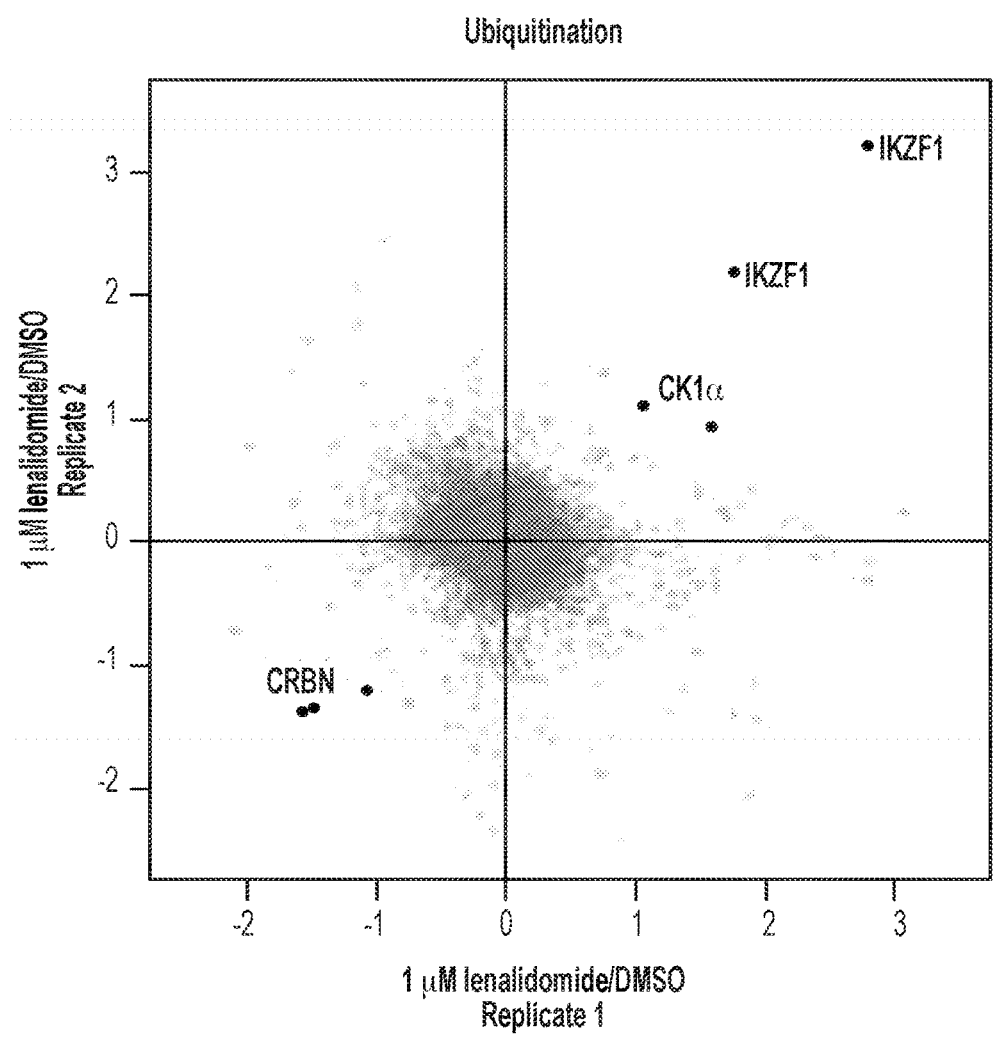
FIGS. 20A-20D show lenalidomide-induced changes in ubiquitination and protein levels in KG-1 cells.
Figure 20B:
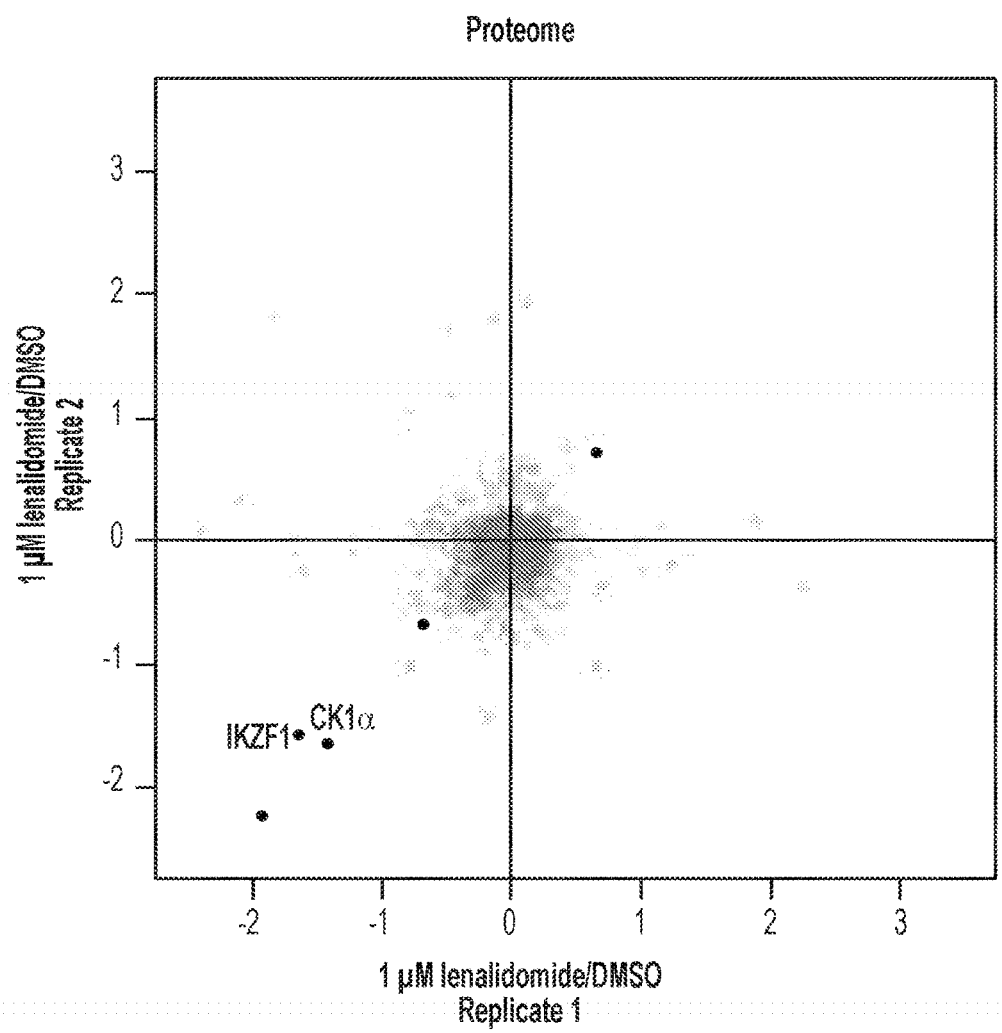
Figure 20C:
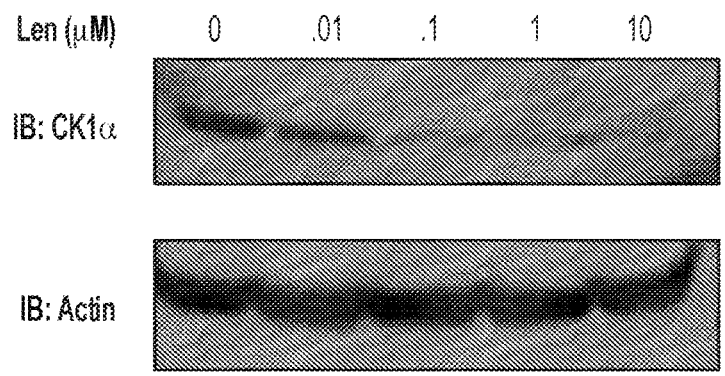
Figure 20D:
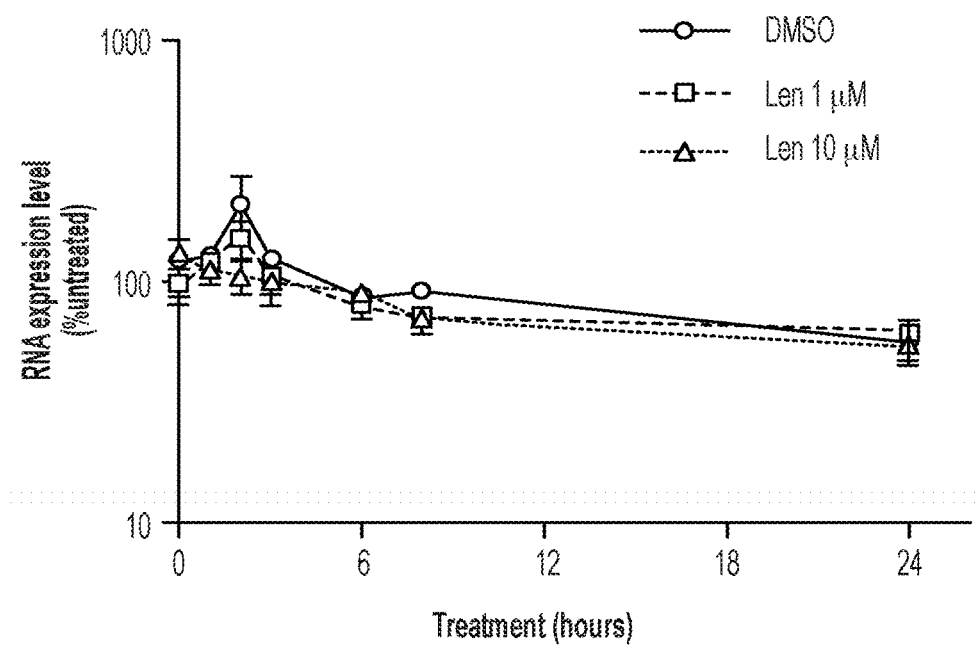
Figure 21D:
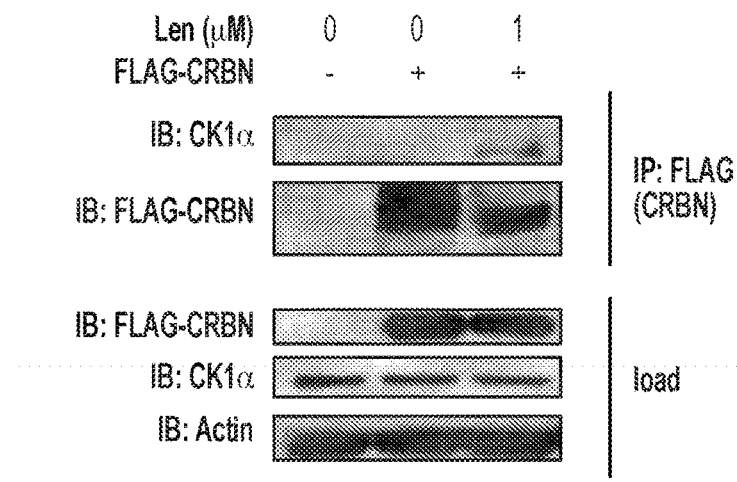
Figure 21E:
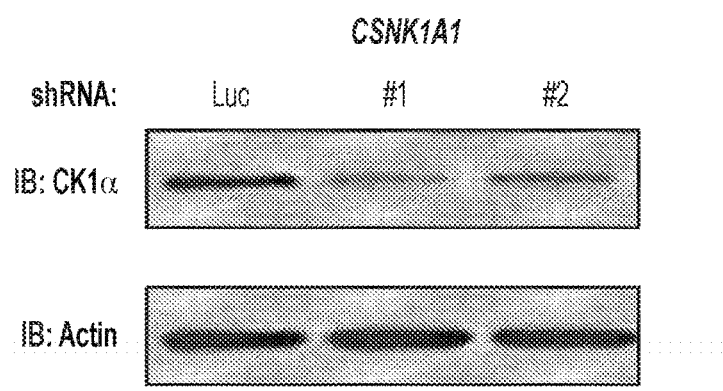

Based on the proteomics results, validation that CSNK1A1 is a lenalidomide-dependent target of the CRBN-CRL4 ubiquitin ligase was sought. It was confirmed that lenalidomide treatment decreased CSNK1A1 protein levels in multiple human cell lines in a dose-dependent fashion (FIGS. 20C, 24D, 25A-25B), decreased the half-life of the CSNK1A1 protein, and did not alter CSNK1A1 mRNA levels (FIGS. 20D and 25C). The lenalidomide-induced decrease in CSNK1A1 protein levels was abrogated by treatment with the proteasome inhibitor MG132 and the NEDD8-activating enzyme inhibitor, MLN-4924, which interferes with the activity of cullin-RING E3 ubiquitin ligases (FIG. 21A). Cells with homozygous genetic inactivation of the CRBN gene by CRISPR-Cas genome engineering were not responsive to lenalidomide (FIG. 21B). Finally, it was demonstrated that CSNK 1A1 co-immunoprecipitates with hemagglutinin (HA)-tagged CRBN, and that lenalidomide increases this association (FIG. 21D). Co-transfection of CRBN with HA-CSNK 1A1 promoted lenalidomide-induced ubiquitination of the tagged CSNK1A1 in 293T cells (FIGS. 21B, 21D). In aggregate, these experiments indicate that CSNK1A1 is a CRBN-CRL4 E3 ligase substrate that is ubiquitinated and degraded in the presence of lenalidomide.

Next, it was examined whether CK1α binds CRBN and is ubiquitinated by the CRL4$^{CRBN}$ E3 ubiquitin ligase. CK1α co-immunoprecipitated with FLAG-tagged CRBN only in the presence of lenalidomide (FIG. 21C). Lenalidomide treatment increased the ubiquitination of FLAG-CK1α in 293T cells (FIG. 21D).

The effects of CSNK1A1 depletion on cell proliferation were assessed. CSNK1A1 is a serine/threonine kinase with multiple cellular activities, including the suppression of TP53 and β-catenin activity. Complete loss of CSNK1A1 induces apoptosis in normal and leukemic stem cells via p53 activation, while heterozygous loss of CSNK1A1 causes stem cell expansion with β-catenin activation. Since p53 activation occurs when CSNK1A1 levels are less than 50% of normal, haploinsufficiency of CSNK1A1 in del (5q) MDS was thought to sensitize cells to a further decrease in CSNK1A1 expression. To address this hypothesis, primary human CD34+ hematopoietic stem and progenitor cells were transduced with lentiviral vectors expressing GFP, as well as CSNK1A1 or control shRNAs. Cells expressing CSNK1A1 shRNAs were depleted in the absence of treatment, confirming that CSNK1A1 depletion inhibited growth of hematopoietic cells. (FIGS. 21E, 21F-1, 21F-2, and 21F-3). The addition of lenalidomide enhanced the depletion of CSNK1A1 shRNA expressing cells, but not cells expressing control shRNAs, demonstrating that reduced CSNK1A1 levels sensitized hematopoietic cells to lenalidomide (FIGS. 21E, 21F-1, 21F-2, 21F-3, 26B, and 26C).

Figure 22A:
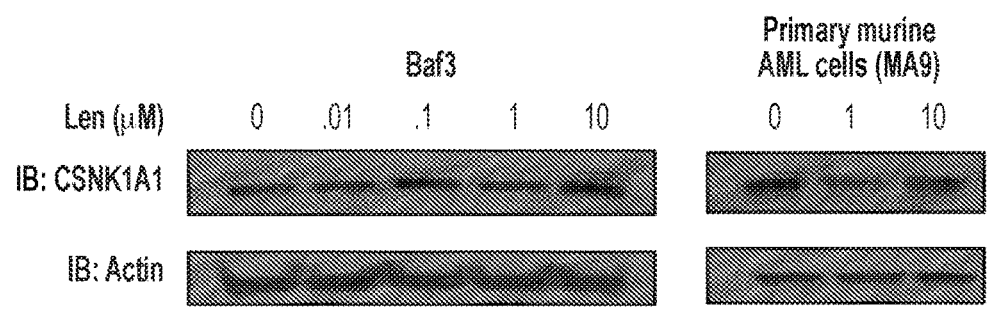
FIGS. 22A-22E show lenalidomide effects on murine cells.
Figure 22B:
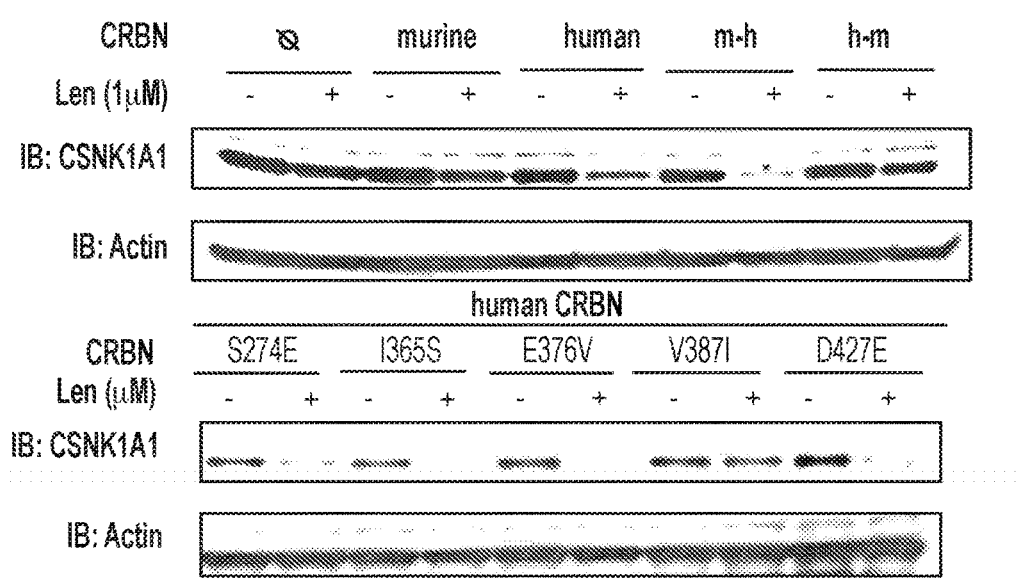
Figure 27A:
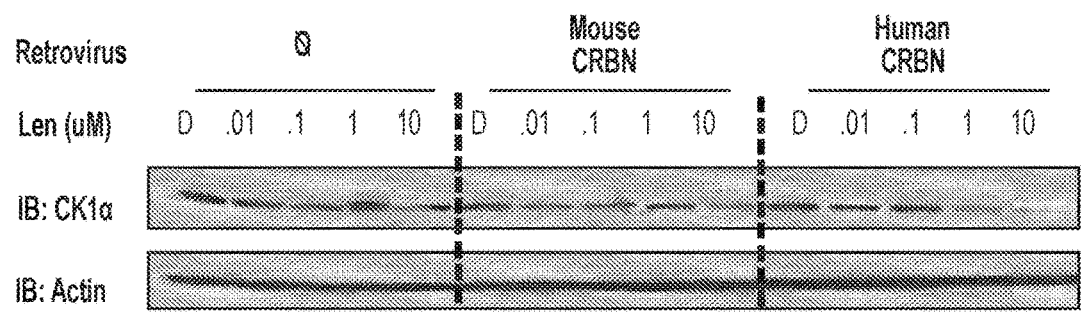
Figure 27B:
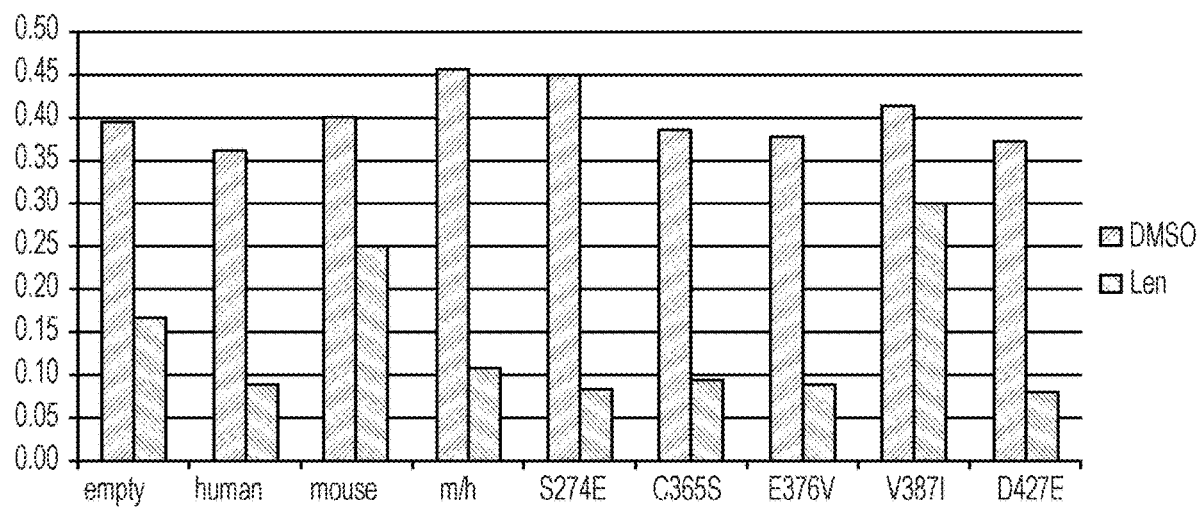

It was determined whether haploinsufficiency for Csnk1a1 sensitizes cells to lenalidomide in a genetically engineered mouse model. In initial experiments, it was found that lenalidomide did not decrease Csnk1a1 protein levels in murine Baf3 cells or primary murine leukemia cells treated with lenalidomide (FIGS. 22A, 27A, 27B). Mice did not develop the specific limb deformations observed in human embryos exposed to thalidomide and primary murine multiple myeloma did not respond to lenalidomide, suggesting that murine cells were intrinsically resistant to IMiDs. Since CRBN is a direct protein target of lenalidomide, it was examined whether expression of the human CRBN could confer drug sensitivity onto murine cells. Overexpression of human, but not murine CRBN, in murine cells resulted in a decrease of CSNK1A1 protein levels, implying amino acid differences between murine CRBN (mCRBN) and human CBRN (hCRBN) were responsible for species-specific response to lenalidomide (FIGS. 22B, 22C, 27A, 27B).

Figure 22C:
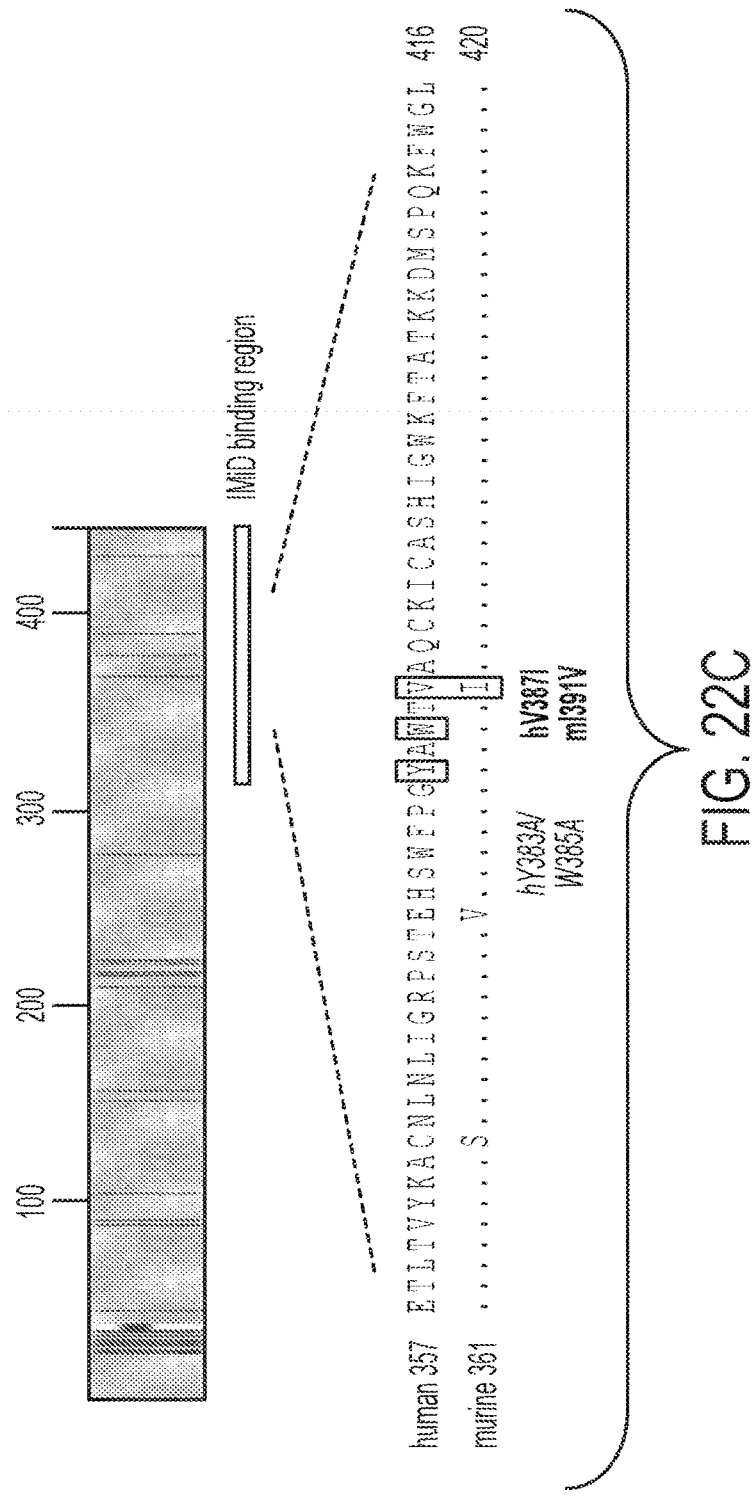
Figure 22D:
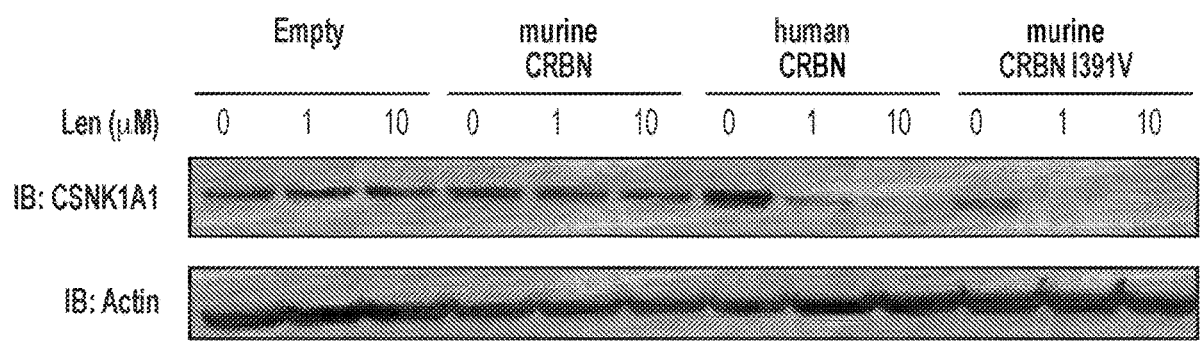
Figure 22E:
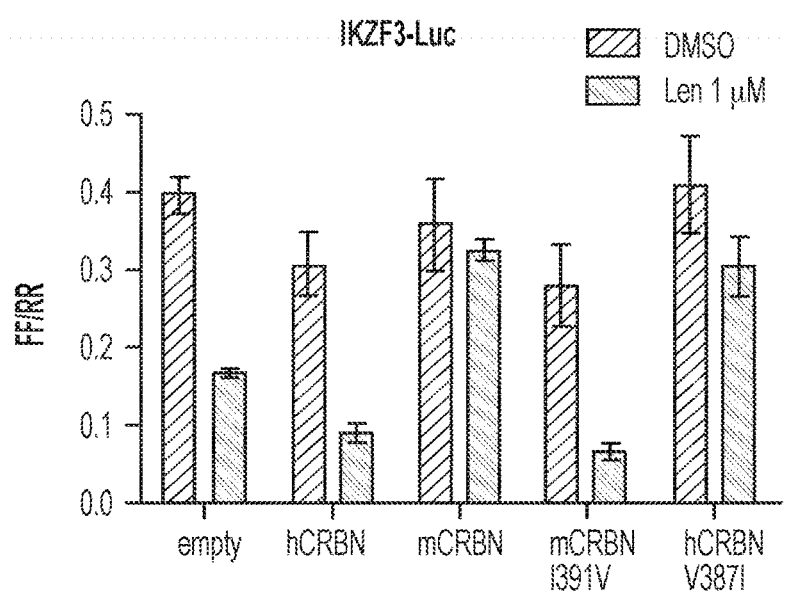

In order to determine the amino acids responsible for the differential sensitivity to lenalidomide between species, a series of human/mouse CRBN chimeric cDNAs and point mutations were tested. A single amino acid in the C-terminus of CRBN (residue I391(murine) and V387 (human)) was identified that determined the response to lenalidomide. (FIGS. 22C, 27C). Expression of a murine CRBN mutant (mCRBV$^{I391V}$) conferred sensitivity to lenalidomide-induced degradation of CSNK1A1 in Baf3 cells. (FIG. 22D). Conversely, expression of the reciprocal human CRBN$^{V387I}$ abrogated sensitivity to lenalidomide in human cells (FIG. 22E). Amino acid 387 of CRBN is located in the IMiD-binding region described by Ito et al., and in close proximity to the CRBN$^{V388A,W385A}$ mutant that does not bind to IMiDs.

Figure 23A:
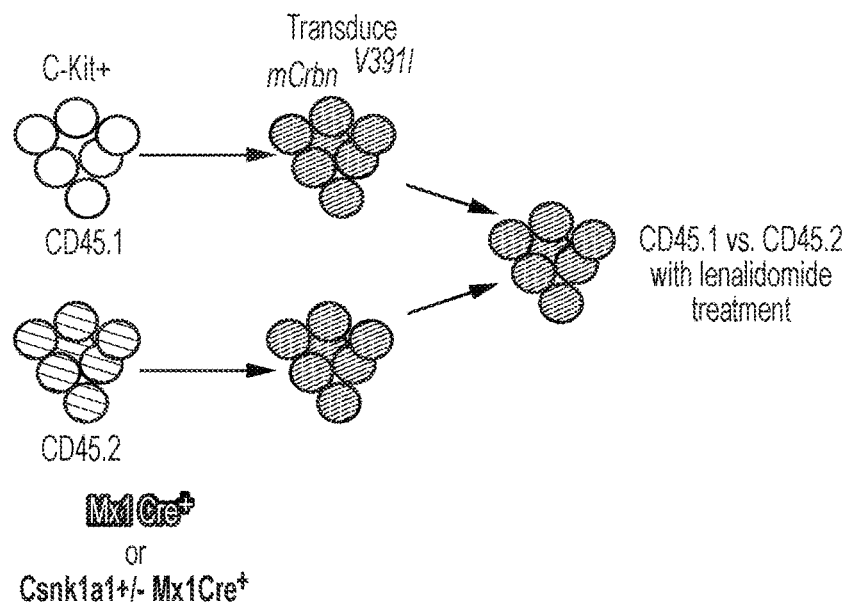
FIGS. 23A-23D show the evaluation of lenalidomide in murine CSNK1A1$^{+/-}$ cells.
Figure 23B:
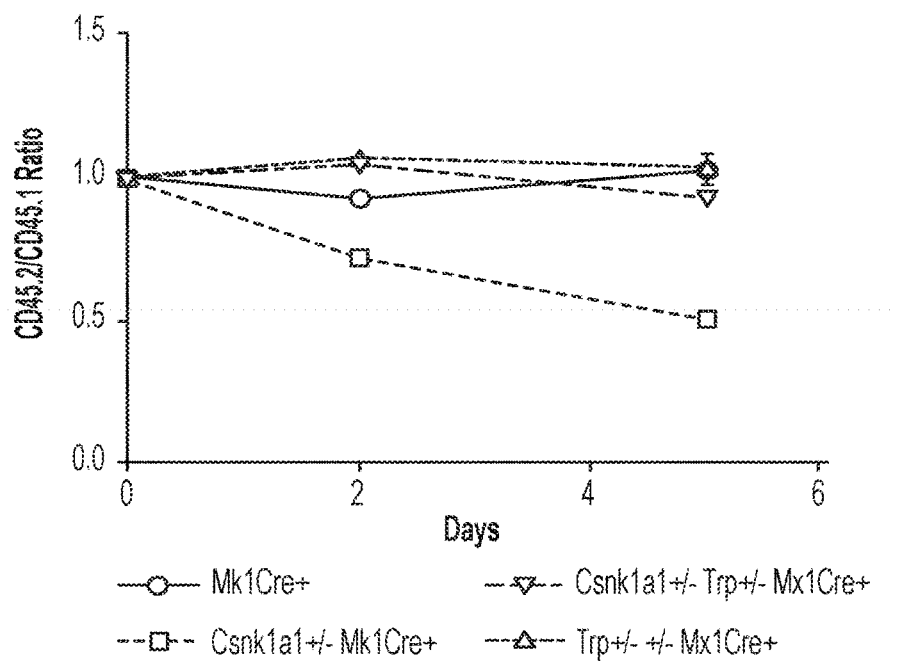
Figure 23C:
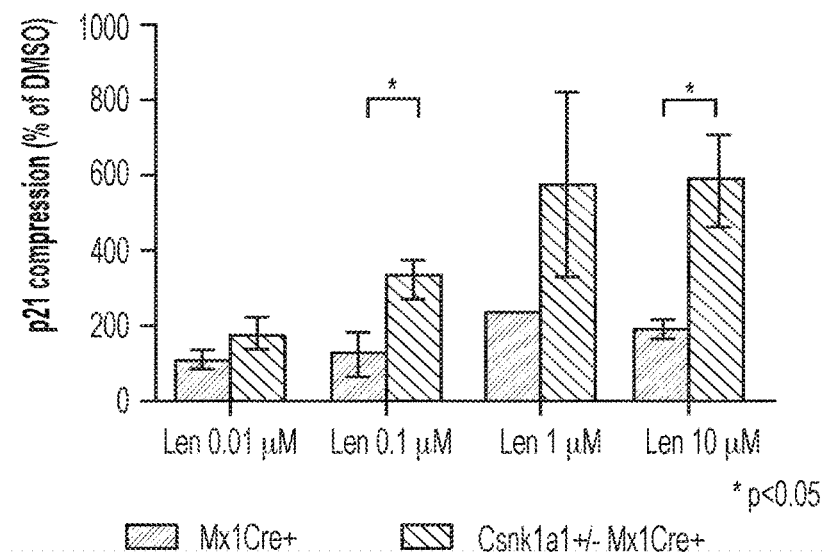
Figure 23D:
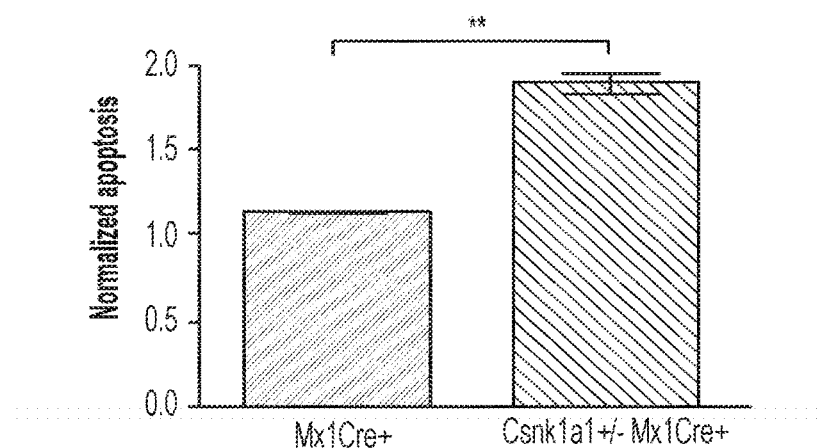
Figure 24A:
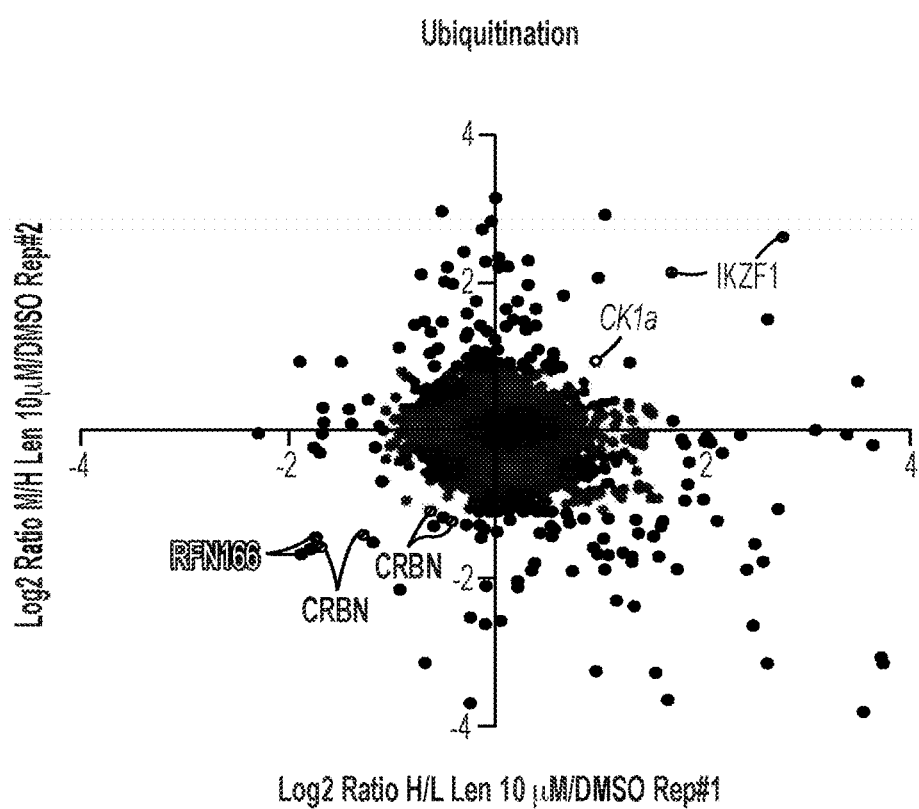
Figure 24B:
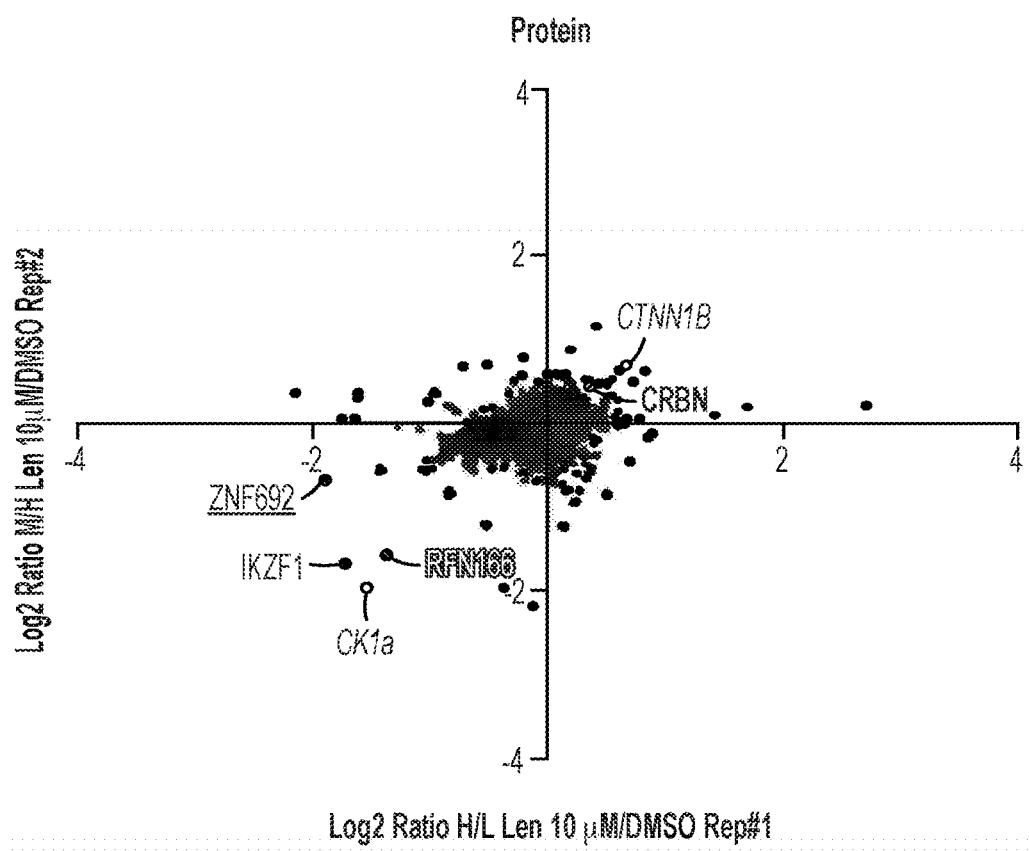
Figures 1, 24C:
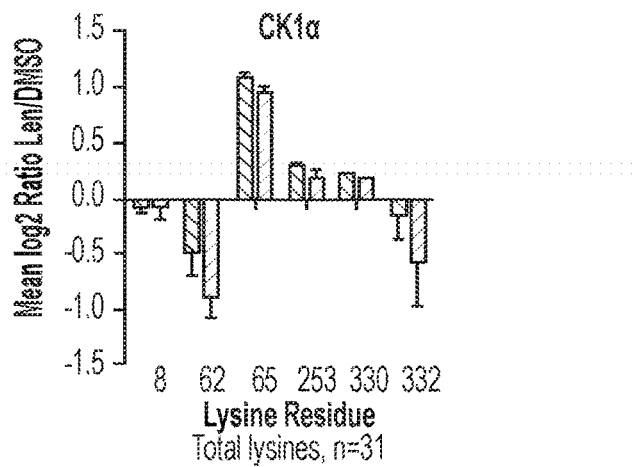
Figures 2, 24C:
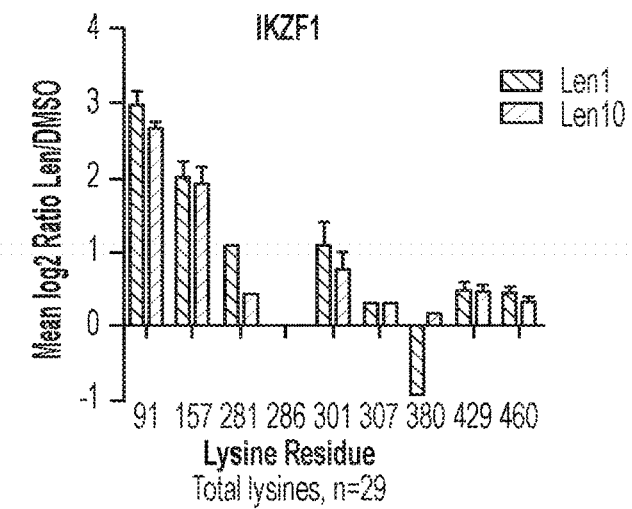
Figures 3, 24C:
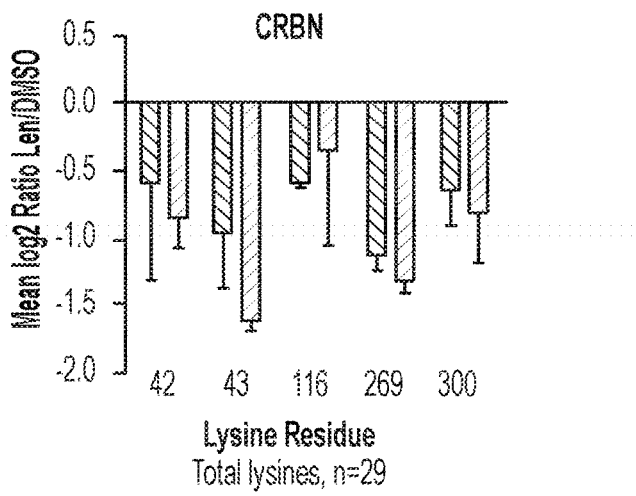
Figure 26A:
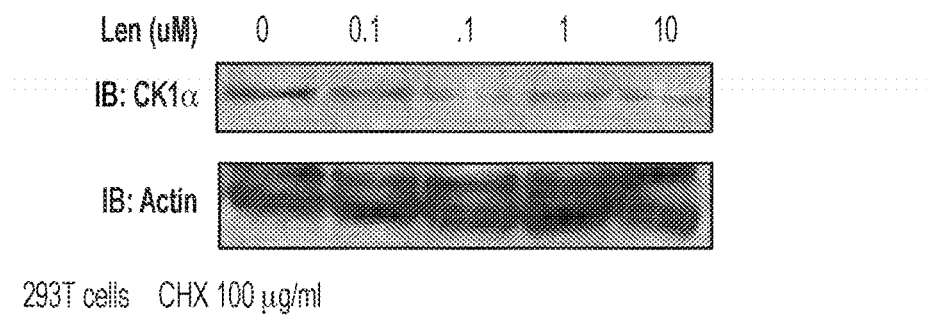
Figure 26B:
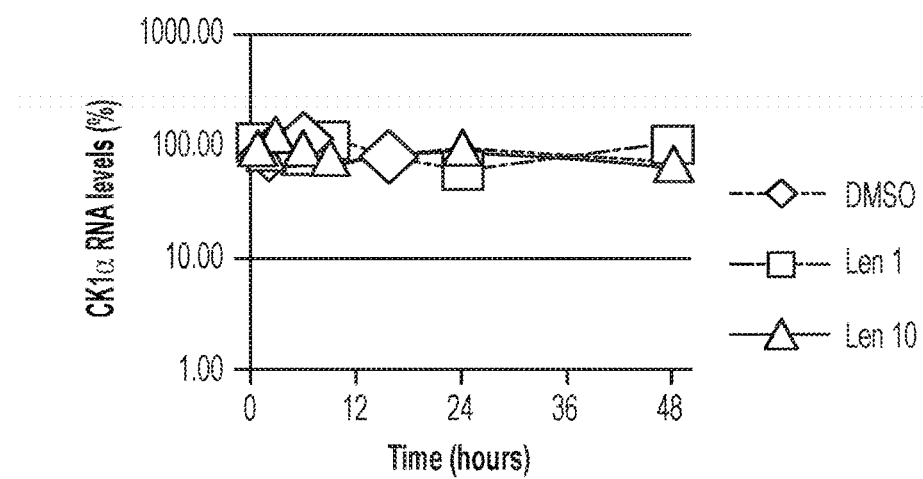
Figure 26C:
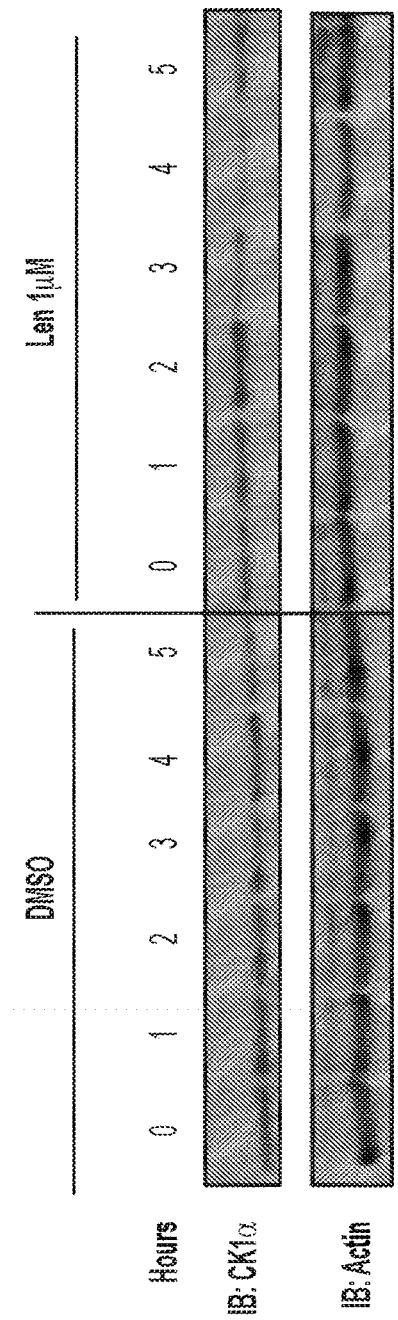
Figures 1, 26D:
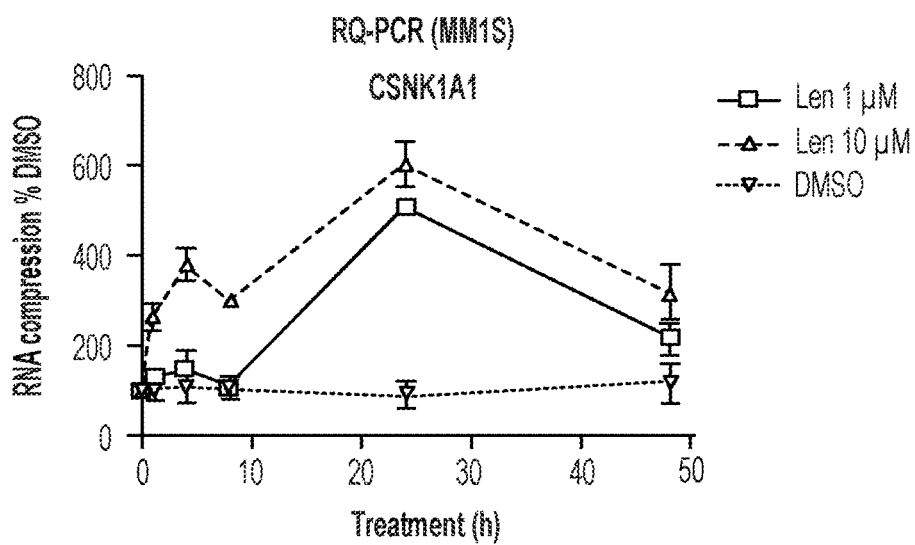
Figures 2, 26D:
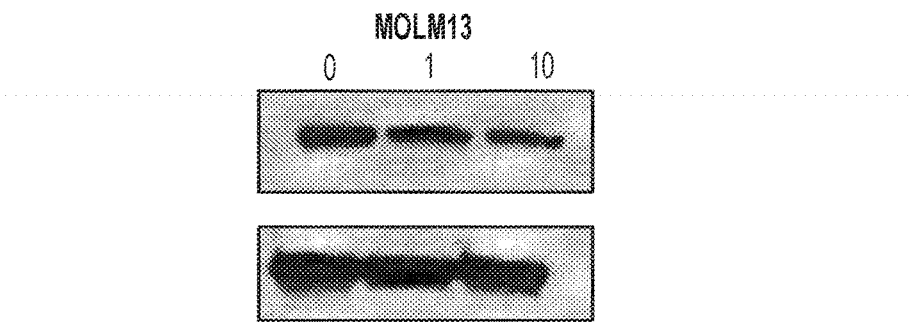

Having determined the mechanism of lenalidomide resistance in murine cells, the mCRBN$^{I391V}$ cDNA was expressed in hematopoietic cells from Csnk1a1 conditional knockout mice to determine the effects of Csnk1a1 haploinsufficiency on drug sensitivity. c-Kit+ hematopoietic stem and progenitor cells were isolated from Csnk1a1+/− and control littermates, transduced with a retroviral vector expressing mCRBN$^{I391V}$, and cultured in competition with a neutral comparator line, SJL, in the presence or absence of lenalidomide (FIG. 23A). Lenalidomide had no effect on the control cells, but Csnk1a1+/− cells were significantly depleted in the presence of lenalidomide (FIG. 23B). The enhanced sensitivity of Csnk1a1+/− cells to lenalidomide was associated with induction of the p53 target gene p21 (FIG. 23C) and rescued by heterozygous deletion of p53 (FIG. 23D), demonstrating a critical down-stream role for p53. These results were consistent with the clinical observation that p53 mutations conferred lenalidomide resistance in MDS with del(5q).

This study demonstrated that the efficacy of lenalidomide in del(5q) MDS was mediated by targeted degradation of a haploinsufficient protein, CSNK1A1. Loss of CSNK1A1 induces p53 activity, and other deleted genes on chromosome 5q, such as RPS14, which may further sensitize cells to p53 activation. Degradation of CSNK1A1 may also contribute to other clinical effects of lenalidomide such as myelosuppression. CSNK1A1 degradation may be involved in the clinical activity of lenalidomide in lymphoid malignancies, including the activated B-cell (ABC) subtype of diffuse large B-cell lymphoma, which requires CSNK 1A1 for constitutive NF-κB activity, and multiple myeloma cells.

The concept that genes within heterozygous deletions could cause vulnerabilities in cancer cells has been confirmed in these cell lines. Heterozygous deletion of CSNK1A1 was demonstrated to create such vulnerability in del(5q) MDS cells, and that lenalidomide-induced degradation of this protein resulted in major significant clinical efficacy. Induction of ubiquitination and degradation of other haploinsufficient proteins may provide a basis for the development of new targeted therapies in cancer.

Example 9: mCRBN$^{I391V}$ Knock-In Mice Responded to Lenalidomide

IMiDs, such as lenalidomide (Len) and pomalidomide (Pom), are structural and functional analogues of thalidomide that act as immunomodulators. Such agents are useful for the treatment of a variety of neoplastic and other diseases. Wild-type rodents do not show teratogenicity in response to IMiDs. Additionally, wild-type mouse cells do not degrade IKZF1/3 or CK1α in response to Len or Pom, and mouse multiple myeloma does not respond to IMiDs. However, mouse CRBN binds IMiDs. As reported herein, a I391V single point mutation renders mouse cells sensitive to IMiDs. A KI mouse of this single point mutation was generated to study the effects of IMiDs in vivo as described herein below.

Figure 28:
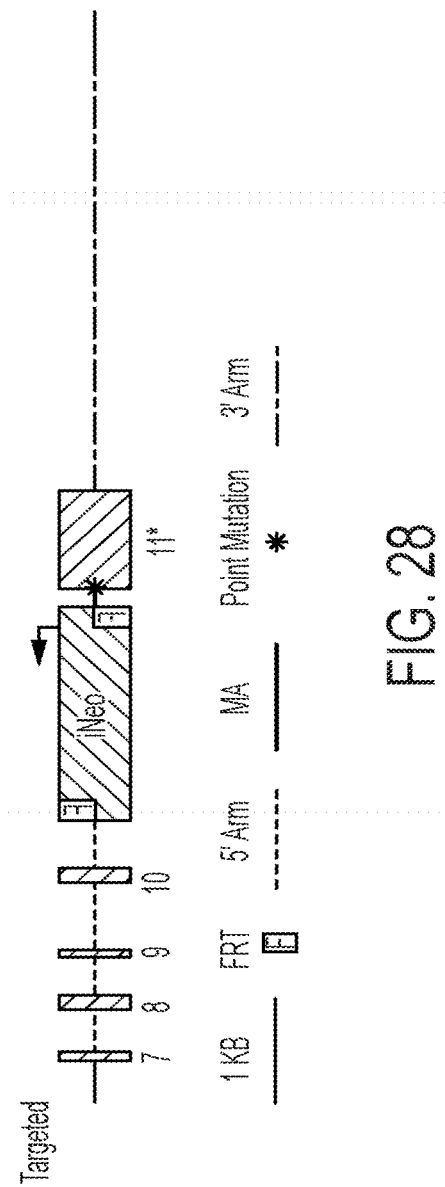
FIG. 28 is a schematic diagram of the targeting vector used for generating a CRBN$^{I391V/+}$ knock-in mouse.
Figure 29:
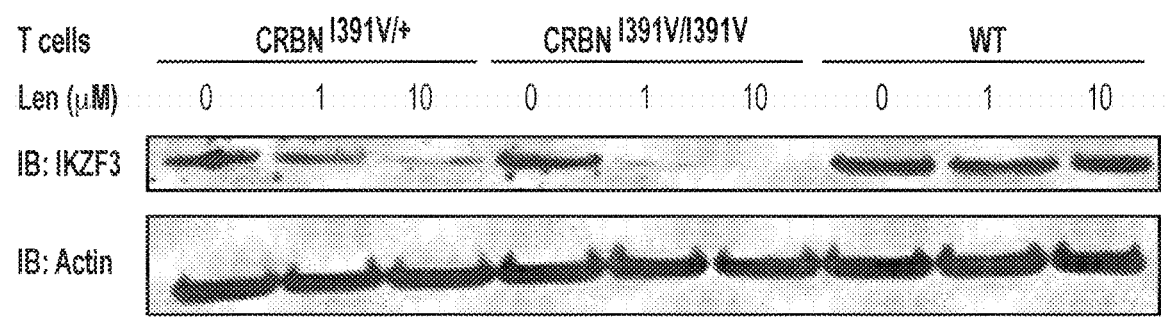
FIG. 29 is an immunoblot showing lenalidomide induced IKZF3 protein degradation in T cells isolated from heterozygous mouse (CRBN$^{I391V/+}$), homozygous knock-in mouse (CRBN$^{I391V/I391V}$) and wild type (WT) mouse. T cells were treated with lenalidomide (Len) at different concentrations (0, 1, or 10 µM). IKZF3 protein levels was detected by immunoblot (IB). Actin was included as a protein loading control. Lenalidomide-induced IKZF3 degradation resulted in increased IL-2 production (and mRNA) as shown in FIG. 30.
Figure 30:
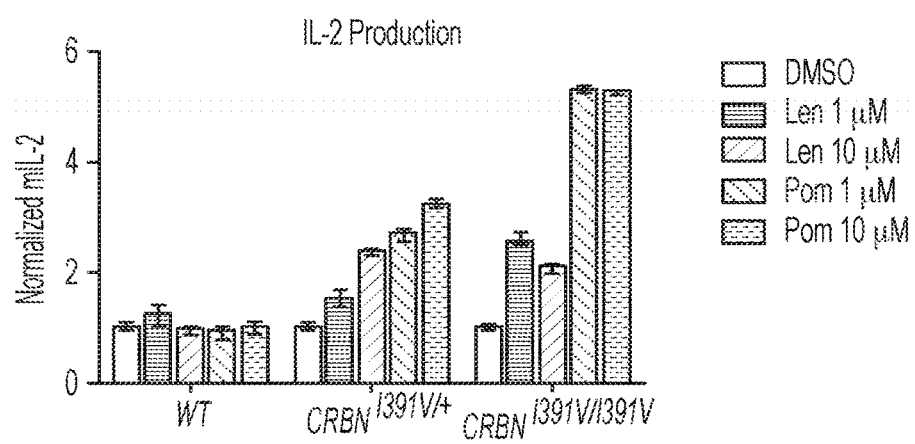
FIG. 30 is a graph that shows the effect of lenalidomide and its analog pomalidomide on Interleukin-2 (IL-2) production in CRBN$^{I391V/+}$), CRBN$^{I391V/I391V}$, and wild type (WT) murine T cells treated with 1 µM or 10 µM lenalidomide (Len) or pomalidomide (Pom).
Figure 31A:
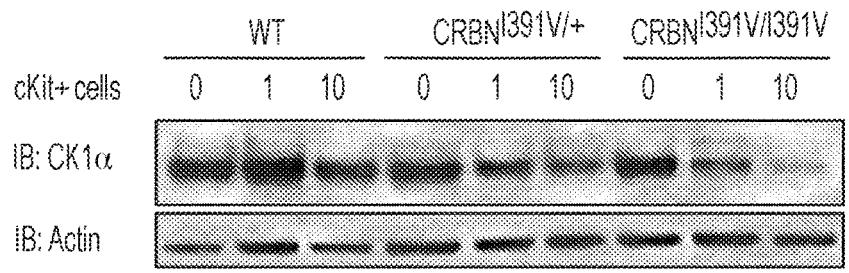
FIGS. 31A and 31B present immunoblots showing lenalidomide-induced casein kinase 1α (CK1α) degradation.
Figure 31B:
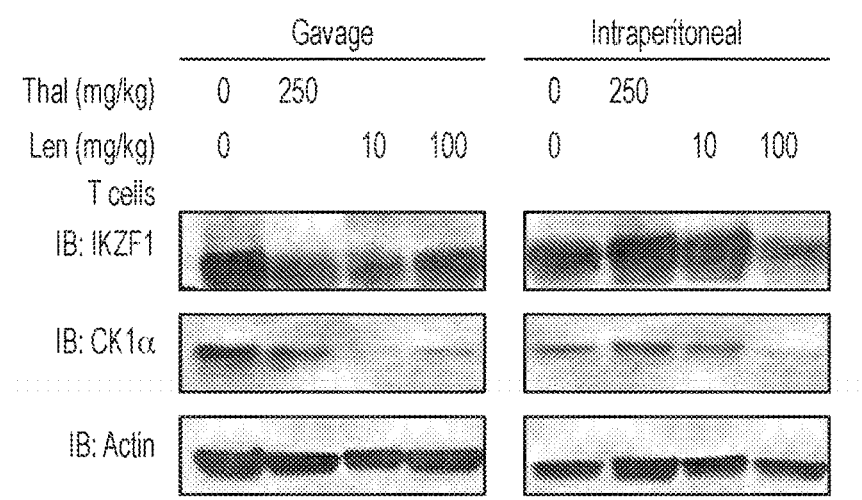
Figure 32:
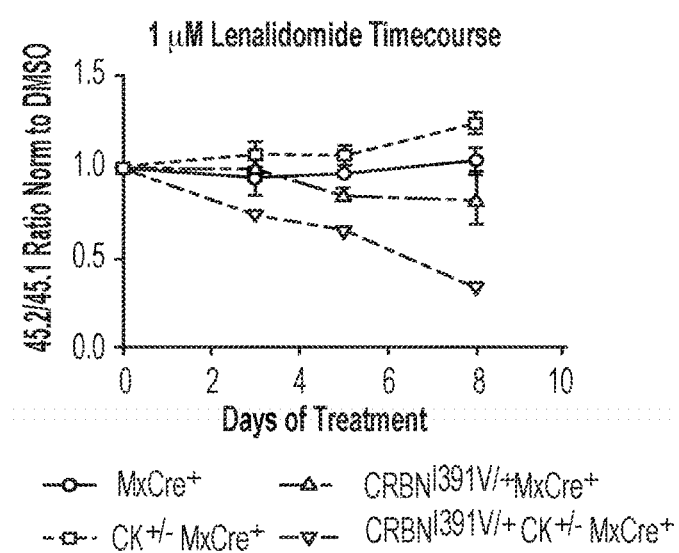
FIG. 32 is a graph showing results of in vitro competition experiments. Cells from mice of specified genotypes (all CD45.2) were mixed in a 1:1 ratio with CD45.1$^+$ cells from SJL strain mice. Cells from MxCre$^+$, CK$^{+/-}$MxCre$^+$, CRBN$^{I391V/+}$MxCre$^+$, and CRBN$^{I391V/+}$ CK$^+$MxCre$^+$ were subject to 1 µM lenalidomide treatment. The percent CD45.1 and CD45.2 cells was followed by flow cytometry over time following cell surface staining. mCRBN$^{I391V/+}$ Csnk1a1$^{+/-}$ cells were significantly depleted in the presence of lenalidomide

FIG. 28 shows a DNA construct used to generate a mCRBN$^{I391V}$ knock-in (KI) mouse. The construct included a single point mutation (I391V) in mouse endogenous CRBN locus (Neo cassette removed) and provided for the constitutive expression of CRBN. KI mice were viable in the homozygous state with no obvious defects. The mCRBN$^{I391V}$ KI mice were tested for responsiveness to lenalidomide and pomalidomide. In contrast to wild-type mice, expression of mCRBN$^{I391V}$ in mice conferred the same responsiveness to lenalidomide and pomalidomide as has been observed in humans. In particular, lenalidomide treatment induced IKZF3 degradation in T cells isolated from mCRBN$^{I391V}$ KI mice (FIG. 29). No IKZF3 degradation was observed in T cells isolated from wild type mice. T cells isolated from mCRBN$^{I391V}$ KI mice also displayed a dose-dependent increase in IL-2 production in response to Len and Pom (FIG. 30). Len also induced degradation of CK1α in cKit+ mCRBN$^{I391V}$ cells isolated from the KI mouse (FIG. 31A). In KI mice, Len and Thal induced degradation of IKZF1 and CK1α in T cells in vivo (FIG. 31B). In cell depletion experiment, Lenalidomide had no effect on the control cells, but mCRBN$^{I391V}$ Csnk1a1$^{+/-}$ cells were significantly depleted in the presence of lenalidomide (FIG. 32).

In sum, IKZF1/3 and CK1α were effectively degraded in I391V cells in response to Len or Pom. In addition, Len and Pom treatment increased IL-2 mRNA and protein levels when assayed by ELISA. Moreover, a competitive disadvantage of CRBN$^{I391V}$ CK1α$^{+/-}$ cells was noted with Len treatment.

The results described in Examples 1-6 were carried out using the following methods and materials.

Synthesis of Lenalidomide Derivative

NMR spectra were recorded on Bruker DRX-600, DRX-500, and AMX-400 instruments and calibrated using residual undeuterated solvent as an internal reference (CHCl$_3$ @ 7.26 ppm 1H NMR, 77.16 ppm 13C NMR). The following abbreviations (or combinations thereof) were used to explain the multiplicities: s=singlet, d=doublet, t=triplet, ap=apparent, m=multiplet, b=broad, ABq=AB quartet.

Compounds were purified by mass-directed purification on a Waters Autopurification system (Milford, Mass.). Collection was triggered on the (M+H)+ and (M+Na)+ ions on a ZQ mass spectrometer using positive electrospray ionization. Mobile phase A consisted of 0.2% ammonium hydroxide in water, while mobile phase B consisted of 0.2% ammonium hydroxide in acetonitrile. An initial hold at 0% mobile phase B for 1.0 minutes was followed by a gradient from 0% to 100% mobile phase B over 11.0 minutes at 24 mL/min. A 2.0 mL/min at-column dilution was present using 100% acetonitrile as well as a 2.0 mL/min make-up flow using 90/10/0.1 methanol/water/formic acid. An XBridge OBD Prep C18, 5 µm, 19×100 mm column was used at room temperature.

Preparation of N-butyl-4-((2-(2,6-dioxopiperidin-3-yl)-1-oxoisoindolin-4-yl)amino)butanamide (Lena-derivative)

Lenalidomide (30 mg, 0.116 mmol) and succinic semialdehyde (0.075 ml, 0.116 mmol) (15% in water) were dissolved in DMF (0.4 ml) and AcOH (8.16 µl). The reaction was stirred at room temperature for 1 hour. Sodium triacetoxyborohydride (36.8 mg, 0.174 mmol) was then added and the reaction is maintained at room temperature. After 4 hours, additional succinic semialdehyde (0.075 ml, 0.116 mmol) and sodium triacetoxyborohydride (36.8 mg, 0.174 mmol) were added and the reaction was stirred for a further 16 hours at room temperature. The reaction mixture was diluted with MeOH, concentrated and purified by HPLC purification to afford the desired carboxylic acid (4-((2-(2,6-dioxopiperidin-3-yl)-1-oxoisoindolin-4-yl)amino)butanoic acid) (16.2 mg, 41%). MS (ESI) calcd for C$_{17}$H$_{19}$N$_3$O$_5$ [M+H]+: 345. Found: 346. The Lenalidomide carboxylic acid derivative (7 mg, 0.020 mmol) was dissolved in DMF (0.5 mL). N-Hydroxysuccinimide (2.333 mg, 0.020 mmol) and 1-ethyl-3-(3-dimethylaminopropyl) carbodiimide (5.83 mg, 0.030 mmol) were then added. After 15 minutes, n-butylamine (10.02 µL, 0.101 mmol) was added. The reaction mixture was concentrated and purified by HPLC purification to afford the desired amide (lena-derivative) (2.6 mg, 32%). MS (ESI) calcd for C$_{21}$H$_{28}$N$_4$O$_4$ [M+H]+: 400. Found: 401. $^1$H NMR (300 MHz, M CD3OD) δ 8.51 (bs, 1H), 7.31 (ap t, J=7.8 Hz, 1H), 7.06 (d, J=7.5 Hz, 1H), 6.81 (d, J=8.1 Hz, 1H), 5.14 (dd, J=13.3, 5.2 Hz, 1H), 4.30, 4.23 (ABq, J$_{AB}$=16.9 Hz, 2H), (3.29-3.02 (m, 4H), 2.97-2.69 (m, 2H), 2.57-2.35 (m, 1H), 2.29 (ap t, J=7.3 Hz, 2H), 2.21-2.07 (m, 1H), 1.99-1.84 (m, 2H), 1.61-1.17 (m, 4H), 0.90 (t, J=7.2 Hz, 3H).

Immobilization of the Lenalidomide Derivative onto Affigel Beads

The solid-phase beads used in small molecule immobilization were Affigel 102 (Bio-Rad) with a loading level of 12 µmol/mL suspension. The bead suspension (1.0 mL) was transferred to a 2.0 mL eppendorf tube and washed with DMSO (6×1.5 mL). The beads were then suspended in anhydrous DMSO (0.5 mL).

The lenalidomide-derived carboxylic acid (4-((2-(2,6-dioxopiperidin-3-yl)-1-oxoisoindolin-4-yl)amino)butanoic acid) (0.277 mL, 10 µmol) was dissolved in DMSO (0.5 mL) and to this were added N-hydroxysuccinimide (1.151 mg, 10.00 µmol) and 1-ethyl-3-(3-dimethylaminopropyl)carbodiimide (2.88 mg, 15.00 µmol). After 45 minutes further N-hydroxysuccinimide (4 mg, 35 µmol) and 1-ethyl-3-(3-dimethylaminopropyl)carbodiimide (6 mg, 31 µmol) were added and the reaction mixture was stirred for a further 60 minutes. At this point LC-MS indicated 60% of the carboxylic acid had been activation with N-hydroxysuccinimide. To achieve a 12.5% loading level of the Affigel beads, 1.5 µmol of activated compound was added to the suspended beads. Thus, the activated acid solution was added to the bead suspension followed by triethylamine (8.36 µL, 60.0 µmol). The suspension was then vortexed at room temperature for 1 hour and the depletion of free activated bait molecule was monitored by LC-MS. After the immobilization, the vials were centrifuged, the supernatant was removed and the beads were washed with DMSO (3×2 mL) and H$_2$O (3×2 mL). The beads were subsequently suspended in PBS (0.8 mL) and stored at 4° C. before use.

SILAC Media Preparation and Cell Culture Conditions

All standard SILAC media preparation and labeling steps were as previously described (E. Ong, Nature protocols 1, 2650 (2006)) with the addition of light proline to prevent the conversion of arginine to proline (S. C. Bendall et al., Mol Cell Proteomics 7, 1587 (September, 2008)). Briefly, L-methionine and 200 mg/L of L-Proline were added to base media according to standard formulations for RPMI (Caisson Labs) or DMEM (Caisson Labs). This base media was divided into three and to each added l-arginine (Arg0) and l-lysine (Lys0) (light), 13C614N4-l-arginine (Arg6) and 4,4,5,5-D4-l-lysine (Lys4) (medium) or 13C615N4-l-arginine (Arg10) and 13C615N2-l-Lysine (Lys8) (heavy) to generate the three SILAC labeling mediums. Each medium with the full complement of amino acids at the standard concentration for each media, was sterile filtered through a 0.22µ filter (Milipore, Bedford Mass.). Each cell type was grown in the corresponding labeling media, prepared as described above, supplemented with 2 mM L-glutamine (Gibco), and 10% dialyzed fetal bovine serum (Sigma) plus antibiotics (Gibco), in a humidified atmosphere with 5% CO2 in air. Cells were grown for at least six cell divisions in labeling media.

Biochemical Purification with Lenalidomide-Derivative Beads

Separate cultures of K562 cells SILAC labeled either with L-arginine and L-lysine (light) or L-arginine-13C6 and L-lysine-13C6-15N2 (heavy) were lysed in ice-chilled Mod-RIPA buffer containing 1% NP-40, 0.1% Na deoxycholate, 150 mM NaCl, 1 mM EDTA, 50 mM Tris, pH 7.5, and protease inhibitors (Complete™ tablets, RocheApplied Science, Indianapolis, Ind.). Lysates were vortexed intermittently while chilled on ice for 10 min and clarified by spinning at 14,000×g. Protein concentrations of light and heavy lysates were estimated with the Protein Assay Dye Reagent Concentrate (Biorad, Hercules Calif.) and equalized. The protein concentrations of lysates varied between 1.7 to 2.2 mg/mL, affinity enrichments were performed in lysate volumes of 1.4 mL in a 1.5 mL microcentrifuge tube.

Lenalidomide (in DMSO) at 100-fold excess over the amount of lenalidomide-derivative on beads was added to 2 mg of light lysate. An equal volume of DMSO was then added to 2 mg of heavy lysate as a control and pre-incubated for 30 minutes. Thirty microliters of a 50% slurry in phosphate buffered saline (PBS) of lenalidomide-derivative bead was added to both light and heavy lysates.

Affinity enrichments were incubated overnight (approx. 16 hrs) on an end-over-end rotator at 4° C. Following incubation, the tubes were spun at 1000×g on a benchtop centrifuge to pellet the beads. The supernatant was aspirated, taking care to avoid disturbing the beads. Each tube in a set was washed with ModRIPA buffer twice to remove excess soluble small molecule competitor. Beads from the two tubes were then be combined for an extra washing step in ModRIPA. After the third and final wash, beads were collected by spinning at 1000×g and the wash aspirated leaving approximately 20 µL of buffer in the tube.

The experiment was done in process replicate in which the labels were swapped, with lenalidomide being pre-incubated in the heavy and DMSO in the light.

1D-SDS-PAGE and MS Analysis for Lenalidomide-Protein Interaction Studies.

Proteins enriched in SILAC affinity pull-downs were reduced and alkylated, on bead, in 2 mM DTT and 10 mM iodoacetamide respectively. One part LDS buffer (Invitrogen) was added to three parts sample (including beads) and tubes heated to 70° C. for 10 minutes. Proteins were resolved on a 4-12% gradient 1.5 mm thick Bis-Tris gel with MES running buffer (Nupage, Invitrogen) and Coomassie stained (Simply Blue, Invitrogen). Gel lanes were excised into six pieces and then further cut into 1.5 mm cubes. The gel pieces were further destained in a solution containing 50% EtOH and 50% 50 mM ammonium bicarbonate, then dehydrated in 100% EtOH before addition of sufficient trypsin (12.5 ng/µL) to swell the gel pieces completely. An additional 100 µL of 50 mM ammonium bicarbonate was added before incubating at 37° C. overnight on a thermomixer (Eppendorf). Enzymatic digestion was stopped by the addition of 100 µL of 1% TFA to tubes. A second extraction with 300 µL of 0.1% TFA was combined with the first extract and the peptides from each gel slice cleaned up on C18 StageTips (Rappsilber et al., *Nature protocols* 2, 1896 (2007)). Peptides were eluted in 50 µL of 80% acetonitrile/0.1% TFA and dried down in an evaporative centrifuge to remove organic solvents. The peptides were then resuspended by vortexing in 7 µL of 0.1% TFA and analyzed by nanoflow-LCMS with an Agilent 1100 with autosampler and a LTQ Orbitrap. Peptides were resolved on a 10 cm column, made in-house by packing a self-pulled 75 µm I.D. capillary, 15 µm tip (P-2000 laser based puller, Sutter Instruments) column with 3 µm Reprosil-C18-AQ beads (Dr. Maisch GmbH, Ammerbuch-Entringen, Germany) with an analytical flowrate of 200 nL/min and a 58 min linear gradient (~0.57% B/min) from 0.1% formic acid in water to 0.1% formic acid/90% acetonitrile. The run time was 108 min for a single sample, including sample loading and column reconditioning. An MS method was used a with a master Orbitrap full scan (60,000 resolution) and data dependent LTQ MS/MS scans for the top five precursors (excluding z=1) from the Orbitrap scan. Each cycle was approximately 2 secs long.

Identification and Quantification of Proteins for Lenalidomide-Protein Interaction Studies All mass spectra were analyzed with Max Quant software version 1.1.1.36[4]. using a human IPI database v3.68. MS/MS searches for the proteome data sets were performed with the following parameters: Oxidation of methionine and protein N-terminal acetylation as variable modifications; carbamidomethylation as fixed modification. Trypsin/P was selected as the digestion enzyme, and a maximum of 3 labeled amino acids and 2 missed cleavages per peptide were allowed. The mass tolerance for precursor ions was set to 20 p.p.m. for the first search (used for nonlinear mass re-calibration) and 6 p.p.m. for the main search. Fragment ion mass tolerance was set to 20 p.p.m. For identification a maximum FDR of 1% was applied separately on protein, peptide and PTM-site level. 2 or more unique/razor peptides were required for protein identification and a ratio count of 2 or more for protein quantification per replicate measurement.

CRBN-Protein Interaction Studies

MMS1 cells stably expressing FLAG- or HA-tagged CRBN were grown for 2 weeks (~6 cell doublings) in RPMI depleted of L-arginine and L-lysine (Caisson Labs Inc.) and supplemented with 10% dialyzed FBS (Sigma) and amino acids as described above to generate light-, medium- and heavy-labeled cells. FLAG-CRBN expressing cells were cultured in light media, HA-CRBN expressing cells were grown in medium and heavy media. On day 14, HA-CRBN expressing cells grown in medium media were treated with DMSO and HA-CRBN cells grown in heavy media with 1 µM lenalidomide for 6 hours. For a second replicate labels were swapped such that HA-tagged CRBN expressing cells grown in medium media were treated with lenalidomide and cells grown in heavy media treated with DMSO. Cells were lysed in IP lysis buffer (Pierce) containing protease and phosphatase inhibitor cocktail (Pierce). For immunoprecipitation of HA-tagged proteins, 1000 µg protein was incubated together with HA-Tag Rabbit mAb Sepharose (C29F4) Bead Conjugate (Cell Signaling) over night at 4° C. in the presence of 1 µM lenalidomide or DMSO. Lysates of FLAG-CRBN expressing cells served as negative control to exclude non-specific binding to the anti-HA sepharose conjugates used for immunoprecipitation. For a schematic presentation of the experiment see FIG. 4.

1D-SDS-PAGE and MS Analysis for CRBN-Protein Interaction Studies.

The beads from immunopurification samples were washed once with IP lysis buffer (Pierce), then the three different lysates of each replicate combined, washed again and reduced and alkylated, on bead, in 2 mM DTT and 10 mM iodoacetamide respectively. One part LDS buffer (Invitrogen) was added to three parts sample (including beads) and tubes heated to 70° C. for 10 minutes. Proteins were resolved on a 4-12% gradient 1.5 mm thick Bis-Tris gel with MES running buffer: 50 mM (2-[N-morpholino]ethanesulfonic acid); 50 mM Tris base; 1 mM EDTA; 1% (w/v) SDS (Nupage, Invitrogen) and Coomassie stained (Simply Blue, Invitrogen). Gel lanes were excised into nine pieces and then further cut into 1.5 mm cubes. The gel pieces were further destained in a solution containing 50% EtOH and 50% 50 mM ammonium bicarbonate, then dehydrated in 100% EtOH before addition of sufficient trypsin (12.5 ng/µL) to swell the gel pieces completely. An additional 100 µL of 50 mM ammonium bicarbonate was added before incubating at 37° C. overnight on a thermomixer (Eppendorf). Enzymatic digestion was stopped by the addition of 100 µL of 1% trifluoracetic acid (TFA) to tubes. A second extraction with 300 µL of 0.1% TFA was combined with the first extract and the peptides from each gel slice cleaned up on C18 StageTips (Rappsilber et al., Nature protocols 2, 1896 (2007)). Peptides were eluted in 50 µL of 80% acetonitrile/0.1% TFA and dried down in an evaporative centrifuge to remove organic solvents. The peptides were then reconstituted with 3% ACN in 0.1% formic acid. Reconstituted peptides were separated on an online nanoflow EASY-nLC 1000 UHPLC system (Thermo Fisher Scientific) and analyzed on a benchtop Orbitrap Q Exactive mass spectrometer (Thermo Fisher Scientific). The peptide samples were injected onto a capillary column (Picofrit with 10 µm tip opening/75 µm diameter, New Objective, PF360-75-10-N-5) packed in-house with 20 cm C18 material (1.9 µm ReproSil-Pur C18-AQ medium, Dr. Maisch GmbH, r119.aq). The UHPLC setup was connected with a custom-fit microadapting tee (360 µm, IDEX Health Science, UH-753), and capillary columns were heated to 50° C. in column heater sleeves (Phoenix-ST) to reduce backpressure during UHPLC separation. Injected peptides were separated at a flow rate of 200 nL/min with a linear 80 min gradient from 100% solvent A (3% acetonitrile, 0.1% formic acid) to 30% solvent B (90% acetonitrile, 0.1% formic acid), followed by a linear 6 min gradient from 30% solvent B to 90% solvent B. Each sample was run for 150 min, including sample loading and column equilibration times. Data-dependent acquisition was obtained using Xcalibur 2.2 software in positive ion mode at a spray voltage of 2.00 kV. MS1 Spectra were measured with a resolution of 70,000, an AGC target of 3e6 and a mass range from 300 to 1800 m/z. Up to 12 MS2 spectra per duty cycle were triggered at a resolution of 17,500, an AGC target of 5e4, an isolation window of 2.5 m/z and a normalized collision energy of 25. Peptides that triggered MS2 scans were dynamically excluded from further MS2 scans for 20 s.

Identification and Quantification of Proteins for CRBN-Protein Interaction Studies.

All mass spectra were analyzed with MaxQuant software version 1.3.0.5. (J. Cox et al., Journal of proteome research 10, 1794 (Apr. 1, 2011)) Using a human Uniprot database. MS/MS searches for the proteome data sets were performed with the following parameters: Oxidation of methionine and protein N-terminal acetylation as variable modifications; carbamidomethylation as fixed modification. Trypsin/P was selected as the digestion enzyme, and a maximum of 3 labeled amino acids and 2 missed cleavages per peptide were allowed. The mass tolerance for precursor ions was set to 20 p.p.m. for the first search (used for nonlinear mass re-calibration) and 6 p.p.m. for the main search. Fragment ion mass tolerance was set to 20 p.p.m. For identification a maximum FDR of 1% was applied separately on protein, peptide and PTM-site level. 2 or more unique/razor peptides were required for protein identification and a ratio count of 2 or more for protein quantification per replicate measurement. To assign interacting proteins the Limma package was used in the R environment to calculate moderated t-test p, as described previously (9).

Cell Culture and Treatment for K-ε-GG and Proteome Profiling

MM1S cells were cultured for 2 weeks (~6 cell doublings) in RPMI depleted of L-arginine and L-lysine (Caisson Labs Inc.) and supplemented with 10% dialyzed FBS (Sigma) and amino acids as described above to generate light-, medium- and heavy-labeled cells. Media was exchanged every 3rd day. On day 14 cells were treated for 12 hours with 1 µM lenalidomide, 20 µM thalidomide or DMSO. For each of the three replicates SILAC labels were flipped:

| | SILAC labelling | | |
|---|---|---|---|
| | Light | Medium | Heavy |
| Replicate 1 | DMSO | Thal 20 uM | Len 1 uM |
| Replicate 2 | Len 1 uM | DMSO | Thal 20 uM |
| Replicate 3 | Thal 20 uM | Len 1 uM | DMSO |

For the last 3 hours cells determined for K-ε-GG profiling were treated with 5 µM MG132 together with lenalidomide, thalidomide or DMSO. K-ε-GG profiling was later performed for all 3 replicates and proteome profiling for replicate 1 and 2.

Cell Lysis and Trypsin Digestion for K-ε-GG and Proteome Profiling

SILAC-labeled cell pellets were lysed in 8 M urea, 50 mM Tris-HCl, pH 7.5, 150 mM NaCl, 1 mM EDTA, 2 ug/ml aprotinin (Sigma-Aldrich), 10 ug/ml leupeptin (Roche Applied Science), 1 mM phenylmethylsulfonyl fluoride (PMSF), 50 µM PR-619, and 1 mM chloroacetamide at 4° C. Following lysis, samples were centrifuged at 20,000×g for 15 minutes at 4 C to remove insoluble material. Protein concentrations were determined using a bicincohoninic acid (BCA) protein assay (Pierce) and samples were mixed equitably at 10 mg per SILAC state. Proteins were reduced with 5 mM dithiothreitol for 45 minutes at room temperature (RT) and subsequently carbamidomethylated with 10 mM iodoacetamide for 30 min at RT in the dark. Samples were diluted to 2 M urea with 50 mM Tris-HCl, pH 7.5, and digested with sequencing grade trypsin (Promega) at 25° C. o/n using an enzyme to substrate ratio of 1:50. Digested samples were acidified to 1% formic acid (FA) (Sigma-Aldrich).

Tryptic peptides were desalted on 500-mg tC18 Sep-Pak SPE cartridges (Waters). Cartridges were conditioned with 5 ml of 100% acetonitrile (MeCN), 5 ml of 50% MeCN/0.1% FA, and four times with 5 ml of 0.1% trifluoroacetic acid (TFA). Up to 15 mg of sample was loaded onto a single cartridge, and subsequently washed 3× with 5 ml of 0.1% TFA. Samples were eluted from cartridges by washing 2× with 3 ml of 50% MeCN/0.1% FA. Desalted samples were dried overnight in a Savant SC210A SpeedVac concentrator (Thermo Scientific).

Basic pH Reverse Phase (bRP) Fractionation

Offline bRP fractionation was completed using a custom-manufactured Zorbax 300 Extend-C18 column (9.4×250 mm, 300 Å, 5 µm, Agilent) on an Agilent 1100 series HPLC system. Approximately 15 mg of peptide sample was resuspended in 1.8 ml of basic RP solvent A (2% MeCN, 5 mM ammonium formate, pH 10), separated into 2 HPLC vials and injected with Solvent A at flow rate of 3 ml/min. A 64-min method was used for fractionation. The gradient was composed of an initial increase to 8% Solvent B (1.1% B/min) (90% MeCN, 5 mM ammonium formate), followed by a 38-minute linear phase (0.5% B/min) where the amount of solvent B was increased from 8% to 27% and ramp phases where the Solvent B amount was increased from 31% (1% B/min) to 39% (0.5% B/min), and finally to 60% (3% B/min). A total of 96 2 ml fractions were collected every 0.66 min at a flow rate of 3 ml/min. For the proteome profiling, 5% of each fraction was pooled into 22 fractions. For ubiquitination profiling, 95% of each fraction was pooled into 8 fractions using a concatenated pooling strategy. Pooled samples were dried using a SpeedVac concentrator.

K-ε-GG Enrichment

The anti-K-ε-GG antibody was obtained from the PTMScan® ubiquitin remnant motif (K-ε-GG) kit (Cell Signaling Technology). Prior to enrichment, the antibody was covalently coupled to Protein A agarose beads by chemical cross-linking with DMP. For cross-linking, the antibody bound beads were first washed 3× with 1 ml of 100 mM sodium borate, pH 9 and then incubated in 1 ml of 20 mM dimethyl pimelimidate (DMP) for 30 minutes with rotation at RT. The reaction was stopped by washing beads 2× with 1 ml of 200 mM ethanolamine, pH 8 followed by incubation for 2 hours at 4C with rotation. Antibody-bound beads were washed three times in 1.5 ml of ice cold immunoprecipitation (IAP) buffer (50 mM MOPS, pH 7.2, 10 mM sodium phosphate, 50 mM NaCl), resuspended in IAP buffer, and stored at 4° C.

For K-ε-GG enrichment, bRP fractions were reconstituted in 1.5 ml of IAP buffer and each fraction was incubated with 32 ug of cross-linked anti-K-ε-GG antibody for 1 hour, at 4° C., while rotating. Following incubation, samples were spun down at 2000× g and the supernatant was removed. Antibody-bound beads were washed 4× with 1.5 ml of ice cold PBS and peptides were then eluted from the beads with 2×50 µl of 0.15% TFA. Eluted peptides were desalted using C18 StageTips. Each StageTip was packed with two plugs of C18 material (Empore™ C18 Extraction Disk; 3M) and then conditioned with 100 µl of MeOH, 100 µl of 50% MeCN/ 0.1% FA, and 2× with 100 µl of 0.1% FA. K-ε-GG peptides were loaded onto the condition StageTips, washed 2× with 100 µl of 0.1% FA, eluted with 50 µl of 50% MeCN/0.1% FA, and dried to completeness.

LC-MS/MS Analysis

K-ε-GG and global proteome fractions were reconstituted in 8 ul and 20 ul of 3% MeCN/1% FA, respectively, and analyzed by nanoflow-UPLC-HCD-MS/MS using Q Exactive mass spectrometer (Thermo Fishes Scientific) coupled on-line to a Proxeon Easy-nLC 1000 system. 4 ul and 1 ul of K-ε-GG and global proteome samples was injected, respectively, for each analysis. Samples were injected onto a microcapillary column (360 um OD×75 um ID) packed with 24 cm of ReproSil-Pul C18-AQ 1.9 um beads (Dr. Maisch GmbH) that was equipped with an integrated electrospray emitter tip (10 um). For online analyses, the column was heated to 50 C using a 20 cm column heater (Phoenix S&T). For LC separation, solvent A was 0.1% FA/3% MeCN and solvent B was 90% MeCN/0.1% FA. Peptides were eluted on the mass spectrometer at a flow rate of 200 nl/min using a gradient consisting of a linear phase at 0.3% B/min, followed by a ramp to 60% B (10% B/min). The total analysis time for each sample was 150 minutes. The Q Exactive instrument was operated in the data-dependent mode acquiring HCD MS/MS scans (R=17,500) after each MS1 scan (R=70,000) on the 12 top most abundant ions using an MS1 ion target of 3×10$^6$ ions and an MS2 target of 5×10$^4$ ions. The maximum ion time utilized for the MS/MS scans was 120 ms; the HCD-normalized collision energy was set to 25; the dynamic exclusion time was set to 20s, and the peptide match and isotope exclusion functions were enabled.

K-ε-GG and Proteome MS Data Analysis

MS data was analyzed with the MaxQuant software version 1.3.0.5 and searched against the human Uniprot database that contained 248 common laboratory contaminants was provided by the MaxQuant software package. The search parameters were as follows: enzyme specificity was set to trypsin, maximum number of mixed cleavages to 2, precursor mass tolerance was at 20 ppm for the first search (used for nonlinear mass re-calibration), and set to 6 ppm for the main search. Oxidized methionines and N-terminal protein acetylation were searched as variable modifications, with carbamidomethylation of cysteines set to fixed modification. For searching K-ε-GG data files, Gly-Gly addition to lysines was also searched as a variable modification. The minimum peptide length was set to 6, and false discovery rate for peptide, protein, and side identification was set to 1%. The filter labeled amino acids and peptide quantification functions were enabled. For proteome data, proteins were considered in the dataset if they were identified by 2 or more razor/unique peptides and quantified by 3 or more ratio counts in bot biological replicates. For the K-ε-GG data, K-ε-GG sites were considered if they were confidently localized (>0.75) and quantified in all three biological replicates.

Cell Lines and Primary Cells

MM1S, NCI-H929, U266, Namalwa, Jurakat, K562, HEL and 293T cells were obtained from American Type Culture Collection. Cells were cultured in RPMI 1640 (Mediatech) or DMEM (Mediatech) supplemented with 10-20% heat-inactivated fetal bovine serum (Omega Scientific) and 1% penicillin, streptomycin, and L-glutamine (Mediatech). Cells were grown at 37° C. in a humidified incubator under 5% CO2.

Primary T cells were obtained from healthy donors under an Institutional Review Board approved protocol at the Dana-Farber Cancer Institute. PBMCs were isolated using Ficoll (Ficoll-Paque PLUS, GE Healthcare) according to the protocol. After positive selection with CD3+ MACS beads (Miltenyi), T cells were cultured in RPMI with 10% human Serum (Sigma) and 100 U/ml recombinant IL-2 (Miltenyi). For stimulation, tissue culture plates were pre-coated with 2.5 µg/ml CD3 (OKT3, Biolegend) and CD28 (CD28.2, Pharmingen).

Antibodies

The following antibodies were used: HA-HRP (Miltenyi, GG8-1F3.3), Flag-HRP (M2, Sigma Aldrich), Actin-HRP (Abcam), rabbit IKZF3 (Imginex), IKZF1 (H-100, Santa Cruz), FK2-HRP (Enzo Lifescience), DDB1 (Abcam), and p27 (Cell Signaling).

Virus Constructs

For cDNA over-expression, the RSF91 retrovirus backbone (kind gift of Prof. Dr. Christopher Baum of Hanover Medical School) was used. For certain constructs GFP was replaced by GFP-T2A-Puro or dTomato. The Gateway Vector Conversion System (Invitrogen) was used to converted RSF91 to a Gateway Destination vector. Entry clones were obtained from the Broad Institute Orfeome collection and cloned into RSF91-Gateway with LR clonase enzyme mix II (Invitrogen). IKZF4 cDNA was obtained from GeneCopeia. The CRBN YWAA mutant, IZKF3 and IKZF4 mutants, IKZF2 Isoform 1 were cloned by PCR using overlapping primers containing the respective mutations.

| ORF | Origin | Clone |
| --- | --- | --- |
| IKZF1 | Broad Institute | ORF016074.1_s300c1 |
| IKZF2 | Broad Institute | ORF018485.1_s300c1 |
| IZKF3 | Broad Institute | ORF000952.1_s304c1 |
| IKZF4 | GeneCopoeia | # GC-Z2828 |
| IZKF5 | Broad Institute | ORF004130.1_s300c1 |
| RAB28 | Broad Institute | ORF011035.1_s304c1 |
| IRF4 | Broad Institute | ORF002494.1_s304c1 |
| HOXA9 | Broad Institute | ORF016570.1_s300c1 |
| CRBN | Broad Institute | ORF007943.1_s300c1 |

Lentiviral vectors expressing shRNAs were obtained from the RNAi consortium (TRC) of the Broad Institute:

| shRNA | Clone Name | Target sequence (SEQ ID NOs: 14-24, respectively, in order of appearance) |
|---|---|---|
| Luciferase#1 | TRCN0000072254 | ATGTTTACTACACTCGGATAT |
| Luciferase#2 | TRCN0000072243 | CTTCGAAATGTCCGTTCGGTT |
| CRBN#1 | TRCN0000141562 | CGCTGGCTGTATTCCTTATAT |
| CRBN#2 | TRCN0000144360 | CAGGATAGTAAAGAAGCCAAA |
| CRBN#3 | TRCN0000139091 | CTTAACGCGATCTGCTCTGTT |
| IKZF1#1 | TRCN0000236419 | CCGCTTCCACATGAGCTAAAG |
| IKZF1#2 | TRCN0000236420 | GCATTTGGAAACGGGAATAAA |
| IKZF1#3 | TRCN0000244221 | GTGATATCTGTGGGATCATTT |
| IKZF3#1 | TRCN0000236419 | CCGCTTCCACATGAGCTAAAG |
| IKZF3#2 | TRCN0000236420 | GCATTTGGAAACGGGAATAAA |
| IKZF3#3 | TRCN0000244221 | GTGATATCTGTGGGATCATTT |

The luciferase reporter plasmid CMV-IRES-RenillaLUC-IRES-Gateway-FireflyLUC (11) was a kind gift from William G. Kaelin (Dana-Farber Cancer Institute). Cloning of cDNAs was performed using Gateway LR reaction (invitrogen). 24 hours after transfection of 40 ng reporter plasmid in 10xe4 293T cells, the media was changed to media containing lenalidomide or the vehicle control. After an additional 24 hours, dual luciferase assays were performed using the Dual-Glo Luciferase Assay System (Promega) according to the manufacturer's protocol.

Transfections, Virus Production and Infections

Retro- or lentiviral vectors were transfected using TRANS-LTI (Mirrus) into 293T cells together with packaging plasmid (retrogagpol or pSPAX2) and envelope plasmids expressing VSV-G. The media was changed after 12 hours, and the viral supernatant was collected 36 hours and 48 hours after transfection.

For viral infection, cells were seeded in high density and supplemented with Polybrene (Sigma) at concentrations of 1 to 2 µg/ml. Primary T cells were stimulated on plates pre-coated with anti-C3/CD28 for 48h before lentiviral transduction. Puromycin selection was started 1 day after transduction at concentrations between 0.5 and 2 µg/ml.

Quantitative RT-PCR

Gene expression was measured by reverse transcription quantitative PCR (RQ-PCR). cDNA was synthesized using the cDNA synthesis Kit for Multimacs (Miltenyi) according to the manufacturer's protocol, and used 1 µl of the product per RQ-PCR reaction in a 384-well plate. The following primer-probe sets from Life Technologies were used: GAPDH ( ), IKZF1 ( ), IKZF3 ( ), CRBN (Hs00372271_m1), IL-2 ( ). Analysis was performed on a 7900HT Fast Real-Time PCR System (Applied Biosystems). Expression levels were calculated using the ΔΔCT method.

Western Blot

Protein lysates were run on Tris-HCl, 1 mm Criterion™ Precast gels (Bio-Rad) at a constant voltage. Proteins were transferred onto Imobilon-P transfer membranes (Millipore) at a constant amperage. Before staining, blots were blocked in 5% BSA in TBST for 30 minutes.

Immunoprecipitation

For immunoprecipitation of HA-tagged proteins, the HA-protein Isolation Kit from Miltenyi was used according to the manufacturer's protocol using an MultiMACS M96 Separator (Miltenyi). Proteins tagged with the FLAG peptide were immunoprecipiated using anti-FLAG M2 Affinity Gel (Sigma-Aldrich) according to the manufacturer's protocol. 500 to 1000 µg protein was incubated together with the specific bead-bound antibody overnight at 4° C. The samples were washed 4 times with RIPA buffer or IP lysis buffer (Pierce) and protein was eluted from the affinity gel or Multimacs columns with 98° C. laemmli buffer (Bio-Rad).

In Vivo Ubiquitination

MM1S or 293T cells expressing tagged IKZF1 or IKZF3 were treated with the respective concentrations of lenalidomide and/or epoxomicin for 1.5 hours. Cells were then washed twice with ice-cold PBS and lysed under denaturing conditions using 2% SDS-containing lysis buffer and boiled for 10 minutes. SDS was diluted with addition of 10×Ip lysis buffer (Pierce), incubated at 4° C. for 30 minutes prior addition of IP antibodies. Immunoprecipitation was performed over night and then washed 4× with 1 ml RIPA buffer. Proteins were eluted from the beads by addition of Laemmli buffer and incubation at 95° C. for 5 minutes. The supernatant was then loaded on a gel and analyzed by Western Blot.

In Vitro Ubiquitination 293T cells were co-transfected with HA-IKZF3 and FLAG-CRBN. After 48 hours cells were treated with DMSO or 1 µM lenalidomide for 20 minutes, lysed in IP lysis buffer (Pierce) and immunoprecipitation was performed overnight with anti-FLAG M2 sepharose beads (Sigma) to obtain CRBN together with CRBN-bound IKZF3. The beads were washed 3× with IP lysis buffer, 1× ubiquitination buffer (Boston Biochem) and eluted with 250 µg/ml FLAG peptide (Sigma) for 30 min at 4° C. The CRBN-IKZF3 complex was incubated for 90 min at 30° C. in ubiquitination reaction mixture containing 200 nM E1, 500 nM E2 (UbcH5a and UbcH5b), 20 µg ubiquitin, 1 µM ubiquitin aldehyde, 1× ubiquitin reaction buffer, 1× Energy Restoration System (all Boston Biochem), and 100 nM MG101 in a total volume of 75 µl. Negative controls did not include E1 and E2 enzymes. 20 µl of the reaction was denatured by adding 5×SDS containing loading buffer (Boston Biochem) and boiling at 95° C. for 5 minutes, separated by SDS-PAGE and transferred to a PVDF membrane in order to detect HA-IKZF3 and its ubiquitinated forms with an HA specific antibody. The remaining 55 µl reaction mix were denatured by adding SDS to a final concentration of 1% and boiling for 10 minutes. 500 µl IP lysis buffer was added for 30 minutes before adding anti-HA magnetic beads (Miltenyi) for 1 hour. After purification on Multimacs columns (Miltenyi) eluates were separated by SDS-PAGE, transferred to a PVDF membrane and stained with anti-ubiquitin antibodies (FK2).

Flow Cytometry

Flow cytometry was performed on a FACS Canto II (BD Bioscience) using PE channel for detection of dTomato-, and FITC for GFP-expressing cells. DAPI staining was performed to exclude dead cells.

For investigating shRNA effects on proliferation 50,000 cells were infected in a 96-well plate with 50 µl lentivirus containing medium in the presence of polybrene. Media was changed after 24 hours. The number of infected cells was determined on day 2 when GFP was fully expressed in all infected cells. The number of viable GFP positive cells on day 2 was set to 100% to normalize for transduction efficiency and every consecutive assessment was calculated in relation to day 2.

To investigate the effect of IKZF3 over-expression on lenalidomide sensitivity, MM1S were separately infected with an empty backbone expressing dTomato or an IKZF3 and GFP expressing vector. After two days cells were washed, combined in a 96-well plate and analyzed by flow cytometry for the relative number of GFP and Tomato expressing cells before start of lenalidomide treatment. Media was changed every $3^{rd}$ day containing the drug. Every experiment was performed in triplicate.

Viability

For assessing the effects of lenalidomide on cell growth cells were plated in a 96-well plate and treated with lenalidomide. On the respective days, total cellular ATP content was assessed using CellTiter-Glo® Luminescent Cell Viability Assay (Promega) according to the protocol. Luminescence was assessed by a multimode detector DTX880(Beckman Coulter).

The results described in Example 8 were carried out using the following methods and materials.

Reagents

Lenalidomide (Toronto Research Chemicals and Selleck Chemicals), Thalidomide (Milipore), Pomalidomide (Selleck Chemicals), MG-132 (Selleck Chemicals), CC-122 (Celgene), PR619 (Lifesensors) and MLN4924 (Active Biochem) were dissolved in DMSO at 10 to 100 mM and stored at −20° C. for up to 6 months. For cell culture experiments drugs were diluted at least by 1:1000 so that the final DMSO concentration was 0.1% or lower.

Cell Lines

KG-1, Ba/F3, K562, MM1S, Jurkat, and 293T cells were obtained from American Type Culture Collection (ATCC). Cells were cultured in RPMI 1640 (Mediatech) or DMEM (Mediatech) supplemented with 10-20% heat-inactivated fetal bovine serum (FBS), (Omega Scientific) and 1% penicillin, streptomycin, and L-glutamine (Mediatech). Cells were grown at 37° C. in a humidified incubator under 5% $CO_2$. Ba/F3 cells were cultured in the presence of 10 ng/ml murine IL-3 (Miltenyi) and MDS-L cells were cultured with 10 ng/ml human GM-CSF. 293T cells were transfected using TransIT-LT1 (Minus Bio) according to the manufacturer's protocol.

Cell Culture and Treatment for K-ε-GG and Proteome Profiling

KG-1 cells were cultured for 2 weeks (~6 cell doublings) in RPMI depleted of L-arginine and L-lysine (Caisson Labs Inc.) and supplemented with 10% dialyzed FBS (Sigma) and L-arginine (Arg0) and L-lysine (Lys0) (light), $^{13}C_6^{14}N_4$-L-arginine (Arg6) and 4,4,5,5-$D_4$-L-lysine (Lys4) (medium) or $^{13}C_6^{15}N_4$-L-arginine (Arg10) and $^{13}C_6^{15}N_2$-L-Lysine (Lys8) (heavy) to generate light-, medium- and heavy-labeled cells. Media was exchanged every $3^{rd}$ day. On day 14 cells were treated with 1 μM lenalidomide, 10 μM lenalidomide or DMSO for 4 hours for ubiquitination profiling and 24 hours for protein level assessment. Experiments were performed in two biological replicates with flipped SILAC labeling: Replicate 1: DMSO/light, lenalidomide 1 μM/medium; lenalidomide 10 μM/heavy; replicate 2: lenalidomide 10 μM/light, DMSO/medium; lenalidomide 1 μM/heavy.

SILAC Based K-ε-GG and Proteome Profiling of KG-1 Cells

Cell lysis and trypsin digestion, basic pH reversed phase fractionation, K-ε-GG enrichment, and LC-MS/MS analysis for KG-1 cells were performed as recently described (*Science* 343, 301-305, (2014)). For this work, 10 mg of protein was input per SILAC state for the ubiquitin workflow. For proteome profiling, 1.5 mg of protein was input per SILAC state and samples were fractionated by bRP using a 4.6 mm×250 mm column (Agilent, 3.5 um bead size) using the method previously described (*Nature methods* 10, 634-637, (2013)).

For data analysis, normalized SILAC ratios for the 2 biological replicates were filtered to retain only those deemed reproducible. Reproducibility was based on replicates being confined within the 95% limits of agreement of a Bland-Altman plot. In the Bland-Altman plot, differences of the replicates are plotted against the average values and the limits of agreement correspond to the prediction confidence interval for a regression line with unit slope. Reproducible replicates were then subjected to a moderated T-test to assess statistical significance. This statistic is similar to the ordinary t-statistic, with the exception that the standard errors are calculated using an empirical Bayes method utilizing information across all proteins, thereby making inference about each individual protein more robust. The nominal p-values arising from the moderated t-statistic are corrected for multiple testing by controlling the false discovery rate (FDR). Proteins with an FDR adjusted p-value of less than 0.05 were deemed to be reproducibly regulated. Figures containing scatter plots of SILAC data show all points regardless of the reproducibility measure. Statistical significance was assessed using only reproducible data points.

Plasmids and Virus Constructs

The following cDNAs were cloned in the RSF91 retrovirus backbone (kind gift of Christopher Baum, Hanover Medical School) or EF1a-IRES-GFP lentiviral backbone: CSNK1A1 Isoform 2 (ccsbBroadEN_06055), CSNK1E (ccsbBroadEN_00379), murine CRBN Isoform 2 (Thermo Scientific), and human CRBN Isoform 2 (ccsbBroadEn_08244). For certain experiments GFP was replaced by dTomato for competition experiments or GFP-T2A-Puro to allow for drug selection of positively transduced cells. Chimeric cDNAs and point mutations were cloned with overlapping PCR primers. Lentivirus was concentrated by ultracentrifugation for transduction of primary cells.

Lentiviral vectors (TRC005 backbone) expressing shRNAs targeting luciferase (TRCN0000072254: ATGTTTAC-TACACTCGGATAT_(SEQ ID NO: 14)) and CSNK1A1 (#1: TRCN0000342505, CATCTATTTGGCGATCAACAT (SEQ ID NO: 25)); #2: TRCN0000342507, GCAGAAT-TTGCGATGTACTTA (SEQ ID NO: 26)) were obtained from The RNAi Consortium (TRC) of the Broad Institute. For certain experiments, the puromycin resistance gene was replaced by GFP.

The luciferase reporter plasmid CMV-IRES-RenillaLUC-IRES-Gateway-FireflyLU was a kind gift from William G. Kaelin (Dana-Farber Cancer Institute). Cloning of cDNAs was performed using Gateway LR reaction (Invitrogen).

CRISPR mediated genetic deletion was performed with the sgRNA-CAS9-T2A-Puro plasmid. A CRBN exon 1-specific guide RNA was cloned in the BsmBI site.

$1×10^5$ 293 T cells were transfected in a 12-well with 1 μg plasmid using TransLTI (Minus). After 24 hours transfected cells were selected with 2 μg/ml puromycin for 4 days. Then 293T cells were diluted to single cell and plated in 96-well. Colonies were tested by western blot and Sanger sequencing of the endogenous CRBN exon1 locus for inactivating biallelic out-of-frame mutations.

Western Blot and Antibodies

Protein lysates were run on Tris-HCl, 1 mm Criterion™ Precast gels (Bio-Rad) or NuPAGE Bas-Tri-s gels (Novex) gels at a constant voltage. Proteins were transferred onto Immobilon-P transfer membranes (Millipore) at a constant amperage. Before staining with primary antibodies, blots were blocked in 5% non-fat dry milk (Santa Cruz) or BSA in TBST for 30 minutes.

For protein detection primary antibodies detecting CK1α (C-19, Santa Cruz or Abcam ab108296), HA (HRP-conjugate, Miltenyi, GG8-1F3.3), FLAG (M2, HRP-conjugate Sigma Aldrich), ubiquitin (FK2, HRP-conjugate Enzo Life Sciences), Actin (HRP-conjugate, Abcam), and GAPDH (Santa Cruz sc-47724) were used. Secondary antibodies were HRP conjugated Bovine anti-Goat (Jackson ImmunoResearch) and HRP conjugated donkey anti-rabbit (GE Healthcare). Supersignal chemi-luminescent substrate was used for detection. For re-probing, blots were stripped in Restore Western Blot Stripping Buffer (Thermo Scientific), activated in methanol, and re-blocked.

Flow Cytometry

Flow cytometry was performed on a FACS Canto II (BD Bioscience) using the PE and FITC channels for the detection of dTomato and GFP, respectively. DAPI staining was performed to exclude dead cells. A High-Throughput Sampler (BD) was used for some experiments.

Quantitative RT-PCR

Gene expression was measured by reverse transcription quantitative PCR (RQ-PCR). For RNA isolation and reverse transcription, a cDNA Synthesis Kit for MultiMacs (Miltenyi) was used according to the manufacturer's protocol. The following primer-probe sets from Life Technologies were used with TaqMan Gene Expression Master Mix (Life Technologies): human GAPDH (402869), human CSNK1A1 (Hs00793391 ml), murine GAPDH (Mm99999915_g1), murine p21 (Mm04205640_g1). Analysis was performed on a 7900HT Fast Real-Time PCR System (Applied Biosystems) in a 384-well plate. Relative expression levels were calculated using the $\Delta\Delta CT$ method.

Immunoprecipitation of FLAG-CRBN $3 \times 10^6$ 293 T cells were plated in a 10 cm dish and transfected with 10 µg FLAG-hCRBN or empty vector. Cells were treated with DMSO or 1 µM lenalidomide and 10 µM MG132 for 3 hours. Cells were lysed in Pierce IP Lysis Buffer and lysates were cleared by centrifugation. FLAG-CRBN was immunoprecipitated overnight using anti-FLAG M2 Affinity Gel (Sigma-Aldrich) in the presence of 10 µM MG132 and DMSO or 1 µM lenalidomide. The beads were washed 3 times with IP lysis buffer (Pierce) and protein was eluted from the affinity gel with 250 µg/ml FLAG peptide (Sigma) after incubation for 30 min at 4° C. Protein lysates were then analyzed as described above.

In Vivo Ubiquitination

For in vivo ubiquitination analysis 300,000 293T cells were plated in a 6-well. The next day, cells were transfected with 100 ng FLAG-CRBN and 300 ng HA-CK1α using TransLTI (Minis). After 48 hours, cells were treated with lenalidomide or DMSO and 10 µM MG132 for 4 hours. Cells were then washed twice with ice-cold PBS and lysed under denaturing conditions using 1% SDS-containing lysis buffer and boiled for 10 minutes at 95° C. The SDS was diluted with the addition of 9 volumes of IP lysis buffer (Pierce) followed by incubation at 4° C. for 30 minutes. Lysates were cleared from debris by centrifugation and incubated with anti-HA microbeads (Miltenyi) in the presence of lenalidomide or DMSO, 10 µM MG132, and 50 µM PR-619 for 1 hour. Samples were applied to columns on a MultiMacs 96 Separation Unit (Miltenyi), washed four times with RIPA buffer, and eluted by addition of 95° C. Lamelli Buffer (Bio Rad) with β-mercaptoethanol (Sigma). Samples were separated by SDS-PAGE, transferred to a PVDF membrane and probed with anti-CK1A antibody, anti-FK2 for polyubiquitinated proteins and anti-actin as a loading control In Vitro Ubiquitination 293T cells were transfected with either HA-CK1A or FLAG-CRBN vectors. After 48 hours, cells were lysed in Pierce IP lysis buffer (Thermo Scientific) and immunoprecipitated overnight with FLAG-Sepharose beads (Anti-FLAG M2 Affinity Gel, Sigma) or HA-Sepharose beads (EZView Red anti-HA affinity gel, Sigma). The beads were washed 3× in IP lysis buffer and 2× in E3 Ligase Reaction buffer (Boston Biochem) and eluted with 250 µg/ml FLAG peptide (Sigma) or 100 µg/ml HA peptide for 30 min at 4° C. The eluates were mixed in a 1:1 ratio and added to a ubiquitination reaction mixture containing 200 nM E1 (UBE1), 2 µM UbcH5a, 1 µM UbcH5c, 1 µg/µL $K_0$ ubiquitin, 1 µM ubiquitin aldehyde, 1× Mg-ATP, 1× E3 Ligase Reaction Buffer (all Boston Biochem), 10 µM MG132, 100 nM MG101 and 1 µM lenalidomide, 10 µM lenalidomide, or DMSO (1:1000) as appropriate in a total volume of 25 µl. Negative controls did not include E1 and E2 enzymes. After a 90 minute incubation at 30° C., the reaction was denatured by adding 5×SDS containing loading buffer (Boston *Biochem*), boiled at 95° C. for 5 minutes, separated by SDS-PAGE and transferred to a PVDF membrane in order to detect HA-CK1A and its ubiquitinated forms with CK1A antibody. The membrane was then stripped and re-probed with anti-FLAG antibody.

Purification, Culture, and Lentiviral Infection of Human CD34$^+$ Cells for shRNA Experiments Research cord blood units were obtained from The New York Blood Center according to an Institutional Review Board-approved protocol. Cord blood CD34$^+$ hematopoietic cells were isolated from Ficoll purified PBMCs with an Indirect CD34 MicroBead kit (Miltenyi) and an Auto MACS Pro (Miltenyi) according to the manufacturer's protocol. Cells were cultured in serum free media (SFEM, stem span) containing 50 ng/ml recombinant human SCF (Miltenyi), 40 ng/µl human FLT3 ligand (Miltenyi), 25 ng/µl recombinant human thrombopoietin (Miltenyi), and 10 ng/µl IL-3 (Miltenyi). For shRNA experiments, CD34$^+$ cells were transduced with a VSV-G pseudotyped TRC pLKO.005 lentiviral vector expressing GFP instead of puromycin resistance gene. Infection was performed after 24 hours in culture in a 96-well using spinfection in the presence of 2 µg/ml polybrene (hexadimethrine bromide, Sigma). 48 hours after transduction the number of transduced cells was analyzed by flow cytometry and was used as baseline. Then cells were cultured in 1 µM lenalidomide or DMSO and the relative number of infected cells was assessed by flow cytometry for 3 weeks.

Purification, Culture, and Lentiviral Infection of Patient Samples

Viably frozen bone marrow mononuclear cells were obtained from healthy donors or patient with del(5q) MDS according to IRB approved protocols at the University of Pennsylvania and Roswell Park Cancer Institute. Samples were thawed and CD34$^+$ hematopoietic cells were isolated 20-24 hours later using an Indirect CD34 MicroBead kit (Miltenyi) and an Auto MACS Pro (Miltenyi). Cells were grown in serum free media (SFEM, StemSpan) supplemented with 25 ng/ml SCF, 40 ng/ml FLT3 ligand, 50 ng/ml thrombopoietin, 40 µg/mL lipids, 100 U/ml Pen/Strep and 2 mM glutamine. 6-8 hours after CD34$^+$ isolation, cells were transduced with concentrated VSV-G pseuotyped EF1a-GFP-IRES-hCSNK1A1 cDNA virus or empty vector control via spinfection in the presence of 4 µg/ml polybrene (Sigma, diluted to 2 µg/ml after spinfection). After 3 days, the initial percentage of transduced cells was determined by flow cytometry and remaining cells were split to treatment with either DMSO or 1 µM lenalidomide. The relative abundance of transduced cells in each condition was assessed by after 5 days by flow cytometry. Control cord-blood CD34+ cells were isolated as above. Adult bone marrow CD34+ cells were purchased as single-donor lots from AllCells (Alameda, Calif.).

For qPCR validation of CSNK1A1 expression, cord blood CD34+ cells were transduced with lentivirus expressing GFP and hCSNK1A1 or empty vector. After 3 days, transduced GFP+ cells were FACS sorted and RNA extraction and qPCR was performed as above.

Expressing Different CRBN Proteins in Ba/F3 Cells

Variants of human and mouse CRBN were cloned into a modified pRSF91 backbone to generate SFFV-CRBN-IRES-GFP-T2A-Puro retroviral constructs. 200,000 Ba/F3 cells were infected with ecotropic retrovirus in the presence of 2 µg/ml polybrene. After 24 hours, 1 µg/ml puromycin (Gibco) was added and cells were selected for 3-4 days. Cells were confirmed to be >90% GFP+ by flow cytometry and 1,000,000 cells were plated per 6-well and treated with DMSO or lenalidomide for 24 hours. Protein lysates were harvested and immunoblotted for CK1α as described above.

IKZF3 Luciferase Reporter Assay 10,000 293T cells were transfected with 40 ng of CMV-IRES-RenillaLUC-IRES-IKZF3-FireflyLUC reporter plasmid. After 24 hours, cells were treated with DMSO and lenalidomide. 4 hours following treatment, luciferase activity was measured using the Dual-Glo Luciferase Assay System (Promega) according to the manufacturer's protocol.

Mouse Experiments

Mouse experiments were performed according to an IUCAC approved protocol at Children's Hospital Boston. Generation and characterization of the conditional Csnk1a1 knockout mouse has been described previously (*Cancer Cell*, 13; 26(4):509-20, 2014). Csnk1a1$^{flox/flox}$ mice were crossed with Mx1Cre mice to obtain Csnk1a1$^{flox/flox}$ Mx1Cre+ mice. Csnk1a1$^{flox/flox}$ Mx1Cre+ or control Csnk1a1+/+ Mx1Cre+ mice were treated with 3 doses of 200 µg poly(I:C) (Invivogen HMW) at 8-10 weeks of age and gene excision was confirmed where applicable. At least 2 weeks following poly(I:C) treatment, the long bones and spines were harvested and crushed and RBC were lysed. CKit+ cells were isolated with a CD117 MicroBead Kit (Miltenyi) and an AutoMacs Pro and grown in SFEM (StemSpan) supplemented with antibiotics and 50 ng/ml mTPO (Peprotech) and 50 ng/ml mSCF (Peprotech) for 24 hours. Ecotropic pseudotyped retrovirus was spun onto Retronectin (Clontech) coated 6 well plates and cells were added in 1 ml of media with 2 µg/ml polybrene. An addition 1 mL media was added after 24 hours. After 48 hours, GFP+ or dTomato+ cells were isolated by FACS sorting (BD FACS Aria II) and CD45.1 and CD45.2 cells were mixed. Cells were treated with various doses of lenalidomide and the percent CD45.1 and CD45.2 cells expressing the fluorescent marker was followed by flow cytometry over time following cell surface staining. Antibodies for flow cytometry were as follows: CD45.1 APC/Cy7 (A20, BioLegend), CD45.2 PE (104, eBioscience), and CD45.2 FITC (104, eBioscience)

The lenalidomide responsive mouse described in Example 9 was generated using the following methods and materials.

Construction of Knock-in Targeting Vector

A knock-in targeting vector was constructed to introduce a mutant murine CRBN gene carrying an I391V mutation into a wild type mouse.

Figure 33:
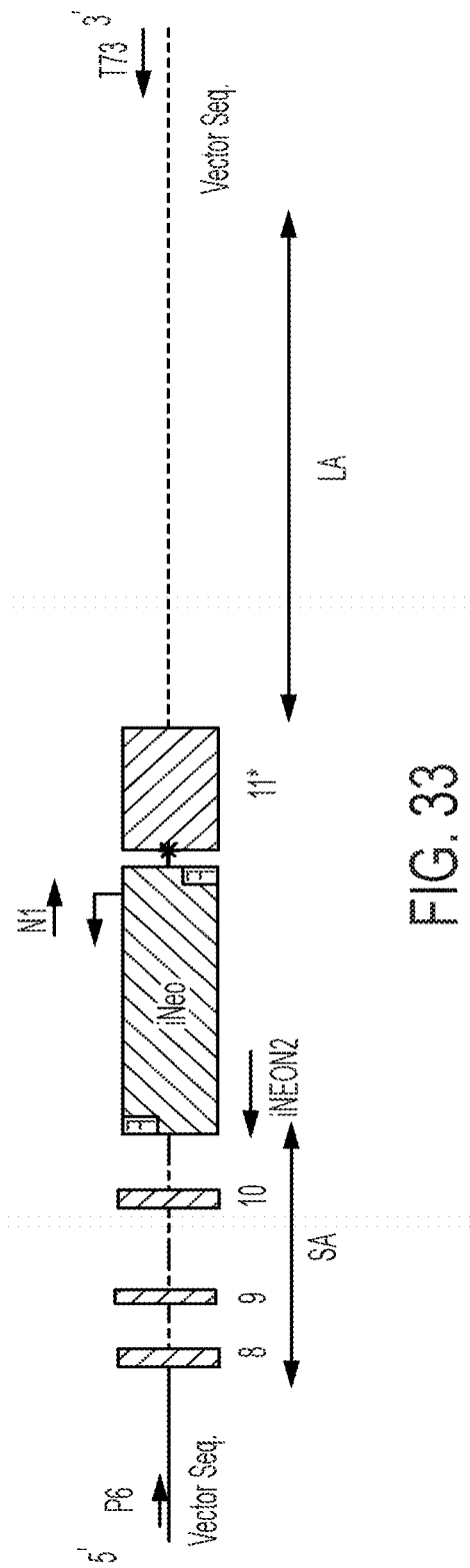
FIG. 33 is a schematic diagram showing the locations of primers (N1, P6, T73 and INEON2) used to sequence the targeting vector.

A ~6.94 kb region of mouse genomic DNA encoding a portion of the CRBN protein was used to construct the targeting vector, which was first sub-cloned from a positively identified C57BL/6 BAC clone (RP23:378L4) (FIG. 33). The region was designed such that the long homology arm (LA) extends ~4.8 kb from the 3' terminus of the site of the point mutation (ATT→GTG) in exon 11 and the FRT-flanked iNeo cassette is inserted 171 bp to the 3' terminus to the point mutation. The short homology arm (SA) extends 1.96 kb from the 5' terminus of the FRT-flanked iNeo cassette. The targeting vector was constructed using Red/ET recombineering technology.

The BAC was sub cloned into a ~2.4 kb backbone vector (pSP72, Promega) containing an ampicillin selection cassette for retransformation of the construct prior to electroporation. A pGK-gb2 FRT-Neo cassette was inserted into the gene as described. The targeting construct can be linearized using Not I prior to electroporation into ES cells.

The total size of the targeting construct (including vector backbone and Neo cassette) is 11.4 Kb.

Generation of the Point Mutation

Figure 34:
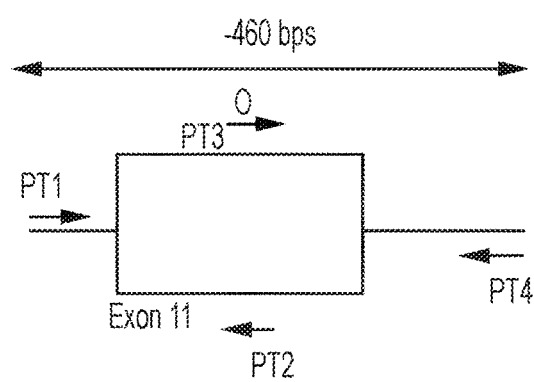
FIG. 34 is a schematic diagram showing the primers (PT1, PT2, PT3, and PT4) used to generate the point mutation I391V.

The mutation was engineered by overlap extension PCR. Two primary PCR fragments that overlap 16 bp 5' of the ATT→GTG point mutation were generated using primers PT1/PT2 and PT3/PT4. The ATT→GTG point mutation was engineered into primer PT3. The two primary products were then mixed and used as a template in a secondary PCR reaction in which PT1/PT4 primer pair amplifies the entire sequence containing the point mutation (FIG. 34).

The oligos used to generate the point mutations are listed below.

```
Oligos used to generate the point mutations
(point mutation indicated in italic and
underlined) (SEQ ID NOs: 34-37, respectively,
in order of appearance):
PT1:
5'-AGC TGG AGC CAA CAG CAA CAT ATA G-3'

PT2:
5'-GGT CCA TGC ATA CCT ATA AAA TGA AGG-3'

PT3:
5'-TAG GTA TGC ATG GAC C*GT G*GC CCA GTG CAA GAT
CTG-3'

PT4:
5'-GCT CTT GAA CTT GGT AGG CAA ATG C-3'
```

The targeting vector was confirmed by restriction analysis after each modification step and by sequencing using primers designed to read from the selection cassette into the 5' terminus of the target region (N1) and from the selection cassette into the 3' terminus of the SA (INEON2). P6 and T73 primers anneal to the BAC subclone sequence and read into the 5' and 3' terminal of the subcloned genomic sequence (FIG. 33)

The primers used for sequencing are listed below:

```
PCR primers used for sequencing (SEQ ID
NOs: 38-41, respectively, inorder of appearance):
Primer P6:
5'-GAG TGC ACC ATA TGG ACA TAT TGT-3'

Primer T73
5'-TAA TGC AGG TTA ACC TGG CTT ATC G-3'

Primer N1:
5'-TGC GAG GCC AGA GGC CAC TTG TGT AGC-3'

Primer INEO N2:
5'-AGT ATG GCT TTC CTT CCC GAT GG-3'
```

The sequence data analysis results are listed below.

Sequencing Data from BAC Sub Clone and Targeting Construct

P6 sequencing data aligned with genomic sequence:

```
Query   16803  GCTACAATGGAATCCTTACTGTTAATTTTCTAACTTAAGTTGAATTGCAGACGTGCCTCT  16862
               ||||||||||||||||||||||||||||||||||||||||||||||||||||||||||||
Sbjct     148  GCTACAATGGAATCCTTACTGTTAATTTTCTAACTTAAGTTGAATTGCAGACGTGCCTCT    207

Query   16863  CATGTAGATACTTCCTGTTCTCTACAGAGCCTTTACAAGTGAAGCTGGCTCCATGACTTA  16922
               ||||||||||||||||||||||||||||||||||||||||||||||||||||||||||||
Sbjct     208  CATGTAGATACTTCCTGTTCTCTACAGAGCCTTTACAAGTGAAGCTGGCTCCATGACTTA    267

Query   16923  CTTTGATATGTCATCTCTATTTGTTTATAAGTCACTTCAAGTATATGTTTGACTTAAAGG  16982
               ||||||||||||||||||||||||||||||||||||||||||||||||||||||||||||
Sbjct     268  CTTTGATATGTCATCTCTATTTGTTTATAAGTCACTTCAAGTATATGTTTGACTTAAAGG    327

Query   16983  AAAGTGACTGAAGTGTATATTAATGACTCCTAAGTTTAAAGCCTGCAAACCTCTCTGTCT  17042
               ||||||||||||||||||||||||||||||||||||||||||||||||||||||||||||
Sbjct     328  AAAGTGACTGAAGTGTATATTAATGACTCCTAAGTTTAAAGCCTGCAAACCTCTCTGTCT    387

Query   17043  TTTAAGACTTTTCTTACAGAGTAGCTGCTTGTCTTCCTATTGATGATGTATTGAGAATTC  17102
               ||||||||||||||||||||||||||||||||||||||||||||||||||||||||||||
Sbjct     388  TTTAAGACTTTTCTTACAGAGTAGCTGCTTGTCTTCCTATTGATGATGTATTGAGAATTC    447

Query   17103  AGCTCCTTAAAATCGGCAGTGCTATTCAACGGCTTCGCTGTGAATTGGACATCATGAACA  17162
               ||||||||||||||||||||||||||||||||||||||||||||||||||||||||||||
Sbjct     448  AGCTCCTTAAAATCGGCAGTGCTATTCAACGGCTTCGCTGTGAATTGGACATCATGAACA    507

Query   17163  AAGTGAGTAAAGCCTCCACGTCATCATTTAGTCAGTCAGGCTACATAGACACATAAGAGA  17222
               ||||||||||||||||||||||||||||||||||||||||||||||||||||||||||||
Sbjct     508  AAGTGAGTAAAGCCTCCACGTCATCATTTAGTCAGTCAGGCTACATAGACACATAAGAGA    567

Query   17223  GTCGAGATCACAAGCTACCTCGACTGTGTAGTAATACAAGCAGATGCTACAAGTACTTGT  17282
               ||||||||||||||||||||||||||||||||||||||||||||||||||||||||||||
Sbjct     568  GTCGAGATCACAAGCTACCTCGACTGTGTAGTAATACAAGCAGATGCTACAAGTACTTGT    627

Query   17283  TTACCTGCCACAGTTTGCAGTAATCTGACATGCTTTATAACTTAGACCATTTCAAATTTG  17342
               ||||||||||||||||||||||||||||||||||||||||||||||||||||||||||||
Sbjct     628  TTACCTGCCACAGTTTGCAGTAATCTGACATGCTTTATAACTTAGACCATTTCAAATTTG    687

Query   17343  GAGGATTAGGAATGTATCAACAATAAAGTCTTGTCCAACTTTGAAT-AAGGTATATTCAG  17401
               |||||||||||||||||||||||||||||||||||||||||||||| |||||||||||||
Sbjct     688  GAGGATTAGGAATGTATCAACAATAAAGTCTTGTCCAACTTTGAATAAAGGTATATTCAG    747

Query   17402  TGTGAAAATTTGAGCCATTTATTTTTGCAGTCAATATAAATTTGCCTGCTTAGGTATGAT  17461
               ||||||||||||||||||||||||||||||||||||||||||||||||||||||||||||
Sbjct     748  TGTGAAAATTTGAGCCATTTATTTTTGCAGTCAATATAAATTTGCCTGCTTAGGTATGAT    807

Query   17462  CTACAGCCCAAGACATTAGTGCCATAGAAAGGTTTGTTTATTCATCATCTGGGTAACATG  17521
               ||||||||||||||||||||||||||||||||||||||||||||||||||||||||||||
Sbjct     808  CTACAGCCCAAGACATTAGTGCCATAGAAAGGTTTGTTTATTCATCATCTGGGTAACATG    867

Query   17522  CCTATTTCTCCATTTAA-CCTTTGTAGTGTACTTCCCTTTGCTGTAAACAATGTCAAGAA  17580
               ||||||||||||||||| |||||||||||||||||||||||||||| |||||| ||||
Sbjct     868  CCTATTTCTCCATTTAACCCTTTGTAGTGTACTTCCCTTTGCTGTAA-CAATGTC-AGAA    925

Query   17581  ACAGAAATAACGACAAAGAATGAAATATTTAGGTAAGATCTTTATTACATTTTTAATATA  17640
               ||||||||||||||  |||||||||||||||||  ||||||||||||| ||||||||||
Sbjct     926  ACAGAAATAACGAC-AAGAATGAAATATTTAGGT-AGATCTTTATTACA-TTTTAATATA    982
```

Query: Genomic Sequence from ENSEMBL Database (SEQ ID NO: 42)
Sbjct: Sequencing data from Targeting Vector (SEQ ID NO: 43)
T73 sequencing data aligned with genomic sequence

```
Query   22997  GGATCCCTCAGTGTTAGGATTATAGGCATATCCACCACCATATCTTGTCATTTATAATAA  23056
               ||||||||||||||||||||||||||||||||||||||||||||||||||||||||||||
Sbjct     949  GGATCCCTCAGTGTTAGGATTATAGGCATATCCACCACCATATCTTGTCATTTATAATAA    890

Query   23057  TAAAGTTAGAGATAAGAGTTAAATAATCTGGACACAAAAAGCCAAGTAATGCATAATACA  23116
               ||||||||||||||||||||||||||||||||||||||||||||||||||||||||||||
Sbjct     889  TAAAGTTAGAGATAAGAGTTAAATAATCTGGACACAAAAAGCCAAGTAATGCATAATACA    830

Query   23117  CATGTAACCAAACTAGGGTAAGCTGAGGACTAGGATATGTTAGTTGACTTATCCATGAGG  23176
               ||||||||||||||||||||||||||||||||||||||||||||||||||||||||||||
Sbjct     829  CATGTAACCAAACTAGGGTAAGCTGAGGACTAGGATATGTTAGTTGACTTATCCATGAGG    770
```

| Sequencing Data from BAC Sub Clone and Targeting Construct |
|---|

```
Query  23177  ACTAAGGTACAAGGACACAGATGACATTCTCATCACTGCTGCAAAGTAGAGGGACTACAG  23236
              ||||||||||||||||||||||||||||||||||||||||||||||||||||||||||||
Sbjct    769  ACTAAGGTACAAGGACACAGATGACATTCTCATCACTGCTGCAAAGTAGAGGGACTACAG    710

Query  23237  ATAACCAAAAAGTTCACAAGGGGATTGAATGCTTTTAGCCTAAACATGATAGCTTTGAGG  23296
              ||||||||||||||||||||||||||||||||||||||||||||||||||||||||||||
Sbjct    709  ATAACCAAAAAGTTCACAAGGGGATTGAATGCTTTTAGCCTAAACATGATAGCTTTGAGG    650

Query  23297  GAAGAGATGTGTTTACCTTCAATACCAATGTATCAAGACATTATATATACATGTATAACT  23356
              ||||||||||||||||||||||||||||||||||||||||||||||||||||||||||||
Sbjct    649  GAAGAGATGTGTTTACCTTCAATACCAATGTATCAAGACATTATATATACATGTATAACT    590

Query  23357  AGTGTTTATGCATCAGTTAAAAATCTACAAAAATTAAAACCACTAATACCCACACAACTA  23416
              ||||||||||||||||||||||||||||||||||||||||||||||||||||||||||||
Sbjct    589  AGTGTTTATGCATCAGTTAAAAATCTACAAAAATTAAAACCACTAATACCCACACAACTA    530

Query  23417  TCACTGCATTTCACACTTAGCCAGTTTCTCCAACTTTTAAGTATCGGAATACTCTGATTT  23476
              ||||||||||||||||||||||||||||||||||||||||||||||||||||||||||||
Sbjct    529  TCACTGCATTTCACACTTAGCCAGTTTCTCCAACTTTTAAGTATCGGAATACTCTGATTT    470

Query  23477  GTTGTACCACTTGCTAGCACTCTCTTTCTGTGTCATTTTTTGGTGAGGCACCGAATATGT  23536
              ||||||||||||||||||||||||||||||||||||||||||||||||||||||||||||
Sbjct    469  GTTGTACCACTTGCTAGCACTCTCTTTCTGTGTCATTTTTTGGTGAGGCACCGAATATGT    410

Query  23537  TCCAGAACATCGACTCTAGGTCCTTGAGGTAGAGCACAGCTTAAGTCATTTCTCTGTAGT  23596
              ||||||||||||||||||||||||||||||||||||||||||||||||||||||||||||
Sbjct    409  TCCAGAACATCGACTCTAGGTCCTTGAGGTAGAGCACAGCTTAAGTCATTTCTCTGTAGT    350

Query  23597  AAGATCACCGAGCACAATACCTGGCCTGTGGCAAGAATTTAAACTACACAATCAATGAAG  23656
              ||||||||||||||||||||||||||||||||||||||||||||||||||||||||||||
Sbjct    349  AAGATCACCGAGCACAATACCTGGCCTGTGGCAAGAATTTAAACTACACAATCAATGAAG    290

Query  23657  GAAAAAGACATTAATGATGTAAAGCTTTTATATAAAACATACTACAAAGAACGGTTTGAT  23716
              ||||||||||||||||||||||||||||||||||||||||||||||||||||||||||||
Sbjct    289  GAAAAAGACATTAATGATGTAAAGCTTTTATATAAAACATACTACAAAGAACGGTTTGAT    230

Query  23717  TATGTATACTTCTGAATAAAAGCCACAGAATGCTACTCAACAGCTACTTGGGTGTCTCAA  23776
              ||||||||||||||||||||||||||||||||||||||||||||||||||||||||||||
Sbjct    229  TATGTATACTTCTGAATAAAAGCCACAGAATGCTACTCAACAGCTACTTGGGTGTCTCAA    170

Query  23777  AGGGTGACACGCAAAACTAAAATTTTCTAGTGTTGAAATTTATAAGTTCTTACCTGAAAT  23836
              ||||||||||||||||||||||||||||||||||||||||||||||||||||||||||||
Sbjct    169  AGGGTGACACGCAAAACTAAAATTTTCTAGTGTTGAAATTTATAAGTTCTTACCTGAAAT    110

Query  23837  ACCTTAAAATTCGAAGATAATCTTCCTGAATTCTCTGTTTTGCATGTCCAACAAATCGAA  23896
              ||||||||||||||||||||||||||||||||||||||||||||||||||||||||||||
Sbjct    109  ACCTTAAAATTCGAAGATAATCTTCCTGAATTCTCTGTTTTGCATGTCCAACAAATCGAA     50

Query  23897  CCt                                                          23899
              |||
Sbjct     49  CCT                                                              47

Query: Genomic Sequence from ENSEMBL Database (SEQ ID NO: 44)
Sbjct: Sequencing data from Targeting Vector (SEQ ID NO: 45)
N1 sequencing data aligned with genomic sequence (exon 11 is underlined and the
mutation is in bold italic)

Query  18807  AGCTGGAGCCAACAGCAACATATAGACACGTGCAGTAATAAATTATCCAGTTATAACAGG  18866
              ||||||||||||||||||||||||||||||||||||||||||||||||||||||||||||
Sbjct    152  AGCTGGAGCCAACAGCAACATATAGACACGTGCAGTAATAAATTATCCAGTTATAACAGG    211

Query  18867  GTGGCTTTGTAAATTTGAGGTGTCAGAGAAATCTCACGAGAAGCCTAGTACAAAGGCTAA  18926
              ||||||||||||||||||||||||||||||||||||||||||||||||||||||||||||
Sbjct    212  GTGGCTTTGTAAATTTGAGGTGTCAGAGAAATCTCACGAGAAGCCTAGTACAAAGGCTAA    271

Query  18927  AAATAGGTTTTAACTTATATCTTTCCTTCATTTTATAGGTATGCATGGACC***ATT***GCCCAG  18986
              |||||||||||||||||||||||||||||||||||||||||||||||||||| |||||||
Sbjct    272  AAATAGGTTTTAACTTATATCTTTCCTTCATTTTATAGGTATGCATGGACC***GTG***GCCCAG    331

Query  18987  TGCAAGATCTGTGCAAGCCATATTGGATGGAAATTTACAGCCACaaaaaaaGACATGTCA  19046
              ||||||||||||||||||||||||||||||||||||||||||||||||||||||||||||
Sbjct    332  TGCAAGATCTGTGCAAGCCATATTGGATGGAAATTTACAGCCACAAAAAAAGACATGTCA    391
```

-continued

Sequencing Data from BAC Sub Clone and Targeting Construct

```
Query  19047  CCTCAAAAATTTTGGGGCTTAACTCGCTCTGCTCTGTTACCCACAATTCCAGAGACTGAA  19106
              ||||||||||||||||||||||||||||||||||||||||||||||||||||||||||||
Sbjct    392  CCTCAAAAATTTTGGGGCTTAACTCGCTCTGCTCTGTTACCCACAATTCCAGAGACTGAA    451

Query  19107  GATGAAATAAGTCCAGACAAAGTAATACTTTGTTTATAAGTGCACCTGTAGGAGTGACTT  19166
              ||||||||||||||||||||||||||||||||||||||||||||||||||||||||||||
Sbjct    452  GATGAAATAAGTCCAGACAAAGTAATACTTTGTTTATAAGTGCACCTGTAGGAGTGACTT    511

Query  19167  CCTGACAGATATTTCCTCAAGTCAGATCTGCCCAGTCATCACTGCCTCTGATATATGTGT  19226
              ||||||||||||||||||||||||||||||||||||||||||||||||||||||||||||
Sbjct    512  CCTGACAGATATTTCCTCAAGTCAGATCTGCCCAGTCATCACTGCCTCTGATATATGTGT    571

Query  19227  ATAGTGGGTTACAGCATTTGCCTACCAAGTTCAAGAGCATATTTAGGGAATGAGAAAGCA  19286
              ||||||||||||||||||||||||||||||||||||||||||||||||||||||||||||
Sbjct    572  ATAGTGGGTTACAGCATTTGCCTACCAAGTTCAAGAGCATATTTAGGGAATGAGAAAGCA    631

Query  19287  GTATAAAACATAAGGCTGGGTTCCAAAATACTTGCTTTTTAGTAGCTTGGTGCCATGGAT  19346
              ||||||||||||||||||||||||||||||||||||||||||||||||||||||||||||
Sbjct    632  GTATAAAACATAAGGCTGGGTTCCAAAATACTTGCTTTTTAGTAGCTTGGTGCCATGGAT    691

Query  19347  TATCCTGTTGAGTCTATGTCATGACAGGATAGGAAAACACAGTTGAAATAATGGGAATGG  19406
              ||||||||||||||||||||||||||||||||||||||||||||||||||||||||||||
Sbjct    692  TATCCTGTTGAGTCTATGTCATGACAGGATAGGAAAACACAGTTGAAATAATGGGAATGG    751

Query  19407  CCATGGAACAGGATAGGGGCACCACTGCTCTAAATGATGAAGCTCTAAATGATGAATGCT  19466
              ||||||||||||||||||||||||||||||||||||||||||||||||||||||||||||
Sbjct    752  CCATGGAACAGGATAGGGGCACCACTGCTCTAAATGATGAAGCTCTAAATGATGAATGCT    811

Query  19467  CCAGAAACTGGGTTGGTAAGCACAAGATAGAGGCAAGGCAGTGTAATTTTAAAAGGACTT  19526
              ||||||||||||||||||||||||||||||||||||||||||||||||||||||||||||
Sbjct    812  CCAGAAACTGGGTTGGTAAGCACAAGATAGAGGCAAGGCAGTGTAATTTTAAAAGGACTT    871

Query  19527  TGCTCCTTTCAATTTTCCTTAGCTTGTCTGAGATACTGACCTGTACATTTTGAACATATT  19586
              ||||||||||||||||||||||||||||||||||||||||||||||| ||||||||||||
Sbjct    872  TGCTCCTTTCAATTTTCCTTAGCTTGTCTGAGATACTGACCTGTACATTTTGACATATT    931

Query  19587  AAAGAGTAACTAAGTATTCTGAGCAGAAATAGCAGCATTTGGTGTAGTTGCACTTTTGAT  19646
               |||||||||||||||||||||||||||||||||||||||||||||||||||||||||||
Sbjct    932  -AAGAGTAACTAAGTATTCTGAGCAGAAATAGCAGCATTTGGTGTAGTTGCACTTTTGAT    990

Query  19647  TTGATGAGCCTGTGATGTGCTAGATCCCTTTAACTAATGTAT-ATGTCCA-TTTTG-CAT  19703
              |||||||||||||||||||||||||||||||||||||||||| ||||||| ||||| |||
Sbjct    991  TTGATGAGCCTGTGATGTGCTAGATCCCTTTAACTAATGTATTATGTCCAATTTTGGCAT   1050
```

Query: Genomic Sequence from ENSEMBL Database (SEQ ID NO: 46)
Sbjct: Sequencing data from Targeting Vector (SEQ ID NO: 47)
LAN1 Raw sequencing data (iNeo sequence is underlined; FRT is bold italic)

AGCGAACCTGCCGGGGCCTGCTTAAGGCGCATGCTTCCAGACTGCCTTGGGAAAAGCGCCTCCCCTACCCGGTAGAAT*GAA*

*GTTCCTATACTTTCTAGAGAATAGGAACTTC*GTTGGTACCGTACGCGGACGACCAACGGGCCCAATTGCTAGCTGGAGCCA

ACAGCAACATATAGACACGTGCAGTAATAAATTATCCAGTTATAACAGGGTGGCTTTGTAAATTTGAGGTGTCAGAGAAAT

CTCACGAGAAGCCTAGTACAAAGGCTAAAAATAGGTTTTAACTTATATCTTTCCTTCATTTTATAGGTATGCATGGACCGT

GGCCCAGTGCAAGATCTGTGCAAGCCATATTGGATGGAAATTTACAGCCACAAAAAAAGACATGTCACCTCAAAAATTTTG

GGGCTTAACTCGCTCTGCTCTGTTACCCACAATTCCAGAGACTGAAGATGAAATAAGTCCAGACAAAGTAATACTTTGTTT

ATAAGTGCACCTGTAGGAGTGACTTCCTGACAGATATTTCCTCAAGTCAGATCTGCCCAGTCATCACTGCCTCTGATATAT

GTGTATAGTGGGTTACAGCATTTGCCTACCAAGTTCAAGAGCATATTTAGGGAATGAGAAAGCAGTATAAAACATAAGGCT

GGGTTCCAAAATACTTGCTTTTTAGTAGCTTGGTGCCATGGATTATCCTGTTGAGTCTATGTCATGACAGGATAGGAAAAC

ACAGTTGAAATAATGGGAATGGCCATGGAACAGGATAGGGGCACCACTGCTCTAAATGATGAAGCTCTAAATGATGAATGC

TCCAGAAACTGGGTTGGTAAGCACAAGATAGAGGCAAGGCAGTGTAATTTTAAAAGGACTTTGCTCCTTTCAATTTTCCTT

AGCTTGTCTGAGATACTGACCTGTACATTTTGACATATTAAGAGTAACTAAGTATTCTGAGCAGAAATAGCAGCATTTGG

| Sequencing Data from BAC Sub Clone and Targeting Construct |
|---|

TGTAGTTGCACTTTTGATTTGATGAGCCTGTGATGTGCTAGATCCCTTTAACTAATGTATTATGTCCAATTTTGGCAT (SEQ ID NO: 48)

iNeoN2 sequencing data aligned with genomic sequence

```
Query  17949  AGGTCAGGAAACTGATATGT-AGGTAAAGTAACTAAATGTCCAAAGATGAAAACATGACC  18007
              |||||||||||||||||||| |||||||||||||||||||||||||||||||||||||||
Sbjct   1038  AGGTCAGGAAACTGATATGTTAGGTAAAGTAACTAAATGTCCAAAGATGAAAACATGAC-   980

Query  18008  TCACTAGGCTTTGTAAACACATA-TATTTACCTTTGAATCATCAAAGAACATTTTTAAGC  18066
              ||||||||||||||||||||||| |||||||||||||||||||||||||||||||||||
Sbjct    979  TCACTAGGCTTTGTAAACACATAATATTTACCTTTGAATCATCAAAGAACATTTTTAAGC   920

Query  18067  AACAGAATATCTGCCAACCTCC-TGTATACTTGTCTTACATTTTACACAAAGTACTATAT  18125
              |||||||||||||||||| ||| |||||||||||||||||||||||||||||||||||||
Sbjct    919  AACAGAATATCTGCCAAC-TCCTTGTATACTTGTCTTACATTTTACACAAAGTACTATAT   861

Query  18126  AATATCTAAAATTCAAAGGTTAAAAAGCATAACTTATGTCCCAAATAAGTAAAAAACTGG  18185
              ||||||||||||||||||||||||||||||||||||||||||||||||||||||||||||
Sbjct    860  AATATCTAAAATTCAAAGGTTAAAAAGCATAACTTATGTCCCAAATAAGTAAAAAACTGG   801

Query  18186  GATTACTATTTTTCTTTTCATTGTCTTATTCTCCACATTATTTCTTTGTCTGTAGTTTAT  18245
              ||||||||||||||||||||||||||||||||||||||||||||||||||||||||||||
Sbjct    800  GATTACTATTTTTCTTTTCATTGTCTTATTCTCCACATTATTTCTTTGTCTGTAGTTTAT   741

Query  18246  CCTTATGTGGTCCAATGGCAGCATATGTGAATCCTCATGGATATGTACATGAGACACTGA  18305
              ||||||||||||||||||||||||||||||||||||||||||||||||||||||||||||
Sbjct    740  CCTTATGTGGTCCAATGGCAGCATATGTGAATCCTCATGGATATGTACATGAGACACTGA   681

Query  18306  CTGTGTATAAAGCGTCCAACCTGAATCTGATAGGCCGGCCTTCTACAGTGCACAGCTGGT  18365
              ||||||||||||||||||||||||||||||||||||||||||||||||||||||||||||
Sbjct    680  CTGTGTATAAAGCGTCCAACCTGAATCTGATAGGCCGGCCTTCTACAGTGCACAGCTGGT   621

Query  18366  TTCCCGGGTAATACAGCTGTTTACTTTTCTTGTTGACTCTTCATTTAGTTTTAGATGAAC  18425
              ||||||||||||||||||||||||||||||||||||||||||||||||||||||||||||
Sbjct    620  TTCCCGGGTAATACAGCTGTTTACTTTTCTTGTTGACTCTTCATTTAGTTTTAGATGAAC   561

Query  18426  TTTCTAGGAAGATACAAAACAAACAGGACAGGAATAGTTTGATCACTTCATGAATGGGTT  18485
              ||||||||||||||||||||||||||||||||||||||||||||||||||||||||||||
Sbjct    560  TTTCTAGGAAGATACAAAACAAACAGGACAGGAATAGTTTGATCACTTCATGAATGGGTT   501

Query  18486  AAAAGCAGGGACATGAGATGTAGAAACCAGTAAATCCTGCTTTCTCTAGCTTGCTTTAAC  18545
              ||||||||||||||||||||||||||||||||||||||||||||||||||||||||||||
Sbjct    500  AAAAGCAGGGACATGAGATGTAGAAACCAGTAAATCCTGCTTTCTCTAGCTTGCTTTAAC   441

Query  18546  CTTGCTCTCCCTTTTACTTTGGAAGTGGCAGAAGAATTAGGGATTAGTGACTTATTATCT  18605
              ||||||||||||||||||||||||||||||||||||||||||||||||||||||||||||
Sbjct    440  CTTGCTCTCCCTTTTACTTTGGAAGTGGCAGAAGAATTAGGGATTAGTGACTTATTATCT   381

Query  18606  TATTATCCTTGAACAAAATCCTCTTATTTGGCATCATTCTTGAGGACTGTAAAGCTAACA  18665
              ||||||||||||||||||||||||||||||||||||||||||||||||||||||||||||
Sbjct    380  TATTATCCTTGAACAAAATCCTCTTATTTGGCATCATTCTTGAGGACTGTAAAGCTAACA   321

Query  18666  TTAATATGCAGAATCCTCTACCTGAGAAAAATGGTACCCTGAGAGCAGAAGTGCCTTGCC  18725
              ||||||||||||||||||||||||||||||||||||||||||||||||||||||||||||
Sbjct    320  TTAATATGCAGAATCCTCTACCTGAGAAAAATGGTACCCTGAGAGCAGAAGTGCCTTGCC   261

Query  18726  TGTCTTCCAGGGGTTCATGCTCTCCTGCATCACCTTCACGTGCATCTCCAACAGAAATGG  18785
              ||||||||||||||||||||||||||||||||||||||||||||||||||||||||||||
Sbjct    260  TGTCTTCCAGGGGTTCATGCTCTCCTGCATCACCTTCACGTGCATCTCCAACAGAAATGG   201

Query  18786  AGAAGAAAGCTGTGAGGTTAA                                        18806
              |||||||||||||||||||||
Sbjct    200  AGAAGAAAGCTGTGAGGTTAA                                          180
```

Query: Genomic Sequence from ENSEMBL Database (SEQ ID NO: 49)
Sbjct: Sequencing data from Targeting Vector (SEQ ID NO: 50)
iNeoN2 RAW sequencing data (iNeo sequence is underlined; FRT is bold italic)

<u>CCTCACCCCGGCCCGATAAAATTGGCCACTGGATTGCAGAAGGTCTCTTCCTGGATCACCTGACAACTCACTCCCATGTCT</u>

<u>TCCAGACTTCTGTCTTACTCTAGATCGG*GAAGTTCCTATTCTCTAGAAAGTATAGGAACTTC*GCGACACGGACACAATCCC</u>

Sequencing Data from BAC Sub Clone and Targeting Construct

ACGAACGTACGCCTAGGTTAACCTCACAGCTTTCTTCTCCATTTCTGTTGGAGATGCACGTGAAGGTGATGCAGGAGAGCA

TGAACCCCTGGAAGACAGGCAAGGCACTTCTGCTCTCAGGGTACCATTTTTCTCAGGTAGAGGATTCTGCATATTAATGTT

AGCTTTACAGTCCTCAAGAATGATGCCAAATAAGAGGATTTTGTTCAAGGATAATAAGATAATAAGTCACTAATCCCTAAT

TCTTCTGCCACTTCCAAAGTAAAAGGGAGAGCAAGGTTAAAGCAAGCTAGAGAAAGCAGGATTTACTGGTTTCTACATCTC

ATGTCCCTGCTTTTAACCCATTCATGAAGTGATCAAACTATTCCTGTCCTGTTTGTTTTGTATCTTCCTAGAAAGTTCATC

TAAAACTAAATGAAGAGTCAACAAGAAAAGTAAACAGCTGTATTACCCGGGAAACCAGCTGTGCACTGTAGAAGGCCGGCC

TATCAGATTCAGGTTGGACGCTTTATACACAGTCAGTGTCTCATGTACATATCCATGAGGATTCACATATGCTGCCATTGG

ACCACATAAGGATAAACTACAGACAAAGAAATAATGTGGAGAATAAGACAATGAAAAGAAAAATAGTAATCCCAGTTTTTT

ACTTATTTGGGACATAAGTTATGCTTTTTAACCTTTGAATTTTAGATATTATATAGTACTTTGTGTAAAATGTAAGACAAG

TATACAAGGAGTTGGCAGATATTCTGTTGCTTAAAAATGTTCTTTGATGATTCAAAGGTAAATATTATGTGTTTACAAAGC

CTAGTGAGTCATGTTTTCATCTTTGGACATTTAGTTACTTTACCTAACATATCAGTTTCCTGACCTCT (SEQ ID NO: 51)

Backbone vector sequence
3' terminus of murine genomic region subcloned from BAC joins here CATCGATGATGGGCCACATTGGCCTCGACGATATCGCGATCGCCGATAAGCCAGGTTAACCTGCATTAACGCGCCGTCGAC GCGGCGCGTTTGCGTATTGGGCGCTCTTCCGCTTCCTCGCTCACTGACTCGCTGCGCTCGGTCGTTCGGCTGCGGCGAGCG GTATCAGCTCACTCAAAGGCGGTAATACGGTTATCCACAGAATCAGGGGATAACGCAGGAAAGAACATGTGAGCAAAAGGC CAGCAAAAGGCCAGGAACCGTAAAAAGGCCGCGTTGCTGGCGTTTTTCCATAGGCTCCGCCCCCCTGACGAGCATCACAAA AATCGACGCTCAAGTCAGAGGTGGCGAAACCCGACAGGACTATAAAGATACCAGGCGTTTCCCCCTGGAAGCTCCCTCGTG CGCTCTCCTGTTCCGACCCTGCCGCTTACCGGATACCTGTCCGCCTTTCTCCCTTCGGGAAGCGTGGCGCTTTCTCATAGC TCACGCTGTAGGTATCTCAGTTCGGTGTAGGTCGTTCGCTCCAAGCTGGGCTGTGTGCACGAACCCCCCGTTCAGCCCGAC CGCTGCGCCTTATCCGGTAACTATCGTCTTGAGTCCAACCCGGTAAGACACGACTTATCGCCACTGGCAGCAGCCACTGGT AACAGGATTAGCAGAGCGAGGTATGTAGGCGGTGCTACAGAGTTCTTGAAGTGGTGGCCTAACTACGGCTACACTAGAAGA ACAGTATTTGGTATCTGCGCTCTGCTGAAGCCAGTTACCTTCGGAAAAAGAGTTGGTAGCTCTTGATCCGGCAAACAAACC ACCGCTGGTAGCGGTGGTTTTTTTGTTTGCAAGCAGCAGATTACGCGCAGAAAAAAAGGATCTCAAGAAGATCCTTTGATC

TTTTCTACGGGGTCTGACGCTCAGTGGAACGAAAACTCACGTTAAGGGATTTTGGTCATGAGATTATCAAAAGGATCTTC

ACCTAGATCCTTTTAAATTAAAAATGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTGCCTGACTCCCCGTCGTGTAGATA

ACTACGATACGGGAGGGCTTACCATCTGGCCCCAGTGCTGCAATGATACCGCGAGACCCACGCTCACCGGCTCCAGATTTA

TCAGCAATAAACCAGCCAGCCGGAAGGGCCGAGCGCAGAAGTGGTCTGCAACTTTATCCGCCTCCATCCAGTCTATTAATT

GTTGCCGGGAAGCTAGAGTAAGTAGTTCGCCAGTTAATAGTTTGCGCAACGTTGTTGCCATTGCTACAGGCATCGTGGTGT

CACGCTCGTCGTTTGGTATGGCTTCATTCAGCTCCGGTTCCCAACGATCAAGGCGAGTTACATGATCCCCCATGTTGTGCA

AAAAAGCGGTTAGCTCCTTCGGTCCTCCGATCGTTGTCAGAAGTAAGTTGGCCGCAGTGTTATCACTCATGGTTATGGCAG

CACTGCATAATTCTCTTACTGTCATGCCATCCGTAAGATGCTTTTCTGTGACTGGTGAGTACTCAACCAAGTCATTCTGAG

AATAGTGTATGCGGCGACCGAGTTGCTCTTGCCCGGCGTCAATACGGGATAATACCGCGCCACATAGCAGAACTTTAAAAG

TGCTCATCATTGGAAAACGTTCTTCGGGGCGAAAACTCTCAAGGATCTTACCGCTGTTGAGATCCAGTTCGATGTAACCCA

CTCGTGCACCCAACTGATCTTCAGCATCTTTTACTTTCACCAGCGTTTCTGGGTGAGCAAAAACAGGAAGGCAAAATGCCG

CAAAAAAGGGAATAAGGGCGACACGGAAATGTTGAATACTCATACTCTTCCTTTTTCAATATTATTGAAGCATTTATCAGG

| Sequencing Data from BAC Sub Clone and Targeting Construct |
|---|

GTTATTGTCTCATGAGCGGATACATATTTGAATGTATTTAGAAAAATAAACAAATAGGGGTTCCGCGCACATTTCCCCGAA

AAGTGCCACCTGACGTCTAAGAAACCATTATTATCATGACATTAACCTATAAAAATAGGCGTATCACGAGGCCCTTTCGTC

TCGCGCGTTTCGGTGATGACGGTGAAAACCTCTGACACATGCAGCTCCCGGAGACGGTCACAGCTTGTCTGTAAGCGGATG

CCGGGAGCAGACAAGCCCGTCAGGGCGCGTCAGCGGGTGTTGGCGGGTGTCGGGGCTGGCTTAACTATGCGGCATCAGAGC

AGATTGTACTGAGAGTGCACCATATGGACATATTGTCGTTAGAACGCGGCTACAATTAATACATAACCTTATGTATCATAC

ACATACGATTTAGGTGACACTATAGAACTCGATGCGGCCCCTGCAGGCGCGCCATTTAAATGCGGCCGCACCTCAGGATGT

CCCCTGAAGCT (SEQ ID NO: 52)

5' terminus of murine genomic region subcloned from BAC joins here
Cassette sequence
FRT-flanked PGK-gb2-Neo Cassette (3'-5' orientation); FRT sites are underlined, bold and italic CCTAGGCGTACGTTCGTGGGATTGTGTCCGTGTCGC*GAAGTTCCTATACTTTCTAGAGAATAGGAACTTC*CCGCGGTTGTA AGTTCTCCAGATCTAGAGTAAGACAGAAGTCTGGAAGACATGGGAGTGAGTTGTCAGGTGATCCAGGAAGAGACCTTCTGC AATCCAGTGACCAATTAATTACAGCAGAAAGGACCATCGGGAAGGAAAGCCATACTCTCCAGGAACGTCATTAGTCGGGAT CTTCAGTTGCTACAAGAAGCAGATGTCAAACGGCCTTCCCCTAACCATGTGAGAAGTGAGCTTTCACTGGCCCGGGTGTGA AGTGATTCTAATGGAATAAATGGATTTGCTAAGGAATAGTTTCCTCAGAAGAAATCCTGGGAGCAAGTGGGGAAAGCTGAC TCAGCAAAACAGAGCTGTTTCTTGAGGACGATGCCAATAGCAATCATTTGACCAAACTGAAGTGGCCGTCAGGAGGCATGA GGATCTGATATCAGGGAGCTCTCAGACGTCGCTTGGTCGGTCTTTATTCGAACCCCAGAGTCCCGCTCAGAAGAACTCGTC AAGAAGGCGATAGAAGGCGATGCGCTGCGAATCGGGAGCGGCGATACCGTAAAGCACGAGGAAGCGGTCAGCCCATTCGCC GCCAAGCTCTTCAGCAATATCACGGGTAGCCAACGCTATGTCCTGATAGCGGTCCGCCACACCCAGCCGGCCACAGTCGAT GAATCCAGAAAAGCGGCCATTTTCCACCATGATATTCGGCAAGCAGGCATCGCCATGGGTCACGACGAGATCCTCGCCGTC GGGCATGCGCGCCTTGAGCCTGGCGAACAGTTCGGCTGGCGCGAGCCCCTGATGCTCTTCGTCCAGATCATCCTGATCGAC AAGACCGGCTTCCATCCGAGTACGTGCTCGCTCGATGCGATGTTTCGCTTGGTGGTCGAATGGGCAGGTAGCCGGATCAAG CGTATGCAGCCGCCGCATTGCATCAGCCATGATGGATACTTTCTCGGCAGGAGCAAGGTGAGATGACAGGAGATCCTGCCC CGGCACTTCGCCCAATAGCAGCCAGTCCCTTCCCGCTTCAGTGACAACGTCGAGCACAGCTGCGCAAGGAACGCCCGTCGT GGCCAGCCACGATAGCCGCGCTGCCTCGTCCTGCAGTTCATTCAGGGCACCGGACAGGTCGGTCTTGACAAAAAGAACCGG GCGCCCCTGCGCTGACAGCCGGAACACGGCGGCATCAGAGCAGCCGATCGTCTGTTGTGCCCAGTCATAGCCGAATAGCCT CTCCACCCAAGCGGCCGGAGAACCTGCGTGCAATCCATCTTGTTCAATGGCCGATCCCATGGTTTAGTTCCTCACCTTGTC GTATTATACTATGCCGATATACTATGCCGATGATTAATTGTCAACACGTGCTGCTGCAGGTCGAAAGGCTCGGAGATGAGG AAGAGGAGAACAGCGCGGCAGACGTGCGCTTTTGAAGCGTGCAGAATGCCGGGCCTCCGGAGGACCTTCGGGCGCCCGCCC CGCCCCTGAGCCCGCCCCTGAGCCCGCCCCCGGACCCACCCCTTCCCAGCCTCTGAGCCCAGAAAGCGAAGGAGCAAAGCT GCTATTGGCCGCTGCCCCAAAGGCCTACCCGCTTCCATTGCTCAGCGGTGCTGTCCATCTGCACGAGACTAGTGAGACGTG CTACTTCCATTTGTCACGTCCTGCACGACGCGAGCTGCGGGGCGGGGGGGAACTTCCTGACTAGGGGAGGAGTGGAAGGTG GCGCGAAGGGGCCACCAAAGAACGGAGCCGGTTGGCGCCTACCGGTGGATGTGGAATGTGTGCGAGGCCAGAGGCCACTTG TGTAGCGCCAAGTGCCCAGCGGGGCTGCTAAAGCGCATGCTCCAGACTGCCTTGGGAAAAGCGCCTCCCCTACCCGGTAGA

AT*GAAGTTCCTATACTTTCTAGAGAATAGGAACTTC*GTTGGTACCGTACGCGGACGACCAACGGGCCCAATT

GCT (SEQ ID NO: 53)

Figure 35:
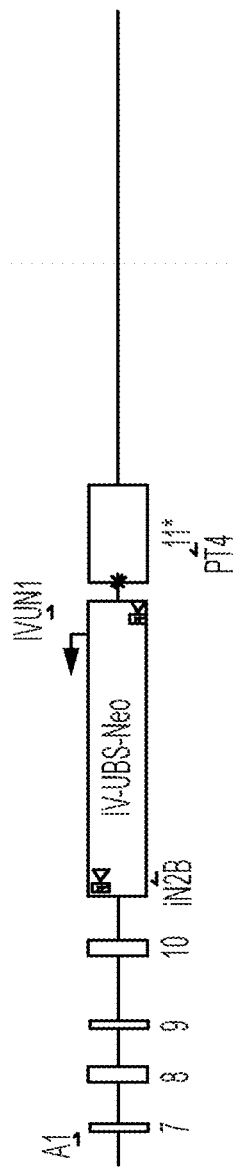
FIG. 35 is a schematic diagram showing the primers (A1, IVUN1, PT4, and iN2B) used to screen the embryonic stem cell clones carrying mutant CRBN$^{I391V}$.

Generation, Screening and Confirmation of Embryonic Stem Cell Clones Carrying mCRBN$^{I391V}$ Ten micrograms of the targeting vector was linearized by Not I and then transfected by electroporation of C57Bl/6 (B6) embryonic stem cells. After selection with G418 antibiotic, surviving clones were expanded for PCR analysis to identify recombinant embryonic stem cell clones. FIG. 35 illustrates the locations of the primers used for PCR screening. The sequences of the primers for PCR screening are listed below.

```
Primers for PCR Screening (SEQ ID NOs:
54-57, respectively, inorder of appearance)
A1:
5'-ACA GAC ATC GTA CGT GGT CTC AG-3'

IVUN1:
5'-GCT CCA GAC TGC CTT GGG AAA AGC-3'

PT4:
5'-GCT CTT GAA CTT GGT AGG CAA ATG C-3' iN2B:
5'-TCC CAT GTC TTC CAG ACT TCT GTC-3'
```

Screening primer A1 was designed upstream of the short homology arm (SA) outside the 5' region used to generate the targeting construct. PCR reactions using A1 with the iN2B primer (located within the Neo cassette) amplify 2.47 kb fragment. Clones 144, 271, 274, 332, and 352 were identified as positive and selected for further expansion.

Reconfirmation of Expanded Clones by PCR

Figure 36:
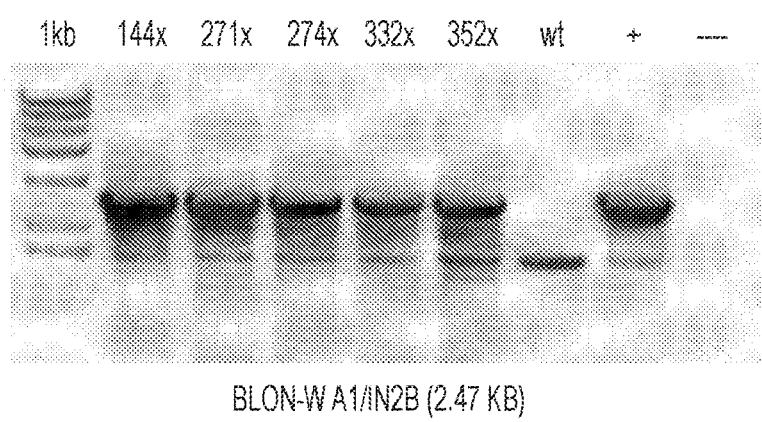
FIG. 36 is a gel showing that short homology arm (SA) integration was present in expanded clones. Each expanded clone was denoted by the clone number (e.g. 144) followed by a "x". "lkb" refers to the reference lkb DNA ladder. DNA from an individual clone (before reconfirmation) was used as a positive control and denoted by a (+). No DNA was used as a negative control and denoted by a (--).

Clones 144, 271, 274, 332, and 352 were expanded and reconfirmed for short homology arm integration (FIG. 36).

Confirmation of Point Mutation by DNA Sequencing

Figure 37:
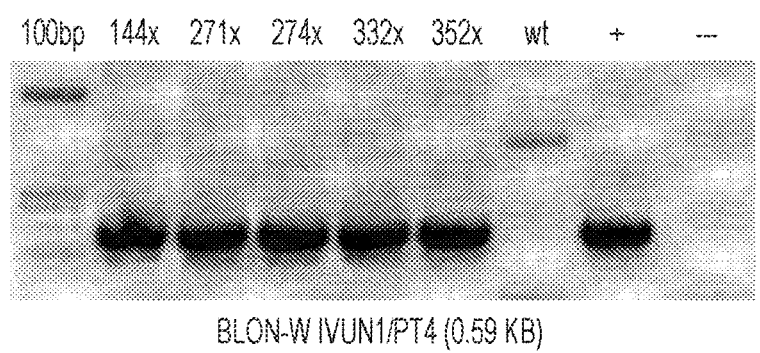
FIG. 37 is a gel showing PCR products comprising the I319V mutation. The products were 0.59 kb as expected.

Confirmation of the point mutation was performed by PCR using the IVUN1 and PT4 primers. This reaction produces a product 0.59 kb in size (FIG. 37). Sequencing was performed on purified PCR DNA to confirm the presence of the point mutation using the IVUN1 primer. The sequence from a confirmed clone is shown below (Query=sequence from clone #271; Sbjct=WT sequences).

the targeting vector. For wild type mice, Mfe I digestion produces a DNA band of about 22.5 kilobases and EcoRI digestion produces a DNA band of about 6.5 kilobases. The digested DNA was electrophoretically separated on a 0.8% agarose gel. After transfer to a nylon membrane, the digested DNA was hybridized with a probe (iNeo) targeted against the Neo Cassette. DNA from C57Bl/6 (B6) mouse strain was used as a wild type control. FIG. 39 shows the results from the Southern Blot. The iNeo probe sequence is listed below.

```
iNeo probe sequence:
                                      (SEQ ID NO: 60)
GTGAGTTGTCAGGTGATCCAGGAAGAGACCTTCTGCAATCCAGTGACCAA

TTAATTACAGCAGAAAGGACCATCGGGAAGGAAAGCCATACTCTCCAGGA

ACGTCATTAGTCGGGATCTTCAGTTGCTACAAGAAGCAGATGTCAAACGG

CCTTCCCCTAACCATGTGAGAAGTGAGCTTTCACTGGCCCGGGTGTGAAG

TGATTCTAATGGAATAAATGGATTTGCTAAGGAATAGTTTCCTCAGAAGA

AATCCTGGGAGCAAGTGGGGAAAGCTGACTCAGCAAAACAGAGCTGTTTC

TTGAGGACGATGCCAATAGCAATCATTTGACCAAACTGAAGTGGCCGTCA

GGAGGCATG
```

Clones 144, 271, 274, 332, and 352 were confirmed as correctly targeted and recommended for injection.

Karyotyping Chromosome Counts for BLON-W

Each clonal cell culture was sampled prior to injection and is of equal passage number to the injected cells. Slides from harvested cultures were made using a CD-4 Thermotron and then G-banded. All slide images were captured and counted using Applied Spectral Imaging's BandView software. For each clone, 15 metaphase spreads were analyzed and the percentage euploidy of each culture was calculated in accordance with Cold Spring Harbor Laboratory's chromosome counting protocol of ignoring metaphase spreads with less than 39 chromosomes.

```
Query    127  AGCTGGAGCCAACAGCAACATATAGACACGTGCAGTAATAAATTATCCAGTTATAACAGG    186
              ||||||||||||||||||||||||||||||||||||||||||||||||||||||||||||
Sbjct  18807  AGCTGGAGCCAACAGCAACATATAGACACGTGCAGTAATAAATTATCCAGTTATAACAGG  18866

Query    187  GTGGCTTTGTAAATTTGAGGTGTCAGAGAAATCTCACGAGAAGCCTAGTACAAAGGCTAA    246
              ||||||||||||||||||||||||||||||||||||||||||||||||||||||||||||
Sbjct  18867  GTGGCTTTGTAAATTTGAGGTGTCAGAGAAATCTCACGAGAAGCCTAGTACAAAGGCTAA  18926

Query    247  AAATAGGTTTTAACTTATATCTTTCCTTCATTTTATAGGTATGCATGGACC*GTG*GCCCAG    306
              |||||||||||||||||||||||||||||||||||||||||||||||||||| ||||||
Sbjct  18927  AAATAGGTTTTAACTTATATCTTTCCTTCATTTTATAGGTATGCATGGACCATTGCCCAG  18986

Query    307  TGCAAGATCTGTGCAAGCCATATTGGATGTAAATTTA                         343 (SEQ
                                                                          ID NO:
                                                                          58)
              |||||||||||||||||||||||||||||||| ||||||||
Sbjct  18987  TGCAAGATCTGTGCAAGCCATATTGGATGGAAATTTA                        19023
                                                                          (SEQ ID
                                                                          NO: 59)
```

The point mutation is indicated in bold italic. The clones 144, 271, 274, 332, and 352 were further analyzed by Southern blot.

Southern Blot Analysis

Secondary confirmation of positive clones identified by PCR was performed by Southern Blotting analysis. FIGS. 38A and 39B illustrate the strategy used for Southern Blot and the expected sizes of the WT Control bands. DNA was digested with Mfe I and EcoR I to confirm the integration of

| Project Number | Project Name | Clone Number | Percentage Euploid |
|---|---|---|---|
| 1605 | BLON-W | 144 | 0.77 |
| 1605 | BLON-W | 271 | 1 |
| 1605 | BLON-W | 274 | 0.7 |
| 1605 | BLON-W | 332 | 0.9 |
| 1605 | BLON-W | 352 | 0.8 |

All clones passed the required 70% euploid cutoff and were recommended for injection.

Generation and Identification of Knock-in Mice

Targeted iTL IC1 (C57BL/6) embryonic stem cells were microinjected into Balb/c blastocysts. Resulting chimeras with a high percentage black coat color were mated to C57BL/6 FLP mice to remove the Neo cassette. Tail DNA was analyzed as shown in FIGS. 40A-40C from pups with black coat color. The primer sequences used for PCR screening are listed below.

```
Primers for PCR Screening (SEQ ID NOs: 54,
61-65, respectively, in order of appearance):
Forward Oligos
A1:
5'-ACA GAC ATC GTA CGT GGT CTC AG-3'

NDEL1:
5'-ACT TTG GAA GTG GCA GAA GAA TTA GGG-3'

Reverse Oligos
RNEOGT:
5'-GAA AGT ATA GGA ACT TCG CGA CAC GGA C-3'

PT4:
5'-GCT CTT GAA CTT GGT AGG CAA ATG C-3'

FLP1:
5'-CAC TGA TAT TGT AAG TAG TTT GC-3'

FLP2:
5'-CTA GTG CGA AGT AGT GAT CAG G-3'
```

Screening for Neo Deletion and Point Mutation

Primer set NDEL1 and PT4 was used to screen mice for the deletion of the Neo cassette. The PCR product for the wild-type is 705 bp. After Neo deletion, one set of LoxP-FRT sites remain (143 bp). A second band with a size of 848 bp indicates Neo deletion. The presence of the Neo cassette is not amplified by this PCR screening because the size is too great. FIG. 41 shows the result of the PCR screening. The PCR parameters for the screening are 94° C. 30 seconds, 60° C. 30 seconds, and 72° C. 1 minute for 30 cycles.

The PCR product was sequenced to confirm the point mutation and the deletion of the Neo cassette. Below is sequencing of representative mouse #582 using primer NDEL1. The sequence shows the deletion of the Neo cassette with the exception of one set of LoxP-FRT sites.

The remaining sequence of the Neo cassette is underlined, the FRT site is in italic text, and the loxP site is in bold text.

```
Query     66 GGACTGTAAAGCTAACATTAATATGCAGAATCCTCTACCTGAGAAAAATGGTACCCTGAG    125
             ||||||||||||||||||||||||||||||||||||||||||||||||||||||||||||
Sbjct  18649 GGACTGTAAAGCTAACATTAATATGCAGAATCCTCTACCTGAGAAAAATGGTACCCTGAG  18708

Query    126 AGCAGAAGTGCCTTGCCTGTCTTCCAGGGGTTCATGCTCTCCTGCATCACCTTCACGTGC    185
             ||||||||||||||||||||||||||||||||||||||||||||||||||||||||||||
Sbjct  18709 AGCAGAAGTGCCTTGCCTGTCTTCCAGGGGTTCATGCTCTCCTGCATCACCTTCACGTGC  18768

Query    186 ATCTCCAACAGAAATGGAGAAGAAAGCTGTGAGGTTAACCTAGGCGTACGTTCGTGGGAT    245
             ||||||||||||||||||||||||||||||||||||||||||||||||||||||||||||
Sbjct  18769 ATCTCCAACAGAAATGGAGAAGAAAGCTGTGAGGTTAACCTAGGCGTACGTTCGTGGGAT  18828

Query    246 TGTGTCCGTGTCGCGAAGTTCCTATACTTTCTAGAGAATAGGAACTTCGTTCGAACATAA    305
             ||||||||||||||||||||||||||||||||||||||||||||||||||||||||||||
Sbjct  18829 TGTGTCCGTGTCGCGAAGTTCCTATACTTTCTAGAGAATAGGAACTTCGTTCGAACATAA  18888

Query    306 CTTCGTATAGCATACATTATACGAAGTTATGGTACGCGGACGACCAACGGGCCCAATTGC    365
             ||||||||||||||||||||||||||||||||||||||||||||||||||||||||||||
Sbjct  18889 CTTCGTATAGCATACATTATACGAAGTTATGGTACGCGGACGACCAACGGGCCCAATTGC  18948

Query    366 TAGCTGGAGCCAACAGCAACATATAGACACGTGCAGTAATAAATTATCCAGTTATAACAG    425
             ||||||||||||||||||||||||||||||||||||||||||||||||||||||||||||
Sbjct  18949 TAGCTGGAGCCAACAGCAACATATAGACACGTGCAGTAATAAATTATCCAGTTATAACAG  19008

Query    426 GGTGGCTTTGTAAATTTGAGGTGTCAGAGAAATCTCACGAGAAGCCTAGTACAAAGGCTA    485
             ||||||||||||||||||||||||||||||||||||||||||||||||||||||||||||
Sbjct  19009 GGTGGCTTTGTAAATTTGAGGTGTCAGAGAAATCTCACGAGAAGCCTAGTACAAAGGCTA  19068

Query    486 AAAATAGGTTTTAACTTATATCTTTCCTTCATTTTATAGGTATGCATGGACCGTGGCCCA    545
             ||||||||||||||||||||||||||||||||||||||||||||||||||||||||||||
Sbjct  19069 AAAATAGGTTTTAACTTATATCTTTCCTTCATTTTATAGGTATGCATGGACCGTGGCCCA  19128

Query    546 GTGCAAGATCTGTGCAAGCCATATTGGATGGAAATTTACAGCCACaaaaaaaGACATGTC    605
             ||||||||||||||||||||||||||||||||||||||||||||||||||||||||||||
Sbjct  19129 GTGCAAGATCTGTGCAAGCCATATTGGATGGAAATTTACAGCCACAAAAAAAGACATGTC  19188
Query: Sequencing data from PCR products (SEQ ID NO: 66)
Sbjct: Respective targeted allele sequence (SEQ ID NO: 67)
```

Sequencing was performed on purified PCR DNA to confirm presence of the point mutations using the PT4 primer. Sequencing from represented mouse #582 is shown below. The point mutations AAT→CAC is highlighted as bold italic text

```
Query     11 ACTAT-C-CATAATATC-TATGCAGTGATGACTGGGCAGATCTGACTTTGAGGAAATATC     67
             ||||| | ||| ||||| | |||||||||||||||||||||||||||| |||||||||||
Sbjct  19231 ACTATACACAT-ATATCAGAGGCAGTGATGACTGGGCAGATCTGACTT-GAGGAAATATC  19174
```

```
Query       68 TGTCAGGAAGTCACTCCTACTGGTGCACTTATAAACAAAGTATTACTTTGTCTGGACTTA      127
               ||||||||||||||||||||| ||||||||||||||||||||||||||||||||||||||
Sbjct    19173 TGTCAGGAAGTCACTCCTACAGGTGCACTTATAAACAAAGTATTACTTTGTCTGGACTTA    19114

Query      128 TTTCATCTTCAGTCTCTGGAATTGTGGGTAACAGAGCAGAGCGAGTTAAGCCCCAAAATT      187
               ||||||||||||||||||||||||||||||||||||||||||||||||||||||||||||
Sbjct    19113 TTTCATCTTCAGTCTCTGGAATTGTGGGTAACAGAGCAGAGCGAGTTAAGCCCCAAAATT    19054

Query      188 TTTGAGGTGACATGTCttttttTGTGGCTGTAAATTTCCATCCAATATGGCTTGCACAGA      247
               |||||||||||||||| |||||||||||||||||||||||||||||||||||||||||||
Sbjct    19053 TTTGAGGTGACATGTCTTTTTTTGTGGCTGTAAATTTCCATCCAATATGGCTTGCACAGA    18994

Query      248 TCTTGCACTGGGCCACGGTCCATGCATACCTATAAAATGAAGGAAAGATATAAGTTAAAA      307
               |||||||||||||  | |||||||||||||||||||||||||||||||||||||||||||
Sbjct    18993 TCTTGCACTGGGCAATGGTCCATGCATACCTATAAAATGAAGGAAAGATATAAGTTAAAA    18934

Query      308 CCTATTTTTAGCCTTTGTACTAGGCTTCTCGTGAGATTTCTCTGACACCTCAAATTTACA      367
               ||||||||||||||||||||||||||||||||||||||||||||||||||||||||||||
Sbjct    18933 CCTATTTTTAGCCTTTGTACTAGGCTTCTCGTGAGATTTCTCTGACACCTCAAATTTACA    18874

Query      368 AAGCCACCCTGTTATAACTGGATAATTTATTACTGCACGTGTCTATATGTTGCTGTTGGC      427
               ||||||||||||||||||||||||||||||||||||||||||||||||||||||||||||
Sbjct    18873 AAGCCACCCTGTTATAACTGGATAATTTATTACTGCACGTGTCTATATGTTGCTGTTGGC    18814

Query      428 TCCAGCT      434
               |||||||
Sbjct    18813 TCCAGCT            18807
Query: Sequencing data from PCR products (SEQ ID NO: 68)
Sbjct: Respective Wild Type Allele (SEQ ID NO: 69)
```

Confirmation of Short Homology Arm Integration

Tail DNA samples from positive mice were amplified with primers A1 and RNEOGT. RNEOGT is located inside the Neo cassette and A1 is located upstream of the short homology arm, outside the region used to create the targeting construct. A1/RNEOGT amplified a fragment of 2.38 kb in length. The PCR results are shown in FIG. 42. The PCR parameters for the reaction were 94° C. 30 seconds, 58° C. 30 seconds, and 72° C. 2 minutes for 35 cycles.

Somatic Neo Deleted Mouse Information

The following heterozygous mice were confirmed for Somatic Neo Deletion.

| Mouse # | Sex | Clone # | Parent Info |
|---|---|---|---|
| 582 | M | 271 | CH × C57BL/6 FLP |
| 584 | M | 271 | CH × C57BL/6 FLP |
| 585 | F | 271 | CH × C57BL/6 FLP |
| 587 | M | 271 | CH × C57BL/6 FLP |
| 589 | F | 271 | CH × C57BL/6 FLP |
| 590 | F | 271 | CH × C57BL/6 FLP |
| 591 | F | 271 | CH × C57BL/6 FLP |
| 592 | M | 271 | CH × C57BL/6 FLP |

Generation and Identification of Germline Neo Deleted Mice

Confirmed Somatic Neo Deleted Mice were set up for mating with C57BL/6 wild-type mice to generate Germline Neo Deleted mice. Resulting pups were genotyped as follows. FIG. 43 provides a schematic diagram for the primers used for PCR screening. The sequences of the primers used for PCR screening are listed below.

```
Primers for PCR Screening (SEQ ID NOs: 61,
63-65, respectively, in order of appearance):
Forward Oligos
NDEL1:
5'-ACT TTG GAA GTG GCA GAA GAA TTA GGG-3'

Reverse Oligos
PT4:
5'-GCT CTT GAA CTT GGT AGG CAA ATG C-3'

FLP1:
5'-CAC TGA TAT TGT AAG TAG TTT GC-3'

FLP2:
5'-CTA GTG CGA AGT AGT GAT CAG G-3'
```

The FLP primers cannot be seen in the schematic diagram in FIG. 43.

Screening for Neo Deletion

Primer set NDEL1 and PT4 was used to screen mice for the deletion of the Neo cassette. The PCR product for the wild-type is 705 bp. After Neo deletion, one set of LoxP-FRT sites remain (143 bp). A second band with a size of 848 bp indicates Neo deletion. The presence of the Neo cassette was not amplified by this PCR screening because the size is too great. FIG. 44 shows the screening results. The PCR parameters for the screening were 94° C. 30 seconds, 60° C. 30 seconds, and 72° C. 1 minute for 30 cycles.

Screening for Absence of FLP Transgene Primer set FLP1 and FLP2 was used to screen mice for absence of the FLP transgene. The amplified product for primer set FLP1 and FLP2 is 725 bp. PCR parameters for this reaction are 94° C. 30 seconds, 55° C. 30 seconds, and 72° C. 1 minute for 30 cycles. FIG. 44 shows the results of the screening. Mice without the FLP transgene were selected for future study.

Germline Neo Deleted Mouse Information

The following heterozygous mice were confirmed for Germline Neo Deletion and FLP absence. These mice are recommended to be mated to each other to generate Homozygote Germline Neo Deleted mice,

| Mouse # | Sex | Clone # | Parent Info |
|---|---|---|---|
| 544 | M | 271 | SND # 582 × C57BL/6 WT |
| 545 | M | 271 | SND # 582 × C57BL/6 WT |
| 546 | F | 271 | SND # 582 × C57BL/6 WT |
| 551 | M | 271 | SND # 587 × C57BL/6 WT |

| Mouse # | Sex | Clone # | Parent Info |
|---------|-----|---------|-------------|
| 552 | F | 271 | SND # 587 × C57BL/6 WT |
| 554 | M | 271 | SND # 590 × C57BL/6 WT |
| 557 | F | 271 | SND # 590 × C57BL/6 WT |

DNA Electrophoresis References

The size of a DNA band on an agarose gel after electrophoresis was estimated by comparing the position of the DNA band to a reference ladder. Two types of ladders are used: 1 kb ladder and 100 bp ladder. FIGS. 45A and 45B show the ladders used.

T Cell Isolation and Experiments:

Mouse T cells were harvested from spleen using a Mouse Pan T cell Isolation kit II (Miltneyi). T cells were activated with CD3/CD28 Mouse Dynabeads (Life Technologies) and treated with DMSO, 1 uM or 10 uM lenalidomide or pomalidomide for 18-24 hours. After 18 hours, the concentration of mIL-2 in the cell culture supernatant was determined by ELISA (Mouse IL-2 Quantikine Kit, R &D Systems). cDNA was synthesized from the cell pellet (Miltenyi MultiMacs cDNA synthesis kit) and qPCR for IL-2 was performed using Taqman probe Mm00434256_m1. Cells were also harvested in IP Lysis buffer (Pierce) for Western Blotting with anti-IKZF1 (Santa Cruz H-100 antibody) and anti-IKZF3 (Imgenex IMG-6283) using anti-Rabbit secondary (GE Healthcare) and anti-Actin-HRP (abcam ab20272).

C-Kit$^+$ Cell Isolation and Experiments:

C-Kit$^+$ cells were isolated with a CD117 MicroBead Kit (Miltenyi) and an AutoMacs Pro and grown in SFEM (StemSpan) supplemented with antibiotics and 50 ng ml$^{-1}$ mTPO (Peprotech) and 50 ng ml$^{-1}$ mSCF (Peprotech). For Western Blot, cells were treated with lenalidomide or DMSO for 24 hours and harvested in IP lysis buffer (Pierce). Lysates were blotted with anti-casein kinase (C-19, Santa Cruz) with anti-goat secondary (Jackson ImmunoResearch.) For in vitro competition experiments, cells from mice of specified genotypes (all CD45.2) were mixed in a 1:1 ratio with CD45.1+ cells from SJL strain mice. Cells grown in SFEM with various doses of lenalidomide and the percent CD45.1 and CD45.2 cells were followed by flow cytometry over time following cell surface staining. Antibodies for flow cytometry were as follows: CD45.2 PE (104, eBioscience), and CD45.2 FITC (104, eBioscience). For these experiments, approximately half of the cells were removed from the culture for flow cytometry every other day and an equal volume of media with fresh drug was added back to maintain the culture volume.

Mice In Vivo Experiments:

CRBN$^{I391V/I391V}$ mice were treated with lenalidomide (10 or 100 mg/kg) or thalidomide (250 mg/kg) by oral gavage or intraperitoneal injection. T cells were isolated from these mice 14 hours after treatment and subjected to Western Blotting for IKZF1 and Ck1α.

Lenalidomide and Thalidomide were purchased from Selleck Chemical. Drugs were suspended in DMSO, then diluted five-fold with saline immediately before injection. Mice were 6-8 weeks old. T cells were isolated from spleen as described above.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications, including U.S. Ser. No. 61/902,066, mentioned in this specification are herein incorporated by reference to the same extent as if each independent patent and publication was specifically and individually indicated to be incorporated by reference.

What is claimed is:

1. A method of reducing the proliferation of a cell, the method comprising: contacting the cell with (i) lenalidomide or a lenalidomide analog; and (ii) an inhibitory nucleic acid molecule that decreases the expression of casein kinase 1A1 (CSNK1A1) polypeptide.

2. The method of claim 1, wherein the inhibitory nucleic acid molecule is a CSNK1A1-specific antisense nucleic acid molecule, shRNA, siRNA molecule, or Crispr.

3. The method of claim 1, wherein the cell is a B cell neoplasia cell, a hematopoietic cell, a mononuclear cell, a myeloid cell, or a myeloma cell.

4. The method of claim 1, wherein the cell is obtained from a subject having myelodysplastic syndrome (MDS) or acute myeloid leukemia (AML).

5. The method of claim 1, wherein the lenalidomide analog is thalidomide or pomalidomide.

6. A method of treating a B cell neoplasia in a subject, the method comprising:
    administering to a subject having a B cell neoplasia a casein kinase inhibitor in an effective amount to inhibit CSNK1A1 expression in the neoplasia cells, thereby treating the B cell neoplasia.

7. A method of identifying an agent that treats myelodysplastic syndrome, the method comprising: contacting a cell with the agent and detecting a decrease in casein kinase 1A1 (CSNK1A1) polypeptide level in the cell compared to the level of (CSNK1A1) polypeptide in an untreated control cell, thereby identifying the agent as treating myelodysplastic syndrome.

8. A method of treating a patient having a hematopoietic or myeloid cell disease or disorder, wherein said patient is pre-selected as having a hematopoietic or myeloid cell disease or disorder which is sensitive to lenalidomide or a lenalidomide analog by:
    (i) contacting a cell from the patient having a hematopoietic or myeloid cell disease or disorder with lenalidomide or a lenalidomide analog; and
    (ii) assaying the cell to detect sensitivity to lenalidomide or a lenalidomide analog by detecting a decrease in the level of casein kinase 1A1 (CSNK1A1) polypeptide in the cell compared to the amount of said polypeptide in an untreated or non-disease control cell, or by detecting an increase in the level of ubiquitinated CSNK1A1 polypeptide in the cell compared to the amount of said ubiquitinated polypeptide in an untreated or non-disease control cell; and
    administering an effective amount of lenalidomide or a lenalidomide analog to the pre-selected patient to treat the hematopoietic or myeloid cell disease or disorder.

9. The method of claim 8, wherein the lenalidomide analog is thalidomide or pomalidomide.

10. The method of claim 8, wherein the hematopoietic or myeloid cell disease or disorder is myelodysplastic syndrome (MDS) or acute myeloid leukemia (AML).

11. A method of treating a patient having a hematopoietic or myeloid cell disease or disorder, wherein said patient is pre-selected for having a hematopoietic or myeloid cell disease or disorder which is resistant to lenalidomide or a lenalidomide analog by:
    (i) contacting a cell from the patient having a hematopoietic or myeloid cell disease or disorder with lenalidomide or a lenalidomide analog; and
    (ii) assaying the cell to detect resistance to lenalidomide or a lenalidomide analog by detecting no significant decrease in the level of casein kinase 1A1 (CSNK1A1) polypeptide in the cell compared to the amount of said polypeptide in an untreated or non-disease control cell, or by detecting no significant increase in the level of ubiquitinated CSNK1A1 polypeptide in the cell compared to the amount of said ubiquitinated polypeptide in an untreated or non-disease control cell; and
    administering an effective amount of a non-lenalidomide or a non-lenalidomide analog drug to the pre-selected patient to treat the hematopoietic or myeloid cell disease or disorder.

12. The method of claim 11, wherein the lenalidomide analog is thalidomide or pomalidomide.

13. The method of claim 11, wherein the hematopoietic or myeloid cell disease or disorder is myelodysplastic syndrome (MDS) or acute myeloid leukemia (AML).

14. The method of claim 11, wherein the patient has myelodysplastic syndrome and is treated with azacitidine or decitabine.

15. The method of claim 6, wherein the casein kinase 1 inhibitor is D4476.

16. The method of claim 11, wherein the non-lenalidomide or non-lenalidomide analog drug is anti-neoplastic therapy, [(1R)-3-methyl-1-[[(2S)-3-phenyl-2-(pyrazine-2-carbonylamino)propanoyl]amino]butyl]boronic acid, or corticosteroids.

* * * * *